(12) United States Patent
Cadilla et al.

(10) Patent No.: US 7,229,998 B2
(45) Date of Patent: Jun. 12, 2007

(54) THIAZOLE AND OXAZOLE DERIVATIVES AS ACTIVATORS OF HUMAN PEROXISOME PROLIFERATOR ACTIVATED RECEPTORS

(75) Inventors: Rodolfo Cadilla, Durham, NC (US); Millard Hurst Lambert, III, Durham, NC (US); Stephen William Rafferty, Durham, NC (US); Daniel David Sternbach, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/550,060

(22) Filed: Oct. 17, 2006

(65) Prior Publication Data

US 2007/0072871 A1 Mar. 29, 2007

Related U.S. Application Data

(63) Continuation of application No. 10/451,295, filed as application No. PCT/US01/51056 on Dec. 19, 2001, now abandoned.

(30) Foreign Application Priority Data

Dec. 20, 2000 (GB) .................... 0031103.5

(51) Int. Cl.
  *A61K 31/496* (2006.01)
  *C07D 417/06* (2006.01)
  *C07D 417/14* (2006.01)
  *C07D 277/30* (2006.01)

(52) U.S. Cl. ............ 514/254.2; 544/367; 544/133; 544/295; 544/357; 546/209; 548/131; 548/204; 548/236

(58) Field of Classification Search ............ 544/367; 514/254.02
  See application file for complete search history.

(56) References Cited

U.S. PATENT DOCUMENTS 5,972,881 A 10/1999 Heyman et al.
2004/0077659 A1 4/2004 Oliver, Jr.

FOREIGN PATENT DOCUMENTS

| WO | 00/08002 | 2/2000 |
| WO | 02/062774 | 8/2000 |
| WO | 01/00603 | 1/2001 |
| WO | 01/40207 | 6/2001 |
| WO | 02/50048 | 6/2002 |

OTHER PUBLICATIONS

J.M. Lehmann et al., "An Antidiabetic Thiazolidinedione is a High Affinity Ligand for Peroxisome Proliferator-Activated Receptor Gamma," *Journal of Biological Chemistry*, V270, N22, Jun. 2, 1995, pp. 12953-12956.
W.R. Oliver et al., "A Selective Peroxisome Proliferator-Activated Receptor Delta Agonist Promotes Reverse Cholesterol Transport," *Proceeding of the National Academy of Sciences of the USA*, V98, N9, Apr. 24, 2001, pp. 5306-5311.
Ellis et al., "Troglitazone Improves Psoriasis and Normalizes Models of Proliferative Skin Disease," *Arch Dermatol*, V136, May 2000, pp. 609-616.
Vippagunta et al., Advanced Drug Delivery Reviews, 2000, V48, pp. 3-26.
Mae et al., American Society for Nutritional Sciences, 2003, 99 3369-3377.
Berger et al., Annu. Rev. Med., 2002, V53, pp. 409-435.
Miyachi, Expert Opin. Ther. Patents, 2004, V14, pp. 607-618.
Rami et al., Exp. Opin. Ther. Patents, 2000, V10, pp. 623-634.
Mukherjee et al., Emerging Therapeutic Targerts, 2000, V4, pp. 377-396.
Bishop-Bailey, British Journal of Pharmacology, 2000, V129, pp. 823-834.

*Primary Examiner*—Emily Bernhardt
(74) *Attorney, Agent, or Firm*—Jennifer L. Fox

(57) ABSTRACT

The present invention provides a compound of formula (I):

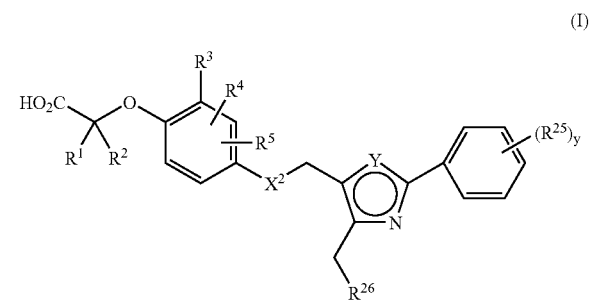

wherein $R_1$–$R_5$, $R_{25}$, $R_{26}$, Y and $X_2$ are as defined herein. The compounds activate human peroxisome proliferator activated receptors (hPPARs) and are useful for the treatment of associated disorders such as cardiovascular disease and hypercholesteremia.

3 Claims, No Drawings

THIAZOLE AND OXAZOLE DERIVATIVES AS ACTIVATORS OF HUMAN PEROXISOME PROLIFERATOR ACTIVATED RECEPTORS

This application is a continuation of Ser. No. 10/451,295 filed Oct. 31, 2003, now abandoned, which is a 371 application of PCT/US01/51056 filed Dec. 19, 2001 which claims priority to 0031103.5 GB filed Dec. 20, 2000. Both applications are incorporated herein by reference in their entirety.

The present invention relates to certain novel compounds. In particular, the present invention relates to compounds that activate human peroxisome proliferator activated receptors ("hPPARs"). The present invention also relates to methods for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. Curr. Pharm. Des. 1998, 4, 53–70).

Syndrome X (including metabolic syndrome) is loosely defined as a collection of abnormalities including hyperinsulinemia, obesity, elevated levels of triglycerides, uric acid, fibrinogen, small dense LDL particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., Curr. Opin. Chem. Biol. (1997) Vol 1 pp 235–241 and Willson T. M. et. al., J. Med. Chem (2000) Vol 43 p527–549. The binding of agonist ligands to the receptor results in changes in the expression level of mRNA's encoded by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, Trends Endocrin. Met 291–296, 4 (1993)).

It has now been reported that thiazolidinediones are potent and selective activators of PPAR-gamma and bind directly to the PPAR-gamma receptor (J. M. Lehmann et. al., J. Biol. Chem. 12953–12956, 270 (1995)), providing evidence that PPAR-gamma is a possible target for the therapeutic actions of the thiazolidinediones.

Activators of the nuclear receptor PPARγ, for example troglitazone, have been shown in the clinic to enhance insulin-action, reduce serum glucose and have small but significant effects on reducing serum triglyceride levels in patients with Type 2 diabetes. See, for example, D. E. Kelly et al., Curr. Opin. Endocrinol. Diabetes, 90–96, 5 (2), (1998); M. D. Johnson et al., Ann. Pharmacother., 337–348, 32 (3), (1997); and M. Leutenegger et al., Curr. Ther. Res., 403–416, 58 (7), (1997).

The mechanism for this triglyceride lowering effect appears to be predominantly increased clearance of very low density lipoproteins (VLDL) through induction of lipoprotein lipase (LPL) gene expression. See, for example, B. Staels et al., Arterioscler. Thromb., Vasc. Biol., 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., Curr. Pharm. Des., 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-II, an inhibitor of LPL activity, increases clearance of VLDL. See, for example, J. Auwerx et al., Atherosclerosis, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.). In a recent report (Berger et al., J. Biol. Chem. 1999), vol. 274, pp. 6718–6725) it was stated that PPAR□ activation does not appear to modulate glucose or triglyceride levels.

In one aspect, the present invention provides compounds of formula (I) and pharmaceutically acceptable salts, solvates, and hydrolysable esters thereof wherein;

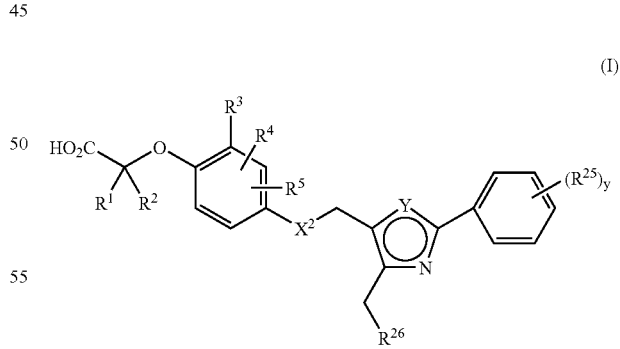

(I)

$R^1$ and $R^2$ are independently hydrogen or $C_{1-3}$ alkyl;

$X^2$ is O, S, or $CH_2$;

$R^3$, $R^4$, and $R^5$ are independently H, $C_{1-3}$alkyl, $OCH_3$, $CF_3$, $OCF_3$, allyl, CN, or halogen;

Y is S or O;

each $R^{25}$ is independently $CH_3$, $OCH_3$, $OCF_3$, $CF_3$, or halogen;

y is 0, 1, 2, 3, 4 or 5; and $R^{26}$ is selected from the group consisting of the moieties A through K depicted below:

A wherein $R^{12}$ is selected from the group consisting of $C_{1-6}$alkyl, $C_{1-6}$alkylenearyl, and the moieties depicted below in Group II, Group II

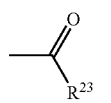 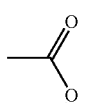 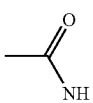 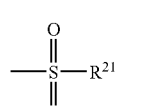

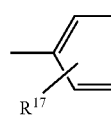 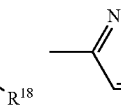 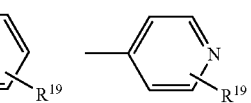

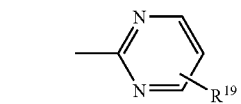 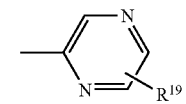

wherein $R^{17}$ and $R^{18}$ are independently hydrogen, halogen, hydroxy, —CN, $C_{1-6}$alkyl, $C_{1-6}$perfluoroalkyl, $C_{1-6}$acyl, —$OC_{1-6}$alkyl, perfluoro$OC_{1-6}$alkyl, or $C_{1-6}$hydroxyalkyl;

$R^{19}$ is hydrogen or $C_{1-6}$alkyl;

$R^{21}$ is $C_{1-6}$alkyl, —$C_{1-6}$alkylenearyl, aryl, or -aryl-heteroaryl;

$R^{22}$ is $C_{1-6}$alkyl, aryl, or —$C_{1-6}$alkylenearyl;

$R^{23}$ is $C_{1-6}$alkyl, $C_{3-6}$cycloalkyl, or aryl;

$R^{24}$ is $C_{1-6}$alkyl, —$C_{1-6}$alkylenearyl, $C_{3-6}$cycloalkyl, or aryl;

B wherein Z is O, N or S (note that when Z is N, the depicted bond can be attached to the nitrogen in the ring as well as any of the carbons in the ring);

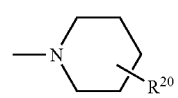

C wherein $R^{20}$ is $C_{1-6}$alkyl, aryl, —$OC_{1-6}$alkyl, hydroxy, $C_{1-6}$hydroxyalkyl, or 1-alkoxy$C_{1-6}$alkyl;

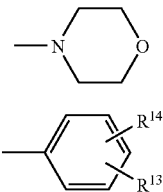

D

E

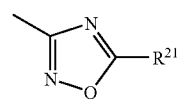

wherein $R^{13}$ and $R^{14}$ are independently hydrogen, halogen, CN, perfluro$C_{1-6}$alkyl, perfluro$OC_{1-6}$alkyl, $C_{1-6}$alkyl, —$OC_{1-6}$alkyl, —$C_{1-6}$alkyleneO$C_{1-6}$alkyl, —$SC_{1-6}$alkyl, or aryl;

F

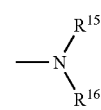

wherein $R^{21}$ is independently as defined above;

G

wherein $R^{15}$ and $R^{16}$ are independently hydrogen, $C_{1-6}$alkyl, $C_{3-6}$cycloalkyl optionally substituted with 1 or 2 $C_{1-3}$alkyl groups, or $R^{12}$ as defined above;

H

I

wherein n is 1-3

J

—O—$R^{21}$ wherein $R^{21}$ is independently as defined above; and

K

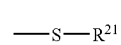

wherein $R^{21}$ is independently as defined above. As used herein "aryl" or in any phrase or term including "aryl" such as "—$C_{1-6}$alkylenearyl", the "aryl" means a phenyl group or a 5 or 6 membered heteroaryl group. As used herein "heteroaryl" means a 5 or 6 membered heteroaryl group. As used herein any such "aryl" or "heteroaryl" group may optionally be substituted with one or two substituents selected from the group consisting of halogen, CN, dimethylamino, perfluro$C_{1-6}$alkyl, perfluro$OC_{1-6}$alkyl, $C_{1-6}$alkyl, —$OC_{1-6}$alkyl, —$C_{1-6}$alkyleneO$C_{1-6}$alkyl, and —$SC_{1-6}$alkyl.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable hydrolyzable ester or, solvate, thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $R^1$ and $R^2$ are independently H or $CH_3$. Most preferably $R^1$ and $R^2$ are either both H or both $CH_3$.

Preferably $X^2$ is O or S. More preferably $X^2$ is S;
Preferably $R^3$ is $CH_3$ or H;
Preferably $R^4$ and $R^5$ are H.
Preferably Y is S.
Preferably y is 1 or 2. When y is 2, preferably one $R^{25}$ is halogen; more preferably one is halogen and the other is $CF_3$. When y is 1, preferably the $R^{25}$ is in the para position on the ring and is more preferably $CF_3$.

Preferably $R^{26}$ is selected from the moieties shown below in Group III.

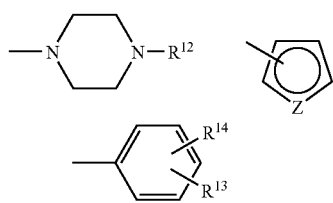

Group III

Preferably $R^{12}$ is selected from the moieties shown below in Group IV.

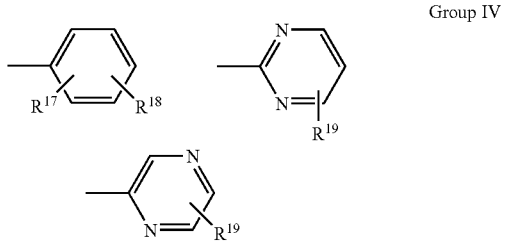

Group IV

Preferably $R^{13}$ or $R^{14}$ are independently fluorine, bromine, phenyl, thienyl, $CF_3$, $OCF_3$, $OCH_3$, $SCH_3$, or t-butyl. Most preferably $R^{14}$ is thienyl, $OCH_3$, $OCF_3$, $CF_3$, or fluorine. Most preferably $R^{14}$ is substituted para to the depicted open valence. Most preferably $R^{13}$ is hydrogen or fluorine.

Preferably $R^{17}$ and $R^{18}$ are independently hydrogen, OH, $OC_{1-3}$alkyl, CN, halogen, $CF_3$, $COCH_3$, $CH(OH)CH_3$, or $OCF_3$. Most preferably $R^{17}$ is fluorine, chlorine, $OC_{1-3}$alkyl, or $COCH_3$ and $R^{18}$ is $OCH_3$ or hydrogen. Most preferably $R^{17}$ is substituted para to the depicted open valence.

Preferably $R^{20}$ is phenyl, methyl, $OCH_3$, OH, or $CH_2OH$.
Preferably $R^{21}$ is —$C_{1-3}$alkylenephenyl, phenyl-5-methyl-1,2,4-oxadiazol-3-yl, or phenyl optionally substituted by methyl or CN.

Preferably $R^{22}$ is $C_{1-6}$alkyl, phenyl, or benzyl.
Preferably $R^{23}$ is $C_{1-6}$alkyl, furanyl, thienyl, methoxymethyl, $C_{3-6}$cyclalkyl, or phenyl optionally substituted by a halogen a methoxy or a dimethylamino group.

Preferably $R^{24}$ is H, $C_{1-6}$alkyl, cyclohexyl, m-methoxyphenyl, p-fluorophenyl, or —$CH_2CH_2$phenyl.
Preferably $R^{19}$ is hydrogen.

Particularly preferred compounds will be those is which most or all of the variables are selected from the preferred or most preferred groups for each variable.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Suitable compounds of formula (1) include:
2-[4-({[4-{[4-(4-acetylphenyl)-1-piperazinyl]methyl}-2-(4-fluorophenyl)-1,3-thiazol-5-yl]methyl}sulfanyl)-2-methylphenoxy]-2-methylpropanoic acid,
2-methyl-2-{2-methyl-4-[({4-[4-(methylsulfanyl)benzyl]-2-[4-(trifluoromethyl)phenyl]-1,3-thiazol-5-yl}methyl) sulfanyl]phenoxy}propanoic acid,
{2-methyl-4-[({4-(3-thienylmethyl)-2-[4-(trifluoromethyl) phenyl]-1,3-thiazol-5-yl}methyl)sulfanyl] phenoxy}acetic acid,
{4-[({4-benzyl-2-[4-(trifluoromethyl)phenyl]-1,3-thiazol-5-yl}methyl)sulfanyl]-2,5-dimethylphenoxy}acetic acid,
2-{4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}propanoic acid,
2-{4-[({4-{[4-(4-acetylphenyl)-1-piperazinyl]methyl}-2-[4-(trifluoromethyl)phenyl]-1,3-thiazol-5-yl}methyl)sulfanyl]-2-ethylphenoxy}propanoic acid,
2-{2-methyl-4-[({4-(2-thienylmethyl)-2-[4-(trifluoromethyl)phenyl]-1,3-thiazol-5-yl}methyl)sulfanyl] phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-{[4-(4-ethoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-methyl-2-{2-methyl-4-[({4-{[4-(phenoxycarbonyl)-1-piperazinyl]methyl}-2-[4-(trifluoromethyl)phenyl]-1,3-thiazol-5-yl}methyl)sulfanyl]phenoxy}propanoic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}propanoic acid, {2-methyl-4-[({4-[4-(3-thienyl)benzyl]-2-[4-(trifluoromethyl)phenyl]-1,3-thiazol-5-yl}methyl)sulfanyl]phenoxy}acetic acid, 2-(4-{[(2-(4-fluorophenyl)-4-{[4-(4-methoxyphenyl)-1-piperazinyl]methyl}-1,3-thiazol-5-yl)methyl]sulfanyl}-2-methylphenoxy)-2-methylpropanoic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]phenoxy}-2-methylpropanoic acid, 2-{4-[({4-{[4-(2,4-dimethoxyphenyl)-1-piperazinyl]methyl}-2-[4-(trifluoromethyl)phenyl]-1,3-thiazol-5-yl}methyl)sulfanyl]-2-methylphenoxy}propanoic acid, {2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-propylphenoxy}propanoic acid, 2-{4-[({4-benzyl-2-[4-(trifluoromethyl)phenyl]-1,3-thiazol-5-yl}methyl)sulfanyl]-2-methylphenoxy}propanoic acid, 2-{2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid, 2-methyl-2-{2-methyl-4-[({4-[4-(trifluoromethyl)benzyl]-2-[4-(trifluoromethyl)phenyl]-1,3-thiazol-5-yl}methyl)sulfanyl]phenoxy}propanoic acid, 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}-2-methylpropanoic acid, {4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}acetic acid, {4-[({4-([1,1'-biphenyl]-4-ylmethyl)-2-[4-(trifluoromethyl)phenyl]-1,3-thiazol-5-yl}methyl)sulfanyl]-2-methylphenoxy}acetic acid, 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}propanoic acid, {4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}acetic acid, 2-{2-methyl-4-[({4-(3-thienylmethyl)-2-[4-(trifluoromethyl)phenyl]-1,3-thiazol-5-yl}methyl)sulfanyl]phenoxy}propanoic acid, {4-[({4-{[4-(2-methoxyphenyl)-1-piperazinyl]methyl}-2-[4-(trifluoromethyl)phenyl]-1,3-thiazol-5-yl}methyl)sulfanyl]-2-methylphenoxy}acetic acid, 2-{2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid, 2-{4-[({4-(4-tert-butylbenzyl)-2-[4-(trifluoromethyl)phenyl]-1,3-thiazol-5-yl}methyl)sulfanyl]-2-methylphenoxy}-2-methylpropanoic acid, 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-benzyl-2-[4-(trifluoromethyl)phenyl]-1,3-thiazol-5-yl}methyl)sulfanyl]-2,3-dimethylphenoxy}propanoic acid, 2-{4-[({4-{[4-(4-chlorophenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-benzyl-2-[4-(trifluoromethyl)phenyl]-1,3-thiazol-5-yl}methyl)sulfanyl]-2-fluorophenoxy}propanoic acid, 2-{4-[({4-{[4-(2,4-difluorophenyl)-1-piperazinyl]methyl}-2-[4-(trifluoromethyl)phenyl]-1,3-thiazol-5-yl}methyl)sulfanyl]-2-methylphenoxy}propanoic acid, {4-[({4-(2,4-difluorobenzyl)-2-[4-(trifluoromethyl)phenyl]-1,3-thiazol-5-yl}methyl)sulfanyl]-2-methylphenoxy}acetic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}-2-methylpropanoic acid, 2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid, {2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid, 2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid, 2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid, 2-methyl-2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid, 2-{4-[({4-{[4-(4-isopropoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{2-methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid, {2-methyl-4-[({4-(3-phenylpropyl)-2-[4-(trifluoromethyl)phenyl]-1,3-thiazol-5-yl}methyl)sulfanyl]phenoxy}acetic acid,

[4-[({4-benzyl-2-[4-(trifluoromethyl)phenyl]-1,3-thiazol-5-yl}methyl)sulfanyl]-2-(trifluoromethyl)phenoxy]acetic acid, {2-methyl-4-[({4-{[4-(5-methyl-1,2,4-oxadiazol-3-yl)phenoxy]methyl}-2-[4-(trifluoromethyl)phenyl]-1,3-thiazol-5-yl}methyl)sulfanyl]phenoxy}acetic acid, {4-[({4-benzyl-2-[4-(trifluoromethyl)phenyl]-1,3-thiazol-5-yl}methyl)sulfanyl]-5-chloro-2-methylphenoxy}acetic acid, {4-[({4-benzyl-2-[4-(trifluoromethyl)phenyl]-1,3-thiazol-5-yl}methyl)sulfanyl]-2-methylphenoxy}acetic acid, {4-[({4-(4-methoxybenzyl)-2-[4-(trifluoromethyl)phenyl]-1,3-thiazol-5-yl}methyl)sulfanyl]-2-methylphenoxy}acetic acid, {2,5-dimethyl-4-[({4-(3-thienylmethyl)-2-[4-(trifluoromethyl)phenyl]-1,3-thiazol-5-yl}methyl)sulfanyl]phenoxy}acetic acid, {2-methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}acetic acid, {4-[({4-benzyl-2-[4-(trifluoromethyl)phenyl]-1,3-thiazol-5-yl}methyl)sulfanyl]-2,3-dimethylphenoxy}acetic acid,
[4-({[2-(4-chlorophenyl)-4-methyl-1,3-thiazol-5-yl]methyl}sulfanyl)-2-methylphenoxy]acetic acid,
{2-methyl-4-[({4-[(4-methyl-2-thienyl)methyl]-2-[4-(trifluoromethyl)phenyl]-1,3-thiazol-5-yl}methyl)sulfanyl]phenoxy}acetic acid,
{4-[({4-benzyl-2-[4-(trifluoromethyl)phenyl]-1,3-thiazol-5-yl}methyl)sulfanyl]-2-bromophenoxy}acetic acid,
{2-methyl-4-[({4-[(2-phenylethoxy)methyl]-2-[4-(trifluoromethyl)phenyl]-1,3-thiazol-5-yl}methyl)sulfanyl]phenoxy}acetic acid,
{2-methyl-4-[({4-(2-phenylethyl)-2-[4-(trifluoromethyl)phenyl]-1,3-thiazol-5-yl}methyl)sulfanyl]phenoxy}acetic acid, and
pharmaceutically acceptable salts, solvates, and hydrolyzable esters thereof.

More preferred compounds of formula (1) include:
2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid,
2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid,
{2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid,
2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid,
2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid,
2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid,
2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid,
2-methyl-2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid,
2-{4-[({4-{[4-(4-isopropoxyphenyl)-1-piperazinyl]methyl}-2-[4-(trifluoromethyl)phenyl]-1,3-thiazol-5-yl}methyl)sulfanyl]-2-methylphenoxy}propanoic acid,
2-{2-methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid, and
pharmaceutically acceptable salts, solvates, and hydrolyzable esters thereof.

Preferably, the compounds of formula (I) are hPPAR agonists. The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 5.0 preferably at least 6.0 to the relevant PPAR, for example hPPAR□ in the binding assay described below, and which achieve at least 30% activation of the relevant PPAR relative to the appropriate indicated positive control in the transfection assay described below at concentrations of $10^{-5}$ M or less. More preferably, the compounds of this invention achieve 30% activation of at least one human PPAR in the relevant transfection assay at concentrations of $10^{-6}$ M or less. More preferably the compounds of the invention achieve 30% activation of at least one human PPAR in the relevant transfection assay at concentrations of $10^{-7}$ M or less.

Preferably the compounds of formula (1) are hPPARδ agonists. More preferably they are also agonists of at least one of PPARγ or PPARα. Most preferably they are pan hPPAR agonists.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

There is further provided processes for the preparation of compounds of 1. Unless otherwise indicated all definitions are as above.

In general when $X^2$ is O or S the compounds could be assembled by coupling through an alkylation step such as that shown below.

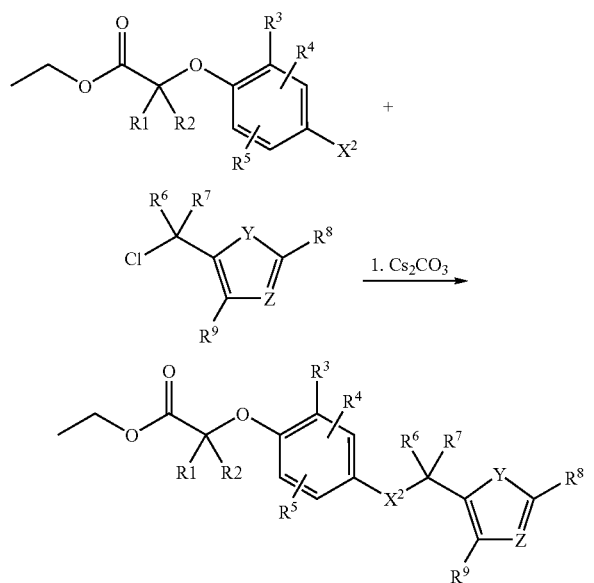

The esters are commercially available or made by the following general route when $X^2$ is S.

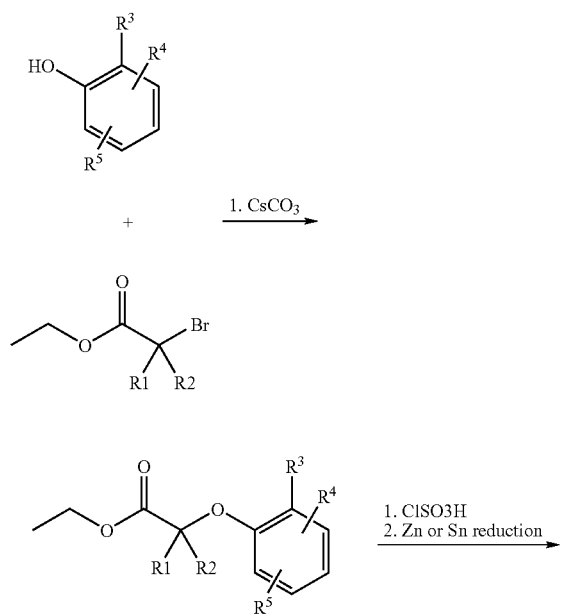

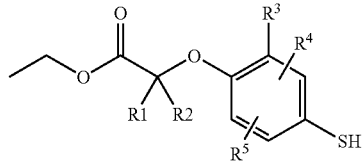

The heterocycle when Y is O or S and Z is N was generally made as shown below from an appropriate amide or thioamide:

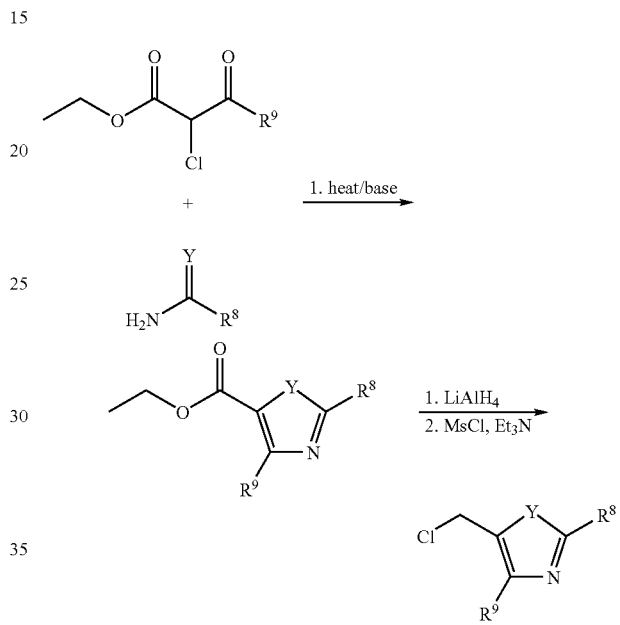

In specific cases the overall coupling step could be carried out directly after chlorosulfonation of the ester component without the need for formation of the chloride of the heterocyclic moiety, as shown below:

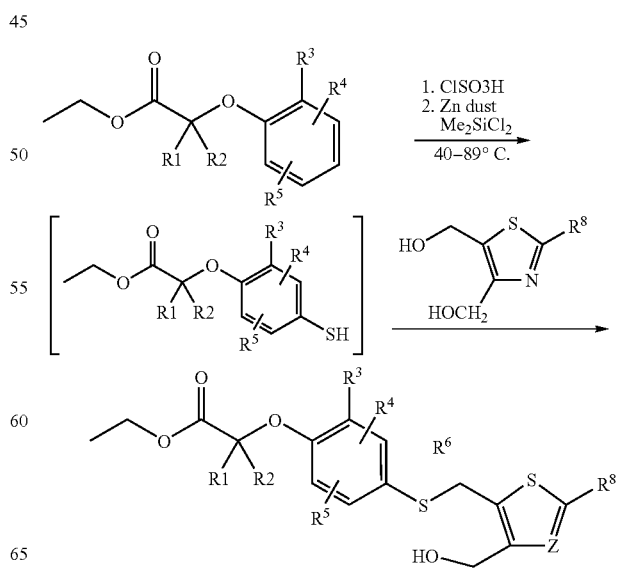

In some cases R⁹ was further elaborated through palladium coupling at the ester stage as shown below:

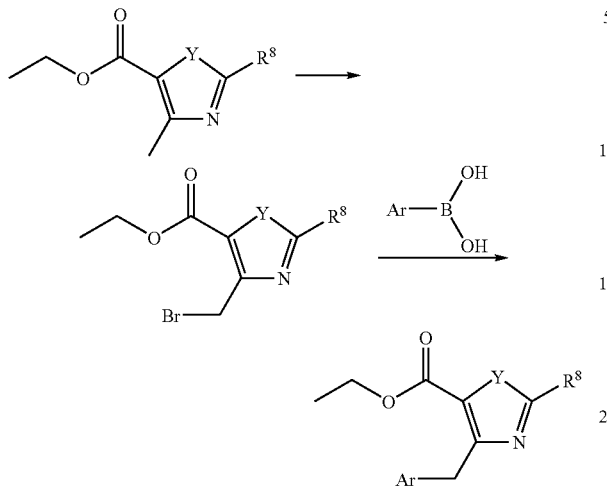

Alternatively R⁹ was elaborated after the coupling reaction by nucleophilic displacement of a mesylate shown below:

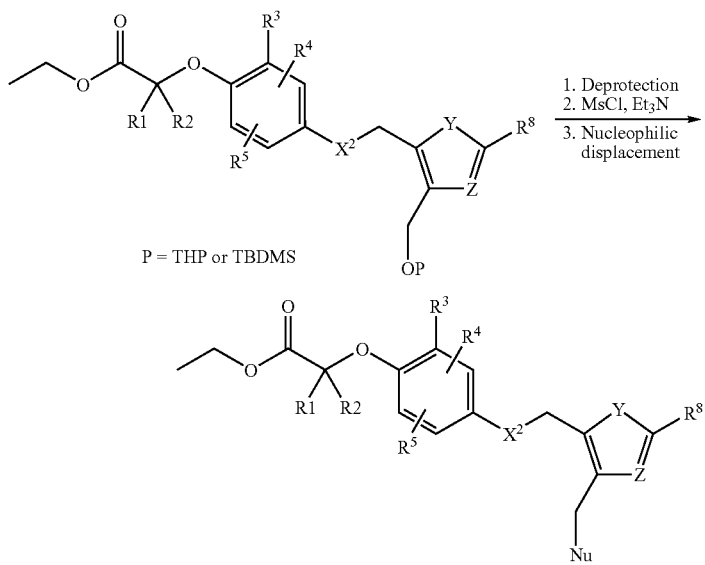

N-bromo succinimide (52.72 g, 1.1 eq) was added as a solid, Benzoyl peroxide (6.5 g, 10 mol %) was added at room temperature all at once as a solid, and the reaction mixture was refluxed for 5 hrs. The reaction was monitored by $^1$H NMR and was determined to be composed of a 9:1 mixture of mono-bromination product (i.e. desired product) and di-bromination product with a 90% conversion. After cooling to 0° C. (to precipitate out the succinimide) the reaction was filtered through Celite and the solvent was removed under reduced pressure to yield a brown oil. The oil was crystallized using hexanes to yield 100 g (94%) of an off-white product of 90% purity.

$^1$H NMR (CDCl$_3$) 400 MHz δ 8.10(d, 2H, J=8.20 Hz), 7.72(d, 2H, J=8.20 Hz), 4.99(s, 2H), 4.40(q, 2H, J=7.18 Hz), 1.41(t, 3H, J=7.18 Hz),

TLC(15% EtOAc/Hexanes) R$_f$=0.55

Ethyl 4-(bromomethyl)-2-phenyl-1,3-thiazole-5-carboxylate

The title compound was made using the same procedure as above.

$^1$H NMR (CDCl$_3$) 400 MHz δ 7.98(dd, 2H, J=7.86, 1.54 Hz), 7.47(m, 3H), 4.99(s, 2H), 4.39(q, 2H, J=7.12 Hz), 1.40(t, 3H, J=7.12 Hz),

TLC(15% EtOAc/Hexanes) R$_f$=0.50

EXAMPLES

The invention is further illustrated by the following Examples which should not be construed as constituting a limitation thereto.

Ethyl 4-(bromomethyl)-2-[4-(trifluoromethyl)phenyl]-1,3-thiazole-5-carboxylate

To a 2-L round-bottom flask equipped with an mechanical overhead stirrer, a reflux condenser and a N$_2$ inlet was added ethyl 4-methyl-2-[4-(trifluoromethyl)phenyl]-1,3-thiazole-5-carboxylate (85 g, 0.27 moles, 1.0 eq) and dry carbon tetrachloride (750 ml, 0.38M). Freshly recrystallized Ethyl 4-(hydroxymethyl)-2-[4-(trifluoromethyl)phenyl]-1,3-thiazole-5-carboxylate To a stirred solution of ethyl 4-(bromomethyl)-2-[4-(trifluoromethyl)phenyl]-1,3-thiazole-5-carboxylate (50 g, 0.127 moles, 1 eq) in dry DMF (300 ml) under a positive N$_2$ flow was added silver trifluoroacetate (42.02 g, 0.191 moles, 1.5 eq) all at once as a solid. This was stirred at room temperature for 3.5 hrs. The reaction was partitioned between ethyl ether (1.5 L) and water (500 ml). The phases were separated and the organic phase was washed twice with water (500 ml). After separation of the phases, the organic fraction was dried with Na$_2$SO$_4$, filtered and concentrated in vacuo. The crude trifluoroacetate product was used without characterization. Ethanol (300 ml) was added and the reaction was refluxed for 10 hrs. After cooling to room temperature the ethanol was removed in vacuo to yield 42 g (100%) of the title compound. The product was used without purification.

$^1$H NMR (CDCl3) 400 MHz δ 8.09(d, 2H, J=8.20 Hz), 7.73(d, 2H, J=8.20 Hz), 5.09(s, 2H), 4.41(q, 2H, J=7.12 Hz), 1.40(t, 3H, J=7.12 Hz),

Ethyl 4-(hydroxymethyl)-2-phenyl-1,3-thiazole-5-carboxylate

The title compound was made using the same procedure as above.

$^1$H NMR (CDCl$_3$) 400 MHz δ 7.95(m, 2H), 7.48(m, 3H), 5.09(s, 2H), 4.40(q, 2H, J=7.12 Hz), 1.41(t, 3H, J=7.12 Hz),

Ethyl 4-[(tetrahydro-2H-pyran-2-yloxy)methyl]-2-[4-(trifluoromethyl)phenyl]-1,3-thiazole-5-carboxylate To a 1-L round-bottom flask equipped with a magnetic stir-bar and a N$_2$ inlet was added Ethyl 4-(hydroxymethyl)-2-[4-(trifluoromethyl)phenyl]-1,3-thiazole-5-carboxylate (42 g, 0.127 moles, 1 eq) and dry CH$_2$Cl$_2$ (300 ml) at room temperature. This was followed by the addition of 3,4-dihydro-2H-pyran (14 ml, 0.152 moles, 1.2 eq) as a neat liquid and pyridinium p-toluenesulfonate (6.4 g, 25.4 mmoles, 20 mol %). The reaction mixture was stirred at room temperature overnight (10 hrs). The volatiles were then removed in vacuo and the residue was purified by flash silica gel chromatography (10% EtOAc/Hexanes to 30% EtOAc/Hexanes) to yield 34 g (64%) of pure title compound.

$^1$H NMR (CDCl$_3$) 400 MHz δ 8.09(d, 2H, J=8.20 Hz), 7.69(d, 2H, J=8.20 Hz), 5.18(d, 1H, J□.30 Hz), 4.99(d, 1H, J□.30 Hz), 4.90(t, 1H, J=3.42 Hz), 4.36(q, 2H, J=7.12 Hz), 3.98(m, 1H), 3.56(m, 1H), 1.69(m, 6H), 1.37(t, 3H, J=7.12 Hz),

TLC(30% EtOAc/Hexanes)=0.64

Ethyl 2-phenyl-4-[(tetrahydro-2H-pyran-2-yloxy)methyl]-1,3-thiazole-5-carboxylate $^1$H NMR (CDCl$_3$) 400 MHz δ 7.97(m, 2H), 7.43(m, 3H), 5.17(d, 1H, J□.13 Hz), 4.98(d, 1H, J□ 13 Hz), 4.91(t, 1H, J=3.33 Hz), 4.35(q, 2H, J=7.12 Hz), 3.98(m, 1H), 3.54(m, 1H), 1.69(m, 6H), 1.36(t, 3H, J=7.12 Hz), Ethyl 2-(4-fluorophenyl)-4-[(tetrahydro-2H-pyran-2-yloxy)methyl]-1,3-thiazole-5-carboxylate $^1$H Nz δ 7.97(m, 2H), 7.11(m, 2H), 5.16(d, 1H, J□.24 Hz), 4.97(d, 1H, J□.24 Hz), 4.90(t, 1H, J=3.36 Hz), 4.34(q, 2H, J=7.13 Hz), 3.98(m, 1H), 3.55(m, 1H), 1.86(m, 2H), 1.70(m, 2H), 1.55(m, 2H), 1.36(t, 3H, J=7.13 Hz), Suzuki Coupling Ethyl 4-[4-(trifluoromethyl)benzyl]-2-[4-(trifluoromethyl)phenyl]-1,3-thiazole-5-carboxylate To a solution of ethyl 4-(bromomethyl)-2-[4-(trifluoromethyl)phenyl]-1,3-thiazole-5-carboxylate (0.25 g, 0.63 mmol) in 4 ml of 2-methoxyethyl ether was added tetrakis(triphenylphosphine)palladium(0), (0.02 g, 0.019 mmol) and then sodium carbonate (0.13 g, 1.2 mmol) in 0.5 ml water. After brief stirring, 4-(trifluoromethyl)phenyl boronic acid (0.13 g, 0.7 mmol) in 1 ml ethanol was added. After heating at 110° C. for 15 hours, the reaction was complete by HPLC and was treated with water (5 ml) and extracted with tert-butyl methyl ether (2×30 ml). The organic layers were dried with magnesium sulfate and immediately loaded onto silica to give a crude residue which was purified on a Biotage FlashElute with a 40M silica cartridge, eluting with 10% ethyl acetate in hexanes to yield ethyl 4-[4-(trifluoromethyl)benzyl]-2-[4-(trifluoromethyl)phenyl]-1,3-thiazole-5-carboxylate as a white solid (0.09 g, 35%).

$^1$H NMR (CDCl$_3$): δ 8.18 (d, 2H), 7.78 (d, 2H), 7.58 (m, 4H), 4.68 (s, 2H), 4.40 (q, 2H), 1.40 (t, 3H); MS m/z 460 (M+1).

The following compounds were made using the same palladium catalyzed coupling procedure using the appropriate boronic acid.

Ethyl 4-[4-(trifluoromethoxy)benzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.25 g, 0.63 mmol), ethyl 4-[4-(trifluoromethoxy)benzyl]-2-[4-(trifluoromethyl)phenyl]-1,3-thiazole-5-carboxylate (0.12 g, 43%) was obtained as a light yellow solid.

$^1$H NMR (CDCl$_3$): δ 8.18 (d, 2H), 7.77 (d, 2H), 7.46 (d, 2H), 7.18 (d, 2H), 4.60 (s, 2H) 4.40 (q, 2H), 1.40 (t, 3H); MS m/z 476 (M+1).

Ethyl 4-[4-methoxybenzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.25 g, 0.63 mmol), ethyl 4-[4-methoxybenzyl]-2-[4-(trifluoromethyl)phenyl]-1,3-thiazole-5-carboxylate (0.16 g, 63%) was obtained as a yellow semi-solid.

$^1$H NMR (CDCl$_3$): δ 8.18 (d, 2H), 7.70 (d, 2H), 7.40 (d, 2H), 6.80 (d, 2H), 4.57 (s, 2H), 4.40 (q, 2H), 3.80 (s, 3H), 1.40 (t, 3H); MS m/z 422 (M+1).

Ethyl 4-[4-(methylsulfanyl)benzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4 g, 1.01 mmol), ethyl 4-[4-(methylsulfanyl)benzyl]-2-[4-(trifluoromethyl)phenyl]-1,3-thiazole-5-carboxylate (0.44 g, 100%) was obtained as a light yellow solid.

$^1$H NMR (CDCl$_3$): δ 8.11 (d, 2H), 7.71 (d, 2H), 7.38 (d, 2H), 7.21 (d, 2H), 4.52 (s, 2H), 4.38 (q, 2H), 2.49 (s, 3H), 1.40 (t, 3H); MS m/z 438 (M+1).

Ethyl 4-[4-tert-butylbenzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4 g, 1.01 mmol), ethyl 4-[4-tert-butylbenzyl]-2-[4-(trifluoromethyl)phenyl]-1,3-thiazole-5-carboxylate (0.24 g, 54%) was obtained as a white solid.

$^1$H NMR (CDCl$_3$): δ 8.11 (d, 2H), 7.73 (d, 2H), 7.56 (d, 1H), 7.49 (d, 1H), 7.34 (m, 2H), 4.58 (s, 2H), 4.40 (q, 2H), 1.40 (t, 3H), 1.27 (s, 9H); MS m/z 448 (M+1).

Ethyl 4-[3-thienylmethyl]-2-[4-(trifluoromethyl) phenyl]-1,3-thiazole-5-carboxylate From ethyl 4-(bromomethyl)-2-[4-(trifluoromethyl)phenyl]-1,3-thiazole-5-carboxylate (0.4 g, 1.01 mmol), ethyl 4-[3-thienylmethyl]-2-[4-(trifluoromethyl)phenyl]-1,3-thiazole-5-carboxylate (0.4 g 100%) was obtained as a yellow solid.

$^1$H NMR (CDCl$_3$): δ 8.12 (d, 2H), 7.77 (d, 2H), 7.40 (d, 1H), 7.28 (d, 1H), 7.20 (s, 1H), 4.61 (s, 2H), 4.41 (q, 2H), 1.40 (t, 3H); MS m/z 398 (M+1).

Ethyl 4-[2-furylmethyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4 g, 1.01 mmol), ethyl 4-[2-furylmethyl]-2-[4-(trifluoromethyl)phenyl]-1,3-thiazole-5-carboxylate (0.204 g, 53%) was obtained as a white solid.

MS m/z 382 (M+1); HPLC RT 4.072 (C18 4.2×100 mm, 0–100% ACN/H$_2$O (0.1% TFA), 6 min @ 2 ml/min @254/220 nm).

Ethyl 4-[3-furylmethyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4 g, 1.01 mmol), ethyl 4-[3-furylmethyl]-2-[4-(trifluoromethyl)phenyl]-1,3-thiazole-5-carboxylate (0.217 g, 56%) was obtained as a white solid.

MS m/z 382 (M+1); HPLC RT 4.091 (C18 4.2×100 mm, 0–100% ACN/H$_2$O (0.1% TFA), 6 min @ 2 ml/min @254/220 nm).

Ethyl 4-[2-thienylmethyl]-2-[4-(trifluoromethyl) phenyl]-1,3-thiazole-5-carboxylate From ethyl 4-(bromomethyl)-2-[4-(trifluoromethyl)phenyl]-1,3-thiazole-5-carboxylate (0.4 g, 1.01 mmol), ethyl 4-[2-thienylmethyl]-2-[4-(trifluoromethyl)phenyl]-1,3-thiazole-5-carboxylate (0.248 g, 62%) was obtained as a yellow solid.

MS m/z 398 (M+1); HPLC RT 4.224 (C18 4.2×100 mm, 0–100% ACN/H$_2$O (0.1% TFA), 6 min @ 2 ml/min @254/220 nm).

Ethyl 4-[(4-methyl-2-thienyl)methyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.6 g, 1.52 mmol), ethyl 4-[(4-methyl-2-thienyl)methyl]-2-[4-(trifluoromethyl)phenyl]-1,3-thiazole-5-carboxylate (0.5 g, 81%) was obtained as a yellow solid.

MS m/z 412 (M+1); HPLC RT 4.682 (C18 4.2×100 mm, 0–100% ACN/H$_2$O (0.1% TFA), 6 min @ 2 ml/min @254/220 nm).

Ethyl 4-[2,4-difluorobenzyl]-2-[4-(trifluoromethyl) phenyl]-1,3-thiazole-5-carboxylate From ethyl 4-(bromomethyl)-2-[4-(trifluoromethyl)phenyl]-1,3-thiazole-5-carboxylate (0.6 g, 1.52 mmol), ethyl 4-[2,4-difluorobenzyl]-2-[4-(trifluoromethyl)phenyl]-1,3-thiazole-5-carboxylate (0.222 g, 35%) was obtained as a white solid.

MS m/z 428 (M+1); HPLC RT 4.618 (C18 4.2×100 mm, 0–100% ACN/H$_2$O (0.1% TFA), 6 min @ 2 ml/min @254/220 nm).

4-[(Tetrahydro-2H-pyran-2-yloxy)methyl]-2-[4-(trifluoromethyl)phenyl]-1,3-thiazol-5-yl}methanol To a stirred solution of lithium aluminum hydride (95%, 3.3 g, 81.84 mmoles, 1 eq) in dry ethyl ether (300 ml) at 0° C. was added ethyl 4-[(tetrahydro-2H-pyran-2-yloxy)methyl]-2-[4-(trifluoromethyl)phenyl]-1,3-thiazole-5-carboxylate (34 g, 81.84 mmoles, 1 eq) in dry ethyl ether (50 ml) dropwise via an addition funnel maintaining the internal reaction temperature below 5° C. This was stirred at 0° C. for 1 hr. At 0° C. 3.5 ml water was added dropwise very carefully and was then allowed to warm to room temperature. This was followed by the addition 3.5 ml 5N NaOH and 10 ml water. The mixture was stirred at room temperature for 2 hrs. At this point a fine white precipitate formed. The reaction was filtered through Celite and the resulting aluminum salts were washed with 500 ml EtOAc. The ether/EtOAc solution was concentrated in vacuo to 30.6 g (100%) of titled alcohol.

$^1$H NMR (CDCl$_3$) 400 MHz δ 8.07(d, 2H, J=8.20 Hz), 7.72(d, 2H, J=8.20 Hz), 4.93(m, 4H), 4.78(t, 1H, J=3.32 Hz), 3.90(m, 1H), 3.61(m, 1H), 1.73(m, 6H),

TLC(30% EtOAc/Hexanes)=0.20

The following intermediates were reduced as above for 4-[(Tetrahydro-2H-pyran-2-yloxy)methyl]-2-[4-(trifluoromethyl)phenyl]-1,3-thiazol-5-yl}methanol.

{4-[(Tetrahydro-2H-pyran-2-yloxy)methyl]-2-[4-(trifluoromethyl)phenyl]-1,3-thiazol-5-yl}methanol $^1$H NMR (CDCl$_3$) 400 MHz δ 8.07(d, 2H, J=8.20 Hz), 7.72(d, 2H, J=8.20 Hz), 4.93(m, 4H), 4.78(t, 1H, J=3.32 Hz), 3.90(m, 1H), 3.61(m, 1H), 1.73(m, 6H), TLC(30% EtOAc/Hexanes)=0.20

{2-(4-Fluorophenyl)-4-[(tetrahydro-2H-pyran-2-yloxy)methyl]-1,3-thiazol-5-yl}methanol $^1$H NMR (CDCl$_3$) 400 MHz δ 7.89(m, 2H), 7.09(m, 2H), 4.81(m, 5H), 3.84(m, 1H), 3.55(m, 1H), 1.67(m, 6H),

{2-Phenyl-4-[(tetrahydro-2H-pyran-2-yloxy)methyl]-1,3-thiazol-5-yl}methanol

1H NMR (CDCl3) 400 MHz δ 7.96(m, 2H), 7.47(m, 3H), 4.92(m, 4H), 4.79(t, 1H, J=3.45 Hz), 3.91(m, 1H), 3.60(m, 1H), 1.73(m, 6H),

{2-(4-{trifuloromethyl}phenyl)-4-[(2-phenylethoxy) methyl]-1,3-thiazol-5-yl}methanol $^1$H (CDCl$_3$) 300 MHz δ 7.99(d, 2H, J=8.79 Hz), 7.67(d, 2H, J=8.79 Hz), 7.26(m, 5H), 4.78(s, 2H), 4.71(s, 2H), 3.84(t, 2H, J=6.94 Hz), 2.95(t, 2H, J=6.94 Hz), 2.63(s, 1H),

[2-(4-{trifuloromethyl}phenyl)-4-(3-phenylpropyl)-1,3-thiazol-5-yl]methanol $^1$H NMR (CDCl$_3$) 300 MHz δ 8.02(d, 2H, J=8.79 Hz), 7.67(d, 2H, J=8.79 Hz), 7.23(m, 4H), 4.76(s, 2H), 2.84(t, 2H, 7.28 Hz), 2.67(t, 2H, 7.28 Hz), 2.12(m, 2H),

[4-benzyl-2-(4-{trifluoromethyl}phenyl)-1,3-thiazol-5-yl]methanol $^1$H (CDCl$_3$) 300 MHz δ 8.01(d, 2H, J=8.79 Hz), 7.65(d, 2H, J=8.79 Hz), 7.26(m, 5H), 4.78(s, 2H), 4.15(s, 2H), TLC(20% EtOAc/Hexanes) R$_f$=0.18
MS(ES$^+$) M+H=350

[2-(4-{trifluoromethyl}phenyl)-4-(2-phenylethyl)-1,3-thiazol-5-yl]methanol $^1$H (CDCl$_3$) 300 MHz δ 8.06(d, 2H, J=9.61 Hz), 7.70(d, 1H, J=9.48 Hz), 7.23(m, 4H), 7.06(m, 2H), 4.40(d, 2H, J=5.63 Hz), 3.07(s, 4H), 1.08(s, 1H),
TLC(20% EtOAc/Hexanes) R$_f$=0.18
MS(ES$^+$) M+H=364

[4-[(Benzyloxy)methyl]-2-(4-{trifluoromethyl}phenyl)-1,3-thiazol-5-yl]methanol $^1$H (CDCl$_3$) 300 MHz δ 8.02(d, 2H, J=8.79 Hz), 7.68(d, 2H, J=8.79 Hz), 7.35(m, 5H), 4.82(m, 4H), 4.68(s, 2H), TLC(20% EtOAc/Hexanes) R$_f$=0.14

[4-(4-Bromobenzyl)-2-(4-{trifluoromethyl}phenyl)-1,3-thiazol-5-yl]methanol $^1$H NMR (CDCl$_3$) 300 MHz δ 7.99(d, 2H, J=8.10 Hz), 7.66(d, 2H, J=8.10 Hz), 7.40(d, 2H, J=8.38 Hz), 7.15(d, 2H, J=8.38 Hz), 4.81(s, 2H), 4.10(s, 2H),
TLC(20% EtOAc/Hexanes) R$_f$=0.14

{4-[4-(trifluoromethyl)benzyl]-2-[4-(trifluoromethyl)phenyl]-1,3-thiazol-5-yl}methanol From ethyl 4-[4-(trifluoromethyl)benzyl]-2-[4-(trifluoromethyl)phenyl]-1,3-thiazole-5-carboxylate (0.096 g, 0.21 mmol), {4-[4-(trifluoromethyl)benzyl]-2-[4-(trifluoromethyl)phenyl]-1,3-thiazol-5-yl}methanol (0.09 g, 100%) was obtained as a white solid.
$^1$H NMR (CDCl$_3$): δ 8.16 (d, 2H), 7.73 (d, 2H), 7.59 (d, 2H), 7.44 (d, 2H), 4.90 (d, 2H), 4.26 (t, 2H); MS m/z 418 (M+1).

{4-[4-(trifluoromethoxy)benzyl]-2-[4-(trifluoromethyl)phenyl]-1,3-thiazol-5-yl}methanol From ethyl 4-[4-(trifluoromethoxy)benzyl]-2-[4-(trifluoromethyl)phenyl]-1,3-thiazole-5-carboxylate (0.123 g 0.26 mmol), {4-[4-(trifluoromethoxy)benzyl]-2-[4-(trifluoromethyl)phenyl]-1,3-thiazol-5-yl}methanol (0.13 g, 99%) was obtained as a white solid.
$^1$H NMR (CDCl$_3$): δ 8.07 (d, 2H), 7.71 (d, 2H), 7.38 (d, 2H), 7.18 (d, 2H), 4.80 (d, 2H), 4.20 (s, 2H); MS m/z 434 (M+1).

{4-(4-methoxybenzyl)-2-[4-(trifluoromethyl)phenyl]-1,3-thiazol-5-yl}methanol

From ethyl 4-[4-methoxybenzyl]-2-[4-(trifluoromethyl)phenyl]-1,3-thiazole-5-carboxylate (0.16 g, 0.38 mmol), {4-(4-methoxybenzyl)-2-[4-(trifluoromethyl)phenyl]-1,3-thiazol-5-yl}methanol (0.06 g, 40%) was obtained as a white solid.
MS m/z 380 (M+1); HPLC RT 3.552 (C18 4.2×100 mm, 0–100% ACN/H$_2$O (0.1% TFA), 6 min @ 2 ml/min @254/220 nm).

{4-[4-(methylsulfanyl)benzyl]-2-[4-(trifluoromethyl)phenyl]-1,3-thiazol-5-yl}methanol From ethyl 4-[4-(methylsulfanyl)benzyl]-2-[4-(trifluoromethyl)phenyl]-1,3-thiazole-5-carboxylate (0.44 g, 1.0 mmol), {4-[4-(methylsulfanyl)benzyl]-2-[4-(trifluoromethyl)phenyl]-1,3-thiazol-5-yl}methanol (0.3 g, 76%) was obtained as a white solid.
MS m/z 396 (M+1); HPLC RT 3.699 (C18 4.2×100 mm, 0–100% ACN/H$_2$O (0.1% TFA), 6 min @ 2 ml/min @254/220 nm).

{4-(4-tert-butylbenzyl)-2-[4-(trifluoromethyl)phenyl]-1,3-thiazol-5-yl}methanol

From ethyl 4-[4-tert-butylbenzyl]-2-[4-(trifluoromethyl)phenyl]-1,3-thiazole-5-carboxylate (0.24 g, 0.54 mmol), {4-(4-tert-butylbenzyl)-2-[4-(trifluoromethyl)phenyl]-1,3-thiazol-5-yl}methanol (0.13 g, 64%) was obtained as a white solid.
MS m/z 406 (M+1); HPLC RT 4.002 (C18 4.2×100 mm, 0–100% ACN/H$_2$O (0.1% TFA), 6 min @ 2 ml/min @254/220 nm).

{4-(3-thienylmethyl)-2-[4-(trifluoromethyl)phenyl]-1,3-thiazol-5-yl}methanol

From ethyl 4-[3-thienylmethyl]-2-[4-(trifluoromethyl)phenyl]-1,3-thiazole-5-carboxylate (0.44 g, 1.11 mmol), {4-(3-thienylmethyl)-2-[4-(trifluoromethyl)phenyl]-1,3-thiazol-5-yl}methanol (0.098 g, 25%) was obtained as a yellow solid.
MS m/z 356 (M+1); HPLC RT 3.513 (C18 4.2×100 mm, 0–100% ACN/H$_2$O (0.1% TFA), 6 min @ 2 ml/min @254/220 nm).

{4-(2-furylmethyl)-2-[4-(trifluoromethyl)phenyl]-1,3-thiazol-5-yl}methanol

From ethyl 4-[2-furylmethyl]-2-[4-(trifluoromethyl)phenyl]-1,3-thiazole-5-carboxylate (0.204 g, 0.53 mmol), {4-(2-furylmethyl)-2-[4-(trifluoromethyl)phenyl]-1,3-thiazol-5-yl}methanol (0.162 g, 89%) was obtained as a white solid.
MS m/z 340 (M+1); HPLC RT 3.382 (C18 4.2×100 mm, 0–100% ACN/H$_2$O (0.1% TFA), 6 min @ 2 ml/min @254/220 nm).

{4-(3-furylmethyl)-2-[4-(trifluoromethyl)phenyl]-1,3-thiazol-5-yl}methanol

From ethyl 4-[3-furylmethyl]-2-[4-(trifluoromethyl)phenyl]-1,3-thiazole-5-carboxylate (0.217 g 0.57 mmol), {4-(3-furylmethyl)-2-[4-(trifluoromethyl)phenyl]-1,3-thiazol-5-yl}methanol (0.180 g, 88%) was obtained as a white solid.
MS m/z 340 (M+1); HPLC RT 3.385 (C18 4.2×100 mm, 0–100% ACN/H$_2$O (0.1% TFA), 6 min @ 2 ml/min @254/220 nm).

{4-(2-thienylmethyl)-2-[4-(trifluoromethyl)phenyl]-1,3-thiazol-5-yl}methanol From ethyl 4-[2-thienylmethyl]-2-[4-(trifluoromethyl)phenyl]-1,3-thiazole-5-carboxylate (0.248 g, 0.62 mmol), {4-(2-thienylmethyl)-2-[4-(trifluoromethyl)phenyl]-1,3-thiazol-5-yl}methanol (0.186 g, 87%) was obtained as a yellow solid.

MS m/z 356 (M+1); HPLC RT 3.528 (C18 4.2×100 mm, 0–100% ACN/$H_2O$ (0.1% TFA), 6 min @ 2 ml/min @254/220 nm).

{4-[(4-Methyl1-2-thienyl)methyl]-2-[4-(trifluoromethyl)phenyl]-1,3-thiazol-5-yl}methanol From ethyl 4-[(4-methyl-2-thienyl)methyl]-2-[4-(trifluoromethyl)phenyl]-1,3-thiazole-5-carboxylate (0.5 g, 1.22 mmol), {4-[(4-methyl-2-thienyl)methyl]-2-[4-(trifluoromethyl)phenyl]-1,3-thiazol-5-yl}methanol (0.084 g, 19%) was obtained as a yellow solid.

MS m/z 370 (M+1); HPLC RT 3.913 (C18 4.2×100 mm, 0–100% ACN/$H_2O$ (0.1% TFA), 6 min @ 2 ml/min @254/220 nm).

{4-(2,4-difluorobenzyl)-2-[4-(trifluoromethyl)phenyl]-1,3-thiazol-5-yl}methanol From ethyl 4-[2,4-difluorobenzyl]-2-[4-(trifluoromethyl)phenyl]-1,3-thiazole-5-carboxylate (0.46 g, 1.08 mmol), {4-(2,4-difluorobenzyl)-2-[4-(trifluoromethyl)phenyl]-1,3-thiazol-5-yl}methanol (0.222 g, 54%) was obtained as a white solid.

MS m/z 386 (M+1); HPLC RT 3.900 (C18 4.2×100 mm, 0–100% ACN/$H_2O$ (0.1% TFA), 6 min @ 2 ml/min @254/220 nm).

5-(Chloromethyl)-4-[(tetrahydro-2H-pyran-2-yloxy)methyl]-2-[4-(trifluoromethyl)phenyl]-1,3-thiazole To a 500-ml round-bottom flask equipped with a magnetic stir-bar, an addition funnel and a $N_2$ inlet was added 4-[(Tetrahydro-2H-pyran-2-yloxy)methyl]-2-[4-(trifluoromethyl)phenyl]-1,3-thiazol-5-yl}methanol (15 g, 40.17 mmoles, 1 eq) and dry $CH_2Cl_2$ (150 ml, 0.27M). Methanesulfonyl chloride (3.73 ml, 48.20 mmoles, 1.2 eq) was added neat all at once followed by the dropwise addition of triethylamine (8.44 ml, 60.26 mmoles, 1.5 eq) over 10 minutes. This solution was stirred at room temperature for 1 hr. The reaction was transferred to a separatory funnel and washed with water and brine. After the phases were separated the $CH_2Cl_2$ fraction was dried over $Na_2SO_4$ and the solvent was removed in vacuo. This yielded 15.74 g (100%) of a brown oil. The crude product was used as is and required no purification.

$^1$H NMR ($CDCl_3$) 300 MHz δ 8.08(d, 2H, J=8.20 Hz), 7.73(d, 2H, J=8.20 Hz), 5.00(m, 3H), 4.80(m, 2H), 3.97(m, 1H), 3.64(m, 1H), 1.77(m, 6H),

TLC(25% EtOAc/Hexanes) $R_f$=0.64

The following intermediates were also prepared using the above mesylation/chloride displacement procedure:

5-(Chloromethyl)-2-(4-fluorophenyl)-4-[(tetrahydro-2H-pyran-2-yloxy)methyl]-1,3-thiazole $^1$H NMR ($CDCl_3$) 400 MHz δ 7.90(m, 2H), 7.11(m, 2H), 4.94(s, 2H), 4.91(d, 1H, J□.45 Hz), 4.76(t, 1H, J=3.39 Hz), 4.72(d, 1H, J□.45 Hz), 3.92(m, 1H), 3.58(m, 1H), 1.69(m, 6H),

[5-(Chloromethyl)-2-phenyl-1,3-thiazol-4-yl]methyl tetrahydro-2H-pyran-2-yl ether $^1$H NMR ($CDCl_3$) 300 MHz δ 7.95(m, 2H), 7.47(m, 3H), 4.98(m, 3H), 4.80(m, 2H), 3.98(m, 1H), 3.63(m, 1H), 1.73(m, 6H), TLC(25% EtOAc/Hexanes) $R_f$=0.57

5-(Chloromethyl)-2-(4-{trifluoromethyl}phenyl)-4-[4-(3-thienyl)benzyl]-1,3-thiazole $^1$H NMR ($CDCl_3$) 300 MHz δ 8.06(d, 2H, J=8.23 Hz), 7.71(d, 2H, J=8.23 Hz), 7.58(d, 2H, J=8.23 Hz), 7.41(m, 5H), 4.84(s, 2H), 4.26(s, 2H), TLC(20% EtOAc/Hexanes) $R_f$=0.66

4-[(Benzyloxy)methyl]-5-(chloromethyl)-2-[4-(trifluoromethyl)phenyl]-1,3-thiazole $^1$H NMR ($CDCl_3$) 300 MHz δ 8.03(d, 2H, J=8.79 Hz), 7.69(d, 2H, J=8.79 Hz), 7.37(m, 5H), 4.90(s, 2H), 4.77(s, 2H), 4.66(s, 2H)

4-Benzyl-5-(chloromethyl)-2-(4-{trifluoromethyl}phenyl)-1,3-thiazole $^1$H ($CDCl_3$) 300 MHz δ 8.02(d, 2H, J=8.79 Hz), 7.67(d, 2H, J=8.79 Hz), 7.26(m, 5H), 4.77(s, 2H), 4.21(s, 2H), TLC(20% EtOAc/Hexanes) $R_f$=0.66

5-(Chloromethyl)-2-(4-{trifluoromethyl}phenyl)-4-(2-phenylethyl)-1,3-thiazole $^1$H ($CDCl_3$) 300 MHz δ 8.05(d, 2H, J=8.79 Hz), 7.70(d, 2H, J=8.79 Hz), 7.22(m, 5H), 4.46(s, 2H), 3.09(s, 4H), TLC(20% EtOAc/Hexanes) $R_f$=0.67

5-(Chloromethyl)-2-(4-{trifluoromethyl}phenyl)-4-[(2-phenylethoxy)methyl]-1,3-thiazole $^1$H NMR ($CDCl_3$) 300 MHz δ 8.01(d, 2H, J=8.79 Hz), 7.68(d, 2H, J=8.79 Hz), 7.26(m, 5H), 4.76(s, 2H), 4.74(s, 2H), 3.78(t, 2H, J=6.94 Hz), 2.94(t, 2H, J=6.94 Hz), TLC(20% EtOAc/Hexanes) $R_f$=0.56

5-(Chloromethyl)-2-(4-{trifluoromethyl}phenyl)-4-(3-phenylpropyl)-1,3-thiazole TLC(20% EtOAc/Hexanes) $R_f$=0.63

4-(4-Bromobenzyl)-5-(chloromethyl)-2-(4-{trifluoromethyl}phenyl)-1,3-thiazole $^1$H NMR ($CDCl_3$) 300 MHz δ 8.00(d, 2H, J=8.10 Hz), 7.67(d, 2H, J=8.10 Hz), 7.42(d, 2H, J=8.38 Hz), 7.18(d, 2H, J=8.38 Hz), 4.77(s, 2H), 4.14(s, 2H), TLC(20% EtOAc/Hexanes) $R_f$=0.66

4-([1,1'-Biphenyl]-4-ylmethl)-5-(chloromethyl)-2-(4-{trifluoromethyl}phenyl)-1,3-thiazole $^1$H NMR ($CDCl_3$) 300 MHz δ 8.07(d, 2H, J=8.23 Hz), 7.72(d, 2H, J=8.23 Hz), 7.57(m, 4H), 7.39(m, 5H), 4.85(s, 2H), 4.28(s, 2H), TLC(20% EtOAc/Hexanes) $R_f$=0.69

5-(chloromethyl)-4-[4-(trifluoromethyl)benzyl]-2-[4-(trifluoromethyl)phenyl]-1,3-thiazole From {4-[4-(trifluoromethyl)benzyl]-2-[4-(trifluoromethyl)phenyl]-1,3-thiazol-5-yl}methanol (0.09 g, 0.216 mmol), 5-(chloromethyl)-4-[4-(trifluoromethyl)benzyl]-2-[4-(trifluoromethyl)phenyl]-1,3-thiazole (0.087 g, 93%) was obtained as a yellow oil and immediately taken on without purification.

5-(chloromethyl)-4-[4-(trifluoromethoxy)benzyl]-2-[4-(trifluoromethyl)phenyl]-1,3-thiazole From {4-[4-(trifluoromethoxy)benzyl]-2-[4-(trifluoromethyl)phenyl]-1,3-thiazol-5-yl}methanol (0.13 g, 0.3 mmol), 5-(chloromethyl)-4-[4-(trifluoromethoxy)benzyl]-2-[4-(trifluoromethyl)phenyl]-1,3-thiazole (0.135 g, 100%) was obtained as a yellow oil and immediately taken on without purification.

5-(chloromethyl)-4-(4-methoxybenzyl)-2-[4-(trifluoromethyl)phenyl]-1,3-thiazole From {4-(4-methoxybenzyl)-2-[4-(trifluoromethyl)phenyl]-1,3-thiazol-5-yl}methanol (0.06 g, 0.158 mmol), 5-(chloromethyl)-4-(4-methoxybenzyl)-2-[4-(trifluoromethyl)phenyl]-1,3-thiazole (0.08 g, 100%) was obtained as a yellow oil and immediately taken on without purification.

5-(chloromethyl)-4-[4-(methylsulfanyl)benzyl]-2-[4-(trifluoromethyl)phenyl]-1,3-thiazole From {4-[4-(methylsulfanyl)benzyl]-2-[4-(trifluoromethyl)phenyl]-1,3-thiazol-5-yl}methanol (0.3 g, 0.76 mmol), 5-(chloromethyl)-4-[4-(methylsulfanyl)benzyl]-2-[4-(trifluoromethyl)phenyl]-1,3-thiazole (0.33 g, 100%) was obtained as a yellow oil and immediately taken on without purification.
MS m/z 414 (M+1).

4-(4-tert-butylbenzyl)-5-(chloromethyl)-2-[4-(trifluoromethyl)phenyl]-1,3-thiazole From {4-(4-tert-butylbenzyl)-2-[4-(trifluoromethyl)phenyl]-1,3-thiazol-5-yl}methanol (0.13 g, 0.32 mmol), 4-(4-tert-butylbenzyl)-5-(chloromethyl)-2-[4-(trifluoromethyl)phenyl]-1,3-thiazole (0.151 g, 100%) was obtained as a yellow oil and immediately taken on without purification.
MS m/z 424 (M+1).

5-(chloromethyl)-4-(3-thienylmethyl)-2-[4-(trifluoromethyl)phenyl]-1,3-thiazole From {4-(3-thienylmethyl)-2-[4-(trifluoromethyl)phenyl]-1,3-thiazol-5-yl}methanol (0.098 g, 0.28 mmol), 5-(chloromethyl)-4-(3-thienylmethyl)-2-[4-(trifluoromethyl)phenyl]-1,3-thiazole (0.105 g, 100%) was obtained as a yellow oil and immediately taken on without purification.
MS m/z 374 (M+1).

5-(chloromethyl)-4-(2-furylmethyl)-2-[4-(trifluoromethyl)phenyl]-1,3-thiazole From {4-(2-furylmethyl)-2-[4-(trifluoromethyl)phenyl]-1,3-thiazol-5-yl}methanol (0.162 g, 0.48 mmol), 5-(chloromethyl)-4-(2-furylmethyl)-2-[4-(trifluoromethyl)phenyl]-1,3-thiazole (0.097 g, 57%) was obtained as a yellow oil and immediately taken on without purification.
MS m/z 358 (M+1).

5-(chloromethyl)-4-(3-furylmethyl)-2-[4-(trifluoromethyl)phenyl]-1,3-thiazole From {4-(3-furylmethyl)-2-[4-(trifluoromethyl)phenyl]-1,3-thiazol-5-yl}methanol (0.18 g, 0.53 mmol), 5-(chloromethyl)-4-(3-furylmethyl)-2-[4-(trifluoromethyl)phenyl]-1,3-thiazole (0.172 g, 91%) was obtained as a yellow oil and immediately taken on without purification.
MS m/z 358 (M+1).

5-(chloromethyl)-4-(2-thienylmethyl)-2-[4-(trifluoromethyl)phenyl]-1,3-thiazole From {4-(2-thienylmethyl)-2-[4-(trifluoromethyl)phenyl]-1,3-thiazol-5-yl}methanol (0.186 g, 0.52 mmol), 5-(chloromethyl)-4-(2-thienylmethyl)-2-[4-(trifluoromethyl)phenyl]-1,3-thiazole (0.185 g, 95%) was obtained as a yellow oil and immediately taken on without purification.
MS m/z 374 (M+1).

5-(chloromethyl)-4-[(4-methyl-2-thienyl)methyl]-2-[4-(trifluoromethyl)phenyl]-1,3-thiazole From {4-[(4-methyl-2-thienyl)methyl]-2-[4-(trifluoromethyl)phenyl]-1,3-thiazol-5-yl}methanol (0.084 g, 0.23 mmol), 5-(chloromethyl)-4-[(4-methyl-2-thienyl)methyl]-2-[4-(trifluoromethyl)phenyl]-1,3-thiazole (0.123 g, 100%) was obtained as a yellow oil and immediately taken on without purification.

5-(chloromethyl)-4-(2,4-difluorobenzyl)-2-[4-(trifluoromethyl)phenyl]-1,3-thiazole From {4-(2,4-difluorobenzyl)-2-[4-(trifluoromethyl)phenyl]-1,3-thiazol-5-yl}methanol (0.222 g, 0.58 mmol), 5-(chloromethyl)-4-(2,4-difluorobenzyl)-2-[4-(trifluoromethyl)phenyl]-1,3-thiazole (0.279 g, 100%) was obtained as a yellow oil and immediately taken on without purification.

Ethyl 2-methyl-2-phenoxypropanoate

To a solution of potassium t-butoxide (1M in THF, 531 ml, 0.531 moles, 1 eq) precooled to 0° C. (ice bath) was added phenol (50 g, 0.531 moles, 1 eq) in dry THF (50 ml) dropwise via an addition funnel over 20 minutes maintaining the internal temperature of the reaction below 5 degrees centigrade. Ethyl-2-bromoisobutyrate (70.14 ml, 0.9 eq, 0.478 moles) in dry THF (20 ml) was added dropwise over 10 minutes maintaining the internal reaction temperature below 5° C. After the addition was complete, the ice bath was removed and the reaction was allowed to warm to room temperature. The reaction was brought to reflux and maintained at this reflux temperature for 8 hours. Following the cooling of the reaction to 0° C. the volatiles were removed in vacuo. The residue was then partitioned between EtOAc and 1N NaOH. The phases were separated and the organic phase was washed with 1N NaOH, $H_2O$, brine and dried over $Na_2SO_4$. After filtration the solution was concentrated under reduced pressure to yield 83 g (75%) of clean title compound.
$^1$H NMR (CDCl$_3$) 400 MHz δ 7.21(m, 2H), 6.95(t, 1H, J=7.41 Hz), 6.82(m, 2H), 4.21(q, 2H, J=7.13 Hz), 1.57(s, 6H), 1.22(t, 3H, J=7.13 Hz),

Ethyl (2-ethylphenoxy)acetate

To a stirred solution of 2-ethylphenol (5 ml, 42.4 mmoles, 1 eq) in dry DMF (120 ml, 0.35M) was added potassium carbonate (6.45 g, 46.6 mmoles, 1.1 eq) and ethylbromoacetate (4.7 ml, 42.2 mmoles, 1 eq) and heated to 60° C. overnight. After cooling to room temperature the reaction mixture was partitioned between ethyl ether and 1N NaOH. The phases were separated and the organic portion was washed twice with 1N NaOH, twice with $H_2O$, brine, dried over $Na_2SO_4$, filtered and concentrated in vacuo to yield 7.2 g (82%) of product.

$^1$H NMR (CDCl$_3$) 400 MHz δ 7.14(m, 2H), 6.92(t, 1H, J=8.24 Hz), 6.70(d, 1H, J=8.24 Hz), 4.62(s, 2H), 4.24(q, 2H, J=7.14 Hz), 2.70(q, 2H, J=7.51 Hz), 1.27(t, 3H, J=7.14 Hz), 1.21(t, 3H, J=7.51 Hz),

The following were compounds were made using the same alkylation procedure:

Ethyl (2-isopropylphenoxy)acetate $^1$H NMR (CDCl$_3$) 400 MHz δ 7.23(d, 1H, J=7.69 Hz), 7.11(t, 1H, J=7.69 Hz), 6.96(t, 1H, J=7.69 Hz), 6.70(d, 1H, J=7.69 Hz), 4.62(s, 2H), 4.25(q, 2H, J=7.14 Hz), 3.41(m, 1H), 1.26(m, 9H),

Ethyl (2-propylphenoxy)acetate $^1$H NMR (CDCl$_3$) 400 MHz δ 7.12(m, 2H), 6.90(t, 1H, J=8.24 Hz), 6.69(d, 1H, J=8.24 Hz), 4.61(s, 2H), 4.24(q, 2H, J=7.14 Hz), 2.64(t, 2H, J=7.33 Hz), 1.64(m, 2H), 1.27(t, 3H, J=7.14 Hz), 0.94(t, 3H, J=7.33 Hz),

Ethyl [4-(chlorosulfonyl)-2-ethylphenoxy]acetate

To a 250 ml round-bottom flask containing chlorosulfonic acid (30 ml) cooled to 0° C. was added ethyl (2-ethylphenoxy)acetate (7.2 g, 34.6 mmoles) dropwise. Once the addition was complete the ice-bath was removed and the reaction was allowed to warm to room temperature at which the reaction was stirred for 3 hours. The reaction was then slowly added to ice, once the excess chlorosulfonic acid was quenched, the mixture was diluted with $CH_2Cl_2$ (200 ml). The phases were separated and the aqueous fraction was washed with $CH_2Cl_2$ twice. The combined organic fractions were dried over $Na_2SO_4$ and filtered and concentrated in vacuo to yield 7.2 g (70%) of crude product. The crude product was used with no purification.

$^1$H NMR (CDCl$_3$) 400 MHz δ 7.84(m, 2H), 6.79(d, 1H, J=8.24 Hz), 4.75(s, 2H), 4.26(q, 2H, J=7.14 Hz), 2.77(q, 2H, J=7.51 Hz), 1.26(m, 6H),

The following were compounds were made using the same chlorosulfonation procedure:

Ethyl [4-(chlorosulfonyl)-2-methylphenoxy]acetate $^1$H NMR (d6-DMSO) 300 MHz δ 7.41(m, 2H), 6.79(d, 1H, J=8.23 Hz), 4.82(s, 2H), 4.16(q, 2H, J=7.17 Hz), 2.21(s, 3H), 1.21(t, 3H, J=7.17 Hz),

Ethyl 2-[4-(chlorosulfonyl)-2-methylphenoxy]propanoate $^1$H NMR (d6-DMSO) 300 MHz δ 7.44(m, 1H), 7.39(dd, 1H, J=8.23, 2.39 Hz), 6.74(d, 1H, J=8.23 Hz), 4.96(q, 1H, J=6.81 Hz), 4.13(q, 2H, J=7.08 Hz), 2.20(s, 3H), 1.54(d, 3H, J=6.81 Hz), 1.18(t, 3H, J=7.08 Hz),

Ethyl 2-[4-(chlorosulfonyl)-2-isopropylphenoxy]propanoate $^1$H NMR (CDCl$_3$) 400 MHz δ 7.81(m, 2H), 6.76(d, 1H, J=8.42 Hz), 4.87(q, 1H, J=6.78 Hz), 4.21(q, 2H, J=7.14 Hz), 3.40(m, 1H), 1.65(d, 3H, J=6.78 Hz), 1.24(m, 9H),

Ethyl [4-(chlorosulfonyl)-2-isopropylphenoxy]acetate $^1$H NMR (CDCl$_3$) 400 MHz δ 7.84(m, 2H), 6.80(d, 1H, J=8.42 Hz), 4.75(s, 2H), 4.26(q, 2H, J=7.14 Hz), 3.42(m, 1H), 1.27(m, 9H),

Ethyl 2-[4-(chlorosulfonyl)-2-propylphenoxy]propanoate $^1$H NMR (CDCl$_3$) 400 MHz δ 7.80(m, 2H), 6.75(d, 1H, J=8.42 Hz), 4.85(q, 1H, J=6.78 Hz), 4.21(q, 2H, J=7.14 Hz), 2.69(t, 2H, J=7.51 Hz), 1.66(m, 5H), 1.23(t, 3H, J=7.14 Hz), 0.95(t, 3H, J=7.51 Hz),

Ethyl [4-(chlorosulfonyl)-2-propylphenoxy]acetate $^1$H NMR (CDCl$_3$) 400 MHz δ 7.83(m, 2H), 6.79(d, 1H, J=8.42 Hz), 4.73(s, 2H), 4.26(q, 2H, J=7.14 Hz), 2.70(t, 2H, J=7.51 Hz), 1.67(m, 2H), 1.29(t, 3H, J=7.14 Hz), 0.95(t, 3H, J=7.51 Hz),

Ethyl 2-[4-(chlorosulfonyl)-2-ethylphenoxy]propanoate $^1$H NMR (CDCl$_3$) 400 MHz δ 7.81(m, 2H), 6.75(d, 1H, J=8.42 Hz), 4.86(q, 1H, J=6.78 Hz), 4.21(q, 2H, J=7.08 Hz), 2.75(m, 2H), 1.68(d, 3H, J=6.78 Hz), 1.23(m, 6H),

Ethyl 2-[4-(chlorosulfonyl)phenoxy]-2-methylpropanoate

To a 3-L three-neck round-bottom flask equipped with a magnetic stir-bar, low temperature thermometer with thermometer adapter, addition funnel and a $N_2$ inlet was added ethyl 2-methyl-2-phenoxypropanoate (83 g, 0.399 moles, 1 eq) and dry $CH_2Cl_2$ (1 L, 0.4M). After cooling the reaction to 0° C. (ice bath) chlorosulfonic acid (26.5 ml, 0.399 moles, 1 eq) in dry $CH_2Cl_2$ (50 ml) was added dropwise over 30 minutes via addition funnel maintaining the internal temperature below 5° C. Following this dropwise addition the reaction was allowed to stir at 0° C. for 3 hours. The reaction was monitored by HPLC and after 3 hours complete conversion was observed [(C-18, 3 μm) 0%–95% Acetonitrile/Water over 8 minutes $R_t$=2.96 minutes]. At this point dry DMF (124 ml, 4 eq) was added slowly maintaining the internal temperature below 5° C. This was followed by the dropwise addition of thionyl chloride (43.77 ml, 0.599 moles, 1.5 eq) in dry $CH_2Cl_2$ (50 ml) over 25 minutes maintaining the internal temperature below 5° C. After stirring at 0° C. for 1.5 hours and monitoring by HPLC [(C-18, 3 μm) 0%–95% Acetonitrile/Water over 8 minutes $R_t$=5.97 minutes] the reaction was allowed to warm to room temperature. The reaction mixture was then washed with 0.1N HCl and the phases were separated, with discarding the aqueous fraction. The organic fraction was washed with 0.1N HCl, $H_2O$, brine and dried over $Na_2SO_4$. The solution was filtered and concentrated in vacuo to yield 119.95 g (98%) of pure sulfonyl chloride.

¹H NMR (CDCl₃) 400 MHz δ 7.89(d, 2H, J=9.31 Hz), 6.89(d, 2H, J=9.31 Hz), 4.21(q, 2H, J=7.16 Hz), 1.66(s, 6H), 1.20(t, 3H, J=7.16 Hz),

HPLC (C-18, 3 μm) 0%–95% Acetonitrile/Water over 8 minutes $R_t$=5.97 minutes

Ethyl 2-methyl-2-(4-sulfanyl phenoxy)propanoate

To a 3-L three-neck round-bottom flask equipped with an overhead mechanical stirrer, addition funnel and a N₂ inlet was added ethyl 2-[4-(chlorosulfonyl)phenoxy]-2-methyl-propanoate (53 g, 0.173 moles, 1 eq) and absolute EtOH (500 ml). Tin powder (325 mesh, 123.06 g, 1.04 moles, 6 eq) was added as a solid. The overhead stirrer was adjusted so that the rotor is as close as possible to the bottom of the round-bottom flask and stirring speed was accelerated to a very high setting before adding the HCl to prevent the clumping of the tin metal. Hydrogen chloride (4N in dioxane, 300 ml) was added dropwise over the course of 1 hour. The reaction mixture was refluxed for 4 hours at which point the hot ethanolic solution was poured into a 2-L Erlenmeyer flask containing CH₂Cl₂ (1 L) and ice. After stirring for 10 minutes the biphasic mixture was filtered through Celite. After transferring to a separatory funnel the phases were separated and the aqueous fraction was washed with CH₂Cl₂ (2×100 ml). The combined organic fractions were dried over Na₂SO₄, filtered and concentrated in vacuo. A bright yellow oil with a white precipitate suspended resulted. This yellow mixture was dissolved in a minimum amount of CH₂Cl₂ and filtered once again through Celite to yield 30 g (75%) of a bright yellow oil.

¹H NMR (CD₃OD) 300 MHz δ 7.18(m, 2H), 6.73(d, 2H, J=8.00 Hz), 4.23(q, 2H, J=7.17 Hz), 3.69(s, 1H), 1.59(s, 6H), 1.26(t, 3H, J=7.17 Hz),

The following were compounds were made using the same reduction procedure:

Ethyl (2-methyl-4-sulfanylphenoxy)acetate

¹H NMR (CDCl₃) 400 MHz δ 7.15(m, 2H), 6.63(d, 1H, J=8.23 Hz), 4.64(s, 2H), 4.29(q, 2H, J=7.17 Hz), 3.36(s, 1H), 2.29(s, 3H), 1.33(t, 3H, J=7.17 Hz),

Ethyl 2-(2-methyl-4-sulfanylphenoxy)propanoate

¹H NMR (CDCl₃) 400 MHz δ 7.12(d, 1H, J=2.39 Hz), 7.04(dd, 1H, J=8.37, 2.39 Hz), 6.56(d, 1H, J=8.37 Hz), 4.67(q, 1H, J=6.72 Hz), 4.19(q, 2H, J=7.12 Hz), 3.31(s, 1H), 2.22(s, 3H), 1.61(d, 3H, J=6.72 Hz), 1.23(t, 3H, J=7.12 Hz), TLC(20% EtOAc/Hexanes) $R_f$=0.60

Ethyl (2-ethyl-4-sulfanylphenoxy)acetate

¹H NMR (CDCl₃) 400 MHz δ 7.13(d, 1H, J=2.20 Hz), 7.08(dd, 1H, J=8.42, 2.38 Hz), 6.58(d, 1H, J=8.42 Hz), 4.59(s, 2H), 4.24(q, 2H, J=7.14 Hz), 3.33(s, 1H), 2.64(q, 2H, J=7.51 Hz), 1.28(t, 3H, J=7.14 Hz), 1.18(t, 3H, J=7.51 Hz),

Ethyl 2-(2-ethyl-4-sulfanylphenoxy)propanoate

¹H NMR (CDCl₃) 400 MHz δ 7.15(d, 1H, J=2.20 Hz), 7.07(dd, 1H, J=8.42, 2.20 Hz), 6.55(d, 1H, J=8.42 Hz), 4.74(q, 1H, J=6.78 Hz), 4.17(m, 2H), 3.32(s, 1H), 2.61(q, 2H, J=7.51 Hz), 1.61(d, 3H, J=6.59 Hz), 1.19(m, 6H),

The following four compounds were made in the same way and used without further purification.
Ethyl (2-propyl-4-sulfanylphenoxy)acetate
Ethyl 2-(2-propyl-4-sulfanylphenoxy)propanoate
Ethyl (2-isopropyl-4-sulfanylphenoxy)acetate
Ethyl 2-(2-isopropyl-4-sulfanylphenoxy)propanoate Ethyl 2-methyl-2-{4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate To a 250 ml round-bottom flask equipped with a magnetic stir-bar and N₂ inlet was added 5-(chloromethyl)-4-[(tetrahydro-2H-pyran-2-yloxy)methyl]-2-[4-(trifluoromethyl)phenyl]-1,3-thiazole (7.87 g, 20.09 mmoles, 1 eq) and dry CH₃CN (100 ml, 0.27M). Solid cesium carbonate (16.4 g, 50.22 mmoles, 2.5 eq) was added all at once followed by the quick addition of ethyl 2-methyl-2-(4-sulfanylphenoxy)propanoate (5.79 g, 24.11 mmoles, 1.2 eq) in dry CH₃CN (10 ml). The reaction was allowed to stir at room temperature for 2 hours at which point the solvent was removed under reduced pressure. The resulting residue was partitioned between EtOAc and 1N NaOH. After the phases were separated the organic fraction was washed with H₂O, brine and dried over Na₂SO₄. After filtration the volatiles were removed in vacuo to yield the titled compound in >100% yield. Sometimes because of the difficult separation between the thiophenol and the product, the crude product was carried forward without purification.

The following compounds were made using the same alkylation procedure. Where selectivity was an issue the alkylations were carried out below room temperature.

Ethyl 2-{2-methyl-4-[({2-phenyl-4-[(tetrahydro-2H-pyran-2-yloxy)methyl]-1,3-thiazol-5-yl}methyl)sulfanyl]phenoxy}propanoate ¹H NMR (CDCl₃) 300 MHz δ 7.93(m, 2H), 7.44(m, 3H), 7.28(d, 1H, J=2.39 Hz), 7.15(dd, 1H, J=8.23, 2.39 Hz), 6.61(d, 1H, J=8.23 Hz), 4.72(m, 3H), 4.50(d, 1H, J□.21 Hz), 4.32(s, 2H), 4.23(q, 2H, J=7.08 Hz), 3.93(m, 1H), 3.59(m, 1H), 2.26(s, 3H), 1.71(m, 9H), 1.28(t, 3H, J=7.08 Hz), Ethyl 2-{2-methyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate ¹H NMR (CDCl₃) 300 MHz δ 8.04(d, 2H, J=8.23 Hz), 7.70(d, 2H, J=8.23 Hz), 7.27(d, 1H, J=2.39 Hz), 7.15(dd, 1H, J=8.49, 2.39 Hz), 6.60(d, 1H, J=8.49 Hz), 4.73(m, 3H), 4.51(d, 1H, J□.21 Hz), 4.32(s, 2H), 4.20(q, 2H, J=7.17 Hz), 3.93(m, 1H), 3.60(m, 1H), 2.27(m, 3H), 1.71(m, 9H), 1.27(t, 3H, J=7.17 Hz),
TLC(30% EtOAc/Hexanes)=0.73

Ethyl 2-{4-[({2-(4-fluorophenyl)-4-[(tetrahydro-2H-pyran-2-yloxy)methyl]-1,3-thiazol-5-yl}methyl)sulfanyl]-2-methylphenoxy}propanoate ¹H NMR (CDCl₃) 400 MHz δ 7.88(m, 2H), 7.19(d, 1H, J=2.24 Hz), 7.08(m, 3H), 6.54(d, 1H, J=8.45 Hz), 4.65(m, 3H), 4.44(m, 1H), 4.24(s, 2H), 4.16(q, 2H, J=7.13 Hz), 3.86(m, 1H), 3.53(m, 1H), 2.21(s, 3H), 1.66(m, 9H), 1.20(t, 3H, J=7.13 Hz), Ethyl {2-ethyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate ¹H NMR (CDCl₃) 400 MHz δ 7.98(d, 2H, J=8.24 Hz), 7.64(d, 2H, J=8.24 Hz), 7.20(d, 1H, J=2.20 Hz), 7.15(dd, 1H, J=8.42, 2.20 Hz), 6.60(d, 1H, J=8.42 Hz), 4.63(m, 4H), 4.42(d, 1H, J□.27 Hz), 4.24(m, 4H), 3.87(m, 1H), 3.54(m, 1H), 2.64(q, 2H, J=7.51 Hz), 1.66(m, 6H), 1.26(t, 3H, J=7.14 Hz), 1.15(t, 3H, J=7.51 Hz),

Ethyl 2-{2-ethyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate $^1$H NMR (CDCl$_3$) 400 MHz δ 7.98(d, 2H, J=8.24 Hz), 7.64(d, 2H, J=8.24 Hz), 7.17(d, 1H, J=2.38 Hz), 7.11(dd, 1H, J=8.42, 2.38 Hz), 6.56(d, 1H, J=8.42 Hz), 4.71(q, 1H, J=6.78 Hz), 4.66(t, 1H, J=3.39 Hz), 4.60(d, 1H, J□.27 Hz), 4.41(d, 1H, J□.27 Hz), 4.26(s, 2H), 4.16(q, 2H, J=7.14 Hz), 3.87(m, 1H), 3.54(m, 1H), 2.62(q, 2H, J=7.51 Hz), 1.60(m, 9H), 1.20(t, 3H, J=7.14 Hz), 1.15(t, 3H, J=7.51 Hz),

Ethyl {2-propyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate $^1$H NMR (CDCl$_3$) 400 MHz δ 7.97(d, 2H, J=8.20 Hz), 7.64(d, 2H, J=8.20 Hz), 7.16(m, 2H), 6.59(d, 1H, J=8.24 Hz), 4.66(m, 1H), 4.61(m, 3H), 4.43(d, 1H, J□.27 Hz), 4.23(m, 4H), 3.88(m, 1H), 3.54(m, 1H), 2.57(t, 2H, J=7.33 Hz), 1.68(m, 8H), 1.26(t, 3H, J=7.14 Hz), 0.88(t, 3H, J=7.33 Hz),

Ethyl 2-{2-propyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate $^1$H NMR (CDCl$_3$) 400 MHz δ 7.97(d, 2H, J=8.24 Hz), 7.64(d, 2H, J=8.24 Hz), 7.17(d, 1H, J=2.38 Hz), 7.11(dd, 1H, J=8.42, 2.38 Hz), 6.55(d, 1H, J=8.42 Hz), 4.70(q, 1H, J=6.78 Hz), 4.66(t, 1H, J=3.39 Hz), 4.62(d, 1H, J□.27 Hz), 4.43(d, 1H, J□.27 Hz), 4.25(s, 2H), 4.15(q, 2H, J=7.14 Hz), 3.88(m, 1H), 3.54(m, 1H), 2.56(t, 2H, J=7.33 Hz), 1.60(m, 11H), 1.21(t, 3H, J=7.14 Hz), 0.88(t, 3H, J=7.33 Hz),

Ethyl {2-isopropyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate $^1$H NMR (CDCl$_3$) 400 MHz δ 7.98(d, 2H, J=8.24 Hz), 7.64(d, 2H, J=8.24 Hz), 7.20(d, 1H, J=2.38 Hz), 7.15(dd, 1H, J=8.42, 2.38 Hz), 6.60(d, 1H, J=8.42 Hz), 4.65(t, 1H, J=3.48 Hz), 4.60(s, 2H), 4.56(d, 1H, J□.09 Hz), 4.38(d, 1H, J□.09 Hz), 4.23(m, 4H), 3.87(m, 1H), 3.53(m, 1H), 3.32(m, 1H), 1.66(m, 6H), 1.26(t, 3H, J=7.14 Hz), 1.15(d, 6H, J=6.96 Hz),

Ethyl 2-{4-[({4-(2-furylmethyl)-2-[4-(trifluoromethyl)phenyl]-1,3-thiazol-5-yl}methyl)sulfanyl]-2-methylphenoxy}propanoate From 5-(chloromethyl)-4-(2-furylmethyl)-2-[4-(trifluoromethyl)phenyl]-1,3-thiazole (0.097 g, 0.27 mmol), ethyl 2-{4-[({4-(2-furylmethyl)-2-[4-(trifluoromethyl)phenyl]-1,3-thiazol-5-yl}methyl)sulfanyl]-2-methylphenoxy}propanoate (0.091 g, 60%) was obtained as a white solid.

$^1$H NMR (CDCl$_3$): δ 8.00 (d, 2H), 7.68 (d, 2H), 7.23 (m, 2H), 6.62 (m 2H), 6.30 (s, 1H), 6.02 (s, 1H), 4.76 (q, 1H), 4.21 (q, 2H), 4.17 (s, 2H), 3.98 (s, 2H), 2.29 (s, 3H), 1.63 (s, 3H), 1.24 (t, 3H); MS m/z 562 (M+1).

Ethyl 2-{4-[({4-(3-furylmethyl)-2-[4-(trifluoromethyl)phenyl]-1,3-thiazol-5-yl}methyl)sulfanyl]-2-methylphenoxy}propanoate From 5-(chloromethyl)-4-(3-furylmethyl)-2-[4-(trifluoromethyl)phenyl]-1,3-thiazole (0.172 g, 0.48 mmol), ethyl 2-{4-[({4-(3-furylmethyl)-2-[4-(trifluoromethyl)phenyl]-1,3-thiazol-5-yl}methyl)sulfanyl]-2-methylphenoxy}propanoate (0.177 g, 65%) was obtained as a white solid.

$^1$H NMR (CDCl$_3$): δ 8.00 (d, 2H), 7.70 (d, 2H), 7.28 (m, 2H), 7.16, (d, 1H), 6.61 (m, 2H), 6.31 (s, 1H), 4.78 (q, 1H), 4.27 (q, 2H), 4.18 (s, 2H), 3.68 (s, 2H), 2.22 (s, 3H), 1.68 (s, 3H), 1.30 (t, 3H); MS m/z 578 (M+1).

Ethyl 2-{4-[({4-(2-thienylmethyl)-2-[4-(trifluoromethyl)phenyl]-1,3-thiazol-5-yl}methyl)sulfanyl]-2-methylphenoxy}propanoate From 5-(chloromethyl)-4-(3-furylmethyl)-2-[4-(trifluoromethyl)phenyl]-1,3-thiazole (0.185 g, 0.50 mmol), ethyl 2-{4-[({4-(2-thienylmethyl)-2-[4-(trifluoromethyl)phenyl]-1,3-thiazol-5-yl}methyl)sulfanyl]-2-methylphenoxy}propanoate (0.21 g, 73%) was obtained as a yellow solid.

$^1$H NMR (CDCl$_3$): δ 8.01 (d, 2H), 7.70 (d, 2H), 7.20 (s, 1H), 7.17 (m, 1H), 6.93 (m, 1H), 6.80 (s, 1H), 6.60 (m, 2H), 4.74 (q, 1H), 4.20 (q, 2H), 4.19 (s, 2H), 4.17 (s, 2H), 2.29 (s, 3H), 1.67 (s, 3H), 1.30 (t, 3H); MS m/z 578 (M+1).

Ethyl 2-methyl-2-{4-[({4-[4-(trifluoromethoxy)benzyl]-2-[4-(trifluoromethyl)phenyl]-1,3-thiazol-5-yl}methyl)sulfanyl]phenoxy}propanoate From 5-(chloromethyl)-4-[4-(trifluoromethoxy)benzyl]-2-[4-(trifluoromethyl)phenyl]-1,3-thiazole (0.166 g, 0.37 mmol) (prepared as in U16097-118-2), ethyl 2-methyl-2-{4-[({4-[4-(trifluoromethoxy)benzyl]-2-[4-(trifluoromethyl)phenyl]-1,3-thiazol-5-yl}methyl)sulfanyl]phenoxy}propanoate (0.210 g, 87%) was obtained as a white solid.

MS m/z 656 (M+1); HPLC RT 4.862 (C18 4.2×100 mm, 0–100% ACN/H$_2$O (0.1% TFA), 6 min @ 2 ml/min @254/220 nm).

Ethyl 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoate From 5-(chloromethyl)-4-(2-thienylmethyl)-2-[4-(trifluoromethyl)phenyl]-1,3-thiazole (0.062 g, 0.16 mmol), ethyl 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoate (0.17 g, 100%) was obtained as a yellow oil.

MS m/z 592 (M+1); HPLC RT 4.534 (C18 4.2×100 mm, 0–100% ACN/H$_2$O (0.1% TFA), 6 min @ 2 ml/min @254/220 nm).

Ethyl {2-methyl-4-[({4-[(4-methyl-2-thienyl)methyl]-2-[4-(trifluoromethyl)phenyl]-1,3-thiazol-5-yl}methyl)sulfanyl]phenoxy}acetate From 5-(chloromethyl)-4-(2-thienylmethyl)-2-[4-(trifluoromethyl)phenyl]-1,3-thiazole (0.062 g, 0.16 mmol), ethyl {2-methyl-4-[({4-[(4-methyl-2-thienyl)methyl]-2-[4-(trifluoromethyl)phenyl]-1,3-thiazol-5-yl}methyl)sulfanyl] phenoxy}acetate (0.13 g, 100%) was obtained as a yellow oil.

MS m/z 578 (M+1); HPLC RT 4.338 (C18 4.2×100 mm, 0–100% ACN/H$_2$O (0.1% TFA), 6 min @ 2 ml/min @254/ 220 nm).

Ethyl {4-[({4-(2,4-difluorobenzyl)-2-[4-(trifluoromethyl)phenyl]-1,3-thiazol-5-yl}methyl)sulfanyl]-2-methylphenoxy}acetate From 5-(chloromethyl)-4-(2,4-difluorobenzyl)-2-[4-(trifluoromethyl)phenyl]-1,3-thiazole (0.139 g, 0.34 mmol), ethyl {4-[({4-(2,4-difluorobenzyl)-2-[4-(trifluoromethyl) phenyl]-1,3-thiazol-5-yl}methyl)sulfanyl]-2-methylphenoxy}acetate, (0.1 g, 49%) was obtained as a white solid.

MS m/z 594 (M+1); HPLC RT 4.337 (C18 4.2×100 mm, 0–100% ACN/H$_2$O (0.1% TFA), 6 min @ 2 ml/min @254/ 220 nm).

Ethyl {4-[({4-(4-methoxybenzyl)-2-[4-(trifluoromethyl)phenyl]-1,3-thiazol-5-yl}methyl)sulfanyl]-2-methyl phenoxy}acetate From 5-(chloromethyl)-4-(4-methoxybenzyl)-2-[4-(trifluoromethyl)phenyl]-1,3-thiazole (0.09 g, 0.4 mmol) (prepared as in U17097-118-3), ethyl {4-[({4-(4-methoxybenzyl)-2-[4-(trifluoromethyl)phenyl]-1,3-thiazol-5-yl}methyl) sulfanyl]-2-methylphenoxy}acetate (0.160 g, 68%) was obtained as a white solid.

MS m/z 588 (M+1); HPLC RT 4.631 (C18 4.2×100 mm, 0–100% ACN/H$_2$O (0.1% TFA), 6 min @ 2 ml/min @254/ 220 nm).

2-Methyl-4-[({4-[(tetrahydro-2H-pyran-2-yloxy) methyl]-2-[4-(trifluoromethyl)phenyl]-1,3-thiazol-5-yl}methyl)sulfanyl]phenol $^1$H NMR (CDCl$_3$) 400 MHz δ 7.97(d, 2H, J=8.10 Hz), 7.63(d, 2H, J=8.10 Hz), 7.16(d, 1H, J=2.24 Hz), 7.06(dd, 1H, J=8.28, 2.24 Hz), 6.63(d, 1H, J=8.28 Hz), 4.64(t, 1H, J=3.53 Hz), 4.59(d, 1H, J□.24 Hz), 4.40(d, 1H, J□.24 Hz), 4.23(s, 2H), 3.86(m, 1H), 3.53(m, 1H), 2.16(s, 3H), 1.66(m, 6H), 2-Methyl-4-[({4-(4-trifluoromethyl)benzyl]-2-[4-(trifluoromethyl)phenyl]-1,3-thiazol-5-yl}methyl) sulfanyl]phenol From 5-(chloromethyl)-4-[4-(trifluoromethyl)benzyl]-2-[4-(trifluoromethyl)phenyl]-1,3-thiazole (0.82 g, 0.19 mmol), 2-methyl-4-[({4-(4-trifluoromethyl)benzyl]-2-[4-(trifluoromethyl)phenyl]-1,3-thiazol-5-yl}methyl)sulfanyl] phenol (0.021 g, 21%) was obtained as a white solid.

$^1$H NMR (CDCl$_3$): δ 8.00 (d, 2H), 7.69 (d, 2H), 7.52 (d, 2H), 7.29 (d, 2H), 7.18 (s, 1H), 7.16 (d 1H), 6.70 (d, 1H), 4.15 (s, 2H), 4.00 (s, 2H), 2.20 (s, 3H); MS m/z 540 (M+1).

2-Methyl-4-[({4-(4-(trifluoromethoxy)benzyl]-2-[4-(trifluoromethyl)phenyl]-1,3-thiazol-5-yl}methyl) sulfanyl]phenol From 5-(chloromethyl)-4-[4-(trifluoromethoxy)benzyl]-2-[4-(trifluoromethyl)phenyl]-1,3-thiazole (0.147 g, 0.33 mmol), 2-methyl-4-[({4-(4-trifluoromethoxy)benzyl]-2-[4-(trifluoromethyl)phenyl]-1,3-thiazol-5-yl}methyl)sulfanyl] phenol (0.048 g, 27%) was obtained as a white solid.

$^1$H NMR (CDCl$_3$): δ 8.01 (d, 2H), 7.71 (d, 2H), 7.13 (m, 6H), 6.69 (d, 1H), 4.18 (s, 2H), 3.96 (s, 2H), 2.22 (s, 3H); MS m/z 556 (M+1).

4-[({4-(4-methoxybenzyl)-2-[4-(trifluoromethyl) phenyl]-1,3-thiazol-5-yl}methyl)sulfanyl]-2-methylphenol From 5-(chloromethyl)-4-(4-methoxybenzyl)-2-[4-(trifluoromethyl)phenyl]-1,3-thiazole (0.063 g, 0.16 mmol), 4-[({4-(4-methoxybenzyl)-2-[4-(trifluoromethyl)phenyl]-1, 3-thiazol-5-yl}methyl)sulfanyl]-2-methylphenol (0.022 g, 28%) was obtained as a white solid.

$^1$H NMR (CDCl$_3$): δ 8.00 (d, 2H), 7.68 (d, 2H), 7.19 (s, 1H), 7.09 (m, 3H), 6.82 (d, 2H), 6.70 (d, 1H), 4.14 (s, 2H), 3.90 (s, 2H), 2.20 (s, 3H); MS m/z 502 (M+1).

2-Methyl-4-[({4-(4-methylsulfanyl)benzyl]-2-[4-(trifluoromethyl)phenyl]-1,3-thiazol-5-yl}methyl) sulfanyl]phenol From 5-(chloromethyl)-4-[4-(methylsulfanyl)benzyl]-2-[4-(trifluoromethyl)phenyl]-1,3-thiazole (0.33 g, 0.78 mmol), 2-methyl-4-[({4-(4-methylsulfanyl)benzyl]-2-[4-(trifluoromethyl)phenyl]-1,3-thiazol-5-yl}methyl)sulfanyl] phenol (0.296 g, 72%) was obtained as a white solid.

MS m/z 518 (M+1).

4-[({4-(4-tert-butylbenzyl)-2-[4-(trifluoromethyl) phenyl]-1,3-thiazol-5-yl}methyl)sulfanyl]-2-methylphenol From 4-(4-tert-butylbenzyl)-5-(chloromethyl)-2-[4-(trifluoromethyl)phenyl]-1,3-thiazole (0.151 g, 0.36 mmol), 4-[({4-(4-tert-butylbenzyl)-2-[4-(trifluoromethyl)phenyl]-1, 3-thiazol-5-yl}methyl)sulfanyl]-2-methylphenol (0.113 g, 60%) was obtained as a white solid. MS m/z 528 (M+1).

2-Methyl]-4-[({4-(3-thienylmethyl)-2-[4-(trifluoromethyl)phenyl]-1,3-thiazol-5-yl}methyl)sulfanyl] phenol From 5-(chloromethyl)-4-(3-thienylmethyl)-2-[4-(trifluoromethyl)phenyl]-1,3-thiazole (0.105 g, 0.28 mmol), 2-methyl-4-[({4-(3-thienylmethyl)-2-[4-(trifluoromethyl)phenyl]-1,3-thiazol-5-yl}methyl)sulfanyl]phenol (0.072 g, 54%) was obtained as a yellow oil. MS m/z 478 (M+1).

The following three compounds were also prepared by the same route but were carried on without purification:

Ethyl 2-{2-isopropyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate 4-[({4-[(Tetrahydro-2H-pyran-2-yloxy)methyl]-2-[4-(trifluoromethyl)phenyl]-1,3-thiazol-5-yl}methyl)sulfanyl] phenol 4-[({2-(4-Fluorophenyl)-4-[(tetrahydro-2H-pyran-2-yloxy) methyl-1,3-thiazol-5-yl}methyl)sulfanyl]-2-methyl phenol Ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate From 2-methyl-4-[({4-(4-trifluoromethoxy)benzyl]-2-[4-(trifluoromethyl)phenyl]-1,3-thiazol-5-yl}methyl)sulfanyl]

phenol (0.17 g, 0.31 mmol), ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate (0.17 g, 83%) was obtained as a white solid.

MS m/z 656 (M+1); HPLC RT 4.553 (C18 4.2×100 mm, 0–100% ACN/H$_2$O (0.1% TFA), 6 min @ 2 ml/min @254/220 nm).

Methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate From 2-methyl-4-[({4-(4-trifluoromethoxy)benzyl]-2-[4-(trifluoromethyl)phenyl]-1,3-thiazol-5-yl}methyl)sulfanyl] phenol (0.17 g, 0.31 mmol), methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate (0.15 g, 80%) was obtained as a white solid. MS m/z 628 (M+1); HPLC RT 4.398 (C18 4.2×100 mm, 0–100% ACN/H$_2$O (0.1% TFA), 6 min @ 2 ml/min @254/220 nm).

Ethyl 2-{2-methyl-4-[({4-(3-thienylmethyl)-2-[4-(trifluoromethyl)phenyl]-1,3-thiazol-5-yl}methyl)sulfanyl]phenoxy}propanoate From 2-methyl-4-[({4-(3-thienylmethyl)-2-[4-(trifluoromethyl)phenyl]-1,3-thiazol-5-yl}methyl)sulfanyl]phenol, ethyl 2-{2-methyl-4-[({4-(3-thienylmethyl)-2-[4-(trifluoromethyl)phenyl]-1,3-thiazol-5-yl}methyl)sulfanyl] phenoxy}propanoate (0.225 g, 0.47 mmol), (0.255 g, 91%) was obtained as a yellow oil.

MS m/z 578 (M+1); HPLC RT 4.412 (C18 4.2×100 mm, 0–100% ACN/H$_2$O (0.1% TFA), 6 min @ 2 ml/min @254/220 nm).

Methyl {2-methyl-4-[({4-(3-thienylmethyl)-2-[4-(trifluoromethyl)phenyl]-1,3-thiazol-5-yl}methyl)sulfanyl]phenoxy}acetate From 2-methyl-4-[({4-(3-thienylmethyl)-2-[4-(trifluoromethyl)phenyl]-1,3-thiazol-5-yl}methyl)sulfanyl]phenol, methyl {2-methyl-4-[({4-(3-thienylmethyl)-2-[4-(trifluoromethyl)phenyl]1,3-thiazol-5-yl}methyl)sulfanyl] phenoxy}acetate (0.225 g, 0.47 mmol), (0.259 g, 94%) was obtained as a yellow oil.

MS m/z 550 (M+1); HPLC RT 4.243 (C18 4.2×100 mm, 0–100% ACN/H$_2$O (0.1% TFA), 6 min @ 2 ml/min @254/220 nm).

Ethyl 2-{4-[({4-(hydroxymethyl)-2-[4-(trifluoromethyl)phenyl]-1,3-thiazol-5-yl}methyl)sulfanyl]phenoxy}-2-methylpropanoate To a stirred solution of crude ethyl {2-methyl-4-[({4-[(tetrahydro-2H-pyran-2-yloxy)methyl]-2-[4-(trifluoromethyl)phenyl]-1,3-thiazol-5-yl}methyl)sulfanyl] phenoxy}acetate (11.98 g, 20.09 mmoles, 1 eq) in MeOH (100 ml, 0.20M) was added as a solid p-toluenesulfonic acid (800 mg, 25 mol %) at room temperature. The reaction mixture was stirred at room temperature for 3 hours. The MeOH was removed in vacuo and the residue was purified by silica gel chromatography (15% EtOAc/Hexanes to 30% EtOAc/Hexanes) to yield 8 g (78%) of pure titled alcohol.

$^1$H NMR (CDCl$_3$) 400 MHz δ 7.96(d, 2H, J=8.06 Hz), 7.65(d, 2H, J=8.06 Hz), 7.23(d, 2H, J=8.79 Hz), 6.73(d, 2H, J=8.79 Hz), 4.44(s, 2H), 4.17(m, 4H), 2.33(br s, 1H), 1.56(s, 6H), 1.21(t, 3H, J=7.14 Hz),

TLC(30% EtOAc/Hexanes) R$_f$=0.32

4-[({4-(Hydroxymethyl)-2-[4-(trifluoromethyl)phenyl]-1,3-thiazol-5-yl}methyl)sulfanyl]-2-methylphenol $^1$H NMR (CDCl$_3$) 400 MHz δ 7.95(d, 2H, J=7.93 Hz), 7.64(d, 2H, J=7.93 Hz), 7.15(d, 1H, J=2.07 Hz), 6.98(dd, 1H, J=8.10, 2.07 Hz), 6.62(d, 1H, J=8.10 Hz), 4.39(s, 2H), 4.11(s, 2H), 2.14(s, 3H),

Ethyl 2-{4-[({4-(hydroxymethyl)-2-[4-(trifluoromethyl)phenyl]-1,3-thiazol-5-yl}methyl)sulfanyl]-2-propylphenoxy}propanoate $^1$H NMR (CDCl$_3$) 400 MHz δ 7.97(d, 2H, J=8.06 Hz), 7.66(d, 2H, J=8.06 Hz), 7.13(d, 1H, J=2.38 Hz), 7.10(dd, 1H, J=8.24, 2.38 Hz), 6.55(d, 1H, J=8.24 Hz), 4.70(q, 1H, J=6.78 Hz), 4.43(s, 2H), 4.14(m, 4H), 2.55(t, 2H, J=7.33 Hz), 2.19(br s, 1H), 1.55(m, 5H), 1.21(t, 3H, J=7.14 Hz), 0.85(t, 3H, J=7.33 Hz),

Methyl {4-[({4-(hydroxymethyl)-2-[4-(trifluoromethyl)phenyl]-1,3-thiazol-5-yl}methyl)sulfanyl]-2-isopropylphenoxy}acetate $^1$H NMR (CDCl$_3$) 400 MHz δ 7.97(d, 2H, J=8.42 Hz), 7.66(d, 2H, J=8.42 Hz), 7.15(m, 2H), 6.60(d, 1H, J=8.79 Hz), 4.64(s, 2H), 4.38(s, 2H), 4.15(s, 2H), 3.77(s, 3H), 3.31(m, 1H), 2.03(br s, 1H), 1.12(d, 6H, J=6.96 Hz),

Ethyl 2-{4-[({4-(hydroxymethyl)-2-[4-(trifluoromethyl)phenyl]-1,3-thiazol-5-yl}methyl)sulfanyl]-2-isopropylphenoxy}propanoate $^1$H NMR (CDCl$_3$) 400 MHz δ 7.97(d, 2H, J=8.24 Hz), 7.66(d, 2H, J=8.24 Hz), 7.15(d, 1H, J=2.38 Hz), 7.11(dd, 1H, J=8.42, 2.38 Hz), 6.56(d, 1H, J=8.42 Hz), 4.73(q, 1H, J=6.78 Hz), 4.38(s, 2H), 4.14(m, 4H), 3.30(m, 1H), 1.60(d, 3H, J=6.78 Hz), 1.17(m, 9H),

Ethyl 2-[(4-[({4-(hydroxymethyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.23 Hz), 7.69(d, 2H, J=8.23 Hz), 7.22(d, 1H, J=2.39 Hz), 7.12(dd, 1H, J=8.23, 2.39 Hz), 6.59(d, 1H, J=8.23 Hz), 4.74(q, 1H, J=6.77 Hz), 4.51(s, 2H), 4.19(m, 4H), 3.68(br s, 1H), 2.26(s, 3H), 1.65(d, 3H, J=6.77 Hz), 1.26(t, 3H, J=7.17 Hz), TLC(50% EtOAc/Hexanes) R$_f$=0.40

The following four compounds were deprotected as above but used without further purification:

Ethyl 2-[4-({[2-(4-fluorophenyl)-4-(hydroxymethyl)-1,3-thiazol-5-yl]methyl}sulfanyl)-2-methylphenoxy]propanoate Ethyl {2-ethyl-4-[({4-(hydroxymethyl)-2-[4-(trifluoromethyl)phenyl]-1,3-thiazol-5-yl}methyl)sulfanyl] phenoxy}acetate Ethyl 2-{2-ethyl-4-[({4-(hydroxymethyl)-2-[4-(trifluoromethyl)phenyl]-1,3-thiazol-5-yl}methyl)sulfanyl] phenoxy}propanoate Ethyl {4-[({4-(hydroxymethyl)-2-[4-(trifluoromethyl)phenyl]-1,3-thiazol-5-yl}methyl)sulfanyl]-2-propylphenoxy}acetate

Ethyl {[tert-butyl(diphenyl)silyl]oxy}acetate

To a 500 ml round-bottom flask equipped with a magnetic stir-bar, $N_2$ inlet was added ethyl glycolate (10 g, 96.0 mmoles, 1 eq) and dry $CH_2Cl_2$ (200 ml, 0.5M). This was followed by the addition of triethylamine (40 ml, 0.288 moles, 3 eq) and DMAP (1.17 g, 9.6 mmoles, 10 mol %) followed by the dropwise addition of TBDPSCl (27.5 ml, 0.106 moles, 1.1 eq) in dry $CH_2Cl_2$ (20 ml). The reaction mixture was allowed to stir at room temperature overnight at which time the reaction mixture was diluted with $CH_2Cl_2$ and washed with 1N HCl, saturated sodium bicarbonate, $H_2O$ and dried over $Na_2SO_4$. After filtration the volatiles were removed in vacuo to yield 30 g (91%) of titled compound.

$^1$H NMR ($CDCl_3$) 300 MHz δ 7.69(m, 4H), 7.39(m, 6H), 4.23(s, 2H), 4.14(q, 2H, J=7.14 Hz), 1.22(t, 3H, J=7.14 Hz), 1.08(m, 9H),

TLC(20% EtOAc/Hexanes) $R_f$=0.67

{[tert-Butyl(diphenyl)silyl]oxy}acetic acid

To a stirred solution of ethyl {[tert-butyl(diphenyl)silyl]oxy}acetate (20 g, 58.4 mmoles, 1 eq) in THF (100 ml, 0.58M) was added 1N NaOH (6 ml, 0.117 moles, 2 eq) and was allowed to stir at room temperature overnight. The THF was removed in vacuo and the residue was partitioned between $CH_2Cl_2$ and 1N HCl until a pH of 2 was reached. The phases were separated and the aqueous phase was washed twice with $CH_2Cl_2$. The combined organic fractions were dried over $Na_2SO_4$, filtered and concentrated in vacuo to yield 17 g (90%) of product.

$^1$H NMR ($CDCl_3$) 300 MHz δ 7.68(m, 4H), 7.41(m, 6H), 4.22(s, 2H), 1.11(s, 9H),

TLC(5% MeOH/$CH_2Cl_2$) $R_f$=0.37

{[tert-Butyl(diphenyl)silyl]oxy}acetyl chloride

In a 500 ml round-bottom flask was mixed {[tert-butyl(diphenyl)silyl]oxy}acetic acid (17 g, 54.0 mmoles, 1 eq), thionyl chloride (11.7 g, 0.162 moles, 3 eq) and dry $CH_2Cl_2$ (120 ml, 0.45M). This mixture was refluxed for 5 hours. After cooling to room temperature the volatiles were removed in vacuo. The resulting residue was washed twice with toluene and the toluene was subsequently removed in vacuo to remove excess thionyl chloride. This resulted in 18 g (100%) of titled compound.

$^1$H NMR ($CDCl_3$) 300 MHz δ 7.72(m, 4H), 7.44(m, 6H), 4.54(s, 2H), 1.11(m, 9H),

Ethyl 4-{[tert-butyl(diphenyl)silyl]oxy}-3-oxobutanoate

To a 1-L round-bottom flask equipped with a magnetic stir-bar, addition funnel, low temperature thermometer with thermometer adapter and a $N_2$ inlet was added monoethyl malonate (14.53 g, 0.1 moles, 2 eq) in dry THF (150 ml, 0.73M) and 20 mg of 2,2'-dipyridyl. After cooling the reaction mixture to −78° C. (dry ice/acetone), n-BuLi (2.5M in Hexanes, 88 ml, 0.22 moles, 4 eq) was added at a rate to maintain the internal temperature below −10° C. Once the addition was complete the reaction was allowed to warm to −10° C. by removal of the cold bath. The reaction remained a light pink color; this designates that there was ample amount of n-BuLi to deprotonate the monoethyl malonate. (If the color had turned yellow the reaction would have had to have been re-cooled to −78° C. and additional n-BuLi would have had to have been added followed be re-warming to −10° C.) At this point the reaction mixture was cooled to −78° C. followed by the dropwise addition of neat {[tert-Butyl(diphenyl)silyl]oxy}acetyl chloride (18 g, 54 mmoles, 1 eq) over a period of 15 minutes maintaining the internal reaction temperature below −60° C. This was allowed to stir at −78° C. for 10 minutes at which point the reaction was transferred to a separatory funnel containing diethyl ether (900 ml) and 1N HCl (450 ml). This was agitated and vented until further gas evolution ceased after which the phases were separated and the organic phase was washed with saturated sodium bicarbonate, brine and dried over $Na_2SO_4$. This was then filtered, concentrated in vacuo and purified by silica gel chromatography (5% EtOAc/Hexanes to 20% EtOAc/Hexanes) to yield 12.2 g (60%) of product.

$^1$H NMR ($CDCl_3$) 300 MHz δ 7.63(m, 4H), 7.41(m, 6H), 4.19(m, 4H), 3.63(s, 2H), 1.27(t, 3H, J=7.14 Hz), 1.08(s, 9H),

TLC(20% EtOAc/Hexanes) $R_f$=0.53

The following compounds were made according to W. Wierenga (J. Org. Chem. 1979 vol 44 p 310):

Ethyl 4-(4-bromophenyl)-3-oxobutanoate $^1$H NMR ($CDCl_3$) 300 MHz δ 7.45(d, 2H, J=8.38 Hz), 7.10(d, 2H, J=8.38 Hz), 4.17(q, 2H, J=7.14 Hz), 3.79(s, 2H), 3.45(s, 2H), 1.26(t, 3H, J=7.14 Hz),

Ethyl 3-oxo-4-(2-phenylethoxy)butanoate $^1$H NMR ($CDCl_3$) 300 MHz δ 7.26(m, 5H), 4.15(q, 4H, J=7.14 Hz), 3.71(t, 2H, J=6.94 Hz), 3.46(s, 2H), 2.92(t, 2H, J=6.94 Hz), 1.27(t, 3H, J=7.14 Hz),

Ethyl 3-oxo-6-phenylhexanoate $^1$H NMR ($CDCl_3$) 300 MHz δ 7.22(m, 5H), 4.18(q, 2H, J=7.14 Hz), 3.39(s, 2H), 2.62(t, 2H, J=7.28 Hz), 2.53(t, 2H, J=7.28 Hz), 1.92(m, 2H), 1.25(t, 3H, J=7.14 Hz),

Ethyl 3-oxo-4-phenylbutanoate $^1$H ($CDCl_3$) 300 MHz 7.29(m, 5H), 4.18(q, 2H, J=7.14 Hz), 3.83(s, 2H), 3.44(s, 2H), 1.26(t, 3H, J=7.14 Hz), TLC(20% EtOAc/Hexanes) $R_f$=0.36

Ethyl 4-(benzyloxy)-3-oxobutanoate $^1$H ($CDCl_3$) 300 MHz 7.35(m, 5H), 4.59(s, 2H), 4.16(q, 4H, J=7.14 Hz), 3.53(s, 2H), 1.26(t, 3H, J=7.14 Hz),

Ethyl 3-oxo-5-phenylpentanoate $^1$H NMR ($CDCl_3$) 300 MHz 7.24(m, 5H), 4.18(q, 2H, J=7.14 Hz), 3.42(s, 2H), 2.90(m, 4H), 1.27(t, 3H, J=7.14 Hz)

Ethyl 4-{[tert-butyl(diphenyl)silyl]oxy}-2-chloro-3-oxobutanoate

To a 100 ml round-bottom flask equipped with a magnetic stir-bar and a $N_2$ inlet was added ethyl 4-{[tert-butyl(diphenyl)silyl]oxy}-3-oxobutanoate (4 g, 10.4 mmoles, 1 eq) and dry $CH_2Cl_2$ (25 ml, 0.42M) at room temperature. This was followed by the addition of neat sulfuryl chloride (0.833 ml, 10.4 mmoles, 1 eq) and the reaction was allowed to stir overnight at room temperature. After dilution with $CH_2Cl_2$ (50 ml) the reaction mixture was treated with saturated sodium bicarbonate until bubbling ceased. The phases were separated and the organic fraction was washed with sat. NaHCO$_3$, brine and dried over Na$_2$SO$_4$. After filtration and concentration in vacuo was yielded 4.2 g (96%) of crude chloride. This crude product was used without purification.

$^1$H NMR (CDCl$_3$) 400 MHz δ 7.62(m, 4H), 7.41(m, 6H), 5.26(s, 1H), 4.40(m, 2H), 4.25(m, 2H), 1.28(t, 3H, J=7.14 Hz), 1.09(s, 9H),

The following intermediates were made by the same procedure as that used for Ethyl 4-{[tert-butyl(diphenyl)silyl]oxy}-2-chloro-3-oxobutanoate

Ethyl 4-(benzyloxy)-2-chloro-3-oxobutanoate $^1$H (CDCl$_3$) 300 MHz δ 7.36(m, 5H), 5.10(s, 1H), 4.59(s, 2H), 4.32(s, 2H), 4.23(q, 2H, J=7.23 Hz), 1.28(t, 3H, J=7.14 Hz),

Ethyl 2-chloro-3-oxo-6-phenylhexanoate $^1$H (CDCl$_3$) 300 MHz δ 7.23(m, 5H), 4.75(s, 1H), 4.27(q, 2H, J=7.14 Hz), 2.72(t, 2H, J=7.28 Hz), 2.63(t, 2H, J=7.28 Hz), 1.97(m, 2H, J=7.28 Hz), 1.28(t, 3H, J=7.14 Hz),

Ethyl 2-chloro-3-oxo-4-(2-phenylethoxy)butanoate $^1$H NMR (CDCl$_3$) 300 MHz δ 7.25(m, 5H), 5.03(s, 1H), 4.29(m, 2H), 4.24(q, 2H, J=7.14 Hz), 3.73(t, 2H, J=7.00 Hz), 2.91(t, 2H, J=7.00 Hz), 1.29(t, 3H, J=7.14 Hz),

Ethyl 2-chloro-3-oxo-4-phenylbutanoate $^1$H (CDCl$_3$) 300 MHz 7.29(m, 5H), 4.87(s, 1H), 4.23(m, 2H, J=7.14, 7.00, 7.14, 1.10, 1.24, 1.24, 0.82 Hz), 4.02(d, 2H, J=4.53 Hz), 1.31(t, 3H, J=7.14 Hz), TLC(20% EtOAc/Hexanes) R$_f$=0.51

Ethyl 2-chloro-3-oxo-5-phenylpentanoate $^1$H (CDCl$_3$) 300 MHz 7.25(m, 5H), 4.76(s, 1H), 4.25(q, 2H, J=7.14 Hz), 2.99(m, 4H), 1.31(t, 3H, J=7.14 Hz), TLC(20% EtOAc/Hexanes) R$_f$=0.46

Ethyl 4-(4-bromophenyl)-2-chloro-3-oxobutanoate $^1$H NMR (CDCl$_3$) 300 MHz δ 7.48(d, 2H, J=8.51 Hz), 7.10(d, 2H, J=8.51 Hz), 4.84(s, 1H), 4.25(q, 2H, J=7.14 Hz), 3.97(s, 2H), 1.29(t, 3H, J=7.14 Hz), TLC(20% EtOAc/Hexanes) R$_f$=0.58

Ethyl 4-({[tert-butyl(diphenyl)silyl]oxy}methyl)-2-(4-{trifluoromethyl}phenyl)-1,3-thiazole-5-carboxylate To a 500 ml round-bottom flask equipped with a magnetic stir-bar was mixed ethyl 4-{[tert-butyl(diphenyl)silyl]oxy}-2-chloro-3-oxobutanoate (20.4 g, 52.88 mmoles, 1 eq), 4-trifluoromethylthiobenzamide (12.2 g, 59.5 mmoles, 1.1 eq), 1,2-dichloroethane (150 ml, 0.44M) and H$_2$O (3 ml). This mixture was refluxed for 12 hrs. After cooling to room temperature, the reaction mixture was diluted with CH$_2$Cl$_2$ (100 ml) and washed with sat. NaHCO$_3$. Once the phases were separated, the organic phase was washed with water, brine and dried over Na$_2$SO$_4$. This was then filtered, concentrated in vacuo and purified via silica gel chromatography (5% EtOAc/Hexanes to 20% EtOAc/Hexanes) to yield 20.3 g (76%) of the titled compound.

$^1$H NMR (CDCl$_3$) 400 MHz δ 8.07(d, 2H, J=8.37 Hz), 7.76(m, 4H), 7.71(d, 2H, J=8.37 Hz), 7.37(m, 6H), 5.24(s, 2H), 4.26(q, 2H, J=7.18 Hz), 1.29(t, 3H, J=7.18 Hz), 1.11(s, 9H),

TLC(20% EtOAc/Hexanes) R$_f$=0.72

Ethyl 4-({[tert-butyl(diphenyl)silyl]oxy}methyl)-2-phenyl-1,3-thiazole-5-carboxylate Analogous procedure to that used for ethyl 4-({[tert-butyl(diphenyl)silyl]oxy}methyl)-2-(4-{trifluoromethyl}phenyl)-1,3-thiazole-5-carboxylate except thiobenzamide is the starting material.

$^1$H NMR (CDCl$_3$) 400 MHz δ 7.98(m, 2H), 7.76(m, 4H), 7.40(m, 9H), 5.21(s, 2H), 4.23(q, 2H, J=7.12 Hz), 1.28(t, 3H, J=7.12 Hz), 1.08(s, 9H),

TLC(20% EtOAc/Hexanes) R$_f$=0.67

The following intermediates were made using the same procedure as Ethyl 4-({[tert-butyl(diphenyl)silyl]oxy}methyl)-2-(4-{trifluoromethyl}phenyl)-1,3-thiazole-5-carboxylate:

Ethyl 2-(4-{trifluoromethyl}phenyl)-4-[(2-phenylethoxy)methyl-1,3-thiazole-5-carboxylate $^1$H (CDCl$_3$) 300 MHz δ 8.10(d, 2H, J=8.79 Hz), 7.71(d, 2H, J=8.79 Hz), 7.23(m, 5H), 5.02(s, 2H), 4.37(q, 2H, J=7.14 Hz), 3.86(t, 2H, J=7.42 Hz), 2.99(t, 2H, J=7.42 Hz), 1.41(t, 3H, J=7.14 Hz),

Ethyl 2-(4-{trifluoromethyl}phenyl)-4-(3-phenylpropyl)-1,3-thiazole-5-carboxylate $^1$H (CDCl$_3$) 300 MHz δ 8.08(d, 2H, J=8.24 Hz), 7.71(d, 2H, J=8.24 Hz), 7.23(m, 5H), 4.34(q, 2H, J=7.14 Hz), 3.25(t, 2H, J=7.69 Hz), 2.71(t, 2H, J=7.69 Hz), 2.13(m, 2H), 1.35(t, 3H, J=7.14 Hz),

Ethyl 4-[(benzyloxy)methyl]-2-(4-{trifluoromethyl}phenyl)-1,3-thiazole-5-carboxylate $^1$H (CDCl$_3$) 300 MHz δ 8.12(d, 2H, J=8.79 Hz), 7.72(d, 2H, J=8.79 Hz), 7.35(m, 5H), 5.04(s, 2H), 4.74(s, 2H), 4.36(q, 2H, J=7.10 Hz), 1.38(t, 3H, J=7.14 Hz), TLC(20% EtOAc/Hexanes) R$_f$=0.49

Ethyl 4-(4-bromobenzyl)-2-(4-{trifluoromethyl}phenyl)-1,3-thiazole-5-carboxylate $^1$H NMR (CDCl$_3$) 300 MHz δ 8.07(d, 2H, J=8.79 Hz), 7.69(d, 2H, J=8.79 Hz), 7.43(d, 2H, J=8.51 Hz), 7.28(d, 2H, J=8.51 Hz), 4.51(s, 2H), 4.38(q, 2H, J=7.14 Hz), 1.39(t, 3H, J=7.14 Hz), TLC(20% EtOAc/Hexanes) R$_f$=0.66

Ethyl 4-(2-phenylethyl)-2-[4-(trifluoromethyl)phenyl]-1,3-thiazole-5-carboxylate $^1$H (CDCl$_3$) 300 MHz 8.10(d, 2H, J=8.79 Hz), 7.72(d, 2H, J=8.79 Hz), 7.24(m, 5H), 4.37(q, 2H, J=7.14 Hz), 3.51(m, 2H), 3.10(m, 2H), 1.40(t, 3H, J=7.14 Hz),

MS(ES$^+$) M+H=405.99

Ethyl 4-benzyl-2-[4-(trifluoromethyl)phenyl]-1,3-thiazole-5-carboxylate

¹H (CDCl₃) 300 MHz 8.08(d, 2H, J=8.79 Hz), 7.70(d, 2H, J=8.79 Hz), 7.42(d, 2H, J=9.61 Hz), 7.23(m, 3H), 4.58(s, 2H), 4.38(q, 2H, J=7.14 Hz), 1.39(t, 3H, J=7.14 Hz),
TLC(20% EtOAc/Hexanes) R$_f$=0.57
MS(ES⁺) M+H=391.9

{4-({[tert-Butyl(diphenyl)silyl]oxy}methyl)-2-[4-(trifluoromethyl)phenyl]-1,3-thiazol-5-yl}methanol Analogous reduction as in the synthesis of 4-[(tetrahydro-2H-pyran-2-yloxy)methyl]-2-[4-(trifluoromethyl)phenyl]-1,3-thiazol-5-yl}methanol.
¹H NMR (CDCl₃) 400 MHz δ 7.97(d, 2H, J=8.03 Hz), 7.68(m, 6H), 7.41(m, 6H), 4.97(s, 2H), 4.84(s, 2H), 1.08(s, 9H),

[4-({[tert-Butyl(diphenyl)silyl]oxy}methyl)-2-phenyl-1,3-thiazol-5-yl}methanol Analogous reduction as in the synthesis of 4-[(tetrahydro-2H-pyran-2-yloxy)methyl]-2-[4-(trifluoromethyl)phenyl]-1,3-thiazol-5-yl}methanol.
¹H NMR (CDCl₃) 300 MHz δ 7.90(m, 2H), 7.75(m, 4H), 7.45(m, 9H), 5.00(s, 2H), 4.86(s, 2H), 1.13(s, 9H), The following compounds were all made by the general alkylation procedure with the appropriate thiols made above and the alkyl halides made from either {4-({[tert-Butyl(diphenyl)silyl]oxy}methyl)-2-[4-(trifluoromethyl)phenyl]-1,3-thiazol-5-yl}methanol or {4-({[tert-Butyl(diphenyl)silyl]oxy}methyl)-2-[4-(trifluoromethyl)phenyl]-1,3-thiazol-5-yl}methanol via the chlorides as described above.

Ethyl [4-({[4-({[tert-butyl(diphenyl)silyl]oxy}methyl)-2-phenyl-1,3-thiazol-5-yl]methyl}sulfanyl)-2-methylphenoxy]acetate ¹H NMR (CDCl₃) 400 MHz δ 7.85(m, 2H), 7.68(m, 4H), 7.39(m, 9H), 7.12(d, 1H, J=2.39 Hz), 7.03(dd, 1H, J=8.37, 2.39 Hz), 6.50(d, 1H, J=8.37 Hz), 4.61(s, 2H), 4.55(s, 2H), 4.24(q, 2H, J=7.12 Hz), 4.10(s, 2H), 2.18(s, 3H), 1.26(t, 3H, J=7.12 Hz), 1.05(s, 9H),
TLC(20% EtOAc/Hexanes) R$_f$=0.43

Ethyl 2-{4-[({4-({[tert-butyl(diphenyl)silyl]oxy}methyl)-2-[4-(trifluoromethyl)phenyl]-1,3-thiazol-5-yl}methyl)sulfanyl]-2-methylphenoxy}propanoate ¹H NMR (CDCl₃) 400 MHz δ 7.94(d, 2H, J=8.20 Hz), 7.67(m, 6H), 7.39(m, 6H), 7.11(d, 1H, J=2.39 Hz), 7.00(dd, 1H, J=8.37, 2.39 Hz), 6.49(d, 1H, J=8.37 Hz), 4.65(m, 2H), 4.17(q, 2H, J=7.18 Hz), 4.09(s, 2H), 2.17(s, 3H), 1.60(d, 3H, J=6.84 Hz), 1.21(t, 3H, J=7.18 Hz), 1.05(s, 9H),
TLC(20% EtOAc/Hexanes) R$_f$=0.57

Ethyl 2-[4-({[4-({[tert-butyl(diphenyl)silyl]oxy}methyl)-2-phenyl-1,3-thiazol-5-yl]methyl}sulfanyl)-2-methylphenoxy]propanoate ¹H NMR (CDCl₃) 400 MHz δ 7.85(m, 2H), 7.68(m, 4H), 7.38(m, 9H), 7.11(d, 1H, J=2.39 Hz), 6.99(dd, 1H, J=8.55, 2.39 Hz), 6.49(d, 1H, J=8.55 Hz), 4.64(m, 3H), 4.16(q, 2H, J=7.12 Hz), 4.07(s, 2H), 2.17(s, 3H), 1.59(d, 3H, J=6.84 Hz), 1.20(t, 3H, J=7.12 Hz), 1.05(m, 9H),
TLC(20% EtOAc/Hexanes) R$_f$=0.48

Ethyl {4-[({3-({[tert-butyl(diphenyl)silyl]oxy}methyl)-5-[4-(trifluoromethyl)phenyl]-2-thienyl}methyl)sulfanyl]-2-methylphenoxy}acetate ¹H NMR (CDCl₃) 400 MHz δ 7.94(d, 2H, J=8.20 Hz), 7.66(m, 6H), 7.38(m, 6H), 7.11 (d, 1H, J=2.22 Hz), 7.03(dd, 1H, J=8.37, 2.22 Hz), 6.50(d, 1H, J=8.37 Hz), 4.63(s, 2H), 4.56(s, 2H), 4.23(q, 2H, J=7.12 Hz), 4.10(s, 2H), 2.18(s, 3H), 1.27(t, 3H, J=7.12 Hz), 1.04(s, 9H),
TLC(20% EtOAc/Hexanes) R$_f$=0.50

Ethyl [4-({[4-(hydroxymethyl)-2-(4-{trifluoromethyl}phenyl)-1,3-thiazol-5-yl]methyl}sulfanyl)-2-methylphenoxy]acetate ¹H NMR (CDCl₃) 300 MHz δ 7.97(d, 2H, J=8.23 Hz), 7.67(d, 2H, J=8.23 Hz), 7.22(d, 1H, J=2.39 Hz), 7.14(dd, 1H, J=8.23, 2.39 Hz), 6.61(d, 1H, J=8.23 Hz), 4.63(s, 2H), 4.50(s, 2H), 4.26(q, 2H, J=7.17 Hz), 4.18(s, 2H), 2.83(s, 1H), 2.25(s, 3H), 1.29(t, 3H, J=7.17 Hz),
TLC(50% EtOAc/Hexanes) R$_f$=0.51

(4-Bromophenyl)acetyl chloride

To a stirred solution of 4-bromophenylacetic acid (10 g, 46.5 mmoles, 1 eq) in dry CH₂Cl₂ (100 ml, 0.47M) was added thionyl chloride (20.2 ml, 0.280 moles, 6 eq) and refluxed for 36 hours. After cooling to room temperature the reaction was concentrated in vacuo to yield 10.86 g (100%) of acid chloride.
¹H (CDCl₃) 300 MHz δ 7.50(d, 2H, J=8.38 Hz), 7.14(d, 2H, J=8.38 Hz), 4.09(s, 2H),

4-Phenylbutanoyl chloride

¹H NMR (CDCl₃) 300 MHz δ 7.25(m, 5H), 2.90(t, 2H, J=7.28 Hz), 2.69(t, 2H, J=7.28 Hz), 2.05(m, 2H),

(2-Phenylethoxy)acetyl chloride

¹H NMR (CDCl₃) 300 MHz δ 7.26(m, 5H), 4.39(s, 2H), 3.80(t, 2H, J=6.94 Hz), 2.93(t, 2H, J=6.94 Hz)

[4-([1,1'-Biphenyl]-4-ylmethyl)-2-(4-{trifluoromethyl}phenyl)-1,3-thiazol-5-yl]methanol To a stirred solution of [4-(4-Bromobenzyl)-2-(4-{trifluoromethyl}phenyl)-1,3-thiazol-5-yl]methanol (0.33 g, 0.78 mmoles, 1 eq) in dry 1,2-dimethoxyethane (5 ml, 0.16M) was added tetrakis(triphenylphosphino) palladium I (0.45 g, 0.39 mmoles, 0.5 eq) and stirred for 5 minutes at room temperature. Phenylboronic acid (0.143 g, 1.2 mmoles, 1.5 eq) was then added followed by the addition of sodium carbonate (2M aqueous solution, 2.3 ml, 4.68 mmoles, 6 eq). The reaction mixture was heated at 100 degrees centigrade for 13 hours at which point, after cooling to room temperature, the reaction was partitioned between EtOAc and water. After separation of the phases the organic phase was washed with brine, dried over anhydrous sodium sulfate, filtered, concentrated in vacuo to yield after purification by silica gel chromatography (CH₂Cl₂ to 2% MeOH/CH₂Cl₂) 268 mg (80%) of product.
¹H NMR (CDCl₃) 400 MHz δ 8.03(d, 2H, J=8.20 Hz), 7.67(d, 2H, J=8.20 Hz), 7.54(m, 4H), 7.36(m, 5H), 4.85(s, 2H), 4.22(s, 2H), The following intermediate was prepared in using the same procedure:

{2-(4-{trifluoromethyl}phenyl)-4-[4-(3-thienyl)benzyl]-1,3-thiazol-5-yl}methanol $^1$H NMR (CDCl$_3$) 400 MHz δ 8.03(d, 2H, J=8.20 Hz), 7.67(d, 2H, J=8.20 Hz), 7.52(d, 2H, J=8.37 Hz), 7.35(m, 5H), 4.84(s, 2H), 4.20(s, 2H), The following compounds were made by the same procedure for phenol alkylation.

Ethyl {2-methyl-4-[({4-[(tetrahydro-2H-pyran-2-yloxy)methyl]-2-[4-(trifluoromethyl)phenyl-1,3-thiazol-5-yl}methyl)sulfanyl]phenoxy}acetate To a 250 ml round-bottom flask equipped with a magnetic stir-bar and N$_2$ inlet was added 5-(chloromethyl)-4-[(tetrahydro-2H-pyran-2-yloxy)methyl]-2-[4-(trifluoromethyl)phenyl]-1,3-thiazole (7.87 g, 20.09 mmoles, 1 eq) and dry CH$_3$CN (100 ml, 0.27M). Solid cesium carbonate (16.4 g, 50.22 mmoles, 2.5 eq) was added all at once followed by the quick addition of ethyl 2-methyl-2-(4-sulfanylphenoxy)propanoate (5.79 g, 24.11 mmoles, 1.2 eq) in dry CH$_3$CN (10 ml). The reaction was allowed to stir at room temperature for 2 hours at which point the solvent was removed under reduced pressure. The resulting residue was partitioned between EtOAc and 1N NaOH. After the phases were separated the organic fraction was washed with H$_2$O, brine and dried over Na$_2$SO$_4$. After filtration the volatiles were removed in vacuo to yield the titled compound in >100% yield. Because of the difficult separation between the thiophenol and the product, the crude product was carried forward without purification.

4-[({4-(Bromomethyl)-2-[4-(trifluoromethyl)phenyl]-1,3-thiazol-5-yl}methyl)sulfanyl]-2-methylphenol $^1$H NMR (CDCl$_3$) 400 MHz δ 8.01(d, 2H, J=8.10 Hz), 7.68(d, 2H, J=8.10 Hz), 7.17(d, 1H, J=2.41 Hz), 7.08(dd, 1H, J=8.10, 2.41 Hz), 6.67(d, 1H, J=8.10 Hz), 4.63(s, 2H), 4.14(s, 2H), Ethyl 2-{4-[({4-{[4-(4-methoxyphenyl)-1-piperazinyl]methyl}-2-[4-(trifluoromethyl)phenyl]-1,3-thiazol-5-yl]methyl)sulfanyl]phenoxy}-2-methylpropanoate To a 500 ml 3-neck round-bottom flask equipped with a magnetic stir-bar, low temperature thermometer with thermometer adapter, addition funnel and N$_2$ inlet was added ethyl 2-{4-[({4-(hydroxymethyl)-2-[4-(trifluoromethyl)phenyl]-1,3-thiazol-5-yl}methyl)sulfanyl]phenoxy}-2-methylpropanoate (16 g, 31.28 mmoles, 1 eq) and dry CH$_2$Cl$_2$ (120 ml, 0.26M) and cooled to 0° C. Methanesulfonyl chloride (2.91 ml, 37.54 mmoles, 1.2 eq) was added neat all at once. Triethylamine (6.6 ml, 46.92 mmoles, 1.5 eq) was added dropwise over 20 minutes maintaining the internal temperature below 5° C. and was stirred at 0° C. for 30 minutes. The reaction mixture was transferred to a separatory funnel and washed with H$_2$O, brine and the organic fraction was dried over Na$_2$SO$_4$. After filtration the solvent was removed under reduced pressure to yield the corresponding mesylate in quantitative yield. Because of the unstable nature of the mesylate, the product was not characterized and was progressed onto the next stage without purification.

To the crude mesylate dissolved in dry THF (200 ml, 0.16M) was added 4-methoxyphenyl piperazine (13 g, 62.56 mmoles, 2 eq) and the reaction mixture was refluxed for 5 hours. After cooling to room temperature the solvent was removed in vacuo to yield a yellow solid residue. The residue was washed with a minimal amount of EtOAc and filtered through Celite to remove the 4-methoxyphenyl piperazine hydrochloride salt. The EtOAc was removed in vacuo and the resulting solid was filtered through a "plug" of silica gel using 30% EtOAc/Hexanes to yield 20.37 g (95%) of a light-yellow solid.

$^1$H NMR (CDCl$_3$) 400 MHz δ 7.96(d, 2H, J=8.24 Hz), 7.63(d, 2H, J=8.24 Hz), 7.27(d, 2H, J=8.79 Hz), 6.87(d, 2H, J=9.16 Hz), 6.80(d, 2H, J=9.16 Hz), 6.74(d, 2H, J=8.79 Hz), 4.32(s, 2H), 4.17(q, 2H, J=7.14 Hz), 3.73(s, 3H), 3.56(s, 2H), 3.06(br s, 4H), 2.59(br s, 4H), 1.55(s, 6H), 1.21(t, 3H, J=7.14 Hz), HPLC (C-18, 3 μm) 0%–95% Acetonitrile/Water over 8 minutes R$_t$=6.06 minutes The follow intermediates were made using the same alkylation conditions:

4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenol $^1$H NMR (CDCl$_3$) 400 MHz δ 7.94(d, 2H, J=8.10 Hz), 7.64(d, 2H, J=8.10 Hz), 7.16(d, 1H, J=2.07 Hz), 7.07(dd, 1H, J=8.10, 2.07 Hz), 6.86(m, 2H), 6.80(d, 2H, J=8.97 Hz), 6.66(d, 1H, J=8.10 Hz), 4.27(s, 2H), 3.73(s, 3H), 3.59(s, 2H), 3.15(br s, 4H), 2.67(br s, 4H), 2.16(s, 3H), Ethyl [2-methyl-4-({[2-(4-{trifluoromethyl}phenyl)-4-(4-morpholinylmethyl)-1,3-thiazol-5-yl]methyl}sulfanyl)phenoxy]acetate $^1$H NMR (CDCl$_3$) 300 MHz δ 8.02(d, 2H, J=8.23 Hz), 7.69(d, 2H, J=8.23 Hz), 7.27(m, 1H), 7.17(dd, 1H, J=8.23, 2.39 Hz), 6.62(d, 1H, J=8.23 Hz), 4.64(s, 2H), 4.36(s, 2H), 4.25(q, 2H, J=7.17 Hz), 3.72(t, 4H, J=4.51 Hz), 3.53(s, 2H), 2.48(t, 4H, J=4.51 Hz), 2.27(s, 3H), 1.32(t, 3H, J=7.17 Hz), TLC(50% EtOAc/Hexanes) R$_f$=0.26

Ethyl [4-({[4-[(4-benzyl-1-piperazinyl)methyl]-2-(4-{trifluoromethyl}phenyl)-1,3-thiazol-5-yl]methyl}sulfanyl)-2-methylphenoxy]acetate $^1$H NMR (CDCl$_3$) 300 MHz δ 8.02(d, 2H, J=8.76 Hz), 7.68(d, 2H, J=8.76 Hz), 7.31(m, 6H), 7.16(dd, 1H, J=8.49, 2.39 Hz), 6.62(d, 1H, J=8.49 Hz), 4.63(s, 2H), 4.35(s, 2H), 4.27(q, 2H, J=7.17 Hz), 3.54(m, 4H), 2.51(br s, 8H), 2.27(s, 3H), 1.32(t, 3H, J=7.17 Hz), TLC(50% EtOAc/Hexanes)=0.19

Ethyl 2-{4-[({4-{[4-(4-methoxyphenyl)-1-piperazinyl]methyl}-2-[4-(trifluoromethyl)phenyl-1,3-thiazol-5-yl}methyl)sulfanyl]-2-methylphenoxy]propanoate $^1$H NMR (CDCl$_3$) 400 MHz. δ 7.99(d, 2H, J=8.20 Hz), 7.66(d, 2H, J=8.20 Hz), 7.23(d, 1H, J=2.39 Hz), 7.13(dd, 1H, J=8.37, 2.39 Hz), 6.89(d, 2H, J=9.23 Hz), 6.83(d, 2H, J=9.23 Hz), 6.57(d, 1H, J=8.37 Hz), 4.70(q, 1H, J=6.84 Hz), 4.34(s, 2H), 4.17(q, 2H, J=7.18 Hz), 3.76(s, 3H), 3.58(s, 2H), 3.09(m, 4H), 2.63(m, 4H), 2.24(s, 3H), 1.62(d, 3H, J=6.84 Hz), 1.21(t, 3H, J=7.18 Hz), TLC(30% EtOAc/Hexanes)=0.29

Ethyl {2-methyl-4-[({2-(4-{trifluoromethyl}phenyl)-4-[(4-phenyl-1-piperazinyl)methyl]-1,3-thiazol-5-yl}methyl)sulfanyl]phenoxy}acetate ¹H NMR (CDCl₃) 300 MHz δ 8.04(d, 2H, J=8.23 Hz), 7.70(d, 2H, J=8.23 Hz), 7.29(m, 3H), 7.21(dd, 1H, J=8.23, 2.39 Hz), 6.92(m, 3H), 6.63(d, 1H, J=8.23 Hz), 4.64(s, 2H), 4.38(s, 2H), 4.27(q, 2H, J=7.17 Hz), 3.63(s, 2H), 3.21(m, 4H), 2.66(m, 4H), 2.28(s, 3H), 1.32(t, 3H, J=7.17 Hz),
TLC(50% EtOAc/Hexanes) R_f=0.52

Ethyl 4-{[5-({[4-(2-ethoxy-2-oxoethoxy)-3-methylphenyl]sulfanyl}methyl)-2-(4-{trifluoromethyl}phenyl)-1,3-thiazol-4-yl]methyl}-1-piperazinecarboxylate ¹H NMR (CDCl₃) 300 MHz δ 7.99(d, 2H, J=8.23 Hz), 7.68(d, 2H, J=8.23 Hz), 7.25(m, 1H), 7.17(dd, 1H, J=8.49, 2.12 Hz), 6.61(d, 1H, J=8.49 Hz), 4.64(s, 2H), 4.28(m, 4H), 4.14(t, 2H, J=7.17 Hz), 3.50(m, 6H), 2.44(br s, 4H), 2.26(s, 3H), 1.29(t, 3H, J=7.17 Hz),
TLC(50% EtOAc/Hexanes) R_f=0.17

Ethyl {2-methyl-4-[({2-(4-{trifluoromethyl}phenyl)-4-[(4-phenyl-1-piperidinyl)methyl]-1,3-thiazol-5-yl}methyl)sulfanyl]phenoxy}acetate ¹H NMR (CDCl₃) 300 MHz δ 8.04(d, 2H, J=8.23 Hz), 7.70(d, 2H, J=8.23 Hz), 7.27(m, 7H), 6.64(d, 1H, J=8.49 Hz), 4.64(s, 2H), 4.41(s, 2H), 4.28(q, 2H, J=7.17 Hz), 3.60(s, 2H), 3.02(m, 2H), 2.53(m, 1H), 2.30(s, 3H), 2.18(m, 2H), 1.84(m, 4H), 1.32(t, 3H, J=7.17 Hz),
TLC(50% EtOAc/Hexanes) R_f=0.48

Ethyl {2-methyl-4-[({2-(4-{trifluoromethyl}phenyl)-4-[(4-methyl-1-piperidinyl)methyl]-1,3-thiazol-5-yl}methyl)sulfanyl]phenoxy}acetate ¹H NMR (CDCl₃) 300 MHz δ 8.02(d, 2H, J=8.23 Hz), 7.68(d, 2H, J=8.23 Hz), 7.28(d, 1H, J=2.39 Hz), 7.19(dd, 1H, J=8.49, 2.39 Hz), 6.62(d, 1H, J=8.49 Hz), 4.64(s, 2H), 4.38(s, 2H), 4.28(q, 2H, J=7.17 Hz), 3.51(s, 2H), 2.84(m, 4H), 2.28(s, 3H), 2.02(m, 4H), 1.61(m, 4H), 1.30(m, 8H), 0.94(d, 3H, J=6.11 Hz),
TLC(50% EtOAc/Hexanes) R_f=0.36

Ethyl (2-methyl-4-{[(2-(4-{trifluoromethyl}phenyl)-4-{[4-(2-methylphenyl)-1-piperazinyl]methyl}-1,3-thiazol-5-yl)methyl]sulfanyl}phenoxy)acetate ¹H (CDCl₃) 400 MHz δ 7.99(d, 2H, J=8.20 Hz), 7.66(d, 2H, J=8.20 Hz), 7.25(m, 1H), 7.16(m, 3H), 6.98(m, 2H), 6.60(d, 1H, J=8.55 Hz), 4.60(s, 2H), 4.37(s, 2H), 4.23(q, 2H, J=7.12 Hz), 3.59(s, 2H), 2.93(s, 4H), 2.63(s, 4H), 2.29(s, 3H), 2.24(s, 3H), 1.27(t, 5H, J=7.12 Hz),
TLC(50% EtOAc/Hexanes) R_f=0.73

Ethyl [4-({[4-{[4-(4-methoxyphenyl)-1-piperazinyl]methyl}-2-(4-{trifluoromethyl}phenyl)-1,3-thiazol-5-yl]methyl}sulfanyl)-2-methylphenoxy]acetate ¹H (CDCl₃) 400 MHz δ 7.99(d, 2H, J=8.20 Hz), 7.65(d, 2H, J=8.20 Hz), 7.24(dd, 1H, J=2.39 Hz), 7.16(dd, 1H, J=8.37, 2.39 Hz), 6.84(m, 4H), 6.58(d, 1H, J=8.37 Hz), 4.59(s, 2H), 4.33(s, 2H), 4.23(q, 2H, J=7.18 Hz), 3.75(s, 3H), 3.57(s, 2H), 3.07(m, 4H), 2.62(s, 4H), 2.24(s, 3H), 1.27(t, 3H, J=7.18 Hz),
TLC(50% EtOAc/Hexanes) R_f=0.44

Ethyl (2-methyl-4-{[(2-(4-{trifluoromethyl}phenyl)-4-{[4-(3-methylphenyl)-1-piperazinyl]methyl}-1,3-thiazol-5-yl)methyl]sulfanyl}phenoxy)acetate ¹H (CDCl₃) 400 MHz δ 7.99(d, 2H, J=8.20 Hz), 7.66(d, 2H, J=8.20 Hz), 7.24(m, 1H), 7.14(m, 2H), 6.70(s, 3H), 6.59(d, 1H, J=8.55 Hz), 4.60(s, 2H), 4.33(s, 2H), 4.23(q, 2H, J=7.12 Hz), 3.57(s, 2H), 3.16(br s, 4H), 2.62(br s, 4H), 2.30(s, 3H), 2.24(s, 3H), 1.26(t, 3H, J=7.12 Hz),
TLC(50% EtOAc/Hexanes) R_f=0.64

Ethyl (2-methyl-4-{[(2-(4-{trifluoromethyl}phenyl)-4-{[4-(4-methylphenyl)-1-piperazinyl]methyl}-1,3-thiazol-5-yl)methyl]sulfanyl}phenoxy)acetate ¹H (CDCl₃) 400 MHz δ 7.99(d, 2H, J=8.20 Hz), 7.65(d, 2H, J=8.20 Hz), 7.24(d, 1H, J=2.39 Hz), 7.15(dd, 1H, J=8.37, 2.39 Hz), 7.04(d, 2H, J=8.55 Hz), 6.82(d, 2H, J=8.55 Hz), 6.58(d, 1H, J=8.37 Hz), 4.60(s, 2H), 4.32(s, 2H), 4.23(q, 2H, J=7.12 Hz), 3.57(s, 2H), 3.10(s, 4H), 2.60(s, 4H), 2.26(s, 3H), 2.23(s, 3H), 1.26(t, 3H, J=7.12 Hz),
TLC(50% EtOAc/Hexanes) R_f=0.64

Ethyl [4-({[4-{[4-(2-furoyl)-1-piperazinyl]methyl}-2-(4-{trifluoromethyl}phenyl)-1,3-thiazol-5-yl]methyl}sulfanyl)-2-methylphenoxy]acetate ¹H (CDCl₃) 400 MHz δ 7.98(d, 2H, J=8.20 Hz), 7.65(d, 2H, J=8.20 Hz), 7.46(m, 1H), 7.22(d, 1H, J=2.39 Hz), 7.13(dd, 1H, J=8.37, 2.39 Hz), 6.96(d, 1H, J=3.42 Hz), 6.59(d, 1H, J=8.37 Hz), 6.46(m, 1H), 4.62(s, 2H), 4.29(s, 2H), 4.21(q, 2H, J=7.12 Hz), 3.80(s, 4H), 3.50(s, 2H), 2.53(s, 4H), 2.23(s, 3H), 1.26(t, 3H, J=7.18 Hz),
TLC(50% EtOAc/Hexanes) R_f=0.06

Ethyl (2-methyl-4-{[(2-(4-{trifluoromethyl}phenyl)-4-{[4-(2-pyridinyl)-1-piperazinyl]methyl}-1,3-thiazol-5-yl)methyl]sulfanyl}phenoxy)acetate ¹H (CDCl₃) 400 MHz δ 8.16(m, 1H), 7.98(d, 2H, J=8.20 Hz), 7.63(d, 2H, J=8.20 Hz), 7.45(s, 1H), 7.25(d, 1H, J=2.22 Hz), 7.15(dd, 1H, J=8.37, 2.22 Hz), 6.56(m, 3H), 4.60(s, 2H), 4.33(s, 2H), 4.21(q, 2H, J=7.12 Hz), 3.53(m, 6H), 2.57(s, 4H), 2.23(s, 3H), 1.27(t, 3H, J=7.12 Hz),
TLC(50% EtOAc/Hexanes) R_f=0.25

Ethyl [4-({[4-{[4-(4-chlorobenzyl)-1-piperazinyl]methyl}-2-(4-{trifluoromethyl}phenyl)-1,3-thiazol-5-yl]methyl}sulfanyl)-2-methylphenoxy]acetate ¹H (CDCl₃) 400 MHz δ 7.96(d, 2H, J=8.20 Hz), 7.64(d, 2H, J=8.20 Hz), 7.25(m, 5H), 7.13(dd, 1H, J=8.37, 2.39 Hz), 6.58(d, 1H, J=8.37 Hz), 4.59(s, 2H), 4.31(s, 2H), 4.22(q, 2H, J=7.18 Hz), 3.52(s, 2H), 3.42(s, 2H), 2.48(br s, 8H), 2.20(s, 3H), 1.26(t, 3H, J=7.18 Hz),
TLC(50% EtOAc/Hexanes) R_f=0.23

Ethyl [4-({[4-{[4-(4-acetylphenyl)-1-piperazinyl]methyl}-2-(4-{trifluoromethyl}phenyl)-1,3-thiazol-5-yl]methyl}sulfanyl)-2-methylphenoxy]acetate ¹H (CDCl₃) 400 MHz δ 7.98(d, 2H, J=8.20 Hz), 7.85(d, 2H, J=9.06 Hz), 7.66(d, 2H, J=8.20 Hz), 7.24(d, 1H, J=2.39 Hz), 7.16(dd, 1H, J=8.20, 2.39 Hz), 6.84(d, 2H, J=9.06 Hz), 6.58(d, 1H, J=8.20 Hz), 4.61(s, 2H), 4.31 (s, 2H), 4.22(q, 2H, J=7.18 Hz), 3.58(s, 2H), 3.33(br s, 4H), 2.60(br s, 4H), 2.50(m, 3H), 2.24(s, 3H), 1.27(t, 3H, J=7.18 Hz), TLC(50% EtOAc/Hexanes) $R_f$=0.23

Ethyl [4-({[4-{[4-(2-hydroxyethyl)-1-piperazinyl]methyl}-2-(4-{trifluoromethyl}phenyl)-1,3-thiazol-5-yl]methyl}sulfanyl)-2-methylphenoxy]acetate $^1$H (CDCl$_3$) 400 MHz δ 7.97(d, 2H, J=8.20 Hz), 7.64(d, 2H, J=8.20 Hz), 7.23(d, 1H, J=2.22 Hz), 7.14(dd, 1H, J=8.37, 2.22 Hz), 6.58(d, 1H, J=8.37 Hz), 4.60(s, 2H), 4.30(s, 2H), 4.22(q, 2H, J=7.12 Hz), 3.60(m, 2H), 3.50(s, 2H), 2.94(s, 1H), 2.53(m, 10H), 2.23(s, 3H), 1.26(t, 3H, J=7.12 Hz),

Ethyl (2-methyl-4-{[(2-(4-{trifluoromethyl}phenyl)-4-{[(3-pyridinylmethyl)amino]methyl-1,3-thiazol-5-yl)methyl]sulfanyl}phenoxy)acetate $^1$H (CDCl$_3$) 400 MHz δ 8.55(m, 1H), 8.50(m, 1H), 7.98(d, 2H, J=8.20 Hz), 7.71(m, 1H), 7.65(m, 2H), 7.24(m, 1H), 7.17(m, 1H), 7.10(m, 1H), 6.55(d, 1H, J=8.37 Hz), 4.58(s, 2H), 4.22(q, 2H, J=7.12 Hz), 4.12(s, 2H), 3.77(s, 2H), 3.63(s, 2H), 2.64(br s, 1H), 2.21(s, 3H), 1.27(t, 3H, J=7.12 Hz),

Ethyl (4-{[(4-{[4-(4-methoxyphenyl)-1-piperazinyl]methyl}-2-phenyl-1,3-thiazol-5-yl)methyl]sulfanyl}-2-methylphenoxy)acetate $^1$H NMR (CDCl$_3$) 400 MHz δ 7.88(m, 2H), 7.40(m, 3H), 7.25(d, 1H, J=2.39 Hz), 7.17(dd, 1H, J=8.37, 2.39 Hz), 6.89(d, 2H, J=9.06 Hz), 6.81(d, 2H, J=9.06 Hz), 6.58(d, 1H, J=8.37 Hz), 4.59(s, 2H), 4.32(s, 2H), 4.23(q, 2H, J=7.12 Hz), 3.74(s, 3H), 3.56(s, 2H), 3.06(m, 4H), 2.62(m, 4H), 2.24(s, 3H), 1.27(t, 3H, J=7.12 Hz),

Ethyl 2-(4-{[(4-{[4-(4-methoxyphenyl)-1-piperazinyl]methyl}-2-phenyl-1,3-thiazol-5-yl)methyl]sulfanyl}-2-methylphenoxy)propanoate $^1$H NMR (CDCl$_3$) 400 MHz. δ 7.88(m, 2H), 7.40(m, 3H), 7.25(d, 1H, J=2.39 Hz), 7.14(dd, 1H, J=8.37, 2.39 Hz), 6.89(d, 2H, J=9.40 Hz), 6.82(d, 2H, J=9.40 Hz), 6.57(d, 1H, J=8.37 Hz), 4.70(q, 1H, J=6.84 Hz), 4.32(s, 2H), 4.17(q, 2H, J=7.18 Hz), 3.76(s, 3H), 3.56(s, 2H), 3.08(m, 4H), 2.63(m, 4H), 2.23(m, 3H), 1.61(d, 3H, J=6.84 Hz), 1.25(t, 3H, J=7.18 Hz),

Ethyl {2-methyl-4-[({2-(4-{trifluoromethyl}phenyl)-4-[(pentylamino)methyl]-1,3-thiazol-5-yl}methyl)sulfanyl]phenoxy}acetate $^1$H (CDCl$_3$) 400 MHz δ 7.97(d, 2H, J=8.20 Hz), 7.65(d, 2H, J=8.20 Hz), 7.20(d, 1H, J=2.39 Hz), 7.12(dd, 1H, J=8.37, 2.39 Hz), 6.58(d, 1H, J=8.37 Hz), 4.60(s, 2H), 4.23(q, 2H, J=7.18 Hz), 4.18(s, 2H), 3.64(s, 2H), 2.58(t, 2H, J=6.92 Hz), 2.22(s, 3H), 1.50(m, 2H), 1.28(m, 7H), 0.87(t, 3H, J=6.92 Hz),

Ethyl 2-{4-[({4-{[4-(4-hydroxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.08(d, 2H, J=8.28 Hz), 7.75(d, 2H, J=8.28 Hz), 7.27(d, 1H, J=2.21 Hz), 7.17(dd, 1H, J=8.28, 2.21 Hz), 6.87(d, 2H, J=8.83 Hz), 6.73(d, 2H, J=8.83 Hz), 6.66(d, 1H, J=8.28 Hz), 4.83(q, 1H, J=6.81 Hz), 4.34(s, 2H), 4.15(q, 2H, J=7.08 Hz), 3.47(s, 2H), 3.00(t, 4H, J=4.83 Hz), 2.57(t, 4H, J=4.83 Hz), 2.20(s, 3H), 1.57(d, 3H, J=6.81 Hz), 1.20(t, 3H, J=7.08 Hz),

Ethyl 2-{4-[({4-{[4-(3,4-dimethoxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.06(d, 2H, J=8.28 Hz), 7.72(d, 2H, J=8.28 Hz), 7.26(d, 1H, J=2.21 Hz), 7.16(dd, 1H, J=8.55, 2.21 Hz), 6.82(d, 1H, J=8.55 Hz), 6.64(m, 2H), 6.47(dd, 1H, J=8.55, 2.21 Hz), 4.81(q, 1H, J=6.99 Hz), 4.34(s, 2H), 4.14(q, 2H, J=7.17 Hz), 3.82(s, 3H), 3.77(s, 3H), 3.52(s, 2H), 3.07(t, 4H, J=4.55 Hz), 2.63(t, 4H, J=4.55 Hz), 2.20(s, 3H), 1.57(d, 3H, J=6.99 Hz), 1.18(t, 3H, J=7.17 Hz),

Ethyl 2-(4-{[(4-{[4-(4-methoxyphenyl)-1-piperazinyl]methyl}-2-phenyl-1,3-thiazol-5-yl)methyl]sulfanyl}phenoxy)-2-methylpropanoate $^1$H NMR (CDCl$_3$) 400 MHz δ 7.87(m, 2H), 7.40(m, 3H), 7.28(d, 2H, J=8.89 Hz), 6.89(d, 2H, J=9.23 Hz), 6.82(d, 2H, J=9.23 Hz), 6.75(d, 2H, J=8.89 Hz), 4.33(s, 2H), 4.19(q, 2H, J=7.18 Hz), 3.76(s, 3H), 3.56(s, 2H), 3.09(br s, 4H), 2.65(br s, 4H), 1.58(s, 6H), 1.20(t, 3H, J=7.18 Hz),

Ethyl {4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400 MHz δ7.99(d, 2H, J=8.20 Hz), 7.66(d, 2H, J=8.20 Hz), 7.35(d, 2H, J=8.89 Hz), 6.88(d, 2H, J=9.40 Hz), 6.83(m, 4H), 4.58(s, 2H), 4.34(s, 2H), 4.24(q, 2H, J=7.18 Hz), 3.76(s, 3H), 3.57(s, 2H), 3.08(m, 4H), 2.63(m, 4H), 1.27(t, 3H, J=7.18 Hz),

Ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400 MHz δ 7.99(d, 2H, J=8.20 Hz), 7.66(d, 2H, J=8.20 Hz), 7.32(d, 2H, J=8.89 Hz), 6.89(d, 2H, J=9.23 Hz), 6.83(d, 2H, J=9.23 Hz), 6.79(d, 2H, J=8.89 Hz), 4.70(q, 1H, J=6.78 Hz), 4.33(s, 2H), 4.16(q, 2H, J=7.09 Hz), 3.75(s, 3H), 3.57(s, 2H), 3.08(m, 4H), 2.63(m, 4H), 1.60(d, 3H, J=6.78 Hz), 1.24(t, 3H, J=7.09 Hz),

Ethyl 2-(4-{[(4-{[4-(4-methoxyphenyl)-1-piperazinyl]methyl}-2-phenyl-1,3-thiazol-5-yl)methyl]sulfanyl}phenoxy)propanoate $^1$H NMR (CDCl$_3$) 400 MHz δ7.87(m, 2H), 7.39(m, 3H), 7.32(d, 2H, J=8.85 Hz), 6.87(d, 2H, J=9.06 Hz), 6.82(d, 2H, J=9.06 Hz), 6.77(d, 2H, J=8.85 Hz), 4.69(q, 1H, J=6.78 Hz), 4.31(s, 2H), 4.18(q, 2H, J=7.12 Hz), 3.75(s, 3H), 3.54(s, 2H), 3.08(m, 4H), 2.62(m, 4H), 1.59(d, 3H, J=6.78 Hz), 1.20(t, 3H, J=7.12 Hz),

Ethyl 2-{4-[({4-{[4-(3-methoxyphenyl)-1-piperazinyl]methyl}-2-[4-(trifluoromethyl)phenyl-1,3-thiazol-5-yl}methyl)sulfanyl]-2-methylphenoxy}-2-methylpropanoate $^1$H NMR (CDCl$_3$) 400 MHz δ 7.96(d, 2H, J=8.28 Hz), 7.63(d, 2H, J=8.28 Hz), 7.21(d, 1H, J=2.41 Hz), 7.13(t, 1H, J=8.10 Hz), 7.07(dd, 1H, J=8.45, 2.41 Hz), 6.53(m, 2H), 6.43(t, 1H, J=2.24 Hz), 6.38(dd, 1H, J=8.10, 2.24 Hz), 4.31(s, 2H), 4.18(q, 2H, J=7.16 Hz), 3.75(s, 3H), 3.55(s, 2H), 3.16(t, 4H, J=4.83 Hz), 2.58(t, 4H, J=4.83 Hz), 2.17(s, 3H), 1.57(s, 6H), 1.22(t, 3H, J=7.16 Hz), Ethyl 2-{4-[({4-{[4-(4-fluorophenyl)-1-piperazinyl]methyl}-2-[4-(trifluoromethyl)phenyl-1,3-thiazol-5-yl}methyl)sulfanyl]-2-methylphenoxy}-2-methylpropanoate $^1$H NMR (CDCl$_3$) 400 MHz δ 7.96(d, 2H, J=8.28 Hz), 7.62(d, 2H, J=8.28 Hz), 7.21(d, 1H, J=2.41 Hz), 7.06(dd, 1H, J=8.45, 2.41 Hz), 6.91(m, 2H), 6.83(m, 2H), 6.53(d, 1H, J=8.45 Hz), 4.30(s, 2H), 4.13(q, 2H, J=7.16 Hz), 3.55(s, 2H), 3.06(t, 4H, J=4.66 Hz), 2.57(t, 4H, J=4.66 Hz), 2.15(s, 3H), 1.55(s, 6H), 1.21(t, 3H, J=7.16 Hz), Ethyl 2-{4-[({4-{[4-(3-methoxyphenyl)-1-piperazinyl]methyl}-2-[4-(trifluoromethyl)phenyl]-1,3-thiazol-5-yl}methyl)sulfanyl]phenoxy}-2-methylpropanoate $^1$H NMR (CDCl$_3$) 400 MHz δ 7.96(d, 2H, J=8.10 Hz), 7.63(d, 2H, J=8.10 Hz), 7.26(d, 2H, J=8.79 Hz), 7.14(t, 1H, J=8.28 Hz), 6.74(d, 2H, J=8.79 Hz), 6.51(dd, 1H, J=8.28, 2.24 Hz), 6.43(t, 1H, J=2.24 Hz), 6.39(dd, 1H, J=8.28, 2.24 Hz), 4.31(s, 2H), 4.16(q, 2H, J=7.07 Hz), 3.74(s, 3H), 3.54(s, 2H), 3.17(t, 4H, J=4.66 Hz), 2.58(t, 4H, J=4.66 Hz), 1.56(s, 6H), 1.20(t, 3H, J=7.07 Hz), Ethyl 2-{4-[({4-{[4-(4-chlorophenyl)-1-piperazinyl]methyl}-2-[4-(trifluoromethyl)phenyl-1,3-thiazol-5-yl}methyl)sulfanyl]phenoxy}-2-methylpropanoate $^1$H NMR (CDCl$_3$) 400 MHz δ 7.96(d, 2H, J=8.10 Hz), 7.63(d, 2H, J=8.10 Hz), 7.27(d, 2H, J=8.79 Hz), 7.15(d, 2H, J=9.14 Hz), 6.80(d, 2H, J=9.14 Hz), 6.73(d, 2H, J=8.79 Hz), 4.30(s, 2H), 4.17(q, 2H, J=7.16 Hz), 3.54(s, 2H), 3.12(t, 4H, J=4.74 Hz), 2.57(m, 4H), 1.55(s, 6H), 1.17(t, 3H, J=7.16 Hz), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]phenoxy}-2-methylpropanoate $^1$H NMR (CDCl$_3$) 400 MHz δ 7.95(d, 2H, J=8.28 Hz), 7.83(d, 2H, J=9.14 Hz), 7.62(d, 2H, J=8.28 Hz), 7.26(d, 2H, J=8.62 Hz), 6.82(d, 2H, J=9.14 Hz), 6.73(d, 2H, J=8.62 Hz), 4.29(s, 2H), 4.17(q, 2H, J=7.07 Hz), 3.53(s, 2H), 3.32(t, 4H, J=4.66 Hz), 2.57(br s, 4H), 2.48(s, 3H), 1.55(s, 6H), 1.17(t, 3H, J=7.07 Hz), Ethyl 2-{4-[({4-{[4-(4-methoxyphenyl)-1-piperazinyl]methyl}-2-[4-(trifluoromethyl)phenyl-1,3-thiazol-5-yl}methyl)sulfanyl]phenoxy}-2-methylpropanoate $^1$H NMR (CDCl$_3$) 400 MHz δ 7.96(d, 2H, J=8.28 Hz), 7.63(d, 2H, J=8.28 Hz), 7.26(d, 2H, J=8.79 Hz), 6.87(d, 2H, J=9.14 Hz), 6.81(d, 2H, J=9.14 Hz), 6.73(d, 2H, J=8.79 Hz), 4.32(s, 2H), 4.17(q, 2H, J=7.16 Hz), 3.73(s, 3H), 3.54(s, 2H), 3.06(t, 4H, J=4.83 Hz), 2.60(br s, 4H), 1.55(s, 6H), 1.20(t, 3H, J=7.16 Hz), Ethyl 2-(4-{[(2-(4-fluorophenyl)-4-{[4-(4-methoxyphenyl)-1-piperazinyl]methyl}-1,3-thiazol-5-yl)methyl]sulfanyl}-2-methylphenoxy)-2-methylpropanoate $^1$H NMR (CDCl$_3$) 400 MHz δ 7.84(m, 2H), 7.20(d, 1H, J=2.20 Hz), 7.07(m, 3H), 6.87(d, 2H, J=9.16 Hz), 6.81(d, 2H, J=9.16 Hz), 6.54(d, 1H, J=8.42 Hz), 4.29(s, 2H), 4.19(q, 2H, J=7.14 Hz), 3.75(s, 3H), 3.54(s, 2H), 3.07(t, 4H, J=4.76 Hz), 2.61(br s, 4H), 2.15(s, 3H), 1.54(s, 6H), 1.21(t, 3H, J=7.14 Hz), Ethyl 2-[4-({[4-{[4-(4-acetylphenyl)-1-piperazinyl]methyl}-2-(4-fluorophenyl)-1,3-thiazol-5-yl]methyl}sulfanyl)-2-methylphenoxy]-2-methylpropanoate $^1$H NMR (CDCl$_3$) 400 MHz δ 7.84(m, 4H), 7.20(d, 1H, J=2.38 Hz), 7.07(m, 3H), 6.83(d, 2H, J=9.16 Hz), 6.53(d, 1H, J=8.42 Hz), 4.28(s, 2H), 4.18(q, 2H, J=7.14 Hz), 3.53(s, 2H), 3.33(t, 4H, J=4.58 Hz), 2.58(br s, 4H), 2.48(s, 3H), 2.16(s, 3H), 1.58(s, 6H), 1.23(t, 3H, J=7.14 Hz), Ethyl 2-(4-{[(2-(4-fluorophenyl)-4-{[4-(3-methoxyphenyl)-1-piperazinyl]methyl}-1,3-thiazol-5-yl)methyl]sulfanyl}-2-methylphenoxy)-2-methylpropanoate $^1$H NMR (CDCl$_3$) 400 MHz δ 7.85(m, 2H), 7.20(d, 1H, J=2.38), 7.14(t, 1H, J=8.24 Hz), 7.07(m, 3H), 6.53(m, 2H), 6.44(t, 1H, J=2.29 Hz), 6.39(dd, 1H, J=8.06, 2.38 Hz), 4.29(s, 2H), 4.19(q, 2H, J=7.14 Hz), 3.76(s, 3H), 3.53(s, 2H), 3.17(t, 4H, J=4.67 Hz), 2.59(br s, 4H), 2.16(s, 3H), 1.55(s, 6H), 1.21(t, 3H, J=7.14 Hz), Ethyl 4-{[5-({[4-(2-ethoxy-1,1-dimethyl-2-oxoethoxy)-3-methylphenyl]sulfanyl}methyl)-2-(4-fluorophenyl)-1,3-thiazol-4-yl]methyl}-1-piperazinecarboxylate $^1$H NMR (CDCl$_3$) 400 MHz δ 7.82(m, 2H), 7.18(d, 1H, J=2.38 Hz), 7.06(m, 3H), 6.53(d, 1H, J=8.61 Hz), 4.25(s, 2H), 4.19(q, 2H, J=7.14 Hz), 4.10(q, 2H, J=7.08 Hz), 3.45(m, 6H), 2.40(br s, 4H), 2.16(s, 3H), 1.55(s, 6H), 1.21(m, 6H), Ethyl 2-{4-[({4-{[4-(4-methoxyphenyl)-1-piperazinyl]methyl}-2-[4-(trifluoromethyl)phenyl-1,3-thiazol-5-yl}methyl)sulfanyl]-2-methylphenoxy}-2-methylpropanoate $^1$H NMR (CDCl$_3$) 400 MHz δ 7.96(d, 2H, J=8.28 Hz), 7.63(d, 2H, J=8.28 Hz), 7.21(d, 1H, J=2.24 Hz), 7.07(dd, 1H, J=8.45, 2.24 Hz), 6.86(d, 2H, J=9.14 Hz), 6.80(d, 2H, J=9.14 Hz), 6.53(d, 1H, J=8.45 Hz), 4.31(s, 2H), 4.17(q, 2H, J=7.16 Hz), 3.72(s, 3H), 3.55(s, 2H), 3.05(t, 4H, J=4.66 Hz), 2.59(t, 4H, J=4.66 Hz), 2.16(s, 3H), 1.55(s, 6H), 1.20(t, 3H, J=7.16 Hz), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}-2-methylpropanoate $^1$H NMR (CDCl$_3$) 400 MHz δ 7.95(d, 2H, J=8.10 Hz), 7.82(d, 2H, J=8.97 Hz), 7.62(d, 2H, J=8.10 Hz), 7.19(d, 1H, J=2.41 Hz), 7.06(dd, 1H, J=8.45, 2.41 Hz), 6.82(d, 2H, J=8.97 Hz), 6.52(d, 1H, J=8.45 Hz), 4.27(s, 2H), 4.16(q, 2H, J=7.07 Hz), 3.53(s, 2H), 3.29(t, 4H, J=4.66 Hz), 2.54(t, 4H, J=4.66 Hz), 2.47(s, 3H), 2.14(s, 3H), 1.55(s, 6H), 1.18(t, 3H, J=7.07 Hz), Ethyl 2-{4-[({4-[(4-acetyl-1-piperazinyl)methyl]-2-[4-(trifluoromethyl)phenyl]-1,3-thiazol-5-yl}methyl)sulfanyl]-2-methylphenoxy}propanoate ¹H NMR (CDCl₃) 300 MHz δ 8.00(d, 2H, J=8.23 Hz), 7.68(d, 2H, J=8.23 Hz), 7.27(d, 1H, J=2.39 Hz), 7.14(dd, 1H, J=8.23, 2.39 Hz), 6.59(d, 1H, J=8.23 Hz), 4.73(q, 1H, J=6.72 Hz), 4.30(s, 2H), 4.20(q, 2H, J=7.17 Hz), 3.65(t, 2H, J=4.65 Hz), 3.54(s, 2H), 3.45(t, 2H, J=4.65 Hz), 2.48(t, 4H, J=4.65 Hz), 2.26(s, 3H), 2.09(s, 3H), 1.65(d, 3H, J=6.72 Hz), 1.25(dd, 3H, J=7.17 Hz), 2-Methyl-2-{4-[({4-{[4-(phenoxycarbonyl)-1-piperazinyl]methyl}-2-]4-(trifluoromethyl)phenyl]-1,3-thiazol-5-yl}methyl)sulfanyl]phenoxy}propanoic acid ¹H NMR (CDCl₃) 400 MHz δ 7.95(d, 2H, J=8.28 Hz), 7.65(d, 2H, J=8.28 Hz), 7.33(m, 2H), 7.26(d, 2H, J=8.79 Hz), 7.17(t, 1H, J=7.59 Hz), 7.06(d, 2H, J=7.59 Hz), 6.74(d, 2H, J=8.79 Hz), 4.32(s, 2H), 4.18(q, 2H, J=7.07 Hz), 3.61(m, 6H), 2.51(br s, 4H), 1.57(s, 6H), 1.20(t, 3H, J=7.07 Hz), tert-Butyl 4-({5-({[4-(2-ethoxy-1,1-dimethyl-2-oxoethoxy)phenyl]sulfanyl}methyl)-2-[4-(trifluoromethyl)phenyl]-1,3-thiazol-4-yl}methyl)-1-piperazinecarboxylate ¹H NMR (CDCl₃) 400 MHz δ 7.94(d, 2H, J=8.28 Hz), 7.63(d, 2H, J=8.28 Hz), 7.24(d, 2H, J=8.79 Hz), 6.72(d, 2H, J=8.79 Hz), 4.29(s, 2H), 4.18(q, 2H, J=7.07 Hz), 3.44(m, 6H), 2.43(br s, 4H), 1.56(s, 6H), 1.42(s, 9H), 1.19(t, 3H, J=7.07 Hz), Ethyl 2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 400 MHz δ 8.12(s, 1H), 8.04(s, 1H), 7.94(d, 2H, J=8.28 Hz), 7.83(s, 1H), 7.65(d, 2H, J=8.28 Hz), 7.26(d, 2H, J=8.79 Hz), 6.73(d, 2H, J=8.79 Hz), 4.32(s, 2H), 4.17(q, 2H, J=7.07 Hz), 3.62(m, 6H), 2.64(br s, 4H), 1.56(s, 6H), 1.18(t, 3H, J=7.07 Hz), Ethyl 2-{4-[({4-{[4-(2-methoxyphenyl)-1-piperazinyl]methyl}-2-[4-(trifluoromethyl)phenyl-1,3-thiazol-5-yl}methyl)sulfanyl]phenoxy}-2-methylpropanoate ¹H NMR (CDCl₃) 400 MHz δ 7.96(d, 2H, J=8.28 Hz), 7.64(d, 2H, J=8.28 Hz), 7.27(d, 2H, J=8.97 Hz), 6.98(m, 1H), 6.90(m, 2H), 6.83(m, 1H), 6.73(d, 2H, J=8.97 Hz), 4.35(s, 2H), 4.17(q, 2H, J=7.07 Hz), 3.83(s, 3H), 3.60(s, 2H), 3.11(br s, 4H), 2.72(br s, 4H), 1.58(s, 6H), 1.18(t, 3H, J=7.07 Hz), tert-Butyl 4-({5-({[4-(2-methoxy-2-oxoethoxy)-3-methylphenyl]sulfanyl}methyl)-2-[4-(trifluoromethyl)phenyl]-1,3-thiazol-4-yl}methyl)-1-piperazinecarboxylate ¹H NMR (CDCl₃) 400 MHz δ 7.90(d, 2H, J=8.28 Hz), 7.58(d, 2H, J=8.28 Hz), 7.16(d, 1H, J=2.24 Hz), 7.08(dd, 1H, J=8.45, 2.24 Hz), 6.52(d, 1H, J=8.45 Hz), 4.56(s, 2H), 4.20(s, 2H), 3.70(s, 3H), 3.44(s, 2H), 3.36(t, 4H, J=4.48 Hz), 2.32(br s, 4H), 2.17(s, 3H), 1.38(s, 9H), Ethyl 2-{2-methyl-4-[({4-{[4-(4-pyridinyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 300 MHz δ 8.28(d, 2H, J=6.37 Hz), 8.02(d, 2H, J=8.23 Hz), 7.69(d, 2H, J=8.23 Hz), 7.28(d, 1H, J=2.39 Hz), 7.16(dd, 1H, J=8.49, 2.39 Hz), 6.68(d, 2H, J=6.37 Hz), 6.60(d, 1H, J=8.49 Hz), 4.73(q, 1H, J=6.72 Hz), 4.32(s, 2H), 4.20(q, 2H, J=7.08 Hz), 3.59(s, 2H), 3.34(t, 4H, J=5.04 Hz), 2.58(t, 4H, J=5.04 Hz), 2.26(s, 3H), 1.65(d, 3H, J=6.72 Hz), 1.25(t, 3H, J=7.08 Hz), Ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 400 MHz 67.99(d, 2H, J=8.20 Hz), 7.66(d, 2H, J=8.20 Hz), 7.23(d, 1H, J=2.39 Hz), 7.13(dd, 1H, J=8.37, 2.39 Hz), 6.89(d, 2H, J=9.23 Hz), 6.83(d, 2H, J=9.23 Hz), 6.57(d, 1H, J=8.37 Hz), 4.70(q, 1H, J=6.84 Hz), 4.34(s, 2H), 4.17(q, 2H, J=7.18 Hz), 3.76(s, 3H), 3.58(s, 2H), 3.09(m, 4H), 2.63(m, 4H), 2.24(s, 3H), 1.62(d, 3H, J=6.84 Hz), 1.21(t, 3H, J=7.18 Hz), TLC(30% EtOAc/Hexanes)=0.29

Ethyl 2-{4-[({4-{[4-(2,4-difluorophenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300 MHz δ 8.03(d, 2H, J=8.28 Hz), 7.69(d, 2H, J=8.28 Hz), 7.27(d, 1H, J=2.21 Hz), 7.17(dd, 1H, J=8.28, 2.21 Hz), 6.86(m, 3H), 6.61(d, 1H, J=8.28 Hz), 4.73(q, 1H, J=6.71 Hz), 4.36(s, 2H), 4.21(q, 2H, J=7.17 Hz), 3.62(s, 2H), 3.06(t, 4H, J=4.55 Hz), 2.67(t, 4H, J=4.55 Hz), 2.27(s, 3H), 1.65(d, 3H, J=6.71 Hz), 1.26(t, 3H, J=7.17 Hz), Ethyl 2-{2-methyl-4-[({4-({4-[4-(trifluoromethoxy)phenyl-1-piperazinyl}methyl)-2-[4-(trifluoromethyl)phenyl]-1,3-thiazol-5-yl}methyl)sulfanyl]phenoxy}propanoate ¹H NMR (CD₃OD) 400 MHz δ 7.97(d, 2H, J=8.24 Hz), 7.63(d, 2H, J=8.24 Hz), 7.19(s, 1H), 7.10(dd, 1H, J=8.42, 2.20 Hz), 7.03(d, 2H, J=9.16 Hz), 6.85(d, 2H, J=9.16 Hz), 6.57(d, 1H, J=8.42 Hz), 4.73(q, 1H, J=6.78 Hz), 4.27(s, 2H), 4.07(m, 2H), 3.41(s, 2H), 3.03(br s, 4H), 2.48(br s, 4H), 2.13(s, 3H), 1.51(d, 3H, J=6.78 Hz), 1.11(t, 3H, J=7.14 Hz), Ethyl 2-{4-[({4-{[4-(4-ethoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CD₃OD) 400 MHz δ 8.01(d, 2H, J=8.28 Hz), 7.70(d, 2H, J=8.28 Hz), 7.21(d, 1H, J=2.24 Hz), 7.11(dd, 1H, J=8.45, 2.24 Hz), 6.86(d, 2H, J=9.14 Hz), 6.76(d, 2H, J=9.14 Hz), 6.61(d, 1H, J=8.45 Hz), 4.77(q, 1H, J=6.72 Hz), 4.29(s, 2H), 4.10(q, 2H, J=7.16 Hz), 3.91(q, 2H, J=6.98 Hz), 3.40(s, 2H), 2.96(t, 4H, J=4.83 Hz), 2.50(t, 4H, J=4.83 Hz), 2.14(s, 3H), 1.52(d, 3H, J=6.72 Hz), 1.30(t, 3H, J=6.98 Hz), 1.14(t, 3H, J=7.16 Hz),

Ethyl 2-{2-methyl-4-[({4-{[4-(4-propoxyphenyl)-1-piperazinyl]methyl}-2-]4-(trifluoromethyl)phenyl]-1,3-thiazol-5-yl}methyl)sulfanyl]phenoxy}propanoate ¹H NMR (CD₃OD) 400 MHz δ 7.96(d, 2H, J=8.10 Hz), 7.63(d, 2H, J=8.10 Hz), 7.18(s, 1H), 7.09(d, 1H, J=8.45 Hz), 6.81(d, 2H, J=8.97 Hz), 6.73(d, 2H, J=8.97 Hz), 6.56(d, 1H, J=8.45 Hz), 4.71(q, 1H, J=6.47 Hz), 4.25(s, 2H), 4.06(q, 2H, J=7.07 Hz), 3.76(t, 2H, J=7.41 Hz), 3.39(s, 2H), 2.92(br s, 4H), 2.48(br s, 4H), 2.12(s, 3H), 1.67(m, 2H), 1.49(d, 3H, J=6.47 Hz), 1.11(t, 3H, J=7.07 Hz), 0.94(t, 3H, J=7.41 Hz),

Ethyl 2-{4-[({4-{[4-(4-isopropoxyphenyl)-1-piperazinyl]methyl}-2-[4-(trifluoromethyl)phenyl-1,3-thiazol-5-yl}methyl)sulfanyl]-2-methylphenoxy}propanoate ¹H NMR (CD₃OD) 400 MHz δ 7.96(d, 2H, J=8.28 Hz), 7.64(d, 2H, J=8.28 Hz), 7.18(d, 1H, J=2.24 Hz), 7.09(dd, 1H, J=8.45, 2.24 Hz), 6.81(d, 2H, J=9.14 Hz), 6.73(d, 2H, J=9.14 Hz), 6.57(d, 1H, J=8.45 Hz), 4.71(q, 1H, J=6.78 Hz), 4.36(m, 1H), 4.24(s, 2H), 4.06(q, 2H, J=7.16 Hz), 3.39(s, 2H), 2.92(t, 4H, J=4.57 Hz), 2.47(t, 4H, J=4.57 Hz), 2.11(s, 3H), 1.48(d, 3H, J=6.78 Hz), 1.19(d, 6H, J=6.21 Hz), 1.11(t, 3H, J=7.16 Hz),

Ethyl 4-({5-({[4-(2-ethoxy-1,1-dimethyl-2-oxoethoxy)phenyl]sulfanyl}methyl)-2-[4-(trifluoromethyl)phenyl]-1,3-thiazol-4-yl}methyl)-1-piperazinecarboxylate ¹H NMR (CDCl₃) 400 MHz δ 7.94(d, 2H, J=8.28 Hz), 7.63(d, 2H, J=8.28 Hz), 7.24(m, 2H), 6.72(d, 2H, J=8.79 Hz), 4.30(s, 2H), 4.18(q, 2H, J=7.07 Hz), 4.10(q, 2H, J=7.13 Hz), 3.49(m, 6H), 2.46(br s, 4H), 1.58(s, 6H), 1.21(m, 6H),

Ethyl 4-({5-({[4-(2-methoxy-2-oxoethoxy)-3-methylphenyl]sulfanyl}methyl)-2-[4-(trifluoromethyl)phenyl]-1,3-thiazol-4-yl}methyl)-1-piperazinecarboxylate ¹H NMR (CDCl₃) 400 MHz δ 7.95(d, 2H, J=8.10 Hz), 7.64(d, 2H, J=8.10 Hz), 7.20(d, 1H, J=2.21 Hz), 7.13(dd, 1H, J=8.45, 2.21 Hz), 6.57(d, 1H, J=8.45 Hz), 4.62(s, 2H), 4.30(s, 2H), 4.10(q, 2H, J=7.16 Hz), 3.77(s, 3H), 3.49(m, 6H), 2.45(br s, 4H), 2.21(s, 3H), 1.23(t, 3H, J=7.16 Hz),

Methyl {4-[({4-{[4-(3-methoxyphenyl)-1-piperazinyl]methyl}-2-[4-(trifluoromethyl)phenyl-1,3-thiazol-5-yl}methyl)sulfanyl]-2-methylphenoxy}acetate ¹H NMR (CDCl₃) 400 MHz δ 7.97(d, 2H, J=8.28 Hz), 7.64(d, 2H, J=8.28 Hz), 7.21(d, 1H, J=2.24 Hz), 7.14(m, 2H), 6.57(d, 1H, J=8.45 Hz), 6.49(dd, 1H, J=8.10, 2.20 Hz), 6.40(s, 2H), 4.60(s, 2H), 4.33(s, 2H), 3.76(s, 6H), 3.59(s, 2H), 3.21(br s, 4H), 2.68(br s, 4H), 2.21(s, 3H),

Methyl {4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}acetate ¹H NMR (CDCl₃) 400 MHz δ 7.93(d, 2H, J=8.28 Hz), 7.82(d, 2H, J=8.97 Hz), 7.61(d, 2H, J=8.28 Hz), 7.20(d, 1H, J=2.24 Hz), 7.13(dd, 1H, J=8.45, 2.24 Hz), 6.80(d, 2H, J=8.97 Hz), 6.55(d, 1H, J=8.45 Hz), 4.57(s, 2H), 4.27(s, 2H), 3.73(s, 3H), 3.52(s, 2H), 3.27(t, 4H, J=4.83 Hz), 2.54(t, 4H, J=4.83 Hz), 2.45(s, 3H), 2.20(s, 3H),

Methyl {4-[({4-{[4-(2-methoxyphenyl)-1-piperazinyl]methyl}-2-[4-(trifluoromethyl)phenyl-1,3-thiazol-5-yl}methyl)sulfanyl]-2-methylphenoxy}acetate ¹H NMR (CDCl₃) 400 MHz δ 7.97(d, 2H, J=8.10 Hz), 7.65(d, 2H, J=8.10 Hz), 7.21 (m, 1H), 7.15(dd, 1H, J=8.45, 2.07 Hz), 6.98(br s, 1H), 6.89(m, 2H), 6.83(d, 1H, J=7.41 Hz), 6.57(d, 1H, J=8.45 Hz), 4.61(s, 2H), 4.35(s, 2H), 3.83(s, 3H), 3.75(s, 3H), 3.61(s, 2H), 3.11(br s, 4H), 2.70(br s, 4H), 2.22(s, 3H),

Methyl {2-methyl-4-[({4-{[4-(2-pyrazinyl)-1-piperazinyl]methyl}-2-[4-(trifluoromethyl)phenyl-1,3-thiazol-5-yl}methyl)sulfanyl]phenoxy}acetate ¹H NMR (CDCl₃) 400 MHz δ 8.07(s, 1H), 7.99(m, 1H), 7.94(d, 2H, J=8.10 Hz), 7.77(d, 1H, J=2.59 Hz), 7.60(d, 2H, J=8.10 Hz), 7.20(d, 1H, J=2.24 Hz), 7.12(dd, 1H, J=8.45, 2.24 Hz), 6.54(d, 1H, J=8.45 Hz), 4.58(s, 2H), 4.26(s, 2H), 3.73(s, 3H), 3.52(m, 6H), 2.52(t, 4H, J=4.83 Hz), 2.19(s, 3H),

Ethyl (4-[{(4-{[4-(4-methoxyphenyl)-1-piperazinyl]methyl}-2-phenyl-1,3-thiazol-5-yl)methyl]sulfanyl}-2-methylphenoxy)acetate ¹H NMR (CDCl₃) 400 MHz 67.88(m, 2H), 7.40(m, 3H), 7.25(d, 1H, J=2.39 Hz), 7.17(dd, 1H, J=8.37, 2.39 Hz), 6.89(d, 2H, J=9.06 Hz), 6.81(d, 2H, J=9.06 Hz), 6.58(d, 1H, J=8.37 Hz), 4.59(s, 2H), 4.32(s, 2H), 4.23(q, 2H, J=7.12 Hz), 3.74(s, 3H), 3.56(s, 2H), 3.06(m, 4H), 2.62(m, 4H), 2.24(s, 3H), 1.27(t, 3H, J=7.12 Hz),

Ethyl 2-(4-{[(4-{[4-(4-methoxyphenyl)-1-piperazinyl]methyl}-2-phenyl-1,3-thiazol-5-yl)methyl]sulfanyl}-2-methylphenoxy)propanoate ¹H NMR (CDCl₃) 400 MHz δ 7.88(m, 2H), 7.40(m, 3H), 7.25(d, 1H, J=2.39 Hz), 7.14(dd, 1H, J=8.37, 2.39 Hz), 6.89(d, 2H, J=9.40 Hz), 6.82(d, 2H, J=9.40 Hz), 6.57(d, 1H, J=8.37 Hz), 4.70(q, 1H, J=6.84 Hz), 4.32(s, 2H), 4.17(q, 2H, J=7.18 Hz), 3.76(s, 3H), 3.56(s, 2H), 3.08(m, 4H), 2.63(m, 4H), 2.23(m, 3H), 1.61(d, 3H, J=6.84 Hz), 1.25(t, 3H, J=7.18 Hz),

Ethyl 2-(4-{[(4-{[4-(4-methoxyphenyl)-1-piperazinyl]methyl}-2-phenyl-1,3-thiazol-5-yl)methyl]sulfanyl}phenoxy)-2-methylpropanoate ¹H NMR (CDCl₃) 400 MHz δ 7.87(m, 2H), 7.40(m, 3H), 7.28(d, 2H, J=8.89 Hz), 6.89(d, 2H, J=9.23 Hz), 6.82(d, 2H, J=9.23 Hz), 6.75(d, 2H, J=8.89 Hz), 4.33(s, 2H), 4.19(q, 2H, J=7.18 Hz), 3.76(s, 3H), 3.56(s, 2H), 3.09(br s, 4H), 2.65(br s, 4H), 1.58(s, 6H), 1.20(t, 3H, J=7.18 Hz),

Ethyl 2-{4-[({4-{[4-(2-methoxyphenyl)-1-piperazinyl]methyl}-2-[4-(trifluoromethyl)phenyl-1,3-thiazol-5-yl}methyl)sulfanyl]-2-methylphenoxy}propanoate ¹H NMR (CDCl₃) 300 MHz δ 8.03(d, 2H, J=8.28 Hz), 7.69(d, 2H, J=8.28 Hz), 7.28(d, 1H, J=2.21 Hz), 7.17(dd, 1H, J=8.28, 2.21 Hz), 7.00(m, 3H), 6.88(d, 1H, J=7.73 Hz), 6.61(d, 1H, J=8.28 Hz), 4.74(q, 1H, J=6.81 Hz), 4.39(s, 2H), 4.21(q, 2H, J=7.17 Hz), 3.89(s, 3H), 3.63(s, 2H), 3.12(br s, 4H), 2.72(br s, 4H), 2.27(s, 3H), 1.65(d, 3H, J=6.81 Hz), 1.26(t, 3H, J=7.17 Hz), Ethyl 2-[2-methyl-4-({[2-[4-(trifluoromethyl)phenyl]-4-({4-[3-(trifluoromethyl)phenyl]-1-piperazinyl}methyl)-1,3-thiazol-5-yl]methyl}sulfanyl)phenoxy]propanoate $^1$H NMR (CDCl$_3$) 300 MHz δ 8.03(d, 2H, J=8.28 Hz), 7.70(d, 2H, J=8.28 Hz), 7.36(t, 1H, J=8.00 Hz), 7.29(d, 1H, J=2.21 Hz), 7.13(m, 4H), 6.61(d, 1H, J=8.28 Hz), 4.74(q, 1H, J=6.90 Hz), 4.36(s, 2H), 4.18(q, 2H, J=7.08 Hz), 3.62(s, 2H), 3.26(t, 4H, J=4.83 Hz), 2.65(t, 4H, J=4.83 Hz), 2.26(s, 3H), 1.65(d, 3H, J=6.90 Hz), 1.27(t, 3H, J=7.08 Hz), Ethyl 2-{2-methyl-4-[({4-({4-]2-oxo-2-(1-pyrrolidinyl)ethyl]-1-piperazinyl}methyl)-2-]4-(trifluoromethyl)phenyl]-1,3-thiazol-5-yl}methyl)sulfanyl]phenoxy}propanoate $^1$H NMR (CDCl$_3$) 300 MHz δ 7.96(d, 2H, J=8.28 Hz), 7.63(d, 2H, J=8.28 Hz), 7.20(d, 1H, J=2.21 Hz), 7.10(dd, 1H, J=8.28, 2.21 Hz), 6.56(d, 1H, J=8.28 Hz), 4.69(q, 1H, J=6.71 Hz), 4.30(s, 2H), 4.16(q, 2H, J=7.08 Hz), 3.47(m, 8H), 3.10(s, 2H), 2.54(m, 6H), 2.20(s, 3H), 1.85(m, 4H), 1.60(d, 3H, J=6.71 Hz), 1.20(t, 3H, J=7.08 Hz), Ethyl 2-{2-methyl-4-[({4-{[4-(2-pyrimidinyl)-1-piperazinyl]methyl}-2-]4-(trifluoromethyl)phenyl]-1,3-thiazol-5-yl}methyl)sulfanyl]phenoxy}propanoate $^1$H NMR (CDCl$_3$) 300 MHz δ 8.31(d, 2H, J=4.69 Hz), 8.01(d, 2H, J=8.28 Hz), 7.68(d, 2H, J=8.28 Hz), 7.27(d, 1H, J=2.21 Hz), 7.16(dd, 1H, J=8.28, 2.21 Hz), 6.60(d, 1H, J=8.28 Hz), 6.48(t, 1H, J=4.69 Hz), 4.74(q, 1H, J=6.71 Hz), 4.35(s, 2H), 4.20(q, 2H, J=7.08 Hz), 3.85(t, 4H, J=4.97 Hz), 3.57(s, 2H), 2.54(t, 4H, J=4.97 Hz), 2.24(s, 3H), 1.64(d, 3H, J=6.71 Hz), 1.24(t, 3H, J=7.08 Hz), Ethyl 2-{2-methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300 MHz δ 8.14(m, 1H), 8.06(m, 1H), 8.01(d, 2H, J=8.28 Hz), 7.85(d, 1H, J=2.48 Hz), 7.67(d, 2H, J=8.28 Hz), 7.27(d, 1H, J=2.21 Hz), 7.15(dd, 1H, J=8.28, 2.21 Hz), 6.59(d, 1H, J=8.28 Hz), 4.73(q, 1H, J=6.71 Hz), 4.33(s, 2H), 4.16(q, 2H, J=7.17 Hz), 3.60(m, 6H), 2.58(t, 4H, J=4.83 Hz), 2.25(s, 3H), 1.64(d, 3H, J=6.71 Hz), 1.25(t, 3H, J=7.17 Hz), Ethyl 2-{2-methyl-4-({[2-[4-(trifluoromethyl)phenyl]-4-({4-[4-(trifluoromethyl)phenyl]-1-piperazinyl}methyl)-1,3-thiazol-5-yl]methyl}sulfanyl)phenoxy]propanoate $^1$H NMR (CDCl$_3$) 300 MHz δ 8.03(d, 2H, J=8.28 Hz), 7.70(d, 2H, J=8.28 Hz), 7.51(d, 2H, J=8.55 Hz), 7.28(d, 1H, J=2.21 Hz), 7.18(dd, 1H, J=8.28, 2.21 Hz), 6.94(d, 2H, J=8.55 Hz), 6.61(d, 1H, J=8.28 Hz), 4.74(q, 1H, J=6.71 Hz), 4.35(s, 2H), 4.21(q, 2H, J=7.17 Hz), 3.62(s, 2H), 3.33(t, 4H, J=4.55 Hz), 2.66(t, 4H, J=4.55 Hz), 2.27(s, 3H), 1.66(d, 3H, J=6.71 Hz), 1.26(t, 3H, J=7.17 Hz), Ethyl 2-{4-[({4-[(4-acetyl-1-piperazinyl)methyl]-2-[4-(trifluoromethyl)phenyl]-1,3-thiazol-5-yl}methyl)sulfanyl]-2-isopropylphenoxy}propanoate $^1$H NMR (CDCl$_3$) 400 MHz δ 7.94(d, 2H, J=8.10 Hz), 7.64(d, 2H, J=8.10 Hz), 7.17(d, 1H, J=2.24 Hz), 7.11(dd, 1H, J=8.45, 2.24 Hz), 6.54(d, 1H, J=8.45 Hz), 4.72(q, 1H, J=6.78 Hz), 4.23(s, 2H), 4.14(q, 2H, J=7.13 Hz), 3.59(s, 2H), 3.42(br s, 4H), 3.30(m, 1H), 2.42(br s, 4H), 2.04(s, 3H), 1.59(d, 3H, J=6.78 Hz), 1.17(m, 9H), Ethyl 2-{4-[({4-{[4-(4-fluorophenyl)-1-piperazinyl]methyl}-2-[4-(trifluoromethyl)phenyl]-1,3-thiazol-5-yl}methyl)sulfanyl]-2-isopropylphenoxy}propanoate $^1$H NMR (CDCl$_3$) 400 MHz δ 7.97(d, 2H, J=8.28 Hz), 7.64(d, 2H, J=8.28 Hz), 7.20(d, 1H, J=2.24 Hz), 7.13(dd, 1H, J=8.45, 2.24 Hz), 6.92(m, 2H), 6.83(m, 2H), 6.55(d, 1H, J=8.45 Hz), 4.71(q, 1H, J=6.78 Hz), 4.28(s, 2H), 4.14(q, 2H, J=7.18 Hz), 3.48(s, 2H), 3.31(m, 1H), 3.07(t, 4H, J=4.83 Hz), 2.59(br s, 4H), 1.59(d, 3H, J=6.78 Hz), 1.15(m, 9H), Ethyl 2-{2-isopropyl-4-[({4-(4-morpholinylmethyl)-2-[4-(trifluoromethyl)phenyl]-1,3-thiazol-5-yl}methyl)sulfanyl]phenoxy}propanoate $^1$H NMR (CDCl$_3$) 400 MHz δ 7.95(d, 2H, J=8.28 Hz), 7.63(d, 2H, J=8.28 Hz), 7.19(d, 1H, J=2.24 Hz), 7.12(dd, 1H, J=8.45, 2.24 Hz), 6.55(d, 1H, J=8.45 Hz), 4.71(q, 1H, J=6.78 Hz), 4.26(s, 2H), 4.14(q, 2H, J=7.13 Hz), 3.67(m, 4H), 3.41(s, 2H), 3.30(m, 1H), 2.42(br s, 4H), 1.59(d, 3H, J=6.78 Hz), 1.16(m, 9H), Ethyl 2-{2-methyl-4-[({4-(1-piperazinylmethyl)-2-[4-(trifluoromethyl)phenyl]-1,3-thiazol-5-yl}methyl)sulfanyl]phenoxy}propanoate $^1$H NMR (CDCl$_3$) 300 MHz δ 8.01(d, 2H, J=8.23 Hz), 7.67(d, 2H, J=8.23 Hz), 7.27(d, 1H, J=2.39 Hz), 7.15(dd, 1H, J=8.23, 2.39 Hz), 6.59(d, 1H, J=8.23 Hz), 4.73(q, 1H, J=6.64 Hz), 4.34(s, 2H), 4.20(q, 2H, J=7.08 Hz), 3.52(s, 2H), 2.91(t, 4H, J=4.91 Hz), 2.46(m, 4H), 2.33(br s, 1H), 2.26(s, 3H), 1.64(d, 3H, J=6.64 Hz), 1.25(t, 3H, J=7.08 Hz), tert-Butyl 4-({5-({[4-(2-ethoxy-1-methyl-2-oxoethoxy)-3-methylphenyl]sulfanyl}methyl)-2-]4-(trifluoromethyl)phenyl]-1,3-thiazol-4-yl}methyl)-1-piperazinecarboxylate $^1$H NMR (CDCl$_3$) 300 MHz δ 8.01(d, 2H, J=8.23 Hz), 7.68(d, 2H, J=8.23 Hz), 7.27(d, 1H, J=2.39 Hz), 7.15(dd, 1H, J=8.49, 2.39 Hz), 6.60(d, 1H, J=8.49 Hz), 4.74(q, 1H, J=6.72 Hz), 4.33(s, 2H), 4.22(q, 2H, J=7.08 Hz), 3.54(s, 2H), 3.46(m, 4H), 2.44(m, 4H), 2.27(s, 3H), 1.65(d, 3H, J=6.72 Hz), 1.48(s, 9H), 1.26(t, 3H, J=7.08 Hz), Ethyl 2-{4-[({4-{[4-(4-chlorophenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.03(d, 2H, J=8.23 Hz), 7.70(d, 2H, J=8.23 Hz), 7.22(m, 4H), 6.86(d, 2H, J=9.03 Hz), 6.61(d, 1H, J=8.49 Hz), 4.73(q, 1H, J=6.81 Hz), 4.36(s, 2H), 4.18(q, 2H, J=7.08 Hz), 3.61(s, 2H), 3.17(m, 4H), 2.64(m, 4H), 2.27(s, 3H), 1.65(d, 3H, J=6.84 Hz), 1.27(t, 3H, J=7.08 Hz), Ethyl 2-{4-[({4-[(3,5-dimethyl-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.01(d, 2H, J=8.23 Hz), 7.68(d, 2H, J=8.23 Hz), 7.27(d, 1H, J=2.39 Hz), 7.15(dd, 1H, J=8.49, 2.39 Hz), 6.60(d, 1H, J=8.49 Hz), 4.74(q, 1H, J=6.72 Hz), 4.35(s, 2H), 4.21(q, 2H, J=7.08 Hz), 3.53(s, 2H), 2.96(m, 2H), 2.78(m, 2H), 2.26(s, 3H), 1.73(m, 2H), 1.65(d, 3H, J=6.72 Hz), 1.26(t, 3H, J=7.08 Hz), 1.09(d, 6H, J=6.37 Hz), Ethyl 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.03(d, 2H, J=8.49 Hz), 7.70(d, 2H, J=8.49 Hz), 7.28(d, 1H, J=2.39 Hz), 7.18(dd, 1H, J=8.23, 2.39 Hz), 6.94(m, 4H), 6.62(d, 1H, J=8.23 Hz), 4.74(q, 1H, J=6.72 Hz), 4.37(s, 2H), 4.21(q, 2H, J=7.08 Hz), 3.63(s, 2H), 3.14(t, 4H, J=4.51 Hz), 2.67(t, 4H, J=4.51 Hz), 2.28(s, 3H), 1.65(d, 3H, J=6.72 Hz), 1.26(t, 3H, J=7.08 Hz), Ethyl 2-}4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.02(d, 2H, J=8.23 Hz), 7.89(d, 2H, J=8.76 Hz), 7.69(d, 2H, J=8.23 Hz), 7.28(br s, 1H), 7.17(dd, 1H, J=8.23, 2.39 Hz), 6.88(d, 2H, J=8.76 Hz), 6.60(d, 1H, J=8.23 Hz), 4.73(q, 1H, J=6.81 Hz), 4.34(s, 2H), 4.18(q, 2H, J=7.17 Hz), 3.60(s, 2H), 3.37(m, 4H), 2.63(m, 4H), 2.54(s, 3H), 2.26(s, 3H), 1.65(d, 3H, J=6.81 Hz), 1.27(t, 3H, J=7.17 Hz), Ethyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl]methyl)-1-piperazinecarboxylate $^1$H NMR (CDCl$_3$) 300 MHz δ 8.00(d, 2H, J=8.23 Hz), 7.68(d, 2H, J=8.23 Hz), 7.27(d, 1H, J=2.39 Hz), 7.14(dd, 1H, J=8.23, 2.39 Hz), 6.60(d, 1H, J=8.23 Hz), 4.73(q, 1H, J=6.81 Hz), 4.31(s, 2H), 4.18(m, 4H), 3.50(m, 6H), 2.44(m, 4H), 2.26(s, 3H), 1.65(d, 3H, J=6.81 Hz), 1.26(m, 6H), Ethyl 2-{2-methyl-4-[({4-(4-morpholinylmethyl)-2-[4-(trifluoromethyl)phenyl]-1,3-thiazol-5-yl]methyl)sulfanyl]phenoxy}propanoate $^1$H NMR (CDCl$_3$) 300 MHz δ 8.01(d, 2H, J=8.23 Hz), 7.68(d, 2H, J=8.23 Hz), 7.27(d, 1H, J=2.39 Hz), 7.16(dd, 1H, J=8.49, 2.39 Hz), 6.60(d, 1H, J=8.49 Hz), 4.73(q, 1H, J=6.72 Hz), 4.34(s, 2H), 4.21(q, 2H, J=7.08 Hz), 3.73(t, 4H, J=4.51 Hz), 3.54(s, 2H), 2.49(t, 4H, J=4.51 Hz), 2.26(s, 3H), 1.65(d, 3H, J=6.72 Hz), 1.26(t, 3H, J=7.08 Hz), Ethyl 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.04(d, 2H, J=8.23 Hz), 7.70(d, 2H, J=8.23 Hz), 7.28(m, 1H), 7.18(m, 2H), 6.62(d, 1H, J=8.23 Hz), 6.56(dd, 1H, J=8.23, 2.39 Hz), 6.50(t, 1H, J=2.26 Hz), 6.45(dd, 1H, J=8.23, 2.39 Hz), 4.74(q, 1H, J=6.81 Hz), 4.37(s, 2H), 4.21(q, 2H, J=7.08 Hz), 3.82(s, 3H), 3.61(s, 2H), 3.22(t, 4H, J=4.65 Hz), 2.65(t, 4H, J=4.65 Hz), 2.28(s, 3H), 1.66(d, 3H, J=6.81 Hz), 1.26(t, 3H, J=7.08 Hz), Ethyl 2-{4-[({4-[(4-acetyl-1-piperazinyl)methyl]-2-[4-(trifluoromethyl)phenyl]-1,3-thiazol-5-yl}methyl)sulfanyl]-2-propylphenoxy}propanoate $^1$H NMR (CDCl$_3$) 400 MHz δ 7.95(d, 2H, J=8.06 Hz), 7.63(d, 2H, J=8.06 Hz), 7.16(d, 1H, J=2.38 Hz), 7.11(dd, 1H, J=8.24, 2.38 Hz), 6.55(d, 1H, J=8.24 Hz), 4.70(q, 1H, J=6.84 Hz), 4.23(s, 2H), 4.13(q, 2H, J=7.14 Hz), 3.59(br s, 2H), 3.47(s, 2H), 3.40(t, 2H, J=4.58 Hz), 2.55(t, 2H, J=7.33 Hz), 2.40(m, 4H), 2.05(s, 3H), 1.56(m, 5H), 1.20(t, 3H, J=7.14 Hz), 0.86(t, 3H, J=7.33 Hz), Ethyl 2-{4-[({4-{[4-(4-fluorophenyl)-1-piperazinyl]methyl}-2-[4-(trifluoromethyl)phenyl]-1,3-thiazol-5-yl}methyl)sulfanyl]-2-propylphenoxy}propanoate $^1$H NMR (CDCl$_3$) 400 MHz δ 7.97(d, 2H, J=8.24 Hz), 7.64(d, 2H, J=8.24 Hz), 7.19(d, 1H, J=2.38 Hz), 7.14(dd, 1H, J=8.42, 2.38 Hz), 6.93(m, 2H), 6.84(m, 2H), 6.56(d, 1H, J=8.42 Hz), 4.69(q, 1H, J=6.78 Hz), 4.30(s, 2H), 4.14(q, 2H, J=7.14 Hz), 3.54(s, 2H), 3.07(t, 4H, J=4.58 Hz), 2.58(m, 6H), 1.57(m, 5H), 1.22(t, 3H, J=7.14 Hz), 0.86(t, 3H, J=7.33 Hz), Ethyl 2-{(4-[({4-(4-morpholinylmethyl)-2-[4-(trifluoromethyl)phenyl]-1,3-thiazol-5-yl}methyl)sulfanyl]-2-propylphenoxy}propanoate $^1$H NMR (CDCl$_3$) 400 MHz δ 7.95(d, 2H, J=8.24 Hz), 7.63(d, 2H, J=8.24 Hz), 7.17(d, 1H, J=2.38 Hz), 7.12(dd, 1H, J=8.42, 2.38 Hz), 6.55(d, 1H, J=8.42 Hz), 4.69(q, 1H, J=6.78 Hz), 4.27(s, 2H), 4.14(q, 2H, J=7.14 Hz), 3.66(t, 4H, J=4.67 Hz), 3.45(s, 2H), 2.56(t, 2H, J=7.33 Hz), 2.42(m, 4H), 1.56(m, 5H), 1.21(t, 3H, J=7.14 Hz), 0.86(t, 3H, J=7.33 Hz), Methyl {4-[({4-[(4-acetyl-1-piperazinyl)methyl]-2-[4-(trifluoromethyl)phenyl]-1,3-thiazol-5-yl}methyl)sulfanyl]-2-isopropylphenoxy}acetate $^1$H NMR (CDCl$_3$) 400 MHz δ 7.95(d, 2H, J=8.61 Hz), 7.64(d, 2H, J=8.61 Hz), 7.20(d, 1H, J=2.20 Hz), 7.15(dd, 1H, J=8.42, 2.20 Hz), 6.59(d, 1H, J=8.42 Hz), 4.63(s, 2H), 4.25(s, 2H), 3.76(s, 3H), 3.56(s, 2H), 3.41(m, 4H), 3.31(m, 1H), 2.38(m, 4H), 2.05(s, 3H), 1.11(d, 6H, J=6.78 Hz), Methyl {4-[({4-{[4-(4-fluorophenyl)-1-piperazinyl]methyl}-2-[4-(trifluoromethyl)phenyl]-1,3-thiazol-5-yl}methyl)sulfanyl]-2-isopropylphenoxy}acetate $^1$H NMR (CDCl$_3$) 400 MHz δ 7.98(d, 2H, J=8.24 Hz), 7.65(d, 2H, J=8.24 Hz), 7.23(d, 1H, J=2.20 Hz), 7.18(dd, 1H, J=8.42, 2.20 Hz), 6.94(m, 2H), 6.83(m, 2H), 6.60(d, 1H, J=8.42 Hz), 4.61(s, 2H), 4.30(s, 2H), 3.76(s, 3H), 3.49(s, 2H), 3.34(m, 1H), 3.07(t, 4H, J=4.58 Hz), 2.59(m, 4H), 1.13(d, 6H, J=6.96 Hz), Methyl {2-isopropyl-4-[({4-(4-morpholinylmethyl)-2-[4-(trifluoromethyl)phenyl]-1,3-thiazol-5-yl}methyl)sulfanyl]phenoxy}acetate $^1$H NMR (CDCl$_3$) 400 MHz δ 7.96(d, 2H, J=8.24 Hz), 7.64(d, 2H, J=8.24 Hz), 7.21(d, 1H, J=2.38 Hz), 7.16(dd, 1H, J=8.42, 2.38 Hz), 6.59(d, 1H, J=8.42 Hz), 4.62(s, 2H), 4.28(s, 2H), 3.76(s, 3H), 3.66(t, 4H, J=4.58 Hz), 3.41(s, 2H), 3.32(m, 1H), 2.42(m, 4H), 1.15(d, 6H, J=6.96 Hz), Methyl {2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400 MHz δ 7.98(d, 2H, J=8.24 Hz), 7.65(d, 2H, J=8.24 Hz), 7.23(d, 1H, J=2.20 Hz), 7.18(dd, 1H, J=8.42, 2.20 Hz), 6.87(d, 2H, J=9.16 Hz), 6.81(d, 2H, J=9.16 Hz), 6.60(d, 1H, J=8.42 Hz), 4.61(m, 2H), 4.31(s, 2H), 3.77(s, 3H), 3.74(s, 3H), 3.50(s, 2H), 3.33(m, 1H), 3.05(m, 4H), 2.60(br s, 4H), 1.15(d, 6H, J=6.96 Hz), Methyl {4-[({4-{[4-(4-acetylphenyl)-1-piperazinyl]methyl}-2-[4-(trifluoromethyl)phenyl]-1,3-thiazol-5-yl}methyl)sulfanyl]-2-isopropylphenoxy}acetate $^1$H NMR (CDCl$_3$) 400 MHz δ 7.95(d, 2H, J=8.28 Hz), 7.84(d, 2H, J=9.14 Hz), 7.62(d, 2H, J=8.28 Hz), 7.21(d, 1H, J=2.24 Hz), 7.16(dd, 1H, J=8.45, 2.24 Hz), 6.80(d, 2H, J=9.14 Hz), 6.58(d, 1H, J=8.45 Hz), 4.59(s, 2H), 4.27(s, 2H), 3.73(s, 3H), 3.46(s, 2H), 3.30(m, 5H), 2.54(t, 4H, J=4.57 Hz), 2.47(s, 3H), 1.12(d, 6H, J=6.90 Hz), Methyl {2-isopropyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400 MHz δ 7.98(d, 2H, J=8.28 Hz), 7.65(d, 2H, J=8.28 Hz), 7.24(d, 1H, J=2.38 Hz), 7.19(dd, 1H, J=8.42, 2.38 Hz), 7.14(t, 1H, J=8.24 Hz), 6.60(d, 1H, J=8.42 Hz), 6.51(dd, 1H, J=8.24, 2.38 Hz), 6.44(t, 1H, J=2.29 Hz), 6.39(dd, 1H, J=8.24, 2.38 Hz), 4.62(s, 2H), 4.30(s, 2H), 3.75(m, 6H), 3.48(s, 2H), 3.34(m, 1H), 3.16(t, 4H, J=4.67 Hz), 2.57(t, 4H, J=4.67 Hz), 1.14(d, 6H, J=6.78 Hz), Ethyl 2-{2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400 MHz δ 8.04(d, 2H, J=8.24 Hz), 7.71(d, 2H, J=8.24 Hz), 7.16(m, 2H), 6.87(d, 2H, J=9.16 Hz), 6.78(d, 2H, J=9.16 Hz), 6.64(d, 1H, J=8.42 Hz), 4.81(q, 1H, J=6.71 Hz), 4.27(s, 2H), 4.11(q, 2H, J=7.08 Hz), 3.69(s, 3H), 3.28(m, 3H), 2.96(t, 4H, J=4.94 Hz), 2.51(t, 4H, J=4.94 Hz), 1.54(d, 3H, J=6.71 Hz), 1.12(m, 9H), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-isopropylphenoxy}propanoate $^1$H NMR (CDCl$_3$) 400 MHz δ 7.96(d, 2H, J=8.28 Hz), 7.83(d, 2H, J=9.14 Hz), 7.64(d, 2H, J=8.28 Hz), 7.19(d, 1H, J=2.24 Hz), 7.12(dd, 1H, J=8.45, 2.24 Hz), 6.81(d, 2H, J=9.14 Hz), 6.55(d, 1H, J=8.45 Hz), 4.71(q, 1H, J=6.78 Hz), 4.26(s, 2H), 4.12(q, 2H, J=7.16 Hz), 3.47(s, 2H), 3.29(m, 5H), 2.56(br s, 4H), 2.48(s, 3H), 1.58(d, 3H, J=6.78 Hz), 1.15(m, 9H), Ethyl 2-{2-isopropyl-4-[({4-{[4-(3-methoxyphenyl)-1-piperazinyl]methyl}-2-]4-(trifluoromethyl)phenyl]-1,3-thiazol-5-yl}methyl)sulfanyl]phenoxy}propanoate $^1$H NMR (CDCl$_3$) 400 MHz δ 7.98(d, 2H, J=8.24 Hz), 7.65(d, 2H, J=8.24 Hz), 7.21(d, 1H, J=2.38 Hz), 7.14(m, 2H), 6.58(d, 1H, J=8.61 Hz), 6.51(dd, 1H, J=8.24, 2.20 Hz), 6.43(t, 1H, J=2.29 Hz), 6.39(dd, 1H, J=8.24, 2.20 Hz), 4.72(q, 1H, J=6.78 Hz), 4.29(s, 2H), 4.15(q, 2H, J=7.14 Hz), 3.76(s, 3H), 3.48(s, 2H), 3.33(m, 1H), 3.16(br s, 4H), 2.59(br s, 4H), 1.60(d, 3H, J=6.78 Hz), 1.16(m, 9H), Ethyl {4-[({4-(4-morpholinylmethyl)-2-[4-(trifluoromethyl)phenyl]-1,3-thiazol-5-yl}methyl)sulfanyl]-2-propylphenoxy}acetate $^1$H NMR (CDCl$_3$) 400 MHz δ 7.95(d, 2H, J=8.24 Hz), 7.63(d, 2H, J=8.24 Hz), 7.19(m, 2H), 6.58(d, 1H, J=8.24 Hz), 4.59(s, 2H), 4.28(s, 2H), 4.21(q, 2H, J=7.14 Hz), 3.66(t, 4H, J=4.49 Hz), 3.45(s, 2H), 2.56(t, 2H, J=7.33 Hz), 2.42(m, 4H), 1.56(m, 2H), 1.24(t, 3H, J=7.14 Hz), 0.87(t, 3H, J=7.33 Hz), Ethyl {4-[({4-{[4-(4-acetylphenyl)-1-piperazinyl]methyl}-2-[4-(trifluoromethyl)phenyl]-1,3-thiazol-5-yl}methyl)sulfanyl]-2-ethylphenoxy}acetate $^1$H NMR (CDCl$_3$) 400 MHz δ 7.97(d, 2H, J=8.24 Hz), 7.83(d, 2H, J=9.16 Hz), 7.63(d, 2H, J=8.24 Hz), 7.21(d, 1H, J=2.20 Hz), 7.16(dd, 1H, J=8.42, 2.20 Hz), 6.82(d, 2H, J=9.16 Hz), 6.59(d, 1H, J=8.42 Hz), 4.59(s, 2H), 4.29(s, 2H), 4.21(q, 2H, J=7.14 Hz), 3.52(s, 2H), 3.31(t, 4H, J=4.80 Hz), 2.64(q, 2H, J=7.51 Hz), 2.55(t, 4H, J=4.80 Hz), 2.47(s, 3H), 1.24(t, 3H, J=7.14 Hz), 1.14(t, 3H, J=7.51 Hz), Ethyl {2-ethyl-4-[({4-{[4-(3-methoxyphenyl)-1-piperazinyl]methyl}-2-]4-(trifluoromethyl)phenyl]-1,3-thiazol-5-yl}methyl)sulfanyl]phenoxy}acetate $^1$H NMR (CDCl$_3$) 400 MHz δ 7.98(d, 2H, J=8.24 Hz), 7.65(d, 2H, J=8.24 Hz), 7.22(s, 1H), 7.16(m, 2H), 6.60(d, 1H, J=8.42 Hz), 6.51(d, 1H, J=8.42 Hz), 6.44(s, 1H), 6.39 (dd, 1H, J=8.24, 1.28 Hz), 4.60(s, 2H), 4.32(s, 2H), 4.22(q, 2H, J=7.14 Hz), 3.76(s, 3H), 3.52(s, 2H), 3.16(t, 4H, J=4.67 Hz), 2.65(q, 2H, J=7.51 Hz), 2.57(t, 4H, J=4.67 Hz), 1.26(t, 3H, J=7.14 Hz), 1.16(t, 3H, J=7.51 Hz), Ethyl {4-[({4-[(4-acetyl-1-piperazinyl)methyl]-2-[4-(trifluoromethyl)phenyl]-1,3-thiazol-5-yl}methyl)sulfanyl]-2-ethylphenoxy}acetate $^1$H NMR (CDCl$_3$) 400 MHz δ 7.93(d, 2H, J=8.28 Hz), 7.61(d, 2H, J=8.28 Hz), 7.16(d, 1H, J=2.24 Hz), 7.12(dd, 1H, J=8.28, 2.24 Hz), 6.56(d, 1H, J=8.28 Hz), 4.58(s, 2H), 4.20(m, 4H), 3.55(t, 4H, J=4.91 Hz), 3.43(s, 2H), 3.37(t, 4H, J=4.91 Hz), 2.60(q, 2H, J=7.50 Hz), 2.02(s, 3H), 1.22(t, 3H, J=7.14 Hz), 1.11(t, 3H, J=7.50 Hz), Ethyl {2-ethyl-4-[({4-{[4-(4-fluorophenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400 MHz δ 8.03(d, 2H, J=8.28 Hz), 7.69(d, 2H, J=8.28 Hz), 7.25(m, 2H), 6.93(m, 4H), 6.64(d, 1H, J=8.28 Hz), 4.64(s, 2H), 4.36(s, 2H), 4.26(q, 2H, J=7.08 Hz), 3.58(s, 2H), 3.11(t, 4H, J=4.97 Hz), 2.66(m, 6H), 1.29(t, 3H, J=7.08 Hz), 1.19(t, 3H, J=7.54 Hz), Ethyl {2-ethyl-4-[({4-(4-morpholinylmethyl)-2-[4-(trifluoromethyl)phenyl]-1,3-thiazol-5-yl}methyl)sulfanyl]phenoxy}acetate $^1$H NMR (CDCl$_3$) 400 MHz δ 8.01(d, 2H, J=8.28 Hz), 7.68(d, 2H, J=8.28 Hz), 7.24(m, 2H), 6.63(d, 1H, J=8.28 Hz), 4.64(s, 2H), 4.34(s, 2H), 4.26(q, 2H, J=7.17 Hz), 3.70(t, 4H, J=4.42 Hz), 3.49(s, 2H), 2.67(q, 2H, J=7.54 Hz), 2.46(t, 4H, J=4.42 Hz), 1.30(t, 3H, J=7.17 Hz), 1.19(t, 3H, J=7.54 Hz), Ethyl 2-{2-ethyl-4-[({4-{[4-(4-methoxyphenyl)-1-piperazinyl]methyl}-2-]4-(trifluoromethyl)phenyl]-1,3-thiazol-5-yl}methyl)sulfanyl]phenoxy}propanoate $^1$H NMR (CDCl$_3$) 400 MHz δ 8.03(d, 2H, J=8.28 Hz), 7.70(d, 2H, J=8.28 Hz), 7.26(d, 1H, J=2.21 Hz), 7.19(dd, 1H, J=8.28, 2.21 Hz), 6.93(d, 2H, J=9.11 Hz), 6.86(d, 2H, J=9.11 Hz), 6.62(d, 1H, J=8.28 Hz), 4.76(q, 1H, J=6.90 Hz), 4.36(s, 2H), 4.19(q, 2H, J=7.17 Hz), 3.80(s, 3H), 3.58(s, 2H), 3.11(t, 4H, J=4.69 Hz), 2.67(m, 6H), 1.65(d, 3H, J=6.90 Hz), 1.24(m, 6H), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-ethylphenoxy}propanoate $^1$H NMR (CDCl$_3$) 400 MHz δ 8.02(d, 2H, J=8.28 Hz), 7.89(d, 2H, J=8.83 Hz), 7.69(d, 2H, J=8.28 Hz), 7.25(d, 1H, J=2.21 Hz), 7.18(dd, 1H, J=8.28, 2.21 Hz), 6.88(d, 2H, J=8.83 Hz), 6.61(d, 1H, J=8.28 Hz), 4.76(q, 1H, J=6.90 Hz), 4.33(s, 2H), 4.18(q, 2H, J=7.17 Hz), 3.57(s, 2H), 3.36(m, 4H), 2.66(m, 6H), 2.53(s, 3H), 1.65(d, 3H, J=6.90 Hz), 1.23(m, 6H), Ethyl 2-{2-ethyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400 MHz δ 8.03(d, 2H, J=8.28 Hz), 7.70(d, 2H, J=8.28 Hz), 7.26(d, 1H, J=2.21 Hz), 7.18(m, 2H), 6.62(d, 1H, J=8.28 Hz), 6.56(dd, 1H, J=8.00, 1.66 Hz), 6.49(m, 1H), 6.44(dd, 1H, J=8.00, 1.66 Hz), 4.76(q, 1H, J=6.62 Hz), 4.35(s, 2H), 4.19(q, 2H, J=7.17 Hz), 3.81(s, 3H), 3.57(s, 2H), 3.21(t, 4H, J=4.83 Hz), 2.66(m, 6H), 1.65(d, 3H, J=6.62 Hz), 1.24(m, 6H), Ethyl 2-{4-[({4-{[4-(4-methoxyphenyl)-1-piperazinyl]methyl}-2-[4-(trifluoromethyl)phenyl-1,3-thiazol-5-yl}methyl)sulfanyl]-2-propylphenoxy}propanoate $^1$H NMR (CDCl$_3$) 400 MHz δ 7.97(d, 2H, J=8.24 Hz), 7.64(d, 2H, J=8.24 Hz), 7.19(d, 1H, J=2.38 Hz), 7.14(dd, 1H, J=8.42, 2.38 Hz), 6.88(d, 2H, J=9.16 Hz), 6.81(d, 2H, J=9.16 Hz), 6.56(d, 1H, J=8.42 Hz), 4.70(q, 1H, J=6.78 Hz), 4.31(s, 2H), 4.15(q, 2H, J=7.14 Hz), 3.74(s, 3H), 3.54(s, 2H), 3.05(t, 4H, J=4.85 Hz), 2.57(m, 6H), 1.56(m, 5H), 1.20(t, 3H, J=7.14 Hz), 0.86(t, 3H, J=7.33 Hz), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}propanoate $^1$H NMR (CDCl$_3$) 400 MHz δ 7.95(d, 2H, J=8.24 Hz), 7.84(d, 2H, J=9.14 Hz), 7.63(d, 2H, J=8.24 Hz), 7.17(d, 1H, J=2.24 Hz), 7.12(dd, 1H, J=8.45, 2.24 Hz), 6.82(d, 2H, J=9.14 Hz), 6.54(d, 1H, J=8.45 Hz), 4.68(q, 1H, J=6.78 Hz), 4.27(s, 2H), 4.13(q, 2H, J=7.07 Hz), 3.51(m, 2H), 3.31(t, 4H, J=4.91 Hz), 2.55(m, 6H), 2.47(s, 3H), 1.55(m, 5H), 1.17(t, 3H, J=7.07 Hz), 0.85(t, 3H, J=7.41 Hz), Ethyl 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-propylphenoxy}propanoate $^1$H NMR (CDCl$_3$) 400 MHz δ 7.97(d, 2H, J=8.28 Hz), 7.64(d, 2H, J=8.28 Hz), 7.15(m, 3H), 6.56(d, 1H, J=8.45 Hz), 6.50(dd, 1H, J=8.10, 2.07 Hz), 6.43(t, 1H, J=2.07 Hz), 6.39(dd, 1H, J=8.10, 2.07 Hz), 4.70(q, 1H, J=6.72 Hz), 4.29(s, 2H), 4.14(q, 2H, J=7.07 Hz), 3.76(s, 3H), 3.52(s, 2H), 3.16(t, 4H, J=4.83 Hz), 2.58(m, 6H), 1.57(m, 5H), 1.19(t, 3H, J=7.07 Hz), 0.87(t, 3H, J=7.33 Hz), Ethyl 2-(4-{[(2-(4-fluorophenyl)-4-{[4-(4-methoxyphenyl)-1-piperazinyl]methyl}-1,3-thiazol-5-yl)methyl]sulfanyl}-2-methylphenoxy)propanoate $^1$H NMR (CDCl$_3$) 400 MHz δ 7.85(m, 2H), 7.22(d, 1H, J=2.38 Hz), 7.09(m, 3H), 6.87(d, 2H, J=9.16 Hz), 6.81(d, 2H, J=9.16 Hz), 6.56(d, 1H, J=8.42 Hz), 4.68(q, 1H, J=6.78 Hz), 4.30(s, 2H), 4.16(q, 2H, J=7.20 Hz), 3.74(s, 3H), 3.53(s, 2H), 3.07(t, 4H, J=4.58 Hz), 2.62(br s, 4H), 2.21(s, 3H), 1.60(d, 3H, J=6.78 Hz), 1.20(t, 3H, J=7.20 Hz), Ethyl 2-[4-({[4-{[4-(4-acetylphenyl)-1-piperazinyl]methyl}-2-(4-fluorophenyl)-1,3-thiazol-5-yl]methyl}sulfanyl)-2-methylphenoxy]propanoate $^1$H NMR (CDCl$_3$) 400 MHz δ 7.85(m, 4H), 7.23(d, 1H, J=2.38 Hz), 7.09(m, 3H), 6.83(d, 2H, J=9.16 Hz), 6.55(d, 1H, J=8.42 Hz), 4.68(q, 1H, J=6.78 Hz), 4.27(s, 2H), 4.16(q, 2H, J=7.14 Hz), 3.52(s, 2H), 3.32(t, 4H, J=4.94 Hz), 2.59(br s, 4H), 2.49(s, 3H), 2.21(s, 3H), 1.60(d, 3H, J=6.78 Hz), 1.21(t, 3H, J=7.14 Hz), Ethyl 2-(4-{[(2-(4-fluorophenyl)-4-{[4-(3-methoxyphenyl)-1-piperazinyl]methyl}-1,3-thiazol-5-yl)methyl]sulfanyl}-2-methylphenoxy)propanoate $^1$H NMR (CDCl$_3$) 400 MHz δ 7.85(m, 2H), 7.23(d, 1H, J=2.20 Hz), 7.11(m, 4H), 6.56(d, 1H, J=8.24 Hz), 6.51(dd, 1H, J=8.24, 2.20 Hz), 6.44(t, 1H, J=2.20 Hz), 6.39(dd, 1H, J=8.24, 2.20 Hz), 4.69(q, 1H, J=6.78 Hz), 4.29(s, 2H), 4.16(q, 2H, J=7.14 Hz), 3.76(s, 3H), 3.52(s, 2H), 3.16(t, 4H, J=4.76 Hz), 2.60(br s, 4H), 2.21(s, 3H), 1.59(d, 3H, J=6.78 Hz), 1.22(t, 3H, J=7.14 Hz), Ethyl 4-{[5-({[4-(2-ethoxy-1-methyl-2-oxoethoxy)-3-methyl phenyl]sulfanyl}methyl)-2-(4-fluorophenyl)-1,3-thiazol-4-yl]methyl}-1-piperazinecarboxylate $^1$H NMR (CDCl$_3$) 400 MHz δ 7.83(m, 2H), 7.20(d, 1H, J=2.20 Hz), 7.08(m, 3H), 6.55(d, 1H, J=8.42 Hz), 4.68(q, 1H, J=6.78 Hz), 4.23(s, 2H), 4.16(q, 2H, J=7.14 Hz), 4.09(q, 2H, J=7.14 Hz), 3.42(m, 6H), 2.38(br s, 4H), 2.18(s, 3H), 1.57(d, 3H, J=6.78 Hz), 1.13(m, 6H), Ethyl {2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400 MHz δ 7.98(d, 2H, J=8.24 Hz), 7.65(d, 2H, J=8.24 Hz), 7.22(s, 1H), 7.17(d, 1H, J=8.42 Hz), 6.87(d, 2H, J=9.16 Hz), 6.81(d, 2H, J=9.16 Hz), 6.59(d, 1H, J=8.42 Hz), 4.60(s, 2H), 4.32(s, 2H), 4.22(q, 2H, J=7.14 Hz), 3.74(s, 3H), 3.53(s, 2H), 3.05(t, 4H, J=4.76 Hz), 2.62(m, 6H), 1.26(t, 3H, J=7.14 Hz), 1.16(t, 3H, J=7.33 Hz), Ethyl 2-{4-[({4-{[4-acetyl-1-piperazinyl)methyl]-2-[4-(trifluoromethyl)phenyl]-1,3-thiazol-5-yl]methyl)sulfanyl]-2-ethylphenoxy}propanoate $^1$H NMR (CDCl$_3$) 400 MHz δ 7.99(d, 2H, J=8.28 Hz), 7.68(d, 2H, J=8.28 Hz), 7.22(d, 1H, J=2.21 Hz), 7.15(dd, 1H, J=8.28, 2.21 Hz), 6.60(d, 1H, J=8.28 Hz), 4.75(q, 1H, J=6.81 Hz), 4.29(s, 2H), 4.19(q, 2H, J=7.17 Hz), 3.62(t, 2H, J=4.69 Hz), 3.50(s, 2H), 3.43(t, 2H, J=4.69 Hz), 2.66(q, 2H, J=7.45 Hz), 2.43(br s, 4H), 2.09(s, 3H), 1.64(d, 3H, J=6.81 Hz), 1.22(m, 6H), Ethyl 2-{2-ethyl-4-[({4-{[4-(4-fluorophenyl)-1-piperazinyl]methyl}-2-[4-(trifluoromethyl)phenyl]-1,3-thiazol-5-yl]methyl)sulfanyl]phenoxy}propanoate $^1$H NMR (CDCl$_3$) 400 MHz δ 8.03(d, 2H, J=8.28 Hz), 7.69(d, 2H, J=8.28 Hz), 7.26(d, 1H, J=2.21 Hz), 7.19(dd, 1H, J=8.55, 2.21 Hz), 6.94(m, 4H), 6.62(d, 1H, J=8.55 Hz), 4.75(q, 1H, J=6.90 Hz), 4.35(s, 2H), 4.19(q, 2H, J=7.17 Hz), 3.58(s, 2H), 3.12(t, 4H, J=4.97 Hz), 2.66(m, 6H), 1.64(d, 3H, J=6.90 Hz), 1.24(m, 6H), Ethyl 2-{2-ethyl-4-[({4-(4-morpholinylmethyl)-2-[4-(trifluoromethyl)phenyl]-1,3-thiazol-5-yl}methyl)sulfanyl]phenoxy}propanoate $^1$H NMR (CDCl$_3$) 400 MHz δ 8.01(d, 2H, J=8.28 Hz), 7.68(d, 2H, J=8.28 Hz), 7.24(d, 1H, J=2.21 Hz), 7.16(dd, 1H, J=8.28, 2.21 Hz), 6.60(d, 1H, J=8.28 Hz), 4.75(q, 1H, J=6.62 Hz), 4.32(s, 2H), 4.17(s, 2H), 3.70(t, 4H, J=4.42 Hz), 3.49(s, 2H), 2.66(q, 2H, J=7.54 Hz), 2.45(t, 4H, J=4.42 Hz), 1.63(d, 3H, J=6.62 Hz), 1.22(m, 6H), Ethyl {4-]({4-{[4-(4-methoxyphenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400 MHz δ 8.03(d, 2H, J=8.28 Hz), 7.69(d, 2H, J=8.28 Hz), 7.23(m, 2H), 6.89(m, 4H), 6.64(d, 1H, J=8.28 Hz), 4.62(s, 2H), 4.36(s, 2H), 4.26(q, 2H, J=7.08 Hz), 3.79(s, 3H), 3.60(s, 2H), 3.11(m, 4H), 2.64(m, 6H), 1.62(m, 2H), 1.30(t, 3H, J=7.08 Hz), 0.93(t, 3H, J=7.45 Hz), Ethyl {4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400 MHz δ 8.02(d, 2H, J=8.28 Hz), 7.89(d, 2H, J=9.11 Hz), 7.69(d, 2H, J=8.28 Hz), 7.24(m, 2H), 6.87(d, 2H, J=9.11 Hz), 6.64(d, 1H, J=8.28 Hz), 4.62(s, 2H), 4.34(s, 2H), 4.26(q, 2H, J=7.17 Hz), 3.58(s, 2H), 3.35(t, 4H, J=4.97 Hz), 2.62(m, 6H), 2.54(s, 3H), 1.61(m, 2H), 1.29(t, 3H, J=7.17 Hz), 0.91(t, 3H, J=7.45 Hz), Ethyl {4-[({4-{[4-(3-methoxyphenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400 MHz δ 7.97(d, 2H, J=8.28 Hz), 7.64(d, 2H, J=8.28 Hz), 7.17(m, 3H), 6.58(d, 1H, J=8.10 Hz), 6.51(dd, 1H, J=8.10, 2.07 Hz), 6.43(t, 1H, J=2.07 Hz), 6.38(dd, 1H, J=8.10, 2.07 Hz), 4.58(s, 2H), 4.30(s, 2H), 4.21(q, 2H, J=7.13 Hz), 3.75(s, 3H), 3.53(s, 2H), 3.15(t, 4H, J=4.66 Hz), 2.57(m, 6H), 1.57(m, 2H), 1.24(t, 3H, J=7.13 Hz), 0.87(t, 3H, J=7.41 Hz), Ethyl {4-[({4-[(4-acetyl-1-piperazinyl)methyl]-2-[4-(trifluoromethyl)phenyl]-1,3-thiazol-5-yl}methyl)sulfanyl]-2-propylphenoxy}acetate $^1$H NMR (CDCl$_3$) 400 MHz δ 7.93(d, 2H, J=8.28 Hz), 7.62(d, 2H, J=8.28 Hz), 7.14(m, 2H), 6.57(d, 1H, J=8.28 Hz), 4.58(s, 2H), 4.20(m, 4H), 3.56(t, 2H, J=4.91 Hz), 3.45(s, 2H), 3.38(t, 2H, J=4.91 Hz), 2.55(t, 2H, J=7.33 Hz), 2.37(m, 4H), 2.03(s, 3H), 1.53(m, 2H), 1.22(t, 3H, J=7.16 Hz), 0.85(t, 3H, J=7.33 Hz), Ethyl {4-[({4-{[4-(4-fluorophenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400 MHz δ 7.97(d, 2H, J=8.28 Hz), 7.64(d, 2H, J=8.28 Hz), 7.19(m, 2H), 6.92(m, 2H), 6.83(m, 2H), 6.58(d, 1H, J=8.28 Hz), 4.56(s, 2H), 4.29(s, 2H), 4.20(q, 2H, J=7.13 Hz), 3.53(s, 2H), 3.06(t, 4H, J=4.91 Hz), 2.57(m, 6H), 1.55(m, 2H), 1.24(t, 3H, J=7.13 Hz), 0.86(t, 3H, J=7.41 Hz), Ethyl 2-{4-[({4-{[4-(2,4-dimethoxyphenyl)-1-piperazinyl]methyl}-2-]4-(trifluoromethyl)phenyl]-1,3-thiazol-5-yl}methyl)sulfanyl]-2-methylphenoxy}propanoate $^1$H NMR (CDCl$_3$) 300 MHz. δ 8.02(d, 2H, J=8.28 Hz), 7.67(d, 2H, J=8.28 Hz), 7.26(d, 1H, J=2.21 Hz), 7.16(dd, 1H, J=8.55, 2.21 Hz), 6.87(d, 1H, J=8.55 Hz), 6.60(d, 1H, J=8.55 Hz), 6.50(d, 1H, J=2.48 Hz), 6.42(dd, 1H, J=8.55, 2.48 Hz), 4.72(q, 1H, J=6.90 Hz), 4.38(s, 2H), 4.21(q, 2H, J=7.08 Hz), 3.85(s, 3H), 3.79(s, 3H), 3.61(s, 2H), 3.04(br s, 4H), 2.70(br s, 4H), 2.26(s, 3H), 1.63(d, 3H, J=6.90 Hz), 1.24(t, 3H, J=7.04 Hz), phenyl 4-({5-({[4-(2-ethoxy-1,1-dimethyl-2-oxoethoxy)phenyl]thio}methyl)-2-[4-(trifluoromethyl)phenyl]-1,3-thiazol-4-yl}methyl)piperazine-1-carboxylate To a 500 ml 3-neck round-bottom flask equipped with a magnetic stir-bar, low temperature thermometer with thermometer adapter, addition funnel and N$_2$ inlet was added ethyl 2-{4-[({4-(hydroxymethyl)-2-[4-(trifluoromethyl)phenyl]-1,3-thiazol-5-yl}methyl)sulfanyl]phenoxy}-2-methylpropanoate (300 mg, 0.59 mmoles, 1 eq) and dry CH$_2$Cl$_2$ (4 ml, 0.15M) and cooled to 0° C. Methanesulfonyl chloride (0.055 ml, 0.71 mmoles, 1.2 eq) was added neat all at once. Triethylamine (0.12 ml, 0.89 mmoles, 1.5 eq) was added dropwise maintaining the internal temperature below 5° C. and was stirred at 0° C. for 30 minutes. The reaction mixture was transferred to a separatory funnel and washed with H$_2$O, brine and the organic fraction was dried over Na$_2$SO$_4$. After filtration the solvent was removed under reduced pressure to yield the corresponding mesylate in quantitative yield. Because of the unstable nature of the mesylate, the product was not characterized and was progressed onto the next stage without purification.

To the crude mesylate dissolved in dry THF (3 ml, 0.20M) was added piperazine (559 mg, 5.9 mmoles, 10 eq) and the reaction mixture was refluxed for 5 hours. After cooling to room temperature the solvent was removed in vacuo. The residue was partitioned between EtOAc and H$_2$O and after the phases were separated the organic fraction was dried over Na$_2$SO$_4$, filtered and concentrated in vacuo to yield a quantitative amount of product. The product was used without characterization and purification.

The crude piperazine was dissolved in dry CH$_2$Cl$_2$ (5 ml, 0.12M) and to it was added phenylchloroformate (0.08 ml, 0.65 mmoles, 1.1 eq) and triethylamine (0.248 ml, 1.8 mmoles, 3 eq) and was stirred at room temperature overnight. The reaction mixture was diluted with EtOAc and washed with 0.1N HCl twice, H$_2$O, brine, dried over Na$_2$SO$_4$, filtered and concentrated in vacuo to yield after silica gel chromatography 125 mg (32% over three steps) of product.

$^1$H NMR (CDCl$_3$) 400 MHz δ 7.95(d, 2H, J=8.28 Hz), 7.65(d, 2H, J=8.28 Hz), 7.33(m, 2H), 7.26(d, 2H, J=8.79 Hz), 7.17(t, 1H, J=7.59 Hz), 7.06(d, 2H, J=7.59 Hz), 6.74(d, 2H, J=8.79 Hz), 4.32(s, 2H), 4.18(q, 2H, J=7.07 Hz), 3.61 (m, 6H), 2.51(br s, 4H), 1.57(s, 6H), 1.20(t, 3H, J=7.07 Hz),

The following compounds were made the same procedure used for phenyl 4-({5-({[4-(2-ethoxy-1,1-dimethyl-2-oxoethoxy)phenyl]thiomethyl)-2-[4-(trifluoromethyl)phenyl]-1,3-thiazol-4-yl}methyl)piperazine-1-carboxylate except no extra base was used when the other reactant was an isocyanate.

Phenyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 300 MHz δ 7.97(d, 2H, J=8.28 Hz), 7.77(d, 2H, J=8.28 Hz), 7.60(m, 5H), 7.20(d, 1H, J=2.21 Hz), 7.10(dd, 1H, J=8.55, 2.21 Hz), 6.57(d, 1H, J=8.55 Hz), 4.74(q, 1H, J=6.71 Hz), 4.20(m, 4H), 3.48(s, 2H), 3.06(br s, 4H), 2.56(br s, 4H), 2.24(s, 3H), 1.65(d, 3H, J=6.71 Hz), 1.25(t, 3H, J=7.04 Hz), benzyl 4-({5-({[4-(2-ethoxy-1-methyl-2-oxoethoxy)-3-methylphenyl]thio}methyl)-2-[4-(trifluoromethyl)phenyl]-1,3-thiazol-4-yl}methyl)piperazine-1-carboxylate $^1$H NMR (CDCl$_3$) 300 MHz δ 8.01(d, 2H, J=8.00 Hz), 7.69(d, 2H, J=8.00 Hz), 7.36(m, 5H), 7.26(d, 1H, J=2.21 Hz), 7.15(dd, 1H, J=8.55, 2.21 Hz), 6.60(d, 1H, J=8.55 Hz), 5.16(s, 2H), 4.74(q, 1H, J=6.62 Hz), 4.31(s, 2H), 4.21(q, 2H, J=7.08 Hz), 3.55(m, 6H), 2.47(br s, 4H), 2.26(s, 3H), 1.65(d, 3H, J=6.62 Hz), 1.25(t, 3H, J=7.08 Hz),

Isopropyl 4-{15-({[4-(2-ethoxy-1-methyl-2-oxoethoxy)-3-methylphenyl]sulfanyl}methyl)-2-(4-fluorophenyl)-1,3-thiazol-4-yl]methyl}-1-piperazinecarboxylate $^1$H NMR (CDCl$_3$) 400 MHz δ 7.84(m, 2H), 7.22(d, 1H, J=2.20 Hz), 7.09(m, 3H), 6.55(d, 1H, J=8.42 Hz), 4.89(m, 1H), 4.68(q, 1H, J=6.78 Hz), 4.26(s, 2H), 4.16(q, 2H, J=7.20 Hz), 3.47(m, 6H), 2.40(br s, 4H), 2.22(s, 3H), 1.61(d, 3H, J=6.78 Hz), 1.27(m, 9H),

Ethyl 2-{4-[({4-{[4-(cyclopentylcarbonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.67(d, 2H, J=8.28 Hz), 7.24(d, 1H, J=2.21 Hz), 7.14(dd, 1H, J=8.28, 2.21 Hz), 6.59(d, 1H, J=8.28 Hz), 4.73(q, 1H, J=6.71 Hz), 4.31(s, 2H), 4.19(q, 2H, J=7.17 Hz), 3.65(br s, 2H), 3.50(br s, 4H), 2.87(m, 1H), 2.45(t, 4H, J=4.69 Hz), 2.23(s, 3H), 1.73(m, 11H), 1.24(t, 3H, J=7.17 Hz),

Ethyl 2-{4-[({4-{[4-(cyclopropylcarbonyl)-1-piperazinyl]methyl}-2-]4-(trifluoromethyl)phenyl]-1,3-thiazol-5-yl}methyl)sulfanyl]-2-methyl phenoxy}propanoate $^1$H NMR (CDCl$_3$) 300 MHz δ 8.00(d, 2H, J=8.28 Hz), 7.68(d, 2H, J=8.28 Hz), 7.27(d, 1H, J=2.21 Hz), 7.15(dd, 1H, J=8.28, 2.21 Hz), 6.59(d, 1H, J=8.28 Hz), 4.73(q, 1H, J=6.71 Hz), 4.31(s, 2H), 4.20(q, 2H, J=7.08 Hz), 3.67(br s, 4H), 3.55(s, 2H), 2.49(br s, 4H), 2.26(s, 3H), 1.74(m, 1H), 1.64(d, 3H, J=6.71 Hz), 1.25(t, 3H, J=7.08 Hz), 1.00(m, 2H), 0.76(m, 2H),

Ethyl 2-{4-[({4-{[4-(cyclobutylcarbonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 7.99(d, 2H, J=8.28 Hz), 7.67(d, 2H, J=8.28 Hz), 7.24(d, 1H, J=2.21 Hz), 7.13(dd, 1H, J=8.28, 2.21 Hz), 6.58(d, 1H, J=8.28 Hz), 4.73(q, 1H, J=6.71 Hz), 4.28(s, 2H), 4.19(q, 2H, J=7.17 Hz), 3.64(t, 2H, J=4.83 Hz), 3.52(s, 2H), 3.36(t, 2H, J=4.83 Hz), 3.24(m, 1H), 2.47(m, 4H), 2.08(m, 9H), 1.63(d, 3H, J=6.71 Hz), 1.24(t, 3H, J=7.17 Hz),

Methyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 300 MHz δ 8.00(d, 2H, J=8.28 Hz), 7.68(d, 2H, J=8.28 Hz), 7.26(d, 1H, J=2.21 Hz), 7.14(dd, 1H, J=8.28, 2.21 Hz), 6.59(d, 1H, J=8.28 Hz), 4.73(q, 1H, J=6.71 Hz), 4.31(s, 2H), 4.20(q, 2H, J=7.17 Hz), 3.71 (s, 3H), 3.50(m, 6H), 2.44(br s, 4H), 2.26(s, 3H), 1.65(d, 3H, J=6.71 Hz), 1.25(t, 3H, J=7.17 Hz),

Ethyl 2-{2-methyl-4-[({4-{[4-(3-methylbutanoyl)-1-piperazinyl]methyl}-2-]4-(trifluoromethyl)phenyl]-1,3-thiazol-5-yl}methyl)sulfanyl]phenoxy}propanoate $^1$H NMR (CDCl$_3$) 300 MHz δ 8.00(d, 2H, J=8.28 Hz), 7.67(d, 2H, J=8.28 Hz), 7.24(d, 1H, J=2.21 Hz), 7.14(dd, 1H, J=8.55, 2.48 Hz), 6.59(d, 1H, J=8.55 Hz), 4.73(q, 1H, J=6.71 Hz), 4.30(s, 2H), 4.20(q, 2H, J=7.08 Hz), 3.65(br s, 2H), 3.54(s, 2H), 3.47(t, 2H, J=4.69 Hz), 2.45(t, 4H, J=4.83 Hz), 2.26(s, 3H), 2.12(m, 3H), 1.64(d, 3H, J=6.71 Hz), 1.24(t, 3H, J=7.08 Hz), 0.96(d, 6H, J=6.35 Hz),

Ethyl 2-{4-[({4-{[4-(4-fluorobenzoyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.69(d, 2H, J=8.28 Hz), 7.43(m, 2H), 7.24(d, 1H, J=2.39 Hz), 7.11(m, 3H), 6.59(d, 1H, J=8.55 Hz), 4.73(q, 1H, J=6.71 Hz), 4.30(s, 2H), 4.19(q, 2H, J=7.17 Hz), 3.65(m, 6H), 2.53(m, 4H), 2.25(s, 3H), 1.64(d, 3H, J=6.71 Hz), 1.25(t, 3H, J=7.17 Hz),

Ethyl 2-{2-methyl-4-[({4-{[4-(propylsulfonyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300 MHz δ, 8.00(d, 2H, J=8.28 Hz), 7.68(d, 2H, J=8.28 Hz), 7.26(d, 1H, J=2.21 Hz), 7.15(dd, 1H, J=8.28, 2.21 Hz), 6.59(d, 1H, J=8.28 Hz), 4.74(q, 1H, J=6.71 Hz), 4.28(s, 2H), 4.20(q, 2H, J=7.08 Hz), 3.55(s, 2H), 3.30(t, 4H, J=4.55 Hz), 2.89(m, 2H), 2.56(t, 4H, J=4.28 Hz), 2.26(s, 3H), 1.87(m, 2H), 1.65(d, 3H, J=6.62 Hz), 1.25(t, 3H, J=7.04 Hz), 1.07(t, 3H, J=7.17 Hz).

Ethyl 2-{4-[({4-{[4-butyryl-1-piperazinyl)methyl]-2-[4-(trifluoromethyl)phenyl]-1,3-thiazol-5-yl}methyl)sulfanyl]-2-methylphenoxy}propanoate ¹H NMR (CDCl₃) 300 MHz δ 8.00(d, 2H, J=8.28 Hz), 7.67(d, 2H, J=8.28 Hz), 7.26(d, 1H, J=2.21 Hz), 7.14(dd, 1H, J=8.55, 2.21 Hz), 6.59(d, 1H, J=8.55 Hz), 4.73(q, 1H, J=6.71 Hz), 4.30(s, 2H), 4.20(q, 2H, J=7.08 Hz), 3.64(m, 2H), 3.54(s, 2H), 3.45(t, 2H, J=4.83 Hz), 2.45(t, 4H, J=4.83 Hz), 2.31(t, 2H, J=7.31 Hz), 2.25(s, 3H), 1.66(m, 5H), 1.24(t, 3H, J=7.08 Hz), 0.98(t, 3H, J=7.31 Hz), Ethyl 2-{2-methyl-4-[({4-{[4-pentanoyl-1-piperazinyl]methyl}-2-[4-(trifluoromethyl)phenyl]-1,3-thiazol-5-yl}methyl)sulfanyl]phenoxy}propanoate ¹H NMR (CDCl₃) 300 MHz δ 8.00(d, 2H, J=8.28 Hz), 7.67(d, 2H, J=8.28 Hz), 7.26(d, 1H, J=2.21 Hz), 7.14(dd, 1H, J=8.28, 2.21 Hz), 6.58(d, 1H, J=8.28 Hz), 4.73(q, 1H, J=6.71 Hz), 4.30(s, 2H), 4.19(q, 2H, J=7.27 Hz), 3.64(m, 2H), 3.54(s, 2H), 3.46(t, 2H, J=4.83 Hz), 2.45(t, 4H, J=4.83 Hz), 2.32(t, 2H, J=7.45 Hz), 2.24(s, 3H), 1.61(m, 5H), 1.37(m, 2H), 1.24(t, 3H, J=7.27 Hz), 0.93(t, 3H, J=7.45 Hz), Ethyl 2-{4-[({4-{[4-(4-methoxybenzoyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300 MHz δ 8.00(d, 2H, J=8.28 Hz), 7.67(d, 2H, J=8.28 Hz), 7.40(d, 2H, J=8.83 Hz), 7.24(d, 1H, J=2.21 Hz), 7.14(dd, 1H, J=8.28, 2.21 Hz), 6.92(d, 2H, J=8.83 Hz), 6.59(d, 1H, J=8.28 Hz), 4.73(q, 1H, J=6.71 Hz), 4.30(s, 2H), 4.19(q, 2H, J=7.08 Hz), 3.84(s, 3H), 3.63(m, 6H), 2.49(br s, 4H), 2.25(s, 3H), 1.64(d, 3H, J=6.71 Hz), 1.24(t, 3H, J=7.08 Hz), Ethyl 2-{4-[({4-{[4-benzoyl-1-piperazinyl)methyl]-2-[4-(trifluoromethyl)phenyl]-1,3-thiazol-5-yl}methyl)sulfanyl]-2-methylphenoxy}propanoate ¹H NMR (CDCl₃) 300 MHz δ 7.99(d, 2H, J=8.55 Hz), 7.67(d, 2H, J=8.55 Hz), 7.41(m, 5H), 7.24(d, 1H, J=2.21 Hz), 7.15(dd, 1H, J=8.55, 2.21 Hz), 6.59(d, 1H, J=8.55 Hz), 4.73(q, 1H, J=6.71 Hz), 4.30(s, 2H), 4.19(q, 2H, J=7.04 Hz), 3.83(br s, 2H), 3.56(s, 2H), 3.39(br s, 2H), 2.50(br s, 4H), 2.25(s, 3H), 1.64(d, 3H, J=6.71 Hz), 1.24(t, 3H, J=7.04 Hz), isobutyl 4-({5-({[4-(2-ethoxy-1-methyl-2-oxoethoxy)-3-methylphenyl]sulfanyl}methyl)-2-]4-(trifluoromethyl)phenyl]-1,3-thiazol-4-yl}methyl)-1-piperazinecarboxylate ¹H NMR (CDCl₃) 300 MHz δ, 8.00(d, 2H, J=8.28 Hz), 7.68(d, 2H, J=8.28 Hz), 7.26(d, 1H, J=2.21 Hz), 7.14(dd, 1H, J=8.28, 2.21 Hz), 6.59(d, 1H, J=8.55 Hz), 4.73(q, 1H, J=6.71 Hz), 4.32(s, 2H), 4.20(q, 2H, J=7.08 Hz), 3.88(d, 2H, J=6.62 Hz), 3.53(m, 6H), 2.46(br s, 4H), 2.25(s, 3H), 1.94(m, 1H), 1.65(d, 3H, J=6.62 Hz), 1.25(t, 3H, J=7.17 Hz), 0.95(d, 6H, J=6.62 Hz).

Ethyl 2-{2-methyl-4-[({4-{[4-(2-thienylcarbonyl)-1-piperazinyl]methyl}-2-]4-(trifluoromethyl)phenyl]-1,3-thiazol-5-yl}methyl)sulfanyl]phenoxy}propanoate ¹H NMR (CDCl₃) 300 MHz δ 8.01(d, 2H, J=8.28 Hz), 7.68(d, 2H, J=8.28 Hz), 7.45(d, 1H, J=4.97 Hz), 7.30(d, 1H, J=3.59 Hz), 7.25(d, 1H, J=2.21 Hz), 7.15(dd, 1H, J=8.28, 2.21 Hz), 7.05(m, 1H), 6.60(d, 1H, J=8.28 Hz), 4.74(q, 1H, J=6.71 Hz), 4.31(s, 2H), 4.19(q, 2H, J=7.08 Hz), 3.78(t, 4H, J=4.69 Hz), 3.56(s, 2H), 2.55(t, 4H, J=4.69 Hz), 2.25(s, 3H), 1.65(d, 3H, J=6.71 Hz), 1.25(t, 3H, J=7.08 Hz), Phenyl 4-{[5-({[4-(2-ethoxy-1-methyl-2-oxoethoxy)-3-methyl phenyl]sulfanyl}methyl)-2-(4-fluorophenyl)-1,3-thiazol-4-yl]methyl}-1-piperazinecarboxylate ¹H NMR (CDCl₃) 400 MHz δ 7.85(m, 2H), 7.33(m, 2H), 7.15(m, 7H), 6.57(d, 1H, J=8.61 Hz), 4.69(q, 1H, J=6.78 Hz), 4.27(s, 2H), 4.14(q, 2H, J=7.14 Hz), 3.63(br s, 4H), 3.50(s, 2H), 2.49(br s, 4H), 2.23(s, 3H), 1.60(d, 3H, J=6.78 Hz), 1.22(t, 3H, J=7.14 Hz), Ethyl 2-{4-[({4-({4-[4-(dimethylamino)benzoyl]-1-piperazinyl}methyl)-2-]4-(trifluoromethyl)phenyl]-1,3-thiazol-5-yl}methyl)sulfanyl]-2-methylphenoxy}propanoate ¹H NMR (CDCl₃) 300 MHz δ 8.01(d, 2H, J=8.28 Hz), 7.68(d, 2H, J=8.28 Hz), 7.37(d, 2H, J=8.83 Hz), 7.25(d, 1H, J=2.21 Hz), 7.15(dd, 1H, J=8.28, 2.21 Hz), 6.68(d, 2H, J=8.83 Hz), 6.60(d, 1H, J=8.28 Hz), 4.73(q, 1H, J=6.71 Hz), 4.32(s, 2H), 4.20(q, 2H, J=7.17 Hz), 3.67(br s, 4H), 3.55(s, 2H), 3.02(s, 6H), 2.51(br s, 4H), 2.26(s, 3H), 1.65(d, 3H, J=6.71 Hz), 1.25(t, 3H, J=7.17 Hz), Ethyl 2-{4-[({4-{[4-(cyclohexylcarbonyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300 MHz δ 8.00(d, 2H, J=8.28 Hz), 7.68(d, 2H, J=8.28 Hz), 7.26(d, 1H, J=2.21 Hz), 7.14(dd, 1H, J=8.28, 2.21 Hz), 6.59(d, 1H, J=8.28 Hz), 4.73(q, 1H, J=6.71 Hz), 4.30(s, 2H), 4.20(q, 2H, J=7.08 Hz), 3.58(m, 6H), 2.47(m, 5H), 2.26(s, 3H), 1.63(m, 11H), 1.27(m, 5H), Ethyl 2-{2-methyl-4-[({4-({4-[(methylamino)carbonyl]-1-piperazinyl}methyl)-2-[4-(trifluoromethyl)phenyl]-1,3-thiazol-5-yl}methyl)sulfanyl]phenoxy}propanoate ¹H NMR (CDCl₃) 300 MHz δ 8.01(d, 2H, J=8.28 Hz), 7.67(d, 2H, J=8.28 Hz), 7.27(d, 1H, J=2.21 Hz), 7.14(dd, 1H, J=8.55, 2.21 Hz), 6.53(d, 1H, J=8.55 Hz), 4.84(m, 1H), 4.70(q, 1H, J=6.90 Hz), 4.25(m, 4H), 3.52(m, 2H), 3.29(m, 4H), 2.80(d, 3H, J=4.42 Hz), 2.35(t, 4H, J=4.83 Hz), 2.22(s, 3H), 1.64(d, 3H, J=6.90 Hz), 1.25(t, 3H, J=7.17 Hz), Ethyl 2-{4-[({4-({4-[(tert-butylamino)carbonyl]-1-piperazinyl}methyl)-2-]4-(trifluoromethyl)phenyl]-1,3-thiazol-5-yl}methyl)sulfanyl]-2-methylphenoxy}propanoate ¹H NMR (CDCl₃) 300 MHz δ 8.00(d, 2H, J=8.28 Hz), 7.67(d, 2H, J=8.28 Hz), 7.27(d, 1H, J=2.21 Hz), 7.14(dd, 1H, J=8.28, 2.21 Hz), 6.56(d, 1H, J=8.28 Hz), 4.72(q, 1H, J=6.81 Hz), 4.42(s, 1H), 4.33(d, 1H, J=.63 Hz), 4.26(d, 1H, J=63 Hz), 4.20(q, 2H, J=7.08 Hz), 3.53(s, 2H), 3.29(m, 4H), 2.40(t, 4H, J=4.69 Hz), 2.25(s, 3H), 1.63(d, 3H, J=6.81 Hz), 1.35(s, 9H), 1.25(t, 3H, J=7.09 Hz), Ethyl 2-{4-[({4-({4-[(4-methoxyanilino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.05(d, 2H, J=8.28 Hz), 7.73(d, 2H, J=8.28 Hz), 7.23(m, 4H), 6.84(d, 2H, J=6.90 Hz), 6.66(d, 1H, J=8.55 Hz), 4.83(q, 1H, J=6.76 Hz), 4.36(d, 1H, J=63 Hz), 4.30(d, 1H, J=0.63 Hz), 4.16(q, 2H, J=7.08 Hz), 3.75(s, 3H), 3.46(m, 6H), 2.43(t, 4H, J=4.83 Hz), 2.21(s, 3H), 1.58(d, 3H, J=6.76 Hz), 1.20(t, 3H, J=7.08 Hz), Ethyl 2-{2-methyl-4-[({4-[(4-{[(2-phenylethyl)amino]carbonyl}-1-piperazinyl)methyl]-2-[4-(trifluoromethyl)phenyl]-1,3-thiazol-5-yl}methyl)sulfanyl]phenoxy}propanoate $^1$H NMR (CDCl$_3$) 300 MHz δ 8.01(d, 2H, J=8.28 Hz), 7.68(d, 2H, J=8.28 Hz), 7.24(m, 7H), 6.57(d, 1H, J=8.55 Hz), 4.74(m, 2H), 4.33(d, 1H, J□.35 Hz), 4.26(d, 1H, J□.35 Hz), 4.20(q, 2H, J=7.04 Hz), 3.50(m, 4H), 3.28(m, 4H), 2.84(t, 2H, J=7.04 Hz), 2.38(t, 4H, J=4.83 Hz), 2.25(s, 3H), 1.65(d, 3H, J=6.62 Hz), 1.26(t, 3H, J=7.04 Hz), Ethyl 2-{2-methyl-4-[({4-{[4-(phenylsulfonyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300 MHz δ 7.97(d, 2H, J=8.28 Hz), 7.77(d, 2H, J=8.28 Hz), 7.59(m, 5H), 7.20(d, 1H, J=2.21 Hz), 7.10(dd, 1H, J=8.55, 2.21 Hz), 6.58(d, 1H, J=8.55 Hz), 4.73(q, 1H, J=6.71 Hz), 4.19(m, 4H), 3.48(s, 2H), 3.07(br s, 4H), 2.56(br s, 4H), 2.25(s, 3H), 1.65(d, 3H, J=6.71 Hz), 1.25(t, 3H, J=7.04 Hz), Ethyl 2-{2-methyl-4-[({2-[4-(trifluoromethyl)phenyl-4-[(4-{[4-(trifluoromethyl)phenyl]sulfonyl}-1-piperazinyl)methyl]-1,3-thiazol-5-yl}methyl)sulfanyl]phenoxy}propanoate $^1$H NMR (CDCl$_3$) 300 MHz δ 7.98(d, 2H, J=8.28 Hz), 7.90(d, 2H, J=8.55 Hz), 7.81(d, 2H, J=8.55 Hz), 7.67(d, 2H, J=8.28 Hz), 7.21(d, 1H, J=2.21 Hz), 7.10(dd, 1H, J=8.28, 2.21 Hz), 6.58(d, 1H, J=8.28 Hz), 4.74(q, 1H, J=6.71 Hz), 4.21(m, 4H), 3.49(s, 2H), 3.09(br s, 4H), 2.58(br s, 4H), 2.24(s, 3H), 1.66(d, 3H, J=6.71 Hz), 1.26(t, 3H, J=7.17 Hz), Ethyl 2-{4-[({4-({4-[(4-methoxyphenyl)sulfonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ 7.97(d, 2H, J=8.28 Hz), 7.67(m, 4H), 7.20(d, 1H, J=2.21 Hz), 7.09(dd, 1H, J=8.55, 2.21 Hz), 6.99(d, 2H, J=8.83 Hz), 6.58(d, 1H, J=8.55 Hz), 4.74(q, 1H, J=6.71 Hz), 4.20(m, 4H), 3.87(s, 3H), 3.49(s, 2H), 3.05(br s, 4H), 2.54(br s, 4H), 2.24(s, 3H), 1.66(d, 3H, J=6.71 Hz), 1.25(t, 3H, J=7.04 Hz), Ethyl 2-{4-[({4-{[4-(ethylsulfonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.68(d, 2H, J=8.28 Hz), 7.26(d, 1H, J=2.48 Hz), 7.15(d, 1H, J=2.48 Hz), 6.59(d, 1H, J=8.28 Hz), 4.74(q, 1H, J=6.81 Hz), 4.28(s, 2H), 4.20(q, 2H, J=7.17 Hz), 3.55(s, 2H), 3.32(t, 4H, J=4.69 Hz), 2.96(q, 2H, J=7.45 Hz), 2.55(br s, 4H), 2.25(s, 3H), 1.65(d, 3H, J=6.81 Hz), 1.38(t, 3H, J=7.45 Hz), 1.25(t, 3H, J=7.17 Hz), Ethyl 2-{2-methyl-4-[({4-{[4-(methylsulfonyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300 MHz δ 8.00(d, 2H, J=8.55 Hz), 7.68(d, 2H, J=8.55 Hz), 7.26(d, 1H, J=2.21 Hz), 7.15(dd, 1H, J=8.55, 2.21 Hz), 6.59(d, 1H, J=8.55 Hz), 4.73(q, 1H, J=6.71 Hz), 4.27(s, 2H), 4.20(q, 2H, J=7.17 Hz), 3.56(s, 2H), 3.24(t, 4H, J=4.55 Hz), 2.78(s, 3H), 2.58(t, 4H, J=4.55 Hz), 2.24(s, 3H), 1.64(d, 3H, J=6.71 Hz), 1.25(t, 3H, J=7.17 Hz), Ethyl 2-{4-[({4-[(4-{[4-(acetylamino)phenyl]sulfonyl}-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.40(s, 1H), 7.96(d, 2H, J=8.28 Hz), 7.66(m, 6H), 7.16(d, 1H, J=2.21 Hz), 7.07(dd, 1H, J=8.28, 2.21 Hz), 6.56(d, 1H, J=8.28 Hz), 4.73(q, 1H, J=6.71 Hz), 4.22(m, 4H), 3.51(s, 2H), 3.03(br s, 4H), 2.55(br s, 4H), 2.19(m, 6H), 1.65(d, 3H, J=6.71 Hz), 1.27(t, 3H, J=7.04 Hz), Ethyl 2-{4-[({4-({4-[(4-fluorophenyl)sulfonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ 7.97(d, 2H, J=8.28 Hz), 7.77(m, 2H), 7.66(d, 2H, J=8.28 Hz), 7.22(m, 3H), 7.10(dd, 1H, J=8.55, 2.21 Hz), 6.58(d, 1H, J=8.55 Hz), 4.74(q, 1H, J=6.81 Hz), 4.20(m, 4H), 3.49(s, 2H), 3.07(br s, 4H), 2.57(t, 4H, J=4.42 Hz), 2.24(s, 3H), 1.65(d, 3H, J=6.81 Hz), 1.27(t, 3H, J=7.17 Hz), Ethyl 2-{4-[({4-{[4-(2-furoyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.67(d, 2H, J=8.28 Hz), 7.48(s, 1H), 7.24(d, 1H, J=2.21 Hz), 7.15(dd, 1H, J=8.28, 2.21 Hz), 6.99(d, 1H, J=3.59 Hz), 6.60(d, 1H, J=8.28 Hz), 6.48(m, 1H), 4.73(q, 1H, J=6.71 Hz), 4.31(s, 2H), 4.20(q, 2H, J=7.08 Hz), 3.83(br s, 4H), 3.55(s, 2H), 2.54(t, 4H, J=4.83 Hz), 2.25(s, 3H), 1.64(d, 3H, J=6.71 Hz), 1.24(t, 3H, J=7.08 Hz), Ethyl 2-{4-[({4-({4-[(isopropylamino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ, 8.01(d, 2H, J=8.28 Hz), 7.67(d, 2H, J=8.28 Hz), 7.27(d, 1H, J=1.93 Hz), 7.14(ddd, 1H, J=8.55, 2.21, 0.55 Hz), 6.55(d, 1H, J=8.28 Hz), 4.72(q, 1H, J=6.81 Hz), 4.47(d, 1H, J=7.17 Hz), 4.26(m, 4H), 3.99(m, 1H), 3.52(m, 2H), 3.29(m, 4H), 2.37(t, 4H, J=4.69 Hz), 2.24(s, 3H), 1.64(d, 3H, J=6.62 Hz), 1.25(t, 3H, J=7.17 Hz), 1.15(m, 6H),

Ethyl 2-{4-[({4-{[4-(methoxyacetyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.67(d, 2H, J=8.28 Hz), 7.24(d, 1H, J=2.21 Hz), 7.14(dd, 1H, J=8.28, 2.21 Hz), 6.58(d, 1H, J=8.28 Hz), 4.73(q, 1H, J=6.71 Hz), 4.29(s, 2H), 4.20(q, 2H, J=7.17 Hz), 4.10(s, 2H), 3.64(m, 2H), 3.54(s, 2H), 3.48(m, 2H), 3.42(s, 3H), 2.47(m, 4H), 2.25(s, 3H), 1.64(d, 3H, J=6.71 Hz), 1.24(t, 3H, J=7.17 Hz),

Ethyl 2-{(4-[({4-[(4-isobutyryl-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.68(d, 2H, J=8.28 Hz), 7.24(d, 1H, J=2.48 Hz), 7.14(dd, 1H, J=8.55, 2.48 Hz), 6.59(d, 1H, J=8.55 Hz), 4.74(q, 1H, J=6.71 Hz), 4.30(s, 2H), 4.20(q, 2H, J=7.17 Hz), 3.58(m, 6H), 2.79(m, 1H), 2.46(t, 4H, J=4.55 Hz), 2.24(s, 3H), 1.64(d, 3H, J=6.71 Hz), 1.24(t, 3H, J=7.17 Hz), 1.13(d, 6H, J=6.71 Hz),

Ethyl 2-{4-[({4-{[4-(2,2-dimethylpropanoyl)-1-piperazinyl]methyl}-2-]4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.68(d, 2H, J=8.28 Hz), 7.24(d, 1H, J=2.21 Hz), 7.15(dd, 1H, J=8.28, 2.21 Hz), 6.60(d, 1H, J=8.28 Hz), 4.73(q, 1H, J=6.71 Hz), 4.31(s, 2H), 4.20(q, 2H, J=7.08 Hz), 3.66(t, 4H, J=4.69 Hz), 3.52(s, 2H), 2.48(t, 4H, J=4.69 Hz), 2.26(s, 3H), 1.65(d, 3H, J=6.71 Hz), 1.27(m, 12H),

Ethyl 2-{4-[({4-({4-[(4-fluoroanilino)carbonyl]-1-piperazinyl}methyl)-2-]4-(trifluoromethyl)phenyl]-1,3-thiazol-5-yl}methyl)sulfanyl]-2-methylphenoxy}propanoate $^1$H NMR (CDCl$_3$) 300 MHz δ 8.04(d, 2H, J=8.28 Hz), 7.69(d, 2H, J=8.28 Hz), 7.33(m, 2H), 7.17(dd, 1H, J=8.55, 2.21 Hz), 6.96(m, 2H), 6.52(d, 1H, J=8.55 Hz), 4.72(q, 1H, J=6.90 Hz), 4.27(m, 4H), 3.59(d, 1H, J□.52 Hz), 3.51(d, 1H, J□.52 Hz), 3.34(m, 4H), 2.33(t, 4H, J=4.97 Hz), 2.22(s, 3H), 1.62(d, 3H, J=6.90 Hz), 1.26(t, 3H, J=7.17 Hz),

Ethyl 2-{4-[({4-({4-[(3-methoxyanilino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.04(d, 2H, J=8.28 Hz), 7.69(d, 2H, J=8.28 Hz), 7.31(d, 1H, J=2.21 Hz), 7.16(m, 2H), 6.89(m, 2H), 6.59(dd, 1H, J=8.28, 2.21 Hz), 6.53(m, 1H), 4.73(q, 1H, J=6.90 Hz), 4.27(m, 4H), 3.79(s, 3H), 3.56(m, 2H), 3.37(m, 4H), 2.36(t, 4H, J=4.69 Hz), 2.23(s, 3H), 1.63(d, 3H, J=6.90 Hz), 1.26(t, 3H, J=7.17 Hz),

Ethyl 2-{4-[({4-{[4-(aminocarbonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.01(d, 2H, J=8.28 Hz), 7.68(d, 2H, J=8.28 Hz), 7.26(d, 1H, J=2.21 Hz), 7.15(dd, 1H, J=8.55, 2.21 Hz), 6.56(d, 1H, J=8.55 Hz), 4.83(s, 2H), 4.71(q, 1H, J=6.81 Hz), 4.26(m, 4H), 3.55(m, 2H), 3.34(m, 4H), 2.41(t, 4H, J=4.55 Hz), 2.24(s, 3H), 1.63(d, 3H, J=6.81 Hz), 1.25(t, 3H, J=7.04 Hz),

Ethyl 2-{4-[({4-({4-[(cyclohexylamino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300 MHz δ 8.00(d, 2H, J=8.28 Hz), 7.67(d, 2H, J=8.28 Hz), 7.26(d, 1H, J=2.21 Hz), 7.14(dd, 1H, J=8.55, 2.21 Hz), 6.54(d, 1H, J=8.55 Hz), 4.72(q, 1H, J=6.81 Hz), 4.49(d, 1H, J=7.45 Hz), 4.25(m, 4H), 3.64(m, 1H), 3.52(m, 2H), 3.28(m, 4H), 2.38(t, 4H, J=4.83 Hz), 2.24(s, 3H), 1.95(m, 2H), 1.65(m, 7H), 1.38(m, 2H), 1.24(t, 3H, J=7.04 Hz), 1.10(m, 2H),

Ethyl 2-{2-methyl-4-[({4-({4-[(propylamino)carbonyl]-1-piperazinyl}methyl)-2-[4-(trifluoromethyl)phenyl]-1,3-thiazol-5-yl}methyl)sulfanyl]phenoxy}propanoate $^1$H NMR (CDCl$_3$) 300 MHz δ 8.01(d, 2H, J=8.00 Hz), 7.68(d, 2H, J=8.00 Hz), 7.27(d, 1H, J=2.21 Hz), 7.14(dd, 1H, J=8.28, 2.21 Hz), 6.54(d, 1H, J=8.28 Hz), 4.75(m, 2H), 4.26(m, 4H), 3.53(m, 2H), 3.33(m, 4H), 3.19(m, 2H), 2.36(t, 4H, J=4.69 Hz), 2.23(s, 3H), 1.64(d, 3H, J=6.90 Hz), 1.52(m, 2H), 1.25(t, 3H, J=7.17 Hz), 0.92(t, 3H, J=7.45 Hz),

Ethyl 2-{4-[({4-({4-[(ethylamino)carbonyl]-1-piperazinyl}methyl)-2-]4-(trifluoromethyl)phenyl]-1,3-thiazol-5-yl}methyl)sulfanyl]-2-methylphenoxy}propanoate $^1$H NMR (CDCl$_3$) 300 MHz δ 8.02(d, 2H, J=8.28 Hz), 7.69(d, 2H, J=8.28 Hz), 7.27(d, 1H, J=2.21 Hz), 7.15(dd, 1H, J=8.55, 2.21 Hz), 6.54(d, 1H, J=8.55 Hz), 4.72(m, 2H), 4.26(m, 4H), 3.54(m, 2H), 3.29(m, 6H), 2.38(t, 4H, J=4.28 Hz), 2.25(s, 3H), 1.65(d, 3H, J=6.90 Hz), 1.26(t, 3H, J=7.04 Hz), 1.15(t, 3H, J=7.31 Hz),

Ethyl [2-methyl-4-({[4-{[3-(5-methyl-1,2,4-oxadiazol-3-yl)phenoxy]methyl}-2-(4-[(trifluoromethyl)phenyl)-1,3-thiazol-5-yl]methyl}sulfanyl)phenoxy]acetate To a stirred solution of ethyl [4-({[4-(hydroxymethyl)-2-(4-{trifluoromethyl}phenyl)-1,3-thiazol-5-yl]methyl}sulfanyl)-2-methylphenoxy]acetate (40 mg, 0.08 mmoles, 1 eq) in dry toluene (2 ml) was added 3-(5-methyl-1,2,4-oxadiazol-3-yl)phenol (15 mg, 0.088 mmoles, 1.1 eq) followed by triphenylphosphine (25 mg, 0.096 mmoles, 1.2 eq) as a solid. Diisopropylazodicarboxylate (0.017 ml, 0.088 mmoles, 1.1 eq) was then added dropwise and the reaction was stirred for 2 hours at room temperature. The reaction was then partitioned between EtOAc and H$_2$O. After the separation of the phases the organic phase was washed with 0.1N NaOH, brine, dried over Na$_2$SO$_4$, filtered, concentrated in vacuo and purified via flash chromatography (10% EtOAc/Hexanes to 35% EtOAc/Hexanes) to yield 40 mg (76%) of product.

$^1$H (CDCl$_3$) 400 MHz δ 8.02(d, 2H, J=8.20 Hz), 7.68(m, 4H), 7.38(t, 1H, J=7.95 Hz), 7.19(d, 1H, J=1.54), 7.12(dd, 1H, J=8.37, 2.39 Hz), 7.06(dd, 1H, J=8.20, 2.39 Hz), 6.57(d, 1H, J=8.20 Hz), 4.95(s, 2H), 4.59(s, 2H), 4.27(s, 2H), 4.22(q, 2H, J=7.12 Hz), 2.65(s, 3H), 2.18(s, 3H), 1.25(t, 3H, J=7.12 Hz). TLC(50% EtOAc/Hexanes) R$_f$=0.76

The following compounds were made using the general Mitsunobu reaction conditions detailed above:

Ethyl 2-{2-methyl-4-[({4-{[3-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoate $^1$H NMR (CDCl$_3$) 400 MHz δ 8.03(d, 2H, J=8.20 Hz), 7.69(m, 4H), 7.39(m, 1H), 7.20(m, 1H), 7.09(m, 2H), 6.55 (d, 1H, J=8.37 Hz), 4.99(d, 1H, J□.62 Hz), 4.95(d, 1H, J□.62 Hz), 4.70(q, 1H, J=6.78 Hz), 4.16(q, 2H, J=7.18 Hz), 2.65(m, 3H), 2.18(s, 3H), 1.61(d, 3H, J=6.78 Hz), 1.20(t, 3H, J=7.18 Hz), Ethyl (2-methyl-4-{[(4-{[3-(5-methyl-1,2,4-oxadiazol-3-yl)phenoxy]methyl}-2-phenyl)-1,3-thiazol-5-yl)methyl]sulfanyl}phenoxy)acetate $^1$H NMR (CDCl$_3$) 400 MHz δ 7.91(m, 2H), 7.69(m, 2H), 7.40(m, 4H), 7.20(d, 1H, J=2.39 Hz), 7.13(dd, 1H, J=8.37, 2.39 Hz), 7.07(dd, 1H, J=8.37, 2.39 Hz), 6.57(d, 1H, J=8.37 Hz), 5.29(s, 2H), 4.59(s, 2H), 4.27(s, 2H), 4.23(q, 2H, J=7.18 Hz), 2.65(s, 3H), 2.19(s, 3H), 1.27(t, 3H, J=7.18 Hz).

Ethyl [2-methyl-4-({[2-(4-{trifluoromethyl}phenyl)-4-(phenoxymethyl)-1,3-thiazol-5-yl]methyl}sulfanyl)phenoxy]acetate $^1$H NMR (CDCl$_3$) 300 MHz δ 8.04(d, 2H, J=8.23 Hz), 7.71(d, 2H, J=8.23 Hz), 7.34(m, 2H), 7.23(d, 1H, J=2.39 Hz), 7.15(dd, 1H, J=8.49, 2.39 Hz), 7.00(m, 3H), 6.59(d, 1H, J=8.49 Hz), 4.94(s, 2H), 4.64(s, 2H), 4.27(m, 4H), 2.26(s, 3H), 1.32(t, 3H, J=7.17 Hz). TLC(30% EtOAc/Hexanes) R$_f$=0.71

Ethyl [2-methyl-4-({[4-[(2-methylphenoxy)methyl]-2-(4-{trifluoromethyl}phenyl)-1,3-thiazol-5-yl]methyl}sulfanyl)phenoxy]acetate $^1$H (CDCl$_3$) 300 MHz δ 8.05(d, 2H, J=8.23 Hz), 7.72(d, 2H, J=8.23 Hz), 7.21(m, 4H), 6.93(m, 2H), 6.59(d, 1H, J=8.49 Hz), 5.00(s, 2H), 4.64(s, 2H), 4.29(m, 4H), 2.26(m, 6H), 1.32(t, 3H, J=7.17 Hz). TLC(20% EtOAc/Hexanes) R$_f$=0.70

Ethyl [2-methyl-4-({[4-(3-methylphenoxy)methyl]-2-(4-{trifluoromethyl}phenyl)-1,3-thiazol-5-yl]methyl}sulfanyl)phenoxy]acetate $^1$H (CDCl$_3$) 300 MHz δ 8.05(d, 2H, J=8.49 Hz), 7.71(d, 2H, J=8.49 Hz), 7.35(m, 1H), 7.26(dd, 1H, J=2.39, 0.53 Hz), 7.21(t, 1H, J=7.43 Hz), 7.15(ddd, 1H, J=8.49, 2.39, 0.53 Hz), 6.81(m, 2H), 6.60(d, 1H, J=8.49 Hz), 4.92(s, 2H), 4.65(s, 2H), 4.29(m, 4H), 2.38(s, 3H), 2.25(s, 3H), 1.32(t, 3H, J=7.17 Hz). TLC(20% EtOAc/Hexanes) R$_f$=0.70

Ethyl [2-methyl-4-({[4-[(4-methylphenoxy)methyl]-2-(4-{trifluoromethyl}phenyl)-1,3-thiazol-5-yl]methyl}sulfanyl)phenoxy]acetate $^1$H (CDCl$_3$) 300 MHz δ 8.04(d, 2H, J=8.23 Hz), 7.71(d, 2H, J=8.23 Hz), 7.27(dd, 1H, J=2.39, 0.80 Hz), 7.14(m, 3H), 6.88(d, 2H, J=8.49 Hz), 6.60(d, 1H, J=8.23 Hz), 4.92(s, 2H), 4.64(s, 2H), 4.29(m, 4H), 2.33(s, 3H), 2.26(s, 3H), 1.32(t, 3H, J=7.17 Hz). TLC(20% EtOAc/Hexanes) R$_f$=0.70

Ethyl [4-({[4-[(3-cyanophenoxy)methyl]-2-(4-{trifluoromethyl}phenyl)-1,3-thiazol-5-yl]methyl}sulfanyl)-2-methyl phenoxy]acetate $^1$H (CDCl$_3$) 300 MHz δ 8.03(d, 2H, J=8.23 Hz), 7.71(d, 2H, J=8.23 Hz), 7.24(m, 6H), 6.61(d, 1H, J=8.23 Hz), 4.88(s, 2H), 4.67(s, 2H), 4.28(m, 4H), 2.24(s, 3H), 1.31(t, 3H, J=7.17 Hz) TLC(20% EtOAc/Hexanes) R$_f$=0.52

Ethyl [4-({[4-[(4-cyanophenoxy)methyl]-2-(4-{trifluoromethyl}phenyl)-1,3-thiazol-5-yl]methyl}sulfanyl)-2-methylphenoxy]acetate $^1$H (CDCl$_3$) 300 MHz δ 8.03(d, 2H, J=8.23 Hz), 7.73(d, 2H, J=8.23 Hz), 7.61(d, 2H, J=9.03 Hz), 7.23(dd, 1H, J=2.39, 0.53 Hz), 7.14(ddd, 1H, J=8.49, 2.39, 0.53 Hz), 7.01(d, 2H, J=9.03 Hz), 6.59(d, 1H, J=8.49 Hz), 4.91(s, 2H), 4.66(s, 2H), 4.28(m, 4H), 2.25(s, 3H), 1.32(t, 3H, J=7.17 Hz). TLC(20% EtOAc/Hexanes) R$_f$=0.52

Ethyl [2-methyl-4-({[4-{[4-(5-methyl-1,2,4-oxadiazol-3-yl)phenoxy]methyl}-2-(4-{trifluoro}methylphenyl)-1,3-thiazol-5-yl]methyl}sulfanyl)phenoxy]acetate $^1$H (CDCl$_3$) 400 MHz δ 7.99(m, 4H), 7.67(d, 2H, J=8.20 Hz), 7.21(dd, 1H, J=2.39, 0.68 Hz), 7.10(m, 1H), 7.02(m, 2H), 6.54(d, 1H, J=8.37 Hz), 4.90(s, 2H), 4.59(s, 2H), 4.23(m, 4H), 2.62(s, 3H), 2.20(s, 3H), 1.26(t, 3H, J=7.18 Hz). TLC(50% EtOAc/Hexanes) R$_f$=0.68

Ethyl (2-methyl-4-{[(4-{[4-(5-methyl-1,2,4-oxadiazol-3-yl)phenoxy]methyl}-2-phenyl-1,3-thiazol-5-yl)methyl]sulfanyl}phenoxy)acetate $^1$H NMR (CDCl$_3$) 400 MHz δ 7.98(d, 2H, J=8.89 Hz), 7.89(m, 2H), 7.42(m, 3H), 7.21(d, 1H, J=2.39 Hz), 7.10(dd, 1H, J=8.37, 2.39 Hz), 7.02(d, 2H, J=8.89 Hz), 6.54(d, 1H, J=8.37 Hz), 4.89(s, 2H), 4.59(s, 2H), 4.23(q, 2H, J=7.18 Hz), 3.47(s, 2H), 2.62(s, 3H), 2.20(s, 3H), 1.27(t, 3H, J=7.18 Hz), Ethyl 2-{2-methyl-4-[({4-{[4-(5-methyl-1,2,4-oxadiazol-3-yl)phenoxy]methyl}-2-]4-(trifluoromethyl)phenyl]-1,3-thiazol-5-yl}methyl)sulfanyl]phenoxy}propanoate $^1$H NMR (CDCl$_3$) 300 MHz δ 8.04(m, 4H), 7.71(d, 2H, J=8.23 Hz), 7.25(d, 1H, J=2.39 Hz), 7.11(dd, 1H, J=8.49, 2.39 Hz), 7.06(d, 2H, J=9.03 Hz), 6.57(d, 1H, J=8.49 Hz), 4.97(d, 1H, J□.68 Hz), 4.91(d, 1H, J□.68 Hz), 4.73(q, 1H, J=6.81 Hz), 4.29(s, 2H), 4.20(q, 2H, J=7.17 Hz), 2.67(s, 3H), 2.23(s, 3H), 1.65(d, 3H, J=6.81 Hz), 1.25(t, 3H, J=7.17 Hz), Ethyl 2-(2-methyl-4-{[(4-{[4-(5-methyl-1,2,4-oxadiazol-3-yl)phenoxy}methyl-2-phenyl-1,3-thiazol-5-yl)methyl]sulfanyl}phenoxy)propanoate $^1$H NMR (CDCl$_3$) 400 MHz δ 7.99(d, 2H, J=9.06 Hz), 7.89(m, 2H), 7.42(m, 3H), 7.20(d, 1H, J=2.22 Hz), 7.06(dd, 1H, J=8.37, 2.22 Hz), 7.02(d, 2H, J=9.06 Hz), 6.52(d, 1H, J=8.37 Hz), 4.89(d, 1H, J□.62 Hz), 4.85(d, 1H, J□.62 Hz), 4.68(q, 1H, J=6.78 Hz), 4.23(s, 2H), 4.17(q, 2H, J=7.12 Hz), 2.62(s, 2H), 2.19(s, 3H), 1.61(d, 3H, J=6.78 Hz), 1.21(t, 3H, J=7.12 Hz),

4-(Chloromethyl)-2-methylphenyl methyl ether

To a stirred solution of (4-methoxy-3-methylphenyl)methanol (2.31 g, 15.18 mmoles, 1 eq) in anhydrous $CH_2Cl_2$ (50 ml, 0.3M) was added hexachloroethane (3.59 g, 15.18 mmoles, 1 eq) and triphenylphosphine (3.98 g, 15.18 mmoles, 1 eq). This mixture was stirred at room temperature overnight at which point the reaction was transferred to a separatory funnel and washed with $H_2O$, brine, dried over $Na_2SO_4$, filtered, concentrated in vacuo and filtered through a plug of silica gel (30% EtOAc/Hexanes) to yield 2.59 g (100%) of product.

$^1$H NMR ($CDCl_3$) 400 MHz δ 7.16(m, 2H), 6.76(d, 1H, J=8.10 Hz), 4.52(s, 2H), 3.81 (s, 3H), 2.19(s, 3H),

(4-Methoxy-3-methylbenzyl)(triphenyl)phosphonium chloride

To a 250 ml round-bottom flask equipped with a magnetic stir-bar and $N_2$ inlet was added 4-(Chloromethyl)-2-methylphenyl methyl ether (2.59 g, 15.18 mmoles, 1 eq), dry toluene (50 ml, 0.3M) and triphenylphosphine (3.98 g, 15.18 mmoles, 1 eq). The reaction mixture was refluxed overnight. After cooling to room temperature the solvent was removed in vacuo, the residue washed with hexanes and the solid/liquid mixture was filtered to yield 4.48 g (71%) of solid product.

$^1$H NMR ($CDCl_3$) 400 MHz δ 7.66(m, 15H), 6.93(m, 1H), 6.54(m, 2H), 5.24(d, 2H, J□.79 Hz), 3.68(s, 3H), 1.90(s, 3H),

4-[(Tetrahydro-2H-pyran-2-yloxy)methyl]-2-[4-(trifluoromethyl)phenyl]-1,3-thiazole-5-carbaldehyde To a stirred mixture of pyridinium chlorochromate (6.9 g, 32.12 mmoles, 4 eq) in dry $CH_2Cl_2$ (40 ml, 0.2M) was added {4-[(tetrahydro-2H-pyran-2-yloxy)methyl]-2-[4-(trifluoromethyl)phenyl]-1,3-thiazol-5-yl}methanol (3.0 g, 8.03 mmoles, 1 eq) in $CH_2Cl_2$ (10 ml). The mixture was stirred at room temperature for 4 hours at which time the reaction mixture was quenched by allowing it to stir with sat. $NaHCO_3$. Once the quenching had ceased the reaction was filtered through Celite and the filtrate was transferred to a separatory funnel where the phases were separated. The organic phase was dried over $Na_2SO_4$ and concentrated in vacuo to yield 2.18 g (73%) of clean aldehyde. The crude product was used without purification.

$^1$H NMR ($CDCl_3$) 400 MHz δ 10.39(s, 1H), 8.09(d, 2H, J=8.28 Hz), 7.70(d, 2H, J=8.28 Hz), 5.22(d, 1H, J□.97 Hz), 4.96(d, 1H, J□.97 Hz), 4.83(m, 1H), 3.87(m, 1H), 3.58(m, 1H), 1.81(m, 2H), 1.61(m, 4H),

5-[(E)-2-(4-Methoxy-3-methylphenyl)ethenyl]-4-[(tetrahydro-2H-pyran-2-yloxy)methyl]-2-[4-(trifluoromethyl)phenyl]-1,3-thiazole To a suspension of NaH (60% dispersion in mineral oil, 242 mg, 6.32 mmoles, 1.4 eq) in dry $CH_2Cl_2$ (15 ml) was added (4-Methoxy-3-methylbenzyl)(triphenyl)phosphonium chloride (2.62 g, 6.32 mmoles, 1.4 eq). This was allowed to stir at room temperature for 1.5 hours followed by the dropwise addition of 4-[(tetrahydro-2H-pyran-2-yloxy)methyl]-2-[4-(trifluoromethyl)phenyl]-1,3-thiazole-5-carbaldehyde (1.68 g, 4.51 mmoles, 1 eq) in anhydrous carbon tetrachloride (25 ml). The resulting reaction mixture was refluxed overnight at which point (after cooling to room temperature) the reaction was washed with 1N NaOH, $H_2O$, brine, dried over $Na_2SO_4$ and concentrated in vacuo to yield a >100% yield of a light green oil. The crude material was used without purification.

$^1$H NMR ($CDCl_3$) 400 MHz δ 8.05(d, 2H, J=8.24 Hz), 7.68(d, 2H, J=8.24 Hz), 7.29(m, 3H), 6.85(m, 2H), 4.98(d, 1H, J=12.09 Hz), 4.81(m, 2H), 4.01(m, 1H), 3.86(s, 3H), 3.62(m, 1H), 2.26(s, 3H), 1.72(m, 6H),

{5-[2-(4-Methoxy-3-methylphenyl)ethyl]-2-[4-(trifluoromethyl)phenyl]-1,3-thiazol-4-yl}methanol To a stirred solution of 5-[(E)-2-(4-Methoxy-3-methylphenyl)ethenyl]-4-[(tetrahydro-2H-pyran-2-yloxy)methyl]-2-[4-(trifluoromethyl)phenyl]-1,3-thiazole (2.20 g, 4.51 mmoles, 1 eq) in EtOH (50 ml, 0.1M) was added 10% Pd/C (500 mg). The system was degassed using an aspirator and $H_2$ was introduced via a balloon. The reaction was heated to 60° C. overnight which, after cooling to room temperature, was filtered through Celite, washed with EtOAc and concentrated in vacuo. This reaction yielded after chromatography 760 mg (41%) of clean alcohol.

$^1$H NMR ($CDCl_3$) 400 MHz δ 7.98(d, 2H, J=8.24 Hz), 7.66(d, 2H, J=8.24 Hz), 6.91(m, 2H), 6.72(d, 1H, J=8.10 Hz), 4.54(s, 2H), 3.80(s, 3H), 3.11(t, 2H, J=7.42 Hz), 2.87(t, 2H, J=7.42 Hz), 2.18(s, 3H), 2.05(br s, 1H),

4-(Bromomethyl)-5-[2-(4-methoxy-3-methylphenyl)ethyl]-2-[4-(trifluoromethyl)phenyl]-1,3-thiazole To a 100 ml round-bottom flask equipped with a magnetic stir-bar and $N_2$ inlet was added {5-[2-(4-Methoxy-3-methylphenyl)ethyl]-2-[4-(trifluoromethyl)phenyl]-1,3-thiazol-4-yl}methanol (0.708 g, 1.74 mmoles, 1 eq), $CH_2Cl_2$ (20 ml), carbon tetrabromide (0.634 g, 1.91 mmoles, 1.1 eq) and triphenylphosphine (0.501 g, 1.91 mmoles, 1.1 eq) in that order. The reaction was stirred overnight at which time it was diluted with $CH_2Cl_2$ and washed with $H_2O$, brine, dried over $Na_2SO_4$, concentrated in vacuo and purified via silica gel chromatography to yield 573 mg (70%) of product.

$^1$H NMR ($CDCl_3$) 400 MHz δ 7.97(d, 2H, J=8.10 Hz), 7.64(d, 2H, J=8.10 Hz), 6.94(m, 2H), 6.73(d, 1H, J=8.10 Hz), 4.46(m, 2H), 3.79(m, 3H), 3.12(t, 2H, J=7.24 Hz), 2.91(t, 2H, J=7.24 Hz), 2.19(s, 3H),

4-(2-{4-(Bromomethyl)-2-[4-(trifluoromethyl)phenyl]-1,3-thiazol-5-yl}ethyl)-2-methylphenol To a 50 ml round-bottom flask equipped with a magnetic stir-bar, an addition funnel and $N_2$ inlet was added 4-(Bromomethyl)-5-[2-(4-methoxy-3-methylphenyl)ethyl]-2-[4-(trifluoromethyl)phenyl]-1,3-thiazole (468 mg, 1.0 mmoles, 1 eq) and dry $CH_2Cl_2$ (15 ml, 0.1M). The mixture was cooled to −78° C. (dry ice/acetone) after which boron tribromide (1M in $CH_2Cl_2$, 3 ml, 3.0 mmoles, 3 eq) was added dropwise over the course of 15 minutes. After the addition was complete, the cold bath was removed and the reaction was allowed to warm to room temperature and stirred for 1 hour. After this time, the reaction was cooled to 0° C. and quenched very carefully with water. Once the reaction was quenched, it was transferred to a separatory funnel where the phases were separated. The aqueous fraction was washed three times with $CH_2Cl_2$ and the combined organic fractions were dried over $Na_2SO_4$, filtered, concentrated in vacuo to yield a quantitative yield of the titled phenol. The product was used without purification.

$^1$H NMR ($CDCl_3$) 400 MHz δ 7.96(d, 2H, J=8.28 Hz), 7.65(d, 2H, J=8.28 Hz), 6.93(m, 1H), 6.85(d, 1H, J=8.10

Hz), 6.68(d, 1H, J=8.10 Hz), 5.42(br s, 1H), 4.45(s, 2H), 3.10(t, 2H, J=7.41 Hz), 2.89(t, 2H, J=7.41 Hz), 2.20(s, 3H),

The following compounds were made by amine displacement as described above for General Alkylation with an Amine:

4-(2-{4-{[4-(4-Methoxyphenyl)-1-piperazinyl]methyl}-2-[4-(trifluoromethyl)phenyl]-1,3-thiazol-5-yl}ethyl)-2-methylphenol $^1$H NMR (CDCl$_3$) 400 MHz δ 7.94(d, 2H, J=8.28 Hz), 7.59(d, 2H, J=8.28 Hz), 6.91(d, 1H, J=2.24 Hz), 6.86(d, 2H, J=9.31 Hz), 6.80(d, 2H, J=9.31 Hz), 6.74(dd, 1H, J=8.10, 2.24 Hz), 6.58(s, 1H), 6.51(d, 1H, J=8.10 Hz), 3.73(s, 3H), 3.58(s, 2H), 3.12(t, 2H, J=7.50 Hz), 3.05(t, 4H, J=4.48 Hz), 2.84(t, 2H, J=7.50 Hz), 2.64(t, 4H, J=4.48 Hz), 2.20(s, 3H),

1-{4-[4-({5-[2-(4-Hydroxy-3-methylphenyl)ethyl]-2-[4-(trifluoromethyl)phenyl]-1,3-thiazol-4-yl}methyl)-1-piperazinyl]phenyl}ethanone $^1$H NMR (CD$_3$OD) 400 MHz δ 8.07(d, 2H, J=8.28 Hz), 7.85(d, 2H, J=9.14 Hz), 7.73(d, 2H, J=8.28 Hz), 6.92(d, 2H, J=9.14 Hz), 6.88(d, 1H, J=2.24 Hz), 6.77(dd, 1H, J=8.28, 2.24 Hz), 6.60(d, 1H, J=8.28 Hz), 3.49(s, 2H), 3.32(t, 4H, J=4.83 Hz), 3.18(t, 2H, J=7.07 Hz), 2.88(t, 2H, J=7.07 Hz), 2.51(t, 4H, J=4.83 Hz), 2.47(s, 3H), 2.10(s, 3H),

4-(2-{4-{[4-(3-Methoxyphenyl)-1-piperazinyl]methyl}-2-[4-(trifluoromethyl)phenyl]-1,3-thiazol-5-yl}ethyl)-2-methylphenol $^1$H NMR (CD$_3$OD) 400 MHz δ 8.07(d, 2H, J=8.10 Hz), 7.72(d, 2H, J=8.10 Hz), 7.09(t, 1H, J=8.28 Hz), 6.88(s, 1H), 6.77(dd, 1H, J=8.45, 2.24 Hz), 6.59(d, 1H, J=8.45 Hz), 6.51 (dd, 1H, J=8.28, 2.24 Hz), 6.46(t, 1H, J=2.24 Hz), 6.38(dd, 1H, J=8.28, 2.24 Hz), 3.72(s, 3H), 3.49(s, 2H), 3.18(t, 2H, J=6.47 Hz), 3.09(br s, 4H), 2.87(t, 2H, J=6.47 Hz), 2.52(br s, 4H), 2.10(s, 3H),

4-(2-{4-{[4-(4-Chlorophenyl)-1-piperazinyl]methyl}-2-[4-(trifluoromethyl)phenyl]-1,3-thiazol-5-yl}ethyl)-2-methylphenol $^1$H NMR (CD$_3$OD) 400 MHz δ 8.07(d, 2H, J=8.10 Hz), 7.73(d, 2H, J=8.10 Hz), 7.15(d, 2H, J=9.14 Hz), 6.89(m, 3H), 6.77(dd, 1H, J=8.45, 2.41 Hz), 6.59(d, 1H, J=8.45 Hz), 3.49(s, 2H), 3.18(t, 2H, J=7.16 Hz), 3.09(t, 4H, J=5.09 Hz), 2.87(t, 2H, J=7.16 Hz), 2.53(t, 4H, J=5.09 Hz), 2.10(s, 3H),

2-[4-(2-{4-{[4-(4-Methoxyphenyl)-1-piperazinyl] methyl}-2-[4-(trifluoromethyl)phenyl]-1,3-thiazol-5-yl}ethyl)-2-methylphenoxy]-2-methylpropanoic acid To a 25 ml round-bottom flask equipped with a magnetic stir-bar and N$_2$ inlet was added 4-(2-{4-{[4-(4-Methoxyphenyl)-1-piperazinyl]methyl}-2-[4-(trifluoromethyl)phenyl]-1,3-thiazol-5-yl}ethyl)-2-methylphenol (53 mg, 0.094 mmoles, 1 eq) in acetone (2 ml, 0.05M) followed by the addition of 2-trichloromethyl-2-propanol (33 mg, 0.188 mmoles, 2 eq) and NaOH (pellets, 30 mg, 0.752 mmoles, 8 eq). This was stirred at room temperature overnight after which the acetone was removed in vacuo and the resulting residue was partitioned between EtOAc and 1N HCl. The phases were then separated and the organic fraction was washed with brine, dried over Na$_2$SO$_4$ and concentrated in vacuo to yield after chromatography 23 mg (40%) of product.

$^1$H NMR (CDCl$_3$) 400 MHz δ 7.95(d, 2H, J=8.28 Hz), 7.62(d, 2H, J=8.28 Hz), 6.88(m, 5H), 6.67(br s, 1H), 6.54(br s, 1H), 3.72(s, 3H), 3.61(s, 2H), 3.23(m, 8H), 2.80(m, 4H), 2.15(s, 3H), 1.54(s, 6H),

MS(ES$^-$) M–H=652.2

The following compounds were also made by alkylation of a phenol with trichloromethyl-2-propanol as above:

2-[4-(2-{4-{[4-(4-Chlorophenyl)-1-piperazinyl]methyl}-2-[4-(trifluoromethyl)phenyl]-1,3-thiazol-5-yl}ethyl)-2-methylphenoxy]-2-methylpropanoic acid $^1$H NMR (CD$_3$OD) 400 MHz δ 7.99(d, 2H, J=8.28 Hz), 7.66(d, 2H, J=8.28 Hz), 7.55(s, 1H), 7.14(d, 2H, J=8.10 Hz), 6.91(s, 1H), 6.82(d, 2H, J=8.10 Hz), 6.66(br s, 1H), 3.55(s, 2H), 3.28(m, 2H) buried under MeOH signal, 3.12(br s, 4H), 2.85(s, 2H), 2.65(br s, 4H), 2.13(s, 3H), 1.52(s, 6H),

MS(ES$^+$) M+H=659.0

2-[4-(2-{4-{[4-(3-Methoxyphenyl)-1-piperazinyl] methyl}-2-[4-(trifluoromethyl)phenyl]-1,3-thiazol-5-yl}ethyl)-2-methylphenoxy]-2-methylpropanoic acid $^1$H NMR (CD$_3$OD) 400 MHz δ 8.02(d, 2H, J=8.10 Hz), 7.68(d, 2H, J=8.10 Hz), 7.09(t, 1H, J=8.10 Hz), 6.92(s, 1H), 6.76(m, 2H), 6.50(dd, 1H, J=8.10, 2.07 Hz), 6.42(t, 1H, J=2.07 Hz), 6.37(dd, 1H, J=8.10, 2.07 Hz), 3.72(s, 3H), 3.51(s, 2H), 3.28(m, 2H) buried under MeOH signal, 3.12 (m, 4H), 2.83(t, 2H, J=7.16 Hz), 2.61(m, 4H), 2.15(s, 3H), 1.48(s, 6H),

MS(ES$^-$) M–H=652.1

2-[4-(2-{4-{[4-(4-Acetylphenyl)-1-piperazinyl]methyl}-2-[4-(trifluoromethyl)phenyl]-1,3-thiazol-5-yl}ethyl)-2-methylphenoxy]-2-methylpropanoic acid $^1$H NMR (CD$_3$OD) 400 MHz δ 8.01(d, 2H, J=8.10 Hz), 7.82(d, 2H, J=9.14 Hz), 7.67(d, 2H, J=8.10 Hz), 6.90(m, 3H), 6.66(m, 2H), 3.61 (s, 2H), 3.37(br s, 4H), 3.13(t, 2H, J=6.81 Hz), 2.82(t, 2H, J=6.81 Hz), 2.68(br s, 4H), 2.44(s, 3H), 2.11(s, 3H), 1.50(s, 6H),

2-Methyll-2-{2-methyl-4-[({4-[4-(trifluoromethyl) benzyl]-2-[4-(trifluoromethyl)phenyl]-1,3-thiazol-5-yl}methyl)sulfanyl]phenoxy}propanoic acid From 2-methyl-4-[({4-(4-trifluoromethyl)benzyl]-2-[4-(trifluoromethyl)phenyl]-1,3-thiazol-5-yl}methyl)sulfanyl] phenol (0.021 g, 0.04 mmol), 2-methyl-2-{2-methyl-4-[({4-[4-(trifluoromethyl)benzyl]-2-[4-(trifluoromethyl)phenyl]-1,3-thiazol-5-yl}methyl)sulfanyl]phenoxy}propanoic acid (0.006 g, 25%) was obtained as a white solid.

$^1$H NMR (CD$_3$OD): δ 8.02 (d, 2H), 7.78 (d, 2H), 7.60 (d, 2H), 7.30 (d, 2H), 7.23 (s, 1H), 7.16 (d, 1H), 6.73 (d, 1H), 4.29 (s, 2H), 4.00 (s, 2H), 2.17 (s, 3H), 1.61 (s, 6H); $^{19}$F NMR (CD$_3$OD): δ −64.18 (s), −64.73 (s); MS m/z 626 (M+1); HPLC RT 4.273 (C18 4.2×100 mm, 0–100% ACN/ H$_2$O (0.1% TFA), 6 min @ 2 ml/min @254/220 nm).

2-Methyll-2-{2-methyl-4-[({4-[4-(trifluoromethoxy) benzyl]-2-[4-(trifluoromethyl)phenyl]-1,3-thiazol-5-yl}methyl)sulfanyl]phenoxy}propanoic acid From 2-methyl-4-[({4-(4-trifluoromethoxy)benzyl]-2-[4-(trifluoromethyl)phenyl]-1,3-thiazol-5-yl}methyl)sulfanyl] phenol (0.048 g, 0.086 mmol), 2-methyl-2-{2-methyl-4-[({4-[4-(trifluoromethoxy)benzyl]-2-[4-(trifluoromethyl)

phenyl]-1,3-thiazol-5-yl}methyl)sulfanyl]phenoxy}propanoic acid (0.013 g, 23%) was obtained as a white solid.

$^1$H NMR (CD$_3$OD): δ 8.04 (d, 2H), 7.74 (d, 2H), 7.20 (m, 6H), 6.72 (d, 1H), 4.26 (s, 2H), 3.95 (s, 2H), 2.15 (s, 3H), 1.61 (s, 6H); $^{19}$F NMR (CD$_3$OD): δ–59.86 (s), –64.72 (s); MS m/z 642 (M+1); HPLC RT 4.307 (C18 4.2×100 mm, 0–100% ACN/H$_2$O (0.1% TFA), 6 min @ 2 ml/min @254/220 nm).

2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid From 4-[({4-(4-methoxybenzyl)-2-[4-(trifluoromethyl)phenyl]-1,3-thiazol-5-yl}methyl)sulfanyl]-2-methylphenol (0.022 g, 0.04 mmol), 2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid (0.003 g, 12%) was obtained as a white solid.

$^1$H NMR (CD$_3$OD): δ 8.04 (d, 2H), 7.76 (d, 2H), 7.19 (s, 1H), 7.14 (d, 1H), 7.02 (d, 2H), 6.81 (d, 2H), 6.69 (d, 1H), 4.21 (s, 2H), 3.83 (s, 2H), 3.78 (s, 3H), 2.17 (s, 3H), 1.60 (s, 6H); MS m/z 588 (M+1); HPLC RT 4.136 (C18 4.2×100 mm, 0–100% ACN/H$_2$O (0.1% TFA), 6 min @ 2 ml/min @254/220 nm).

2-Methyll-2-{2-methyl-4-[({4-[4-(methylsulfanyl)benzyl]-2-[4-(trifluoromethyl)phenyl]-1,3-thiazol-5-yl}methyl)sulfanyl]phenoxy}propanoic acid From 2-methyl-4-[({4-(4-methylsulfanyl)benzyl]-2-[4-(trifluoromethyl)phenyl]-1,3-thiazol-5-yl}methyl)sulfanyl]phenol (0.296 g, 0.57 mmol), 2-methyl-2-{2-methyl-4-[({4-[4-(methylsulfanyl)benzyl]-2-[4-(trifluoromethyl)phenyl]-1,3-thiazol-5-yl}methyl)sulfanyl]phenoxy}propanoic acid (0.087 g, 25%) was obtained as a white solid.

$^1$H NMR (CD$_3$OD): δ 8.04 (d, 2H), 7.78 (d, 2H), 7.13 (m, 6H), 6.70 (d, 1H), 4.22 (s, 2H), 3.87 (s, 2H), 2.47 (s, 3H), 2.15 (s, 3H), 1.60 (s, 6H); MS m/z 604 (M+1); HPLC RT 4.220 (C18 4.2×100 mm, 0–100% ACN/H$_2$O (0.1% TFA), 6 min @ 2 ml/min @254/220 nm).

2-{4-[({4-(4-tert-butyl benzyl)-2-[4-(trifluoromethyl)phenyl]-1,3-thiazol-5-yl}methyl)sulfanyl]-2-methylphenoxy]-2-methylpropanoic acid From 4-[({4-(4-tert-butylbenzyl)-2-[4-(trifluoromethyl)phenyl]-1,3-thiazol-5-yl}methyl)sulfanyl]-2-methylphenol (0.113 g, 0.21 mmol), 2-{4-[({4-(4-tert-butylbenzyl)-2-[4-(trifluoromethyl)phenyl]-1,3-thiazol-5-yl}methyl)sulfanyl]-2-methylphenoxy}-2-methylpropanoic acid (0.012 g, 9%) was obtained as a white solid.

$^1$H NMR (CD$_3$OD): δ 8.04 (d, 2H), 7.76 (d, 2H), 7.29 (d, 2H), 7.22 (s, 1H), 7.16 (d, 1H), 7.03 (d, 2H), 6.74 (d, 1H); MS m/z 614 (M+1); HPLC RT 4.464 (C18 4.2×100 mm, 0–100% ACN/H$_2$O (0.1% TFA), 6 min @ 2 ml/min @254/220 nm).

2-Methyll-2-{2-methyl-4-[({4-(3-thienylmethyl)-2-[4-(trifluoromethyl)phenyl]-1,3-thiazol-5-yl}methyl)sulfanyl]phenoxy}propanoic acid From 2-methyl-4-[({4-(3-thienylmethyl)-2-[4-(trifluoromethyl)phenyl]-1,3-thiazol-5-yl}methyl)sulfanyl]phenol (0.072 g, 0.15 mmol), 2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid (0.039 g, 46%) was obtained as a cream solid.

$^1$H NMR (CD$_3$OD): δ 8.05 (d, 2H), 7.76 (d, 2H), 7.37 (t, 1H), 7.20 (s, 1H), 7.15 (d, 1H), 7.02 (s, 1H), 6.96 (d, 1H), 6.70 (d, 1H), 4.23 (s, 2H), 3.96 (s, 2H), 2.20 (s, 3H), 1.60 (s, 6H); MS m/z 564 (M+1); HPLC RT 4.112 (C 18 4.2×100 mm, 0–100% ACN/H$_2$O (0.1% TFA), 6 min @ 2 ml/min @254/220 nm).

Ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate From 2-methyl-4-[({4-[4-(4-trifluoromethoxy)benzyl]-2-[4-(trifluoromethyl)phenyl]-1,3-thiazol-5-yl}methyl)sulfanyl]phenol (0.17 g, 0.31 mmol), ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate (0.17 g, 83%) was obtained as a white solid. MS m/z 656 (M+1); HPLC RT 4.553 (C18 4.2×100 mm, 0–100% ACN/H$_2$O (0.1% TFA), 6 min @ 2 ml/min @254/220 nm).

Methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate From 2-methyl-4-[({4-[4-(trifluoromethoxy)benzyl]-2-[4-(trifluoromethyl)phenyl]-1,3-thiazol-5-yl}methyl)sulfanyl]phenol (0.17 g, 0.31 mmol), methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate (0.15 g, 80%) was obtained as a white solid. MS m/z 628 (M+1); HPLC RT 4.398 (C18 4.2×100 mm, 0–100% ACN/H$_2$O (0.1% TFA), 6 min @ 2 ml/min @254/220 nm).

Ethyl 2-}2-methyl-4-[({4-(3-thienylmethyl)-2-[4-(trifluoromethyl)phenyl]-1,3-thiazol-5-yl}methyl)sulfanyl]phenoxy}propanoate From 2-methyl-4-[({4-(3-thienylmethyl)-2-[4-(trifluoromethyl)phenyl]-1,3-thiazol-5-yl}methyl)sulfanyl]phenol, ethyl 2-{2-methyl-4-[({4-(3-thienylmethyl)-2-[4-(trifluoromethyl)phenyl]-1,3-thiazol-5-yl}methyl)sulfanyl]phenoxy}propanoate (0.225 g, 0.47 mmol), (0.255 g, 91%) was obtained as a yellow oil.

MS m/z 578 (M+1); HPLC RT 4.412 (C18 4.2×100 mm, 0–100% ACN/H$_2$O (0.1% TFA), 6 min @ 2 ml/min @254/220 nm).

Methyl {2-methyl-4-[({4-(3-thienylmethyl)-2-[4-(trifluoromethyl)phenyl]-1,3-thiazol-5-yl}methyl)sulfanyl]phenoxy}acetate From 2-methyl-4-[({4-(3-thienylmethyl)-2-[4-(trifluoromethyl)phenyl]-1,3-thiazol-5-yl}methyl)sulfanyl]phenol, methyl {2-methyl-4-[({4-(3-thienylmethyl)-2-[4-(trifluoromethyl)phenyl]-1,3-thiazol-5-yl}methyl)sulfanyl]phenoxy}acetate (0.225 g, 0.47 mmol), (0.259 g, 94%) was obtained as a yellow oil.

MS m/z 550 (M+1); HPLC RT 4.243 (C18 4.2×100 mm, 0–100% ACN/H$_2$O (0.1% TFA), 6 min @ 2 ml/min @254/220 nm).

The following 2 compounds were made by the Mitsunobu reaction of 4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenol with R and S Methyl lactate:

Methyl (2S)-2-[(4-[({4-{[4-(4-methoxyphenyl)-1-piperazinyl]methyl}-2-]4-(trifluoromethyl)phenyl]-1,3-thiazol-5-yl}methyl)sulfanyl]-2-methylphenoxy}propanoate ¹H NMR (CDCl₃) 400 MHz δ 7.97(d, 2H, J=8.24 Hz), 7.64(d, 2H, J=8.24 Hz), 7.21(d, 1H, J=2.20 Hz), 7.11(dd, 1H, J=8.42, 2.20 Hz), 6.86(d, 2H, J=9.16 Hz), 6.80(d, 2H, J=9.16 Hz), 6.54(d, 1H, J=8.42 Hz), 4.70(q, 1H, J=6.78 Hz), 4.30(s, 2H), 3.74(s, 3H), 3.69(s, 3H), 3.55(s, 2H), 3.06(br s, 4H), 2.62(br s, 4H), 2.21(s, 3H), 1.60(d, 3H, J=6.78 Hz),

Methyl (2R)-2-}4-[({4-{[4-(4-methoxyphenyl)-1-piperazinyl]methyl}-2-]4-(trifluoromethyl)phenyl]-1,3-thiazol-5-yl}methyl)sulfanyl]-2-methylphenoxy}propanoate ¹H NMR (CDCl₃) 400 MHz δ 7.97(d, 2H, J=8.24 Hz), 7.64(d, 2H, J=8.24 Hz), 7.22(d, 1H, J=2.01 Hz), 7.12(dd, 1H, J=8.42, 2.01 Hz), 6.88(d, 2H, J=9.16 Hz), 6.80(d, 2H, J=9.16 Hz), 6.55(d, 1H, J=8.42 Hz), 4.70(q, 1H, J=6.78 Hz), 4.32(s, 2H), 3.73(s, 3H), 3.69(s, 3H), 3.55(s, 2H), 3.06(t, 4H, J=4.76 Hz), 2.61(br s, 4H), 2.22(s, 3H), 1.60(d, 3H, J=6.78 Hz),

2-{4-[({4-{[4-(4-Methoxyphenyl)-1-piperazinyl]methyl}-2-[4-(trifluoromethyl)phenyl]-1,3-thiazol-5-yl}methyl)sulfanyl]phenoxy}-2-methylpropanoic acid To a stirred solution of ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoate (77.0 g, 0.112 moles, 1 eq) in THF (600 ml, 0.19M) was added MeOH (50 ml) and a 1N LiOH solution (6.18 g in 250 ml H₂O, 2.3 eq). The mixture was refluxed for 5 hrs after which the THF was removed in vacuo. The residue was diluted with EtOAc and to it was added 1N HCl until a pH of about 5 was reached. The phases were separated and the organic fraction was concentrated in vacuo, then titrated with isopropyl acetate twice which was subsequently removed in vacuo each time. The crude product was then recrystallized from EtOH to yield 52 g (71%) of a white solid.

¹H NMR (CD₃OD) 400 MHz δ 8.08(d, 2H, J=8.24 Hz), 7.75(d, 2H, J=8.24 Hz), 7.25(d, 2H, J=8.61 Hz), 6.94(d, 2H, J=9.16 Hz), 6.82(m, 4H), 4.28(s, 2H), 3.72(s, 3H), 3.59(s, 2H), 3.16(t, 4H, J=4.94 Hz), 2.96(t, 4H, J=4.94 Hz), 1.54(s, 6H),

CHN Analysis: Theory (C, 60.26%; H, 5.21%; N, 6.39%) Found (C, 60.11%; H, 5.31%; N, 6.23%)

HPLC (C-18, 3 μm) 0%–95% Acetonitrile/Water over 8 minutes R$_t$=5.48 minutes

{4-[({4-benzyl-2-[4-(trifluoromethyl)phenyl]-1,3-thiazol-5-yl}methyl)sulfanyl]-2,5-dimethylphenoxy}acetic acid Mass spec: calculated for C₂₈H₂₄F₃NO₃S₂: 543. Found: 544 (MH⁺). HPLC trace: retention time=13.5 min (Alltima C₁₈, 5 micron, 250 mm column, Gradient elution with 70–100% CH₃CN/H₂O).

2-{4-[({4-benzyl-2-[4-(trifluoromethyl)phenyl]-1,3-thiazol-5-yl}methyl)sulfanyl]-2-methylphenoxy}propanoic acid Elemental analysis calculated for C₂₈H₂₄F₃NO₃S₂: C, 61.8%, H, 4.5%, N, 2.6%. Found: C, 61.77%, H, 4.64%, N, 2.51%. HPLC trace: retention Time□.7 min (Alltima C₁₈, 5 micron, 250 mm column, gradient elution with 70–100% CH₃CN/H₂O).

2-{4-[({4-benzyl-2-[4-(trifluoromethyl)phenyl]-1,3-thiazol-5-yl}methyl)sulfanyl-2,3-dimethylphenoxy}propanoic acid Elemental analysis calculated for C₂₉H₂₆F₃NO₃S₂: C, 62.4%, H, 4.7%, N, 2.5%. Found: C, 62.58%, H, 4.93%, N, 2.44%. HPLC trace: retention time=14.7 min (Alltima C₁₈, 5 micron, 250 mm column using gradient elution with 70–100% CH₃CN/H₂O).

2-{4-[({4-benzyl-2-[4-(trifluoromethyl)phenyl]-1,3-thiazol-5-yl}methyl)sulfanyl]-2-fluorophenoxy}propanoic acid Mass spec calculated for C₂₇H₂₁F₄NO₃S₂: 547. Found: 548 (MH⁺). HPLC, Trace: retention time=12.1 min (Alltima C₁₈, 5 micron, 250 mm column using gradient elution with 70–100% CH₃CN/H₂O).

(2S)-2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.07(d, 2H, J=8.24 Hz), 7.74(d, 2H, J=8.24 Hz), 7.19(d, 1H, J=2.20 Hz), 7.09(dd, 1H, J=8.42, 2.20 Hz), 6.91(d, 2H, J=9.16 Hz), 6.80(d, 2H, J=9.16 Hz), 6.62(d, 1H, J=8.42 Hz), 4.68(q, 1H, J=6.78 Hz), 4.28(s, 2H), 3.71(s, 3H), 3.48(s, 2H), 3.05(t, 4H, J=4.76 Hz), 2.69(t, 4H, J=4.76 Hz), 2.18(s, 3H), 1.57(d, 3H, J=6.78 Hz), Chiral HPLC (Chiralpak, 2 cm) 75% Carbon Dioxide/ 25% Methanol over 65 minutes R$_t$@0.88 minutes

(2R)-2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.11(d, 2H, J=8.24 Hz), 7.76(d, 2H, J=8.24 Hz), 7.15(d, 1H, J=2.20 Hz), 7.08(dd, 1H, J=8.42, 2.20 Hz), 6.93(d, 2H, J=9.16 Hz), 6.82(d, 2H, J=9.16 Hz), 6.67(d, 1H, J=8.42 Hz), 4.57(q, 1H, J=6.78 Hz), 4.24(s, 2H), 3.71(s, 3H), 3.54(s, 2H), 3.17(t, 4H, J=4.76 Hz), 3.02(t, 4H, J=4.76 Hz), 2.18(s, 3H), 1.55(d, 3H, J=6.78 Hz), Chiral HPLC (Chiralpak, 2 cm) 75% Carbon Dioxide/ 25% Methanol over 65 minutes R$_t$T.58 minutes

2-(4-{[(2-(4-Fluorophenyl)-4-{[4-(4-methoxyphenyl)-1-piperazinyl]methyl}-1,3-thiazol-5-yl)methyl]sulfanyl}-2-methylphenoxy)-2-methylpropanoic acid ¹H NMR (CD₃OD) 400 MHz δ 7.95(m, 2H), 7.18(m, 3H), 7.05(br s, 1H), 6.93(d, 2H, J=8.61 Hz), 6.81(d, 2H, J=8.61 Hz), 6.69(br s, 1H), 4.22(s, 2H), 3.72(s, 3H), 3.55(s, 2H), 3.17(br s, 4H), 2.93(br s, 4H), 2.14(s, 3H), 1.59(s, 6H),

[4-({[4-[(4-Benzyl-1-piperazinyl)methyl]-2-(4-{trifluoromethyl}phenyl)-1,3-thiazol-5-yl]methyl}sulfanyl)-2-methylphenoxy]acetic acid ¹H (CD₃OD) 300 MHz δ 8.15(d, 2H, J=8.23 Hz), 7.81(d, 2H, J=8.23 Hz), 7.48(m, 5H), 7.24(s, 2H), 6.74(s, 1H), 4.55(s, 2H), 4.28(s, 2H), 4.15(s, 2H), 3.46(s, 2H), 3.06(s, {2-Methyl-4-[({2-(4-{trifluoromethyl}phenyl)-4-[(4-methyl-1-piperidinyl)methyl]-1,3-thiazol-5-yl}methyl)sulfanyl]phenoxy}acetic acid ¹H (CD₃OD) 300 MHz δ 8.20(d, 2H, J=7.97 Hz), 7.85(d, 2H, J=7.97 Hz), 7.27(s, 1H), 7.08(s, 1H), 6.68(s, 1H), 4.62(s, 2H), 4.29(s, 2H), 3.70(s, 2H), 2.86(s, 2H), 2.26(s, 3H), 1.90(s, 2H), 1.48(m, 5H), 1.06(s, 3H). MS(ES⁻) M−H=548.91. TLC(10% MeOH/CH₂Cl₂) R*f*=0.24

[2-Methyl-4-({[4-{[4-(5-methyl-1,2,4-oxadiazol-3-yl)phenoxy]methyl}-2-(4-{(trifluoromethyl)phenyl})-1,3-thiazol-5-yl]methyl}sulfanyl)phenoxy]acetic acid ¹H (CDCl₃) 400 MHz δ 8.03(d, 2H, J=8.03 Hz), 7.93(d, 2H, J=8.89 Hz), 7.70(d, 2H, J=8.03 Hz), 7.19(d, 1H, J=2.22 Hz), 7.07(dd, 1H, J=8.37, 2.22 Hz), 6.96(d, 2H, J=8.89 Hz), 6.53(d, 1H, J=8.37 Hz), 4.88(s, 2H), 4.64(s, 2H), 4.27(s, 2H), 2.65(s, 3H), 2.17(s, 3H). TLC(5% MeOH/CH₂Cl₂) R*f*=0.13. MS(ES⁻) M−H=625.92

[2-Methyl-4-({[4-{[3-(5-methyl-1,2,4-oxadiazol-3-yl)phenoxy]methyl}-2-(4-{(trifluoromethyl)phenyl})-1,3-thiazol-5-yl]methyl}sulfanyl)phenoxy]acetic acid ¹H (CDCl₃) 400 MHz δ 8.04(d, 2H, J=8.20 Hz), 7.69(m, 3H), 7.37(s, 2H), 7.16(dd, 1H, J=8.20, 2.22 Hz), 7.05(dd, 1H, J=8.20, 2.22 Hz), 6.91(d, 1H, J=2.22 Hz), 6.62(d, 1H, J=8.20 Hz), 4.72(s, 2H), 4.43(s, 2H), 4.19(s, 2H), 2.73(s, 3H), 2.09(s, 3H). TLC(5% MeOH/CH₂Cl₂) R*f*=0.13. MS(ES⁻) M−H=625.86

[2-Methyl-4-{[(2-(4-{trifluoromethyl}phenyl)-4-{[4-(2-methylphenyl)-1-piperazinyl]methyl}-1,3-thiazol-5-yl)methyl]sulfanyl}phenoxy)acetic acid ¹H (CDCl₃) 400 MHz δ 8.10(d, 2H, J=8.03 Hz), 7.73(d, 2H, J=8.03 Hz), 7.16(m, 4H), 7.01(br s, 2H), 6.73(d, 1H, J=8.37 Hz), 4.79(s, 2H), 4.08(s, 2H), 3.80(m, 4H), 3.53(m, 2H), 3.24(m, 4H), 2.40(s, 3H), 2.18(s, 3H). TLC(5% MeOH/CH₂Cl₂) R*f*=0.10. MS(ES⁻) M−H=625.94

[4-({[4-{[4-(4-Methoxyphenyl)-1-piperazinyl]methyl}-2-(4-{trifluoromethyl}phenyl)-1,3-thiazol-5-yl]methyl}sulfanyl)-2-methylphenoxy]acetic acid ¹H (CDCl₃) 400 MHz δ 8.04(d, 2H, J=8.20 Hz), 7.72(d, 2H, J=8.20 Hz), 7.12(s, 1H), 6.96(m, 3H), 6.81(d, 2H, J=8.89 Hz), 6.74(d, 1H, J=8.37 Hz), 4.76(s, 2H), 4.05(s, 2H), 3.74(s, 3H), 3.38(m, 10H), 2.16(s, 3H). TLC(5% MeOH/CH₂Cl₂) R*f*=0.13. MS(ES⁻) M−H=641.90

(2-Methyl-4-{[(2-(4-{trifluoromethyl}phenyl)-4-{[4-(3-methylphenyl)-1-piperazinyl]methyl}-1,3-thiazol-5-yl)methyl]sulfanyl}phenoxy)acetic acid ¹H (CDCl₃) 400 MHz δ 8.05(d, 2H, J=8.20 Hz), 7.72(d, 2H, J=8.20 Hz), 7.20(s, 1H), 7.06(d, 2H, J=9.06 Hz), 6.91(m, 3H), 6.72(d, 1H, J=8.37 Hz), 4.77(s, 2H), 4.06(s, 2H), 3.54(br s, 8H), 3.27(s, 2H), 2.30(s, 3H), 2.16(s, 3H). TLC (5% MeOH/CH₂Cl₂) R*f*=0.10. MS(ES⁻) M−H=625.99

(2-Methyl-4-{[(2-(4-{trifluoromethyl}phenyl)-4-{[4-(4-methylphenyl)-1-piperazinyl]methyl}-1,3-thiazol-5-yl)methyl]sulfanyl}phenoxy)acetic acid ¹H (CDCl₃) 400 MHz δ 8.03(d, 2H, J=8.20 Hz), 7.71(d, 2H, J=8.20 Hz), 7.02(m, 6H), 6.71(d, 1H, J=8.55 Hz), 4.76(s, 2H), 4.08(s, 2H), 3.52(br s, 8H), 3.31 (s, 2H), 2.27(s, 3H), 2.16(s, 3H). TLC(5% MeOH/CH₂Cl₂) R*f*=0.10. MS(ES⁻) M−H=625.94

[4-({[4-{[4-(2-Furoyl)-1-piperazinyl]methyl}-2-(4-trifluoromethyl}phenyl)-1,3-thiazol-5-yl]methyl}sulfanyl)-2-methylphenoxy]acetic acid ¹H (CDCl₃) 400 MHz δ 8.02(d, 2H, J=8.20 Hz), 7.71(d, 2H, J=8.20 Hz), 7.48(d, 1H, J=2.05 Hz), 7.16(dd, 1H, J=8.20, 2.05 Hz), 7.07(m, 1H), 6.90(d, 1H, J=2.39 Hz), 6.74(d, 1H, J=8.20 Hz), 6.49(m, 1H), 4.77(s, 2H), 4.62(s, 2H), 4.05(s, 2H), 3.46(s, 2H), 3.27(s, 2H), 3.05(br s, 4H), 2.15(s, 3H). TLC(5% MeOH/CH₂Cl₂) R*f*=0.10. MS(ES⁻) M−H=629.83

(2-Methyl-4-{[(2-(4-{trifluoromethylphenyl)-4-{[4-(2-pyridinyl)-1-piperazinyl]methyl}-1,3-thiazol-5-yl)methyl]sulfanyl}phenoxy)acetic acid ¹H (CDCl₃) 400 MHz δ 8.22(m, 1H), 7.99(d, 2H, J=8.20 Hz), 7.68(d, 2H, J=8.20 Hz), 7.60(s, 1H), 7.20(dd, 1H, J=8.37, 2.39 Hz), 7.14(s, 1H), 6.76(m, 1H), 6.68(m, 1H), 4.68(s, 2H), 4.14(s, 2H), 3.72(br s, 4H), 3.59(s, 2H), 2.87(br s, 4H), 2.17(s, 3H). TLC(5% MeOH/CH₂Cl₂) R*f*=0.10. MS(ES⁻) M−H=612.99

[4-({[4-{[4-(4-Chlorobenzyl)-1-piperazinyl]methyl}-2-(4-{trifluoromethyl}phenyl)-1,3-thiazol-5-yl]methyl}sulfanyl)-2-methylphenoxy]acetic acid ¹H (CDCl₃) 400 MHz δ 8.04(d, 2H, J=8.20 Hz), 7.70(d, 2H, J=8.20 Hz), 7.41(m, 4H), 7.14(m, 1H), 7.03(m, 1H), 6.69(d, 1H, J=8.37 Hz), 4.72(s, 2H), 4.02(s, 2H), 3.18(m, 12H), 2.10(s, 3H). TLC(5% MeOH/CH₂Cl₂) R*f*=0.10. MS(ES⁻) M−H=659.78

[4-({[4-{[4-(4-acetylphenyl)-1-piperazinyl]methyl}-2-(4-{trifluoromethyl}phenyl)-1,3-thiazol-5-yl]methyl}sulfanyl)-2-methylphenoxy]acetic acid ¹H (CDCl₃) 400 MHz δ 7.97(d, 2H, J=8.03 Hz), 7.85(d, 2H, J=8.89 Hz), 7.70(d, 2H, J=8.03 Hz), 7.16(dd, 1H, J=8.37, 2.22 Hz), 6.86(m, 3H), 6.75(d, 1H, J=8.37 Hz), 4.77(s, 2H), 4.04(s, 2H), 3.80(m, 4H), 3.45(m, 4H), 3.29(s, 2H), 2.51(s, 3H), 2.17(s, 3H). TLC(5% MeOH/CH₂Cl₂) R*f*=0.10. MS(ES⁻) M−H=653.99

(4-{[(4-{[4-(4-Methoxyphenyl)-1-piperazinyl]methyl}-2-phenyl-1,3-thiazol-5-yl)methyl]sulfanyl}-2-methylphenoxy)acetic acid ¹H NMR (CDCl₃) 400 MHz 9.94(s, 1H), 7.84(m, 2H), 7.41(m, 3H), 7.11(d, 1H, J=2.22 Hz), 7.06(dd, 1H, J=8.37, 2.22 Hz), 6.79(m, 4H), 6.60(d, 1H, J=8.37 Hz), 4.54(s, 2H), 4.18(s, 2H), 3.76(s, 2H), 3.22(m, 8H), 2.18(s, 3H). HPLC (C-18, 3 μm) 1% MeOH/0–90% CH₃CN/Water (0.1% TFA)/ (50 mM Et₃N/TFA) 4 min run R*t*=2.67 min

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400 MHz δ 9.69(s, 1H), 7.96(d, 2H, J=8.20 Hz), 7.65(d, 2H, J=8.20 Hz), 7.07(d, 1H, J=2.05 Hz), 7.02(dd, 1H, J=8.55, 2.05 Hz), 6.87(d, 2H, J=9.23 Hz), 6.80(d, 2H, J=9.23 Hz), 6.66(d, 1H, J=8.55 Hz), 4.66(q, 1H, J=6.95 Hz), 4.10(d, 1H, J□.70 Hz), 4.05(d, 1H, J□.70 Hz), 3.74(s, 3H), 3.57(d, 1H, J□.18 Hz), 3.51(d, 1H, J□.18 Hz), 3.15(br s, 4H), 2.96(br s, 4H), 2.17(s, 3H), 1.59(d, 3H, J=6.95 Hz). HPLC(C-18, 3 μm) 1% MeOH/0–90% CH$_3$CN/Water (0.1% TFA)/(50 mM Et$_3$N/TFA) 4 min run R$_f$=2.91 min

2-(4-{[(4-{[4-(4-Methoxyphenyl)-1-piperazinyl]methyl}-2-phenyl-1,3-thiazol-5-yl)methyl]sulfanyl}-2-methylphenoxy)propanoic acid $^1$H NMR (CDCl$_3$) 400 MHz δ 7.81(m, 2H), 7.34(m, 3H), 7.09(m, 1H), 6.90(m, 1H), 6.79(m, 4H), 6.48(d, 1H, J=8.37 Hz), 4.35(m, 1H), 4.16(s, 2H), 3.70(s, 3H), 3.32(s, 2H), 3.00(m, 4H), 2.60(m, 4H), 2.09(s, 3H), 1.34(m, 3H). HPLC (C-18, 3 μm) 1% MeOH/0–90% CH$_3$CN/Water (0.1% TFA)/(50 mM Et$_3$N/TFA) 4 min run R$_f$=2.78 min

{2-Methyl-4-[({2-(4-trifluoromethyl}phenyl)-4-[(4-phenyl-1-piperazinyl)methyl]-1,3-thiazol-5-yl}methyl)sulfanyl]phenoxy}acetic acid $^1$H (CD$_3$OD) 300 MHz δ 8.16(d, 2H, J=8.49 Hz), 7.81(d, 2H, J=8.49 Hz), 7.26(br s, 3H), 7.09(br s, 1H), 6.98(d, 2H, J=7.96 Hz), 6.88(m, 1H), 6.66(br s, 1H), 4.57(s, 2H), 4.29(s, 2H), 3.55(s, 2H), 3.26(br s, 4H), 2.91(br s, 4H), 2.23(s, 3H). MS(ES$^-$) M−H=611.85. TLC(10% MeOH/CH$_2$Cl$_2$) R$_f$=0.30

[4-({[4-{[4-(Ethoxycarbonyl)-1-piperazinyl]methyl}-2-(4-{trifluoromethyl}phenyl)-1,3-thiazol-5-yl]methyl}sulfanyl)-2-methylphenoxy]acetic acid $^1$H (CD$_3$OD) 300 MHz δ 8.14(d, 2H, J=8.23 Hz), 7.81(d, 2H, J=8.23 Hz), 7.26(s, 1H), 7.12(s, 1H), 6.71(s, 1H), 4.63(s, 2H), 4.32(s, 2H), 4.16(q, 2H, J=7.08 Hz), 3.55(br s, 4H), 3.44(s, 2H), 2.60(br s, 4H), 2.25(s, 3H), 1.30(t, 3H, J=7.08 Hz). MS(ES$^-$) M−H=607.86. TLC(10% MeOH/CH$_2$Cl$_2$) R$_f$=0.28

{2-Methyl-4-[({2-(4-{trifluoromethyl}phenyl)-4-[(4-phenyl-1-piperidinyl)methyl]-1,3-thiazol-5-yl}methyl)sulfanyl]phenoxy}acetic acid $^1$H (CD$_3$OD) 300 MHz δ 8.14(d, 2H, J=8.23 Hz), 7.77(d, 2H, J=8.23 Hz), 7.28(s, 7H), 6.75(d, 1H, J=8.23 Hz), 4.45(s, 2H), 4.34(s, 2H), 3.53(s, 2H), 3.08(m, 2H), 2.57(m, 1H), 2.35(m, 2H), 2.22(s, 3H), 1.80(m, 4H). MS(ES$^-$) M−H=610.91. TLC(10% MeOH/CH$_2$Cl$_2$) R$_f$=0.30

[4-({[4-{[(Cyclopropylmethyl)amino]methyl}-2-(4-{trifluoromethyl}phenyl)-1,3-thiazol-5-yl]methyl}sulfanyl)-2-methylphenoxy]acetic acid $^1$H NMR 300 MHz δ 8.08(d, 2H, J=8.20 Hz), 7.74(d, 2H, J=8.20 Hz), 7.14(dd, 1H, J=8.49, 2.39 Hz), 7.01(s, 1H), 6.72(d, 1H, J=8.49 Hz), 4.77(s, 2H), 4.03(s, 2H), 3.29(s, 2H), 2.77(d, 2H, J=7.43 Hz), 2.17(s, 3H), 1.17(m, 1H), 0.62(m, 2H), 0.28(m, 2H). MS(ES$^-$) M−H=520.90. HPLC (C-18, 3 μm) 1% MeOH/0–90% CH$_3$CN/Water (0.1% TFA)/(50 mM Et$_3$N/TFA) 4 min run R$_f$=2.67 min

{2-Methyl-4-[({2-(4-trifluoromethyl}phenyl)-4-[(pentylamino)methyl]-1,3-thiazol-5-yl}methyl)sulfanyl]phenoxy}acetic acid $^1$H NMR 300 MHz δ 8.06(d, 2H, J=8.23 Hz), 7.69(d, 2H, J=8.23 Hz), 7.05(m, 2H), 6.66(d, 1H, J=8.23 Hz), 4.67(s, 2H), 4.06(s, 2H), 3.35(s, 2H), 2.78(t, 2H, J=6.64 Hz), 2.17(s, 3H), 1.71(m, 2H), 1.22(m, 4H), 0.83(t, 3H, J=6.64 Hz). MS(ES$^-$) M−H=536.90. HPLC(C-18, 3 μm) 1% MeOH/0–90% CH$_3$CN/Water (0.1% TFA)/(50 mM Et$_3$N/TFA) 4 min run R$_f$=2.80 min

4-({[4-{[4-(2-Hydroxyethyl)-1-piperazinyl]methyl}-2-(4-{trifluoromethyl}phenyl)-1,3-thiazol-5-yl]methyl}sulfanyl)-2-methylphenoxy]acetic acid $^1$H NMR (CD$_3$OD) 300 MHz δ 8.16(d, 2H, J=8.23 Hz), 7.80(d, 2H, J=8.23 Hz), 7.26(m, 2H), 6.80(d, 1H, J=8.49 Hz), 4.76(s, 2H), 4.40(s, 2H), 3.95(m, 2H), 3.84(s, 2H), 3.54(br s, 4H), 3.33(m, 2H), 3.20(br s, 4H), 2.22(s, 3H). HPLC(C-18, 3 μm) 1% MeOH/0–90% CH$_3$CN/Water (0.1% TFA)/(50 mM Et$_3$N/TFA) 4 min run R$_f$=2.48 min

(2-Methyl-4-{[(2-(4-{trifluoromethyl}phenyl)-4-{[(3-pyridinylmethyl)amino]methyl}-1,3-thiazol-5-yl)methyl]sulfanyl}phenoxy)acetic acid $^1$H NMR (CDCl$_3$) 300 MHz δ 8.58(d, 1H, J=1.59 Hz), 8.48(dd, 1H, J=4.78, 1.59 Hz), 8.03(m, 3H), 7.66(d, 2H, J=8.23 Hz), 7.24(m, 1H), 7.06(d, 1H, J=2.39 Hz), 6.99(d, 1H, J=2.39 Hz), 6.59(d, 1H, J=8.49 Hz), 4.61(s, 2H), 4.04(s, 2H), 3.93(s, 2H), 3.28(s, 2H), 2.13(s, 3H). MS(ES$^-$) M−H=557.80. HPLC(C-18, 3 μm) 1% MeOH/0–90% CH$_3$CN/Water (0.1% TFA)/(50 mM Et$_3$N/TFA) 4 min run R$_f$=2.44 min

[4-({[4-[(3-Hydroxy-1-piperidinyl)methyl]-2-(4-{trifluoromethyl}phenyl)-1,3-thiazol-5-yl]methyl}sulfanyl)-2-methylphenoxy]acetic acid $^1$H NMR (CDCl$_3$) 300 MHz δ 8.00(d, 2H, J=8.37 Hz), 7.69(d, 2H, J=8.37 Hz), 7.23(dd, 1H, J=8.55, 2.20 Hz), 6.94(d, 1H, J=2.20 Hz), 6.69(d, 1H, J=8.55 Hz), 4.68(s, 2H), 4.21(s, 2H), 3.16(m, 7H), 2.12(s, 3H), 1.63(m, 4H). MS(ES$^-$) M−H=550.8. HPLC(C-18, 3 μm) 1% MeOH/0–90% CH$_3$CN/Water (0.1% TFA)/(50 mM Et$_3$N/TFA) 4 min run R$_f$=2.58 min

[4-({[4-[(4-Hydroxy-1-piperidinyl)methyl]-2-(4-{trifluoromethyl}phenyl)-1,3-thiazol-5-yl]methyl}sulfanyl)-2-methylphenoxy]acetic acid $^1$H NMR (CDCl$_3$) 300 MHz δ 7.97(d, 2H, J=8.23 Hz), 7.65(d, 2H, J=8.23 Hz), 7.11 (m, 2H), 6.58(d, 1H, J=8.23 Hz), 4.53(s, 2H), 4.18(s, 2H), 3.86(br s, 1H), 3.62(m, 2H), 3.12(m, 2H), 2.95(m, 2H), 2.15(s, 3H), 2.04(m, 2H), 1.77(m, 2H). HPLC(C-18, 3 μm) 1% MeOH/0–90% CH$_3$CN/Water (0.1% TFA)/(50 mM Et$_3$N/TFA) 4 min run R$_f$=2.54 min

[4-({[4-{[2-(hydroxymethyl)-1-piperidinyl]methyl}-2-(4-{trifluoromethyl}phenyl)-1,3-thiazol-5-yl]methyl}sulfanyl)-2-methylphenoxy]acetic acid MS(ES⁻) M−H=564.94. HPLC(C-18, 3 μm) 1% MeOH/0–90% CH₃CN/Water (0.1% TFA)/(50 mM Et₃N/TFA) 4 min run R$_t$=2.66 min

[4-({[4-{[4-(Hydroxymethyl)-1-piperidinyl]methyl}-2-(4-{trifluoromethyl}phenyl)-1,3-thiazol-5-yl]methyl}sulfanyl)-2-methylphenoxy]acetic acid ¹H NMR (CDCl₃) 400 MHz δ 7.94(d, 2H, J=8.20 Hz), 7.64(d, 2H, J=8.20 Hz), 7.13(dd, 1H, J=8.55, 2.39 Hz), 7.06(d, 1H, J=2.39 Hz), 6.58(d, 1H, J=8.55 Hz), 4.60(s, 2H), 4.45(s, 2H), 4.18(s, 2H), 3.56(m, 6H), 2.75(br s, 1H), 2.11(s, 3H), 1.68(m, 4H). MS(ES⁻) M−H=564.93. HPLC(C-18, 3 μm) 1% MeOH/0–90% CH₃CN/Water (0.1% TFA)/(50 mM Et₃N/TFA) 4 min run R$_t$=2.56 min

[2-Methyl-4-({[2-(4-{trifluoromethyl}phenyl)-4-(4-morpholinylmethyl)-1,3-thiazol-5-yl]methyl}sulfanyl)phenoxy]acetic acid ¹H NMR (CD₃OD) 300 MHz δ 8.11(d, 2H, J=8.23 Hz), 7.79(d, 2H, J=8.23 Hz), 7.25(br s, 1H), 7.17(dd, 1H, J=8.23, 2.39 Hz), 6.74(d, 1H, J=8.23 Hz), 4.46(s, 2H), 4.32(s, 2H), 3.69(br s, 4H), 3.47(s, 2H), 2.50(br s, 4H), 2.23(s, 3H). MS(ES⁻) M−H=536.43. TLC(20% MeOH/CH₂Cl₂) R$_f$=0.39

[4-({[4-[(Cyclohexylamino)methyl]-2-(4-{trifluoromethyl}phenyl)-1,3-thiazol-5-yl]methyl}sulfanyl)-2-methylphenoxy]acetic acid ¹H NMR (CDCl₃) 400 MHz δ 8.01(d, 2H, J=8.20 Hz), 7.66(d, 2H, J=8.20 Hz), 7.04(m, 2H), 6.61(d, 1H, J=8.20 Hz), 4.64(s, 2H), 4.14(s, 2H), 3.39(s, 2H), 2.86(m, 1H), 2.14(s, 3H), 2.01(m, 2H), 1.73(m, 2H), 1.48(m, 4H), 1.08(m, 2H). MS(ES⁻) M−H=548.7-. HPLC(C-18, 3 μm) 1% MeOH/0–90% CH₃CN/Water (0.1% TFA)/(50 mM Et₃N/TFA) 4 min run R$_t$=2.75 min

[2-Methyl-4-({[4-{[(2-methylcyclohexyl)amino]methyl}-2-(4-{trifluoromethyl}phenyl)-1,3-thiazol-5-yl]methyl}sulfanyl)phenoxy]acetic acid ¹H NMR 400 MHz δ 7.98(d, 2H, J=8.20 Hz), 7.68(d, 2H, J=8.20 Hz), 7.09(dd, 1H, J=8.37, 2.39 Hz), 6.98(d, 1H, J=2.39 Hz), 6.65(d, 1H, J=8.37 Hz), 4.66(s, 2H), 4.15(d, 1H, J☐.70 Hz), 4.00(d, 1H, J☐.70 Hz), 3.53(d, 1H, J☐.04 Hz), 3.33(d, 1H, J☐.04 Hz), 2.53(m, 1H), 2.10(s, 3H), 1.74(m, 7H), 1.37(m, 2H), 1.03(d, 3H, J=6.32 Hz). MS(ES⁻) M−H=562.80. HPLC(C-18, 3 μm) 1% MeOH/0–90% CH₃CN/Water (0.1% TFA)/(50 mM Et₃N/TFA) 4 min run R$_t$=2.87 min

[2-Methyl-4-({[4-{[(3-methylcyclohexyl)amino]methyl}-2-(4-{trifluoromethyl}phenyl)-1,3-thiazol-5-yl]methyl}sulfanyl)phenoxy]acetic acid ¹H NMR 400 MHz δ 8.01(d, 2H, J=8.20 Hz), 7.68(d, 2H, J=8.20 Hz), 7.05(m, 2H), 6.62(d, 1H, J=8.37 Hz), 4.68(s, 2H), 4.29(s, 2H), 3.32(s, 2H), 2.90(m, 1H), 2.15(s, 3H), 2.00(m, 5H), 1.56(m, 4H), 0.89(d, 3H, J=6.32 Hz). MS(ES⁻) M−H=562.9. HPLC(C-18, 3 μm) 1% MeOH/0–90% CH₃CN/Water (0.1% TFA)/(50 mM Et₃N/TFA) 4 min run R$_t$=2.85 min

[2-Methyl-4-({[4-{[(4-methylcyclohexyl)amino]methyl}-2-(4-{trifluoromethyl}phenyl)-1,3-thiazol-5-yl]methyl}sulfanyl)phenoxy]acetic acid ¹H NMR 400 MHz δ 7.99(d, 2H, J=8.20 Hz), 7.64(d, 2H, J=8.20 Hz), 7.02(m, 2H), 6.59(d, 1H, J=8.03 Hz), 4.58(s, 2H), 4.16(s, 2H), 3.44(s, 2H), 2.90(br s, 1H), 2.12(s, 3H), 2.01(m, 3H), 1.62(m, 6H), 0.90(d, 3H, J=6.84 Hz). MS(ES⁻) M−H=562.90. HPLC(C-18, 3 μm) 1% MeOH/0–90% CH₃CN/Water (0.1% TFA)/(50 mM Et₃N/TFA) 4 min run R$_t$=2.85 min

[2-Methyl-4-({[4-](2-methylphenoxy)methyl]-2-(4-{trifluoromethyl}phenyl)-1,3-thiazol-5-yl]methyl}sulfanyl)phenoxy]acetic acid ¹H (CDCl₃) 300 MHz δ 8.03(d, 2H, J=8.23 Hz), 7.72(d, 2H, J=8.23 Hz), 7.17(m, 4H), 6.91(m, 2H), 6.59(d, 1H, J=8.49 Hz), 4.96(s, 2H), 4.67(s, 2H), 2.25(s, 3H), 2.21(s, 3H). MS(ES⁻) M−H=557.8

[2-Methyl-4-({[4-(3-methylphenoxy)methyl]-2-(4-{trifluoromethyl}phenyl)-1,3-thiazol-5-yl]methyl}sulfanyl)phenoxy]acetic acid ¹H (CDCl₃) 300 MHz δ 8.06(d, 2H, J=8.23 Hz), 7.73(d, 2H, J=8.23 Hz), 7.26(dd, 1H, J=2.39, 0.53 Hz), 7.20(t, 1H, J=7.83 Hz), 7.12(ddd, 1H, J=8.49, 2.39, 0.53 Hz), 6.80(m, 3H), 6.61(d, 1H, J=8.49 Hz), 4.86(s, 2H), 4.67(s, 2H), 4.32(s, 2H), 2.36(s, 3H), 2.23(s, 3H). MS(ES⁻) M−H=557.83

[2-Methyl-4-({[4-(4-Methylphenoxy)methyl]-2-(4-{trifluoromethyl}phenyl)-1,3-thiazol-5-yl]methyl}sulfanyl)phenoxy]acetic acid MS(ES⁻) M−H=557.8
CHN Analysis: Theory 1.5H₂O(C, 57.33%; H, 4.64%; N, 2.39%) Found (C, 57.34%; H, 4.24%; N, 2.37%)

[4-({[4-[(3-Cyanophenoxy)methyl]-2-(4-{trifluoromethyl}phenyl)-1,3-thiazol-5-yl]methyl}sulfanyl)-2-Methylphenoxy]acetic acid ¹H (CDCl₃) 300 MHz δ 8.05(d, 2H, J=8.23 Hz), 7.74(d, 2H, J=8.23 Hz), 7.38(m, 2H), 7.17(m, 4H), 6.67(d, 1H, J=8.23 Hz), 4.76(s, 2H), 4.72(s, 2H), 4.25(s, 2H), 2.23(s, 3H). MS(ES⁻) M−H=569.2

[4-({[4-[(4-Cyanophenoxy)methyl]-2-(4-{trifluoromethyl}phenyl)-1,3-thiazol-5-yl]methyl}sulfanyl)-2-methylphenoxy]acetic acid ¹H (CDCl₃) 300 MHz δ 9.94(s, 1H), 8.03(d, 2H, J=8.23 Hz), 7.73(d, 2H, J=8.23 Hz), 7.60(d, 2H, J=9.03 Hz), 7.27(d, 1H, J=2.12 Hz), 7.10(dd, 1H, J=8.49, 2.12 Hz), 7.00(d, 2H, J=9.03 Hz), 6.61(d, 1H, J=8.49 Hz), 4.85(s, 2H), 4.69(s, 2H), 4.25(s, 2H), 2.21(s, 3H). MS(ES⁻) M−H=569.2

(2-Methyl-4-{[(4-{[4-(5-methyl-1,2,4-oxadiazol-3-yl)phenoxy]methyl}-2-phenyl-1,3-thiazol-5-yl)methyl]sulfanyl}phenoxyacetic acid ¹H (CDCl₃) 400 MHz 7.95(d, 2H, J=9.06 Hz), 7.87(m, 2H), 7.43(m, 3H), 7.20(d, 1H, J=2.39 Hz), 7.05(dd, 1H, J=8.55, 2.39 Hz), 6.95(d, 2H, J=9.06 Hz), 6.52(d, 1H, J=8.55 Hz), 4.80(s, 2H), 4.61(s, 2H), 4.24(s, 2H), 2.63(s, 3H), 2.17(s, 3H). MS(ES⁻) M−H=558.40

2-(2-Methyl-4-{[(4-{[4-(5-methyl-1,2,4-oxadiazol-3-yl)phenoxy]methyl}-2-phenyl-1,3-thiazol-5-yl)methyl]sulfanyl}phenoxy)propanoic acid ¹H (CDCl₃) 400 MHz δ 7.93(d, 2H, J=9.06 Hz), 7.85(m, 2H), 7.40(m, 3H), 7.19(d, 1H, J=2.22 Hz), 7.02(dd, 1H, J=8.37, 2.22 Hz), 6.94(d, 2H, J=9.06 Hz), 6.52(d, 1H, J=8.37 Hz), 4.81(d, 1H, J□.79 Hz), 4.74(d, 1H, J□.79 Hz), 4.68(q, 1H, J=6.78 Hz), 4.21(s, 2H), 2.62(m, 3H), 2.16(s, 3H), 1.61(d, 3H, J=6.78 Hz). MS(ES⁻) M−H=571.50

2-{2-Methyl-4-[({4-{[3-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H NMR (CDCl₃) 400 MHz δ 7.99(d, 2H, J=8.20 Hz), 7.67(m, 3H), 7.47(m, 1H), 7.36(t, 1H, J=8.03 Hz), 7.10(dd, 1H, J=8.37, 2.39 Hz), 7.04(dd, 1H, J=8.37, 2.39 Hz), 6.99(m, 1H), 6.61(d, 1H, J=8.37 Hz), 4.75(q, 1H, J=6.84 Hz), 4.62(d, 1H, J□.45 Hz), 4.43(d, 1H, J□.45 Hz), 4.23(d, 1H, J□.70 Hz), 4.16(d, 1H, J□.70 Hz), 2.70(s, 3H), 2.12(s, 3H), 1.68(d, 3H, J=6.84 Hz). MS(ES⁺) M+H=642.00

2-(2-Methyl-4-{[(4-{[3-(5-methyl-1,2,4-oxadiazol-3-yl)phenoxy]methyl}-2-phenyl-1,3-thiazol-5-yl)methyl}sulfanyl]phenoxy)propanoic acid ¹H NMR (CDCl₃) 400 MHz δ 7.90(m, 2H), 7.67(t, 1H, J=7.52 Hz), 7.46(m, 1H), 7.42(m, 3H), 7.35(t, 1H, J=7.52 Hz), 7.08(dd, 1H, J=8.37, 2.39 Hz), 7.04(d, 1H, J=8.37 Hz), 7.00(d, 1H, J=2.39 Hz), 6.61(d, 1H, J=8.37 Hz), 4.73(q, 1H, J=6.84 Hz), 4.58(d, 1H, J□.45 Hz), 4.43(d, 1H, J□.45 Hz), 4.20(d, 1H, J□.70 Hz), 4.15(d, 1H, J□.70 Hz), 2.69(s, 3H), 2.12(s, 3H), 1.66(d, 3H, J=6.84 Hz). MS(ES⁺) M+H=573.80

[2-Methyl-4-({[2-(4-{trifluoromethyl}phenyl)-4-(phenoxymethyl)-1,3-thiazol-5-yl]methyl}sulfanyl)phenoxy]acetic acid ¹H (CDCl₃) 300 MHz δ 8.02(d, 2H, J=8.23 Hz), 7.70(d, 2H, J=8.23 Hz), 7.33(m, 2H), 7.22(s, 1H), 7.12(d, 1H, J=9.03 Hz), 6.98(m, 3H), 6.58(d, 1H, J=8.49 Hz), 4.87(s, 2H), 4.63(s, 2H), 4.30(s, 2H), 2.22(s, 3H). TLC(5% MeOH/CH₂Cl₂) R_f=0.17

(2-Methyl-4-{[(4-{[3-(5-methyl-1,2,4-oxadiazol-3-yl)phenoxy]methyl}-2-phenyl-1,3-thiazol-5-yl)methyl]sulfanyl}phenoxy)acetic acid ¹H NMR (CDCl₃) 400 MHz δ 7.91(m, 2H), 7.95(d, 1H, J=7.69 Hz), 7.47(m, 1H), 7.42(m, 3H), 7.35(t, 1H, J=7.95 Hz), 7.13(dd, 1H, J=8.37, 2.39 Hz), 7.04(s, 2H), 6.60(d, 1H, J=8.37 Hz), 4.67(s, 2H), 4.57(s, 2H), 4.20(s, 2H), 2.69(s, 3H), 2.12(s, 3H),
MS(ES⁺) M+H=560.30

2-{2-Methyl-4-[({4-{[4-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H (CDCl₃) 400 MHz δ 7.94(m, 4H), 7.66(d, 2H, J=8.20 Hz), 7.18(d, 1H, J=2.22 Hz), 7.03(dd, 1H, J=8.20, 2.22 Hz), 6.94(d, 2H, J=8.89 Hz), 6.53(d, 1H, J=8.20 Hz), 4.85(d, 1H, J□.79 Hz), 4.80(d, 1H, J□.79 Hz), 4.69(q, 1H, J=6.84 Hz), 4.26(d, 1H, J□.70 Hz), 4.21(d, 1H, J□.70 Hz), 2.63(m, 3H), 2.18(s, 3H), 1.62(d, 3H, J=6.84 Hz),
MS(ES⁻) M−H=640.00

{2-Ethyl-4-[({4-{[4-(4-fluorophenyl)-1-piperazinyl]methyl}-2-[4-(trifluoromethyl)phenyl]-1,3-thiazol-5-yl}methyl)sulfanyl]phenoxy}acetic acid ¹H NMR (CDCl₃) 400 MHz δ 7.98(d, 2H, J=8.06 Hz), 7.67(d, 2H, J=8.06 Hz), 7.11(dd, 1H, J=8.61, 2.20 Hz), 7.02(d, 1H, J=2.20 Hz), 6.93(m, 2H), 6.82(m, 2H), 6.68(d, 1H, J=8.61 Hz), 4.62(s, 2H), 4.12(s, 2H), 3.44(s, 2H), 3.25(m, 4H), 3.02(br s, 4H), 2.58(q, 2H, J=7.51 Hz), 1.10(t, 3H, J=7.51 Hz),
MS(ES⁻) M−H=644.5

{4-[({4-[(4-Acetyl-1-piperazinyl)methyl]-2-[4-(trifluoromethyl)phenyl]-1,3-thiazol-5-yl}methyl)sulfanyl-2-ethylphenoxy}acetic acid ¹H NMR (CDCl₃) 300 MHz δ 8.04(d, 2H, J=8.28 Hz), 7.75(d, 2H, J=8.28 Hz), 7.22(dd, 1H, J=8.55, 2.21 Hz), 7.03(s, 1H), 6.74(d, 1H, J=8.55 Hz), 4.74(s, 2H), 4.13(s, 2H), 3.76(br s, 4H), 3.36(s, 2H), 2.99(br s, 2H), 2.72(br s, 2H), 2.61(q, 2H, J=7.45 Hz), 2.09(s, 3H), 1.12(t, 3H, J=7.45 Hz),
MS(ES⁺) M+H=594.1

{4-[({4-{[4-(4-Acetylphenyl)-1-piperazinyl]methyl}-2-[4-(trifluoromethyl)phenyl]-1,3-thiazol-5-yl}methyl)sulfanyl]-2-ethylphenoxy}acetic acid ¹H NMR (CDCl₃) 400 MHz δ 7.95(d, 2H, J=8.42 Hz), 7.84(d, 2H, J=8.97 Hz), 7.67(d, 2H, J=8.42 Hz), 7.14(dd, 1H, J=8.42, 2.20 Hz), 6.95(s, 1H), 6.80(d, 2H, J=8.97 Hz), 6.70(d, 1H, J=8.42 Hz), 4.66(s, 2H), 4.08(s, 2H), 3.54(br s, 4H), 3.38(s, 2H), 3.06(br s, 4H), 2.56(q, 2H, J=7.60 Hz), 2.49(s, 3H), 1.08(t, 3H, J=7.60 Hz),

{2-Ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid ¹H NMR (CDCl₃) 400 MHz δ 7.97(d, 2H, J=8.28 Hz), 7.68(d, 2H, J=8.28 Hz), 7.15(dd, 1H, J=8.45, 2.24 Hz), 6.94(d, 1H, J=2.24 Hz), 6.88(d, 2H, J=9.14 Hz), 6.79(d, 2H, J=9.14 Hz), 6.72(d, 1H, J=8.45 Hz), 4.66(s, 2H), 4.08(s, 2H), 3.72(s, 3H), 3.32(m, 6H), 3.09(br s, 4H), 2.56(q, 2H, J=7.50 Hz), 1.08(t, 3H, J=7.50 Hz),
MS(ES⁻) M−H=656.2

2-(4-{[(2-(4-Fluorophenyl)-4-{[4-(phenoxycarbonyl)-1-piperazinyl]methyl}-1,3-thiazol-5-yl)methyl]sulfanyl}-2-methylphenoxy)propanoic acid ¹H NMR (CDCl₃) 400 MHz δ 7.91(m, 2H), 7.35(m, 3H), 7.19(m, 3H), 7.12(br s, 1H), 7.07(d, 2H, J=8.79 Hz), 6.67(br s, 1H), 4.58(br s, 1H), 4.27(s, 2H), 3.59(m, 4H), 3.41(s, 2H), 2.51(br s, 4H), 2.19(s, 3H), 1.54(d, 1H, J=6.59 Hz),
MS(ES⁻) M−H=620.4

2-(4-{[(2-(4-Fluorophenyl)-4-{[4-(isopropoxycarbonyl)-1-piperazinyl]methyl}-1,3-thiazol-5-yl)methyl]sulfanyl}-2-methylphenoxy)propanoic acid ¹H NMR (CDCl₃) 400 MHz δ 7.94(m, 2H), 7.19(m, 3H), 7.05(br s, 1H), 6.64(d, 1H, J=8.42 Hz), 4.69(br s, 1H), 4.47(br s, 1H), 4.21(s, 2H), 3.50(br s, 4H), 3.36(s, 2H), 2.64(br s, 4H), 2.18(s, 3H), 1.57(d, 3H, J=5.68 Hz), 1.22(d, 6H, J=6.23 Hz),
MS(ES⁻) M−H=586.2

2-[4-({[4-{[4-(Ethoxycarbonyl)-1-piperazinyl]methyl}-2-(4-fluorophenyl)-1,3-thiazol-5-yl]methyl}sulfanyl)-2-methylphenoxy]propanoic acid ¹H NMR (CD₃OD) 400 MHz δ 7.93(m, 2H), 7.19(m, 3H), 7.09(br s, 1H), 6.67(br s, 1H), 4.70(br s, 1H), 4.21(s, 2H), 4.10(q, 2H, J=7.14 Hz), 3.49(m, 4H), 3.37(s, 2H), 2.60(br s, 4H), 2.18(s, 3H), 1.58(br s, 3H), 1.23(t, 3H, J=7.14 Hz),
MS(ES⁻) M−H=572.2

2-(4-{[(2-(4-Fluorophenyl)-4-{[4-(3-methoxyphenyl)-1-piperazinyl]methyl}-1,3-thiazol-5-yl)methyl]sulfanyl}-2-methylphenoxy)propanoic acid ¹H NMR (CDCl₃) 400 MHz δ 7.84(m, 2H), 7.13(m, 4H), 6.92(br s, 1H), 6.72(br s, 1H), 6.44(m, 3H), 4.38(br s, 1H), 4.00(s, 2H), 3.74(s, 3H), 3.40(m, 6H), 3.03(m, 4H), 2.17(s, 3H), 1.61(m, 3H),
MS(ES⁻) M−H=606.2

2-[4-({[4-{[4-(4-Acetylphenyl)-1-piperazinyl]methyl}-2-(4-fluorophenyl)-1,3-thiazol-5-yl]methyl}sulfanyl)-2-methylphenoxy]propanoic acid ¹H NMR (CD₃OD) 400 MHz δ 7.94(m, 2H), 7.85(d, 2H, J=8.97 Hz), 7.18(m, 3H), 7.03(br s, 1H), 6.92(d, 2H, J=8.97 Hz), 6.67(br s, 1H), 4.61(br s, 1H), 4.19(s, 2H), 3.41(m, 6H), 2.73(br s, 4H), 2.48(s, 3H), 2.17(s, 3H), 1.61(br s, 3H),
MS(ES⁻) M−H=618.2

2-(4-{[(2-(4-Fluorophenyl)-4-{[4-(4-methoxyphenyl)-1-piperazinyl]methyl}-1,3-thiazol-5-yl)methyl]sulfanyl}-2-methylphenoxy)propanoic acid ¹H NMR (CD₃OD) 400 MHz δ 7.97(m, 2H), 7.18(m, 3H), 7.02(br s, 1H), 6.91(d, 2H, J=8.79 Hz), 6.81(d, 2H, J=8.79 Hz), 6.62(br s, 1H), 4.66(br s, 1H), 4.17(s, 2H), 3.72(s, 3H), 3.41(s, 2H), 3.15(br s, 4H), 2.92(br s, 4H), 2.18(s, 3H), 1.59(br s, 3H),
MS(ES⁻) M−H=606.2

{4-[({4-[(4-Acetyl-1-piperazinyl)methyl]-2-[4-(trifluoromethyl)phenyl]-1,3-thiazol-5-yl}methyl)sulfanyl]-2-propylphenoxy}acetic acid ¹H NMR (CD₃OD) 400 MHz δ 8.07(d, 2H, J=8.28 Hz), 7.75(d, 2H, J=8.28 Hz), 7.21(dd, 1H, J=8.45, 2.41 Hz), 7.09(d, 1H, J=2.41 Hz), 6.74(d, 1H, J=8.45 Hz), 4.65(s, 2H), 4.26(s, 2H), 3.60(br s, 4H), 3.53(s, 2H), 2.75(t, 2H, J=4.74 Hz), 2.69(t, 2H, J=4.74 Hz), 2.52(t, 2H, J=7.41 Hz), 2.07(s, 3H), 1.50(m, 2H), 0.80(t, 3H, J=7.41 Hz),
MS(ES⁻) M−H=606.3

{4-[({4-{[4-(3-Methoxyphenyl)-1-piperazinyl]methyl}-2-[4-(trifluoromethyl)phenyl]-1,3-thiazol-5-yl}methyl)sulfanyl]-2-propylphenoxy}acetic acid ¹H NMR (CD₃OD) 400 MHz δ 8.11(d, 2H, J=8.28 Hz), 7.77(d, 2H, J=8.28 Hz), 7.19(dd, 1H, J=8.28, 2.41 Hz), 7.13(t, 1H, J=8.45 Hz), 7.08(d, 1H, J=2.41 Hz), 6.73(t, 1H, J=8.45 Hz), 6.54(dd, 1H, J=8.28, 2.41 Hz), 6.49(t, 1H, J=2.33 Hz), 6.45(dd, 1H, J=8.28, 2.41 Hz), 4.58(s, 2H), 4.26(s, 2H), 3.73(s, 3H), 3.69(s, 2H), 3.31(m, 4H), 3.11(t, 4H, J=4.66 Hz), 2.52(t, 2H, J=7.33 Hz), 1.49(s, 2H), 0.80(t, 3H, J=7.33 Hz),
MS(ES⁻) M−H=670.3

{4-[({4-{[4-(4-Acetylphenyl)-1-piperazinyl]methyl}-2-[4-(trifluoromethyl)phenyl]-1,3-thiazol-5-yl}methyl)sulfanyl]-2-propylphenoxy}acetic acid ¹H NMR (CDCl₃) 400 MHz δ 7.93(d, 2H, J=8.45 Hz), 7.82(d, 2H, J=8.97 Hz), 7.68(d, 2H, J=8.45 Hz), 7.19(dd, 1H, J=8.45, 2.41 Hz), 6.78(m, 4H), 4.73(s, 2H), 4.03(s, 2H), 3.71(t, 4H, J=5.09 Hz), 3.28(m, 6H), 2.47(m, 5H), 1.46(m, 2H), 0.86(t, 3H, J=7.24 Hz),
MS(ES⁻) M−H=682.1

{4-[({4-{[4-(4-Methoxyphenyl)-1-piperazinyl]methyl}-2-[4-(trifluoromethyl)phenyl]-1,3-thiazol-5-yl}methyl)sulfanyl]-2-propylphenoxy}acetic acid ¹H NMR (CD₃OD) 400 MHz δ 8.11 (d, 2H, J=8.10 Hz), 7.77(d, 2H, J=8.10 Hz), 7.19(dd, 1H, J=8.62, 2.24 Hz), 7.08(d, 1H, J=2.24 Hz), 6.93(d, 2H, J=9.14 Hz), 6.82(d, 2H, J=9.14 Hz), 6.74(d, 1H, J=8.62 Hz), 4.59(s, 2H), 4.26(s, 2H), 3.73(s, 2H), 3.71(s, 3H), 3.18(m, 8H), 2.52(t, 2H, J=7.33 Hz), 1.48(m, 2H), 0.80(t, 3H, J=7.33 Hz),
MS(ES⁺) M+H=672.2

2-{2-Ethyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CDCl₃) 400 MHz δ 7.95(d, 2H, J=8.28 Hz), 7.66(d, 2H, J=8.28 Hz), 7.12(m, 2H), 6.90(s, 1H), 6.76(d, 1H, J=8.28 Hz), 6.45(m, 3H), 4.80(q, 1H, J=6.90 Hz), 4.02(s, 2H), 3.73(s, 3H), 3.35(m, 4H), 3.21(d, 1H, J=13.66 Hz), 3.15(d, 1H, J=13.66 Hz), 2.95(br s, 4H), 2.55(s, 2H), 1.62(d, 3H, J=6.90 Hz), 1.07(t, 3H, J=7.50 Hz),
MS(ES⁻) M−H=670.0

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-ethylphenoxy}propanoic acid ¹H NMR (CDCl₃) 400 MHz δ 7.93(d, 2H, J=8.28 Hz), 7.82(d, 2H, J=8.97 Hz), 7.65(d, 2H, J=8.28 Hz), 7.08(dd, 1H, J=8.62, 2.41 Hz), 6.87(d, 1H, J=2.41 Hz), 6.79(d, 2H, J=8.97 Hz), 6.72(d, 1H, J=8.62 Hz), 4.80(q, 1H, J=6.72 Hz), 4.04(d, 1H, J=13.66 Hz), 3.98(d, 1H, J=13.66 Hz), 3.49(br s, 4H), 3.28(d, 1H, J=13.83 Hz), 3.14(d, 1H, J=13.83 Hz), 3.00(br s, 4H), 2.54(m, 5H), 1.63(d, 3H, J=6.72 Hz), 1.06(t, 3H, J=7.50 Hz),
MS(ES⁻) M−H=682.2

2-{2-Ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CDCl₃) 400 MHz δ 7.97(d, 2H, J=8.45 Hz), 7.66(d, 2H, J=8.45 Hz), 7.10(dd, 1H, J=8.45, 2.24 Hz), 6.94(d, 1H, J=2.24 Hz), 6.89(d, 2H, J=9.14 Hz), 6.80(d, 2H, J=9.14 Hz), 6.75(d, 1H, J=8.45 Hz), 4.77(q, 1H, J=6.72 Hz), 4.04(s, 2H), 3.73(s, 3H), 3.25(m, 6H), 2.96(br s, 4H), 2.57(s, 2H), 1.61(d, 3H, J=6.72 Hz), 1.09(t, 3H, J=7.50 Hz),
MS(ES⁻) M−H=670.3

2-{2-Ethyl-4-[({4-(4-morpholinylmethyl)-2-[4-(trifluoromethyl)phenyl]-1,3-thiazol-5-yl}methyl)sulfanyl]phenoxy}propanoic acid $^1$H NMR (CDCl$_3$) 400 MHz δ 8.01(d, 2H, J=8.42 Hz), 7.70(d, 2H, J=8.42 Hz), 7.13(dd, 1H, J=8.42, 2.20 Hz), 6.86(s, 1H), 6.76(d, 1H, J=8.42 Hz), 4.84(q, 1H, J=6.65 Hz), 4.04(d, 1H, J□.47 Hz), 3.98(d, 1H, J□.47 Hz), 3.87(br s, 4H), 3.21(d, 1H, J□0.83 Hz), 3.08(d, 1H, J□.83 Hz), 2.95(br s, 4H), 2.55(s, 2H), 1.64(d, 3H, J=6.65 Hz), 1.07(t, 3H, J=7.51 Hz),
MS(ES$^-$) M−H=565.0

2-{2-Ethyl-4-[({4-{[4-(4-fluorophenyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400 MHz δ 8.12(d, 2H, J=8.24 Hz), 7.78(d, 2H, J=8.24 Hz), 7.17(dd, 1H, J=8.61, 2.20 Hz), 7.10(d, 1H, J=2.20 Hz), 6.98(m, 4H), 6.71(d, 1H, J=8.61 Hz), 4.71(q, 1H, J=6.90 Hz), 4.27(s, 2H), 3.66(s, 2H), 3.20(m, 8H), 2.59(q, 2H, J=7.51 Hz), 1.57(d, 3H, J=6.90 Hz), 1.09(t, 3H, J=7.51 Hz),
MS(ES$^-$) M−H=658.0

2-{4-[({4-[(4-Acetyl-1-piperazinyl)methyl]-2-[4-(trifluoromethyl)phenyl]-1,3-thiazol-5-yl}methyl)sulfanyl]-2-ethylphenoxy}propanoic acid $^1$H NMR (CD$_3$OD) 400 MHz δ 8.10(d, 2H, J=8.24 Hz), 7.77(d, 2H, J=8.24 Hz), 7.19(t, 1H, J=2.38 Hz), 7.09(d, 1H, J=2.38 Hz), 6.71(d, 1H, J=8.24 Hz), 4.80(q, 1H, J=6.78 Hz), 4.26(s, 2H), 3.65(m, 6H), 3.56(d, 1H, J□.92 Hz), 3.51(d, 1H, J□.92 Hz), 2.83(m, 4H), 2.58(q, 2H, J=7.60 Hz), 2.09(s, 3H), 1.60(d, 3H, J=6.78 Hz), 1.09(t, 3H, J=7.60 Hz),
MS(ES$^-$) M−H=606.0

{2-Ethyl-4-[({4-(4-morpholinylmethyl)-2-[4-(trifluoromethyl)phenyl]-1,3-thiazol-5-yl}methyl)sulfanyl]phenoxy}acetic acid $^1$H NMR (CDCl$_3$) 300 MHz δ 8.05(d, 2H, J=8.28 Hz), 7.75(d, 2H, J=8.28 Hz), 7.19(dd, 1H, J=8.55, 2.21 Hz), 6.98(s, 1H), 6.76(d, 1H, J=8.55 Hz), 4.74(s, 2H), 4.12(s, 2H), 3.95(br s, 4H), 3.32(s, 2H), 3.06(br s, 4H), 2.61(q, 2H, J=7.54 Hz), 1.14(t, 3H, J=7.54 Hz),
MS(ES$^-$) M−H=551.3

2-{2-Isopropyl-4-[({4-(4-morpholinylmethyl)-2-[4-(trifluoromethyl)phenyl]-1,3-thiazol-5-yl}methyl)sulfanyl]phenoxy}propanoic acid $^1$H NMR (CD$_3$OD) 400 MHz δ 8.11(d, 2H, J=8.24 Hz), 7.78(d, 2H, J=8.24 Hz), 7.25(dd, 1H, J=8.42, 2.38 Hz), 7.00(d, 1H, J=2.38 Hz), 6.74(d, 1H, J=8.42 Hz), 4.88(q, 1H, J=6.78 Hz), 4.25(s, 2H), 3.84(m, 5H), 3.66(d, 1H, J□.28 Hz), 3.22(m, 5H), 1.60(d, 3H, J=6.78 Hz), 1.05(m, 6H),
MS(ES$^-$) M−H=579.0

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-isopropylphenoxy}propanoic acid $^1$H NMR (CD$_3$OD) 400 MHz δ 8.13(d, 2H, J=8.06 Hz), 7.79(d, 2H, J=8.06 Hz), 7.26(d, 1H, J=8.42 Hz), 7.06(s, 1H), 6.99(m, 4H), 6.75(d, 1H, J=8.42 Hz), 4.88(q, 1H, J=6.78 Hz), 4.29(s, 2H), 3.91(d, 1H, J□.10 Hz), 3.80(d, 1H, J□.10 Hz), 3.33(m, 9H), 1.60(d, 3H, J=6.78 Hz), 1.08(m, 6H),
MS(ES$^-$) M−H=672.0

2-{4-[({4-[(4-Acetyl-1-piperazinyl)methyl]-2-[4-(trifluoromethyl)phenyl]-1,3-thiazol-5-ylmethyl)sulfanyl]-2-isopropylphenoxy}propanoic acid

MS(ES$^-$) M−H=620.0

2-{2-Isopropyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400 MHz δ 8.13(d, 2H, J=8.06 Hz), 7.79(d, 2H, J=8.06 Hz), 7.26(d, 1H, J=8.42 Hz), 7.16(t, 1H, J=8.42 Hz), 7.06(s, 1H), 6.74(d, 1H, J=8.42 Hz), 6.56(d, 1H, J=8.42 Hz), 6.50(br s, 2H), 4.90(q, 1H, J=6.78 Hz), 4.27(s, 2H), 3.89(d, 1H, J□0.10 Hz), 3.79(d, 1H, J□.10 Hz), 3.74(s, 3H), 3.34(m, 9H), 1.60(d, 3H, J=6.78 Hz), 1.07(m, 6H),
MS(ES$^-$) M−H=684.1

2-{4-[({4-{[4-(4-Acetylphenyl)-1-piperazinyl]methyl-2-[4-(trifluoromethyl)phenyl]-1,3-thiazol-5-yl}methyl)sulfanyl]-2-isopropylphenoxy}propanoic acid $^1$H NMR (CD$_3$OD) 400 MHz δ 8.13(d, 2H, J=8.24 Hz), 7.91(d, 2H, J=8.97 Hz), 7.78(d, 2H, J=8.24 Hz), 7.25(d, 1H, J=8.97 Hz), 7.04(m, 3H), 6.74(d, 1H, J=8.24 Hz), 4.89(q, 1H, J=6.78 Hz), 4.28(s, 2H), 3.90(d, 1H, J□.55 Hz), 3.79(d, 1H, J□.55 Hz), 3.60(br s, 4H), 3.32(m, 5H), 2.50(s, 3H), 1.61(d, 3H, J=6.78 Hz), 1.07(d, 6H, J=7.51 Hz),
MS(ES$^-$) M−H=696.2

2-{2-Isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400 MHz δ 8.13(d, 2H, J=8.24 Hz), 7.79(d, 2H, J=8.24 Hz), 7.27(d, 1H, J=8.61 Hz), 7.05(s, 1H), 6.95(d, 2H, J=8.79 Hz), 6.84(d, 2H, J=8.79 Hz), 6.75(d, 1H, J=8.61 Hz), 4.88(m, 1H) buried under MeOH signal, 4.28(s, 2H), 3.90(d, 1H, J□.28 Hz), 3.80(d, 1H, J□.28 Hz), 3.71(s, 3H), 3.56(br s, 4H), 3.28(m, 1H) buried under MeOH signal, 2.96(br s, 4H), 1.58(d, 3H, J=6.59 Hz), 1.07(m, 6H),
MS(ES$^-$) M−H=684.1

{2-Isopropyl-4-[({4-(4-morpholinylmethyl)-2-[4-(trifluoromethyl)phenyl]-1,3-thiazol-5-yl}methyl)sulfanyl]phenoxy}acetic acid $^1$H NMR (CD$_3$OD) 400 MHz δ 8.12(d, 2H, J=8.06 Hz), 7.79(d, 2H, J=8.06 Hz), 7.27(d, 1H, J=8.42 Hz), 7.04(s, 1H), 6.80(d, 1H, J=8.42 Hz), 4.76(s, 2H), 4.27(s, 2H), 3.87(m, 6H), 3.22(m, 5H), 1.07(d, 6H, J=6.78 Hz),
MS(ES$^-$) M−H=565.0

{4-[({4-{[4-(4-Fluorophenyl)-1-piperazinyl]methyl}-2-[4-(trifluoromethyl)phenyl]-1,3-thiazol-5-yl}methyl)sulfanyl-2-isopropylphenoxy}acetic acid $^1$H NMR (CD$_3$OD) 400 MHz δ 8.13(d, 2H, J=8.06 Hz), 7.79(d, 2H, J=8.06 Hz), 7.28(d, 1H, J=8.42 Hz), 7.09(s, 1H), 6.98(m, 4H), 6.81(d, 1H, J=8.42 Hz), 4.74(s, 2H), 4.28(s, 2H), 3.89(s, 2H), 3.61 (br s, 4H), 3.29(m, 1H) buried under MeOH signal, 3.02(br s, 4H), 1.07(d, 6H, J=6.78 Hz),
MS(ES⁻) M−H=658.0

{4-[({4-[(4-Acetyl-1-piperazinyl)methyl]-2-[4-(trifluoromethyl)phenyl]-1,3-thiazol-5-yl}methyl)sulfanyl]-2-isopropylphenoxy}acetic acid ¹H NMR (CD₃OD) 400 MHz δ 8.13(d, 2H, J=8.06 Hz), 7.79(d, 2H, J=8.06 Hz), 7.28(d, 1H, J=8.42 Hz), 7.03(br s, 1H), 6.80(d, 1H, J=8.42 Hz), 4.76(s, 2H), 4.27(s, 2H), 3.80(m, 6H), 3.21(m, 5H), 2.11(s, 3H), 1.06(d, 6H, J=6.78 Hz),
MS(ES⁻) M−H=606.2

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400 MHz δ 8.12(d, 2H, J=8.28 Hz), 7.79(d, 2H, J=8.28 Hz), 7.23(dd, 1H, J=8.45, 2.24 Hz), 7.09(d, 1H, J=2.24 Hz), 6.95(d, 2H, J=9.14 Hz), 6.84(d, 2H, J=9.14 Hz), 6.71(d, 1H, J=8.45 Hz), 4.81(q, 1H, J=6.72 Hz), 4.29(s, 2H), 3.98(d, 1H, J□.14 Hz), 3.90(d, 1H, J□.14 Hz), 3.71(s, 3H), 3.50(br s, 4H), 3.21(m, 4H), 2.50(t, 2H, J=7.33 Hz), 1.58(d, 3H, J=6.72 Hz), 1.48(m, 2H), 0.79(t, 3H, J=7.33 Hz),
MS(ES⁻) M−H=684.0

{4-[({4-(4-Morpholinylmethyl)-2-[4-(trifluoromethyl)phenyl]-1,3-thiazol-5-yl}methyl)sulfanyl]-2-propylphenoxy}acetic acid ¹H NMR (CD₃OD) 400 MHz δ 8.10(d, 2H, J=8.79 Hz), 7.78(d, 2H, J=8.79 Hz), 7.20(dd, 1H, J=8.42, 2.20 Hz), 7.08(d, 1H, J=2.20 Hz), 6.75(d, 1H, J=8.42 Hz), 4.63(s, 2H), 4.26(s, 2H), 3.79(t, 4H, J=4.21 Hz), 3.64(s, 2H), 2.97(t, 4H, J=4.21 Hz), 2.53(t, 2H, J=7.42 Hz), 1.50(s, 2H), 0.82(t, 3H, J=7.42 Hz),
MS(ES⁻) M−H=658.0

{4-[({4-{[4-(4-Fluorophenyl)-1-piperazinyl]methyl}-2-[4-(trifluoromethyl)phenyl]-1,3-thiazol-5-yl}methyl)sulfanyl]-2-propylphenoxy}acetic acid ¹H NMR (CDCl₃) 400 MHz δ 7.97(d, 2H, J=8.24 Hz), 7.67(d, 2H, J=8.24 Hz), 7.12(dd, 1H, J=8.42, 2.20 Hz), 7.01(d, 1H, J=2.20 Hz), 6.93(m, 2H), 6.83(m, 2H), 6.69(d, 1H, J=8.42 Hz), 4.62(s, 2H), 4.12(s, 2H), 3.45(s, 2H), 3.26(t, 4H, J=4.85 Hz), 3.04(t, 4H, J=4.85 Hz), 2.52(t, 2H, J=7.33 Hz), 1.51(s, 2H), 0.83(t, 3H, J=7.33 Hz),

2-[(4-[({4-[(3,5-Dimethyl-1-piperazinyl)methyl]-2-[4-(trifluoromethyl)phenyl]-1,3-thiazol-5-yl}methyl)sulfanyl]-2-methylphenoxy}propanoic acid ¹H NMR (CDCl₃) 400 MHz δ 8.03(d, 2H, J=8.23 Hz), 7.71(d, 2H, J=8.23 Hz), 7.20(m, 2H), 6.66(d, 1H, J=8.55 Hz), 4.72(q, 1H, J=6.64 Hz), 4.26(d, 1H, J□.87 Hz), 4.18(d, 1H, J□.87 Hz), 3.34(m, 2H), 3.05(m, 2H), 2.71(m, 2H), 2.21(s, 3H), 1.97(m, 2H), 1.63(d, 3H, J=6.64 Hz), 1.35(m, 6H),
MS(ES⁺) M+H=580.1
HPLC(C-18 3 μm) 1% MeOH/0–99% Acetonitrile/Water (0.1% TFA) 5 min run R_f=3.98

2-{4-[({4-{[4-(4-Chlorophenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400 MHz δ 10.42(s, 1H), 7.92(d, 2H, J=8.20 Hz), 7.64(d, 2H, J=8.20 Hz), 7.15(d, 2H, J=9.06 Hz), 7.01(d, 1H, J=2.20 Hz), 6.96(d, 1H, J=8.37 Hz), 6.72(d, 2H, J=9.06 Hz), 6.59(d, 1H, J=8.37 Hz), 4.64(q, 1H, J=6.78 Hz), 4.09(s, 2H), 3.58(d, 1H, J□.18 Hz), 3.49(d, 1H, J□.18 Hz), 3.26(m, 4H), 3.05(m, 4H), 2.13(s, 3H), 1.56(d, 3H, J=6.78 Hz),
MS(ES⁺) M+H=662.0
HPLC(C-18 3 μm) 1% MeOH/0–99% Acetonitrile/Water (0.1% TFA) 5 min run R_f=4.13

2-{4-[({4-{[4-(tert-Butoxycarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400 MHz δ 10.07(s, 1H), 7.93(d, 2H, J=8.23 Hz), 7.63(d, 2H, J=8.23 Hz), 7.04(s, 1H), 6.98(d, 1H, J=8.37 Hz), 6.58(d, 1H, J=8.37 Hz), 4.65(q, 1H, J=6.78 Hz), 4.12(d, 1H, J□.70 Hz), 4.05(d, 1H, J□.70 Hz), 3.47(m, 6H), 2.73(m, 4H), 2.14(s, 3H), 1.57(d, 3H, J=6.78 Hz), 1.38(s, 9H),
MS(ES⁺) M+H=652.0
HPLC(C-18 3 μm) 1% MeOH/0–99% Acetonitrile/Water (0.1% TFA) 5 min run R_f=4.16

2-{2-Methyl-4-[({4-(1-piperazinylmethyl)-2-[4-(trifluoromethyl)phenyl]-1,3-thiazol-5-yl}methyl)sulfanyl]phenoxy}propanoic acid ¹H NMR (CDCl₃) 400 MHz δ 9.26(br s, 1H), 7.97(br s, 2H), 7.63(br s, 2H), 7.10(br s, 2H), 6.67(br s, 1H), 4.56(br s, 1H), 4.11(br s, 2H), 3.39(br s, 2H), 2.98(br s, 4H), 2.41(br s, 4H), 2.07(br s, 3H), 1.44(br s, 3H),
MS(ES⁺) M+H=552
HPLC(C-18 3 μm) 1% MeOH/0–99% Acetonitrile/Water (0.1% TFA) 5 min run R_f=3.80

{2-Isopropyl-4-[({4-{[4-(3-methoxyphenyl)-1-piperazinyl]methyl-2-[4-(trifluoromethyl)phenyl]-1,3-thiazol-5-yl}methyl)sulfanyl]phenoxy}acetic acid ¹H NMR (CD₃OD) 400 MHz δ 8.13(d, 2H, J=8.06 Hz), 7.79(d, 2H, J=8.06 Hz), 7.28(d, 1H, J=8.24 Hz), 7.15(m, 1H), 7.09(s, 1H), 6.80(d, 1H, J=8.24 Hz), 6.52(m, 3H), 4.74(s, 2H), 4.28(s, 2H), 3.88(s, 2H), 3.73(m, 3H), 3.48(br s, 4H), 3.29(m, 1H) buried under MeOH signal, 3.05(s, 4H), 1.06(d, 6H, J=6.59 Hz),
MS(ES⁻) M−H=670.0

{4-[({4-{[4-(4-Acetylphenyl)-1-piperazinyl]methyl}-2-[4-(trifluoromethyl)phenyl]-1,3-thiazol-5-yl}methyl)sulfanyl]-2-isopropylphenoxy}acetic acid ¹H NMR (CD₃OD) 400 MHz δ 8.13(d, 2H, J=7.87 Hz), 7.91(d, 2H, J=8.79 Hz), 7.78(d, 2H, J=7.87 Hz), 7.27(d, 1H, J=8.24 Hz), 7.09(br s, 1H), 7.02(d, 2H, J=8.24 Hz), 6.80(d, 1H, J=8.79 Hz), 4.74(s, 2H), 4.29(s, 2H), 3.89(s, 2H), 3.62(br s, 4H), 3.30(m, 5H), 2.51 (s, 3H), 1.07(d, 6H, J=6.78 Hz),
MS(ES⁻) M−H=682.0

{2-Isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid ¹H NMR (CD₃OD) 400 MHz δ 8.13(d, 2H, J=8.06 Hz), 7.79(d, 2H, J=8.06 Hz), 7.29(d, 1H, J=8.45 Hz), 7.09(s, 1H), 6.98(d, 2H, J=8.45 Hz), 6.83(m, 3H), 4.73(s, 2H), 4.30(s, 2H), 3.90(s, 3H), 3.35(m, 11H), 1.07(d, 6H, J=6.59 Hz),
MS(ES⁻) M−H=670.0

2-{4-[({4-(4-Morpholinylmethyl)-2-[4-(trifluoromethyl)phenyl]-1,3-thiazol-5-yl}methyl)sulfanyl]-2-propylphenoxy}propanoic acid ¹H NMR (CD₃OD) 400 MHz δ 8.18(d, 2H, J=8.00 Hz), 7.84(d, 2H, J=8.00 Hz), 7.30(dd, 1H, J=8.55, 2.48 Hz), 7.11(d, 1H, J=2.48 Hz), 6.78(d, 1H, J=8.55 Hz), 4.91(s, 1H) buried under MeOH signal, 4.33(s, 2H), 3.94(m, 6H), 3.24(br s, 4H), 2.56(t, 2H, J=7.45 Hz), 1.59(m, 5H), 0.86(t, 3H, J=7.45 Hz),
MS(ES⁻) M−H=579.0

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400 MHz δ 8.18(d, 2H, J=8.28 Hz), 7.85(d, 2H, J=8.28 Hz), 7.30(dd, 1H, J=8.55, 2.21 Hz), 7.16(d, 1H, J=2.21 Hz), 7.06(m, 4H), 6.78(d, 1H, J=8.55 Hz), 4.89(br s, 1H) hidden under MeOH signal, 4.35(s, 2H), 4.06(d, 1H, J□.35 Hz), 3.98(d, 1H, J□.35 Hz), 3.68(br s, 4H), 3.08(br s, 4H), 2.56(t, 2H, J=7.45 Hz), 1.57(m, 5H), 0.86(t, 3H, J=7.45 Hz),
MS(ES⁻) M−H=672.0

2-{4-[({4-[(4-Acetyl-1-piperazinyl)methyl]-2-[4-(trifluoromethyl)phenyl]-1,3-thiazol-5-yl}methyl)sulfanyl]-2-propylphenoxy}propanoic acid ¹H NMR (CD₃OD) 400 MHz δ 8.17(d, 2H, J=8.28 Hz), 7.84(d, 2H, J=8.28 Hz), 7.29(dd, 1H, J=8.55, 2.21 Hz), 7.10(d, 1H, J=2.21 Hz), 6.77(d, 1H, J=8.55 Hz), 4.93(q, 1H, J=6.78 Hz), 4.32(s, 2H), 3.86(m, 6H), 3.27(m, 4H), 2.56(m, 2H), 2.18(s, 3H), 1.66(d, 3H, J=6.78 Hz), 1.54(m, 2H), 0.85(t, 3H, J=7.31 Hz),
MS(ES⁻) M−H=620.0

2-{4-[({4-{[4-(3-Methoxyphenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400 MHz δ 8.18(d, 2H, J=8.55 Hz), 7.85(d, 2H, J=8.55 Hz), 7.30(dd, 1H, J=8.55, 2.21 Hz), 7.22(t, 1H, J=8.55 Hz), 7.16(d, 1H, J=2.21 Hz), 6.77(d, 1H, J=8.55 Hz), 6.58(m, 3H), 4.80(m, 1H), 4.34(s, 2H), 4.06(d, 1H, J□.07 Hz), 3.97(d, 1H, J□.07 Hz), 3.79(s, 3H), 3.60(br s, 4H), 3.08(br s, 4H), 2.56(t, 2H, J=7.17 Hz), 1.58(m, 5H), 0.85(t, 3H, J=7.17 Hz),
MS(ES⁻) M−H=684.1

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400 MHz δ 8.12(d, 2H, J=8.28 Hz), 7.91(d, 2H, J=9.14 Hz), 7.78(d, 2H, J=8.28 Hz), 7.22(dd, 1H, J=8.28, 2.24 Hz), 7.10(d, 1H, J=2.24 Hz), 7.03(d, 2H, J=9.14 Hz), 6.71(d, 1H, J=8.28 Hz), 4.81(q, 1H, J=6.72 Hz), 4.29(s, 2H), 3.99(d, 1H, J=0.14 Hz), 3.91(d, 1H, J□.14 Hz), 3.60(br s, 4H), 3.33(m, 4H), 2.48(m, 5H), 1.59(d, 3H, J=6.72 Hz), 1.48(m, 2H), 0.78(t, 3H, J=7.41 Hz),
MS(ES⁻) M−H=696.1

2-{2-Methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 300 MHz δ 8.35(d, 2H, J=4.69 Hz), 8.13(d, 2H, J=8.28 Hz), 7.80(d, 2H, J=8.28 Hz), 7.21(s, 1H), 7.13(d, 1H, J=8.28 Hz), 6.71(d, 1H, J=8.28 Hz), 6.63(t, 1H, J=4.69 Hz), 4.59(m, 1H), 4.31(s, 2H), 3.86(t, 4H, J=4.69 Hz), 3.50(s, 2H), 2.69(t, 4H, J=4.69 Hz), 2.22(s, 3H), 1.59(d, 3H, J=6.78 Hz),
MS(ES⁻) M−H=628.5

2-{4-[({4-{[4-(2,4-Dimethoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.17(d, 2H, J=8.00 Hz), 7.80(d, 2H, J=8.00 Hz), 7.20(br s, 1H), 7.04(br s, 1H), 6.92(d, 1H, J=8.55 Hz), 6.67(br s, 1H), 6.56(m, 1H), 6.48(m, 1H), 4.59(br s, 1H), 4.27(s, 2H), 3.84(s, 3H), 3.78(s, 3H), 3.55(s, 2H), 3.07(m 8H), 2.21(s, 3H), 1.56(br s, 3H),
MS(ES⁻) M−H=685.6

2-{2-Methyl-4-[({4-({4-[2-oxo-2-(1-pyrrolidinyl)ethyl]-1-piperazinyl}methyl)-2-]4-(trifluoromethyl)phenyl]-1,3-thiazol-5-yl}methyl)sulfanyl]phenoxy}propanoic acid MS(ES⁻) M−H=660.7
CHN Analysis 0.3H₂O (Theoretical % C=53.62, % H=6.05, % N=7.82; Found % C=53.33, % H=6.01, % N=7.95)

2-[2-Methyl-4-({[2-[4-(trifluoromethyl)phenyl]-4-({4-[3-(trifluoromethyl)phenyl]-1-piperazinyl}methyl)-1,3-thiazol-5-yl]methyl}sulfanyl)phenoxy]propanoic acid ¹H NMR (CD₃OD) 300 MHz δ 8.09(d, 2H, J=8.28 Hz), 7.77(d, 2H, J=8.28 Hz), 7.40(s, 1H), 7.19(m, 4H), 7.07(d, 1H, J=7.73 Hz), 6.71(d, 1H, J=8.28 Hz), 4.47(m, 1H), 4.33(s, 2H), 3.53(s, 2H), 3.23(m, 4H), 2.64(m, 4H), 2.22(s, 3H), 1.57(d, 3H, J=6.78 Hz),
MS(ES⁻) M−H=694.5

2-{4-[({4-{[4-(2-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.09(d, 2H, J=8.28 Hz), 7.77(d, 2H, J=8.28 Hz), 7.25(s, 1H), 7.17(s, 1H), 6.96(m, 4H), 6.70(s, 1H), 4.51(m, 1H), 4.34(s, 2H), 3.86(s, 3H), 3.57(s, 2H), 3.07(br s, 4H), 2.76(br s, 4H), 2.23(br s, 3H), 1.54(br s, 3H),
MS(ES⁻) M−H=656.5

2-{4-[({4-[(4-Acetyl-1-piperazinyl)methyl]-2-[4-(trifluoromethyl)phenyl]-1,3-thiazol-5-yl}methyl)sulfanyl]-2-methylphenoxy}propanoic acid $^1$H NMR (CDCl$_3$) 400 MHz δ 7.93(d, 2H, J=8.20 Hz), 7.63(d, 2H, J=8.20 Hz), 7.02(m, 2H), 6.57(d, 1H, J=8.20 Hz), 4.65(q, 1H, J=6.78 Hz), 4.16(d, 1H, J□.87 Hz), 4.09(d, 1H, J□.87 Hz), 3.55(m, 6H), 2.74(m, 4H), 2.11(s, 3H), 1.98(s, 3H), 1.55(d, 3H, J=6.78 Hz),
MS(ES$^+$) M+H=594.0
HPLC(C-18 3 μm) 1% MeOH/0–99% Acetonitrile/Water (0.1% TFA) 5 min run R$_t$=3.79

2-{2-Methyl-4-[({4-{[4-(4-pyridinyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400 MHz δ 8.01(d, 2H, J=8.20 Hz), 7.95(d, 2H, J=8.20 Hz), 7.64(d, 2H, J=8.20 Hz), 7.16(d, 1H, J=2.22 Hz), 7.09(dd, 1H, J=8.37, 2.22 Hz), 6.97(d, 2H, J=8.20 Hz), 6.63(d, 1H, J=8.37 Hz), 4.48(q, 1H, J=6.78 Hz), 4.19(s, 2H), 3.57(t, 4H, J=5.10 Hz), 3.48(s, 2H), 2.46(t, 4H, J=5.10 Hz), 2.14(s, 3H), 1.54(d, 3H, J=6.78 Hz),
MS(ES$^+$) M+H=629.0
HPLC(C-18 3 μm) 1% MeOH/0–99% Acetonitrile/Water (0.1% TFA) 5 min run R$_t$=4.22

2-{4-[({4-{[4-(3-Methoxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400 MHz δ 10.57(s, 1H), 7.91(d, 2H, J=8.20 Hz), 7.63(d, 2H, J=8.20 Hz), 7.11(t, 1H, J=8.20 Hz), 6.98(m, 2H), 6.60(d, 1H, J=8.20 Hz), 6.41(dd, 2H, J=8.20, 2.22 Hz), 6.35(t, 1H, J=2.22 Hz), 4.65(q, 1H, J=6.84 Hz), 4.10(s, 2H), 3.72(s, 3H), 3.59(d, 1H, J□.18 Hz), 3.49(d, 1H, J□.18 Hz), 3.35(m, 4H), 3.10(m, 4H), 2.12(s, 3H), 1.55(d, 3H, J=6.84 Hz),
MS(ES$^+$) M+H=658.0
HPLC(C-18 3 μm) 1% MeOH/0–99% Acetonitrile/Water (0.1% TFA) 5 min run R$_t$=4.09

2-{2-Methyl-4-[({4-(4-morpholinylmethyl)-2-[4-(trifluoromethyl)phenyl]-1,3-thiazol-5-yl}methyl)sulfanyl]phenoxy}propanoic acid $^1$H NMR (CDCl$_3$) 400 MHz δ 11.61(s, 1H), 8.00(d, 2H, J=8.23 Hz), 7.69(d, 2H, J=8.23 Hz), 7.10(dd, 1H, J=8.37, 2.20 Hz), 6.83(d, 1H, J=2.20 Hz), 6.71(d, 1H, J=8.37 Hz), 4.84(q, 1H, J=6.72 Hz), 4.12(m, 4H), 3.84(m, 2H), 3.43(m, 3H), 3.19(m, 2H), 2.88(m, 1H), 2.10(s, 3H), 1.61(d, 3H, J=6.72 Hz),
MS(ES$^+$) M+H=553.0
HPLC(C-18 3 μm) 1% MeOH/0–99% Acetonitrile/Water (0.1% TFA) 5 min run R$_t$=3.89

2-{4-[({4-{[4-(Ethoxycarbonyl)-1-piperazinyl]methyl-2-[4-(trifluoromethyl)phenyl]-1,3-thiazol-5-yl}methyl)sulfanyl]-2-methylphenoxy}propanoic acid $^1$H NMR (CDCl$_3$) 400 MHz δ 10.39(s, 1H), 7.93(d, 2H, J=8.23 Hz), 7.64(d, 2H, J=8.23 Hz), 7.05(d, 1H, J=2.39 Hz), 6.97(d, 1H, J=8.37 Hz), 6.57(d, 1H, J=8.37 Hz), 4.65(q, 1H, J=6.78 Hz), 4.09(q, 4H, J=7.06 Hz), 3.58(m, 4H), 3.39(m, 2H), 2.74(m, 4H), 2.14(s, 3H), 1.57(d, 3H, J=6.78 Hz), 1.21(t, 3H, J=7.06 Hz),
MS(ES$^+$) M+H=624.0

HPLC(C-18 3 μm) 1% MeOH/0–99% Acetonitrile/Water (0.1% TFA) 5 min run R$_t$=3.93

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400 MHz δ 9.84(s, 1H), 7.91(d, 2H, J=8.20 Hz), 7.81(d, 2H, J=8.89 Hz), 7.63(d, 2H, J=8.20 Hz), 7.00(d, 1H, J=2.20 Hz), 6.93(dd, 1H, J=8.37, 2.20 Hz), 6.76(d, 2H, J=8.89 Hz), 6.58(d, 1H, J=8.37 Hz), 4.66(q, 1H, J=6.78 Hz), 4.08(s, 2H), 3.45(m, 6H), 2.96(m, 4H), 2.47(s, 3H), 2.13(s, 3H), 1.59(d, 3H, J=6.78 Hz),
MS(ES$^+$) M+H=670.0
HPLC(C-18 3 μm) 1% MeOH/0–99% Acetonitrile/Water (0.1% TFA) 5 min run R$_t$=4.03

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400 MHz δ 7.92(d, 2H, J=8.23 Hz), 7.62(d, 2H, J=8.23 Hz), 7.05(s, 1H), 6.89(m, 2H), 6.75(m, 2H), 6.55(d, 1H, J=8.23 Hz), 4.59(m, 1H), 4.17(m, 2H), 3.53(m, 2H), 3.21(m, 4H), 2.97(m, 4H), 2.12(s, 3H), 1.51(d, 3H, J=6.78 Hz),
MS(ES$^+$) M+H=646.0
HPLC(C-18 3 μm) 1% MeOH/0–99% Acetonitrile/Water (0.1% TFA) 5 min run R$_t$=4.11

2-{4-[({4-({4-[(4-Fluorophenyl)sulfonyl-1-piperazinyl]methyl)-2-[4-(trifluoromethyl)phenyl]-1,3-thiazol-5-yl}methyl)sulfanyl]-2-methylphenoxy}propanoic acid $^1$H NMR (CD$_3$OD) 400 MHz δ 8.03(d, 2H, J=8.20 Hz), 7.83(t, 2H, J=7.69 Hz), 7.73(d, 2H, J=8.20 Hz), 7.33(t, 2H, J=7.69 Hz), 7.17(s, 1H), 7.08(d, 1H, J=8.20 Hz), 6.64(d, 1H, J=8.20 Hz), 4.67(br s, 1H), 4.22(s, 2H), 3.37(s, 2H), 2.99(br s, 4H), 2.50(br s, 4H), 2.16(s, 3H), 1.57(d, 3H, J=6.84 Hz),
MS(ES$^-$) M−H=708.0

2-{2-Methyl-4-[({4-{[4-(3-methylbutanoyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400 MHz δ 8.12(d, 2H, J=8.28 Hz), 7.80(d, 2H, J=8.28 Hz), 7.23(d, 1H, J=2.21 Hz), 7.17(dd, 1H, J=8.28, 2.21 Hz), 6.72(d, 1H, J=8.28 Hz), 4.72(q, 1H, J=6.44 Hz), 4.32(s, 2H), 3.63(br s, 4H), 3.44(s, 2H), 2.59(br s, 4H), 2.31(d, 2H, J=6.90 Hz), 2.21(s, 3H), 2.06(m, 1H), 1.62(d, 3H, J=6.44 Hz), 0.98(d, 6H, J=6.90 Hz),
MS(ES$^-$) M−H=634.0

2-{4-[({4-{[4-(Cyclohexylcarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400 MHz δ 8.06(d, 2H, J=8.10 Hz), 7.74(d, 2H, J=8.10 Hz), 7.16(d, 1H, J=2.24 Hz), 7.09(dd, 1H, J=8.45, 2.24 Hz), 6.64(d, 1H, J=8.45 Hz), 4.68(q, 1H, J=6.78 Hz), 4.25(s, 2H), 3.60(br s, 4H), 3.42(s, 2H), 2.62(br s, 4H), 2.16(s, 3H), 1.72(m, 5H), 1.56(d, 3H, J=6.72 Hz), 1.31(m, 6H),
MS(ES$^-$) M−H=661.0

2-{2-Methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 300 MHz δ
8.17(m, 4H), 7.81(m, 3H), 7.26(br s, 1H), 7.13(br s, 1H), 6.75(br s, 1H), 4.68(br s, 1H), 4.32(s, 2H), 3.65(br s, 4H), 3.48(s, 2H), 2.64(br s, 4H), 2.20(s, 3H), 1.60(br s, 3H),
MS(ES⁻) M−H=628.3

2-{4-[({4-({4-[4-(dimethylamino)benzoyl-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400 MHz δ,
8.12(d, 2H, J=8.28 Hz), 7.80(d, 2H, J=8.28 Hz), 7.35(d, 2H, J=9.11 Hz), 7.21(d, 1H, J=2.21 Hz), 7.14(d, 1H, J=8.55 Hz), 6.78(d, 2H, J=9.11 Hz), 6.70(d, 1H, J=8.55 Hz), 4.68(q, 1H, J=6.62 Hz), 4.31(s, 2H), 3.70(br s, 4H), 3.45(s, 2H), 3.02(s, 6H), 2.63(br s, 4H), 2.19(s, 3H), 1.59(d, 3H, J=6.62 Hz),
MS(ES⁻) M−H=697.0

2-{4-[({4-{[4-(2-Furoyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.06(d, 2H, J=8.28 Hz), 7.73(d, 2H, J=8.28 Hz), 7.65(m, 1H), 7.16(d, 1H, J=2.20 Hz), 7.07(d, 1H, J=8.55 Hz), 7.01(d, 1H, J=3.62 Hz), 6.63(d, 1H, J=8.45 Hz), 6.55(m, 1H), 4.66(q, 1H, J=6.55 Hz), 4.25(s, 2H), 3.77(br s, 4H), 3.39(s, 2H), 2.59(br s, 4H), 2.14(s, 3H), 1.54(d, 3H, J=6.55 Hz),
MS(ES⁻) M−H=644.1

2-{4-[({4-{[4-(Cyclopentylcarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.13(d, 2H, J=8.28 Hz), 7.80(d, 2H, J=8.28 Hz), 7.23(d, 1H, J=2.39 Hz), 7.15(d, 1H, J=8.28 Hz), 6.71(br s, 1H), 4.73(q, 1H, J=6.78 Hz), 4.31(s, 2H), 3.67(br s, 4H), 3.45(s, 2H), 3.06(m, 1H), 2.62(br s, 4H), 2.22(s, 3H), 1.75(m, 14H),
MS(ES⁻) M−H=646.2

2-{4-[({4-{[4-(Cyclobutylcarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.09(d, 2H, J=8.20 Hz), 7.77(d, 2H, J=8.20 Hz), 7.18(d, 1H, J=2.22 Hz), 7.13(dd, 1H, J=8.55, 2.22 Hz), 6.68(d, 1H, J=8.55 Hz), 4.71(q, 1H, J=6.75 Hz), 4.28(s, 2H), 3.60(br s, 2H), 3.46(br s, 2H), 3.41(s, 2H), 2.57(t, 4H, J=4.44 Hz), 2.22(m, 6H), 2.00(m, 2H), 1.83(m, 2H), 1.60(d, 3H, J=6.75 Hz),
MS(ES⁻) M−H=633.1

2-{4-[({4-{[4-(Cyclopropylcarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.10(d, 2H, J=8.23 Hz), 7.76(d, 2H, J=8.23 Hz), 7.21(d, 1H, J=2.20 Hz), 7.11(d, 1H, J=8.20 Hz), 6.67(s, 1H), 4.68(q, 1H, J=6.84 Hz), 4.28(s, 2H), 3.68(br s, 4H), 3.42(s, 2H), 2.59(br s, 4H), 2.19(s, 3H), 1.95(m, 1H), 1.57(d, 3H, J=6.84 Hz), 0.84(m, 4H),
MS(ES⁻) M−H=619.1

2-{2-Methyl-4-[({4-{[4-(2-thienylcarbonyl)-1-piperazinyl]methyl}-2-[4-(trifluoromethyl)phenyl]-1,3-thiazol-5-ylmethyl)sulfanyl]phenoxy}propanoic acid ¹H NMR (CD₃OD) 300 MHz δ 8.10(d, 2H, J=8.20 Hz), 7.76(d, 2H, J=8.20 Hz), 7.63(d, 1H, J=5.13 Hz), 7.37(d, 1H, J=5.13 Hz), 7.22(br s, 1H), 7.10(br s, 1H), 7.02(br s, 1H), 6.64(br s, 1H), 4.67(br s, 1H), 4.27(s, 2H), 3.74(br s, 4H), 3.40(s, 2H), 2.53(br s, 4H), 2.16(br s, 3H), 1.57(br s, 3H),
MS(ES⁻) M−H=660.1

2-{4-[({4-{[4-(2,4-Difluorophenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.10(d, 2H, J=8.28 Hz), 7.73(d, 2H, J=8.28 Hz), 7.20(br s, 1H), 6.92(m, 4H), 6.60(d, 1H, J=8.55 Hz), 4.59(br s, 1H), 4.23(s, 2H), 3.44(s, 2H), 3.06(br s, 4H), 2.80(br s, 4H), 2.17(s, 3H), 1.53(d, 3H, J=6.35 Hz),
MS(ES⁻) M−H=661.2

2-{2-Methyl-4-({[2-[4-(trifluoromethyl)phenyl]-4-({4-[4-(trifluoromethyl)phenyl-1-piperazinyl}methyl)-1,3-thiazol-5-yl]methyl}sulfanyl)phenoxy]propanoic acid ¹H NMR (CD₃OD) 300 MHz δ 8.11(d, 2H, J=8.28 Hz), 7.78(d, 2H, J=8.28 Hz), 7.49(d, 2H, J=8.55 Hz), 7.24(d, 1H, J=2.39 Hz), 7.15(d, 1H, J=8.55 Hz), 7.04(d, 2H, J=8.55 Hz), 6.71(d, 1H, J=8.55 Hz), 4.55(br s, 1H), 4.32(s, 2H), 3.51(s, 2H), 3.31(m, 4H), 2.68(t, 4H, J=4.97 Hz), 2.22(s, 3H), 1.59(d, 3H, J=6.07 Hz),
MS(ES⁻) M−H=694.5

2-{4-[({4-{[4-(Isobutoxycarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.13(d, 2H, J=8.28 Hz), 7.80(d, 2H, J=8.28 Hz), 7.22(d, 1H, J=2.21 Hz), 7.15(dd, 1H, J=8.28, 2.21 Hz), 6.71(d, 1H, J=8.28 Hz), 4.75(q, 1H, J=6.90 Hz), 4.31(s, 2H), 3.89(d, 2H, J=6.90 Hz), 3.57(br s, 4H), 2.68(t, 4H, J=4.69 Hz), 2.22(s, 3H), 1.96(m, 1H), 1.62(d, 3H, J=6.90 Hz), 0.96(d, 6H, J=6.90 Hz),
MS(ES⁻) M−H=650

2-{4-[({4-({4-[(Benzyloxy)carbonyl-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.06(d, 2H, J=8.03 Hz), 7.73(d, 2H, J=8.03 Hz), 7.30(m, 5H), 7.15(br s, 1H), 7.08(dd, 1H, J=8.20, 2.22 Hz), 6.64(d, 1H, J=8.20 Hz), 5.08(s, 2H), 4.65(q, 1H, J=6.72 Hz), 4.23(s, 2H), 3.51 (br s, 4H), 3.37(s, 2H), 2.57(br s, 4H), 2.15(s, 3H), 1.55(d, 3H, J=6.72 Hz),
MS(ES⁻) M−H=684.0

2-{4-[({4-{[4-(Methoxycarbonyl)-1-piperazinyl]
methyl}-2-[4-(trifluoromethyl)phenyl]-1,3-thiazol-5-
yl}methyl)sulfanyl]-2-methylphenoxy}propanoic
acid ¹H NMR (CD₃OD) 400 MHz δ 8.06(d, 2H, J=8.37 Hz), 7.74(d, 2H, J=8.37 Hz), 7.16(d, 1H, J=2.21 Hz), 7.10(dd, 1H, J=8.55, 2.39 Hz), 6.66(d, 1H, J=8.55 Hz), 4.59(br s, 1H), 4.25(s, 2H), 3.65(s, 3H), 3.45(t, 4H, J=4.79 Hz), 3.38(s, 2H), 2.49(br s, 4H), 2.17(s, 3H), 1.55(d, 3H, J=6.32 Hz),
MS(ES⁻) M−H=608.0

2-{2-Methyl-4-[({4-{[4-(phenoxycarbonyl)-1-piper-
azinyl]methyl}-2-[4-(trifluoromethyl)phenyl]-1,3-
thiazol-5-yl}methyl)sulfanyl]phenoxy}propanoic
acid ¹H NMR (CD₃OD) 400 MHz δ 8.08(d, 2H, J=8.20 Hz), 7.75(d, 2H, J=8.20 Hz), 7.34(m, 2H), 7.19(m, 2H), 7.13(dd, 1H, J=8.20, 2.22 Hz), 7.06(m, 2H), 6.66(d, 1H, J=8.20 Hz), 4.69(q, 1H, J=6.78 Hz), 4.27(s, 2H), 3.69(br s, 2H), 3.54(br s, 2H), 3.43(s, 2H), 2.62(br s, 4H), 2.17(s, 3H), 1.54(d, 3H, J=6.78 Hz),
MS(ES⁻) M−H=670.0

2-{2-Methyl-4-[({4-{[4-(phenylsulfonyl)-1-piperazi-
nyl]methyl}-2-[4-(trifluoromethyl)phenyl-1,3-thia-
zol-5-yl}methyl)sulfanyl]phenoxy}propanoic acid ¹H NMR (CD₃OD) 400 MHz δ 8.01(d, 2H, J=8.20 Hz), 7.72(m, 4H), 7.63(d, 1H, J=8.20 Hz), 7.56(M, 2H), 7.13(d, 1H, J=2.22 Hz), 7.05(dd, 1H, J=8.20, 2.22 Hz), 6.62(d, 1H, J=8.20 Hz), 4.70(q, 1H, J=6.61 Hz), 4.19(s, 2H), 3.34(s, 2H), 2.97(br s, 4H), 2.51(br s, 4H), 2.13(s, 3H), 1.57(d, 3H, J=6.61 Hz),
MS(ES⁻) M−H=690.0

2-{2-Methyl-4-[({2-]4-(trifluoromethyl)phenyl]-4-
[(4-{[4-(trifluoromethyl)phenyl]sulfonyl-1-piperazi-
nyl}methyl]-1,3-thiazol-5-yl}methyl)sulfanyl]
phenoxy}propanoic acid ¹H NMR (CD₃OD) 400 MHz δ 8.01(d, 2H, J=8.20 Hz), 7.91(m, 4H), 7.71(d, 2H, J=8.20 Hz), 7.15(d, 1H, J=2.22 Hz), 7.08(dd, 1H, J=8.20, 2.22 Hz), 6.62(d, 1H, J=8.20 Hz), 4.71(q, 1H, J=6.58 Hz), 4.20(s, 2H), 3.33(s, 2H), 3.01(br s, 4H), 2.49(br s, 4H), 2.14(s, 3H), 1.57(d, 3H, J=6.58 Hz),
MS(ES⁻) M−H=758.0

2-{4-[({4-({4-[(4-Methoxyphenyl)sulfonyl-1-
piperazinyl}methyl]-2-]4-(trifluoromethyl)phenyl]-1,
3-thiazol-5-yl}methyl)sulfanyl]-2-
methylphenoxy}propanoic acid ¹H NMR (CD₃OD) 400 MHz δ 8.02(d, 2H, J=8.37 Hz), 7.72(d, 2H, J=8.37 Hz), 7.66(d, 2H, J=8.72 Hz), 7.14(d, 1H, J=2.21 Hz), 7.07(m, 3H), 6.63(d, 1H, J=8.37 Hz), 4.71(q, 1H, J=6.72 Hz), 4.20(s, 2H), 3.84(s, 3H), 3.35(s, 2H), 2.97(br s, 4H), 2.53(t, 4H, J=4.61 Hz), 2.14(s, 3H), 1.58(d, 3H, J=6.72 Hz),
MS(ES⁻) M−H=720.0

2-{2-Methyl-4-[({4-{[4-(propylsulfonyl)-1-piperazi-
nyl]methyl}-2-[4-(trifluoromethyl)phenyl]-1,3-thia-
zol-5-yl}methyl)sulfanyl]phenoxy}propanoic acid ¹H NMR (CD₃OD) 400 MHz δ 8.07(d, 2H, J=8.20 Hz), 7.75(d, 2H, J=8.20 Hz), 7.19(s, 1H), 7.13(d, 1H, J=8.20 Hz), 6.66(d, 1H, J=8.20 Hz), 4.70(q, 1H, J=6.67 Hz), 4.26(s, 2H), 3.40(s, 2H), 3.22(br s, 4H), 2.95(t, 2H, J=7.43 Hz), 2.54(br s, 4H), 2.17(s, 3H), 1.76(m, 2H), 1.57(d, 3H, J=6.67 Hz), 1.02(t, 3H, J=7.43 Hz),
MS(ES⁻) M−H=656.0

2-{4-[({4-{[4-(Ethylsulfonyl)-1-piperazinyl]methyl-
2-[4-(trifluoromethyl)phenyl]-1,3-thiazol-5-
yl}methyl)sulfanyl]-2-methylphenoxy}propanoic
acid ¹H NMR (CD₃OD) 400 MHz δ 8.07(d, 2H, J=8.03 Hz), 7.74(d, 2H, J=8.03 Hz), 7.19(s, 1H), 7.11(d, 1H, J=8.03 Hz), 6.65(d, 1H, J=8.03 Hz), 4.64(q, 1H, J=6.49 Hz), 4.26(s, 2H), 3.39(s, 2H), 3.23(br s, 4H), 2.99(q, 2H, J=7.41 Hz), 2.51(br s, 4H), 2.16(s, 3H), 1.55(d, 3H, J=6.49 Hz), 1.27(t, 3H, J=7.41 Hz),
MS(ES⁻) M−H=642.0

2-{2-Methyl-4-[({4-{[4-(methylsulfonyl)-1-piperazi-
nyl]methyl}-2-[4-(trifluoromethyl)phenyl]-1,3-thia-
zol-5-yl}methyl)sulfanyl]phenoxy}propanoic acid ¹H NMR (CD₃OD) 400 MHz δ 8.06(d, 2H, J=8.03 Hz), 7.74(d, 2H, J=8.03 Hz), 7.19(s, 1H), 7.13(dd, 1H, J=8.03, 2.22 Hz), 6.66(d, 1H, J=8.03 Hz), 4.65(q, 1H, J=6.84 Hz), 4.27(s, 2H), 3.40(s, 2H), 3.17(t, 4H, J=4.19 Hz), 2.80(s, 3H), 2.53(t, 4H, J=4.19 Hz), 2.17(s, 3H), 1.56(d, 3H, J=6.84 Hz),
MS(ES⁻) M−H=628.0

2-{4-[({4-{[4-(4-Fluorobenzoyl)-1-piperazinyl]me-
thyl}-2-[4-(trifluoromethyl)phenyl]-1,3-thiazol-5-
yl}methyl)sulfanyl]-2-methylphenoxy}propanoic
acid ¹H NMR (CD₃OD) 300 MHz δ 8.09(d, 2H, J=8.28 Hz), 7.76(d, 2H, J=8.28 Hz), 7.52(M, 2H), 7.22(M, 3H), 7.13(dd, 1H, J=8.28, 2.20 Hz), 6.68(d, 1H, J=8.28 Hz), 4.67(q, 1H, J=6.81 Hz), 4.32(s, 2H), 3.79(br s, 4H), 3.66(s, 2H), 2.90(br s, 4H), 2.17(s, 3H), 1.59(d, 3H, J=6.81 Hz),
MS(ES⁻) M−H=671.9

2-{4-[({4-{[4-(4-[(Acetylamino)phenyl]sulfonyl}-1-
piperazinyl)methyl]-2-[4-(trifluoromethyl)phenyl]-1,
3-thiazol-5-yl}methyl)sulfanyl]-2-
methylphenoxy}propanoic acid ¹H NMR (CD₃OD) 400 MHz δ 8.07(d, 2H, J=8.28 Hz), 7.83(d, 2H, J=8.83 Hz), 7.77(d, 2H, J=8.28 Hz), 7.71(d, 2H, J=8.83 Hz), 7.18(d, 1H, J=2.20 Hz), 7.10(dd, 1H, J=8.28, 2.20 Hz), 6.68(d, 1H, J=8.28 Hz), 4.71(q, 1H, J=6.53 Hz), 4.26(s, 2H), 3.42(s, 2H), 3.03(br s, 4H), 2.56(t, 4H, J=4.83 Hz), 2.20(m, 6H), 1.63(d, 3H, J=6.53 Hz),
MS(ES⁻) M−H=747.0

2-{4-[({4-({4-[(4-Fluoroanilino)carbonyl]-1-
piperazinyl}methyl)-2-[4-(trifluoromethyl)phenyl]-1,
3-thiazol-5-yl}methyl)sulfanyl]-2-
methylphenoxy}propanoic acid

MS(ES⁻) M−H=687.5

2-{4-[({4-{[4-(4-Methoxybenzoyl)-1-piperazinyl]
methyl}-2-[4-(trifluoromethyl)phenyl]-1,3-thiazol-5-
yl}methyl)sulfanyl]-2-methylphenoxy}propanoic
acid ¹H NMR (CD₃OD) 300 MHz δ 8.02(d, 2H, J=8.20 Hz), 7.69(d, 2H, J=8.20 Hz), 7.38(d, 2H, J=8.79 Hz), 7.12(d, 1H, J=2.24 Hz), 7.06(dd, 1H, J=8.28, 2.24 Hz), 6.95(d, 2H, J=8.79 Hz), 6.61(d, 1H, J=8.28 Hz), 4.58(q, 1H, J=6.78 Hz), 4.25(s, 2H), 3.78(s, 3H), 3.71(br s, 4H), 3.64(s, 2H), 2.88(br s, 4H), 2.10(s, 3H), 1.52(d, 3H, J=6.78 Hz),
MS(ES⁻) M−H=683.6

2-{4-[({4-({4-[(3-Methoxyanilino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CDCl₃) 300 MHz δ 8.04(d, 2H, J=8.28 Hz), 7.69(d, 2H, J=8.28 Hz), 7.31(d, 1H, J=2.21 Hz), 7.16(m, 2H), 6.89(m, 2H), 6.59(dd, 1H, J=8.28, 2.21 Hz), 6.53(d, 1H, J=8.28 Hz), 4.73(q, 1H, J=6.90 Hz), 4.33(d, 1H, J☐.63 Hz), 4.23(d, 1H, J☐.63 Hz), 3.79(s, 3H), 3.45(m, 6H), 2.36(t, 4H, J=4.69 Hz), 2.24(s, 3H), 1.64(d, 3H, J=6.90 Hz),
MS(ES⁻) M−H=699.6

2-{4-[({4-{[4-(Aminocarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.15(d, 2H, J=8.28 Hz), 7.83(d, 2H, J=8.28 Hz), 7.27(d, 1H, J=2.48 Hz), 7.19(dd, 1H, J=8.55, 2.48 Hz), 6.74(d, 1H, J=8.55 Hz), 4.65(br s, 1H), 4.36(s, 2H), 3.57(s, 2H), 3.48(br s, 4H), 2.64(br s, 4H), 2.24(s, 3H), 1.62(d, 3H, J=6.62 Hz),
MS(ES⁻) M−H=593.1

2-{4-[({4-({4-[(Cyclohexylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.15(d, 2H, J=8.28 Hz), 7.81(d, 2H, J=8.28 Hz), 7.24(br s, 1H), 7.13(br s, 1H), 6.73(br s, 1H), 4.75(br s, 1H), 4.30(s, 2H), 3.52(m, 7H), 2.68(br s, 4H), 2.24(s, 3H), 1.75(m, 7H), 1.26(m, 6H),
MS(ES⁻) M−H=675.0

2-{2-Methyl-4-[({4-({4-[(propylamino)carbonyl]-1-piperazinyl}methyl)-2-[4-(trifluoromethyl)phenyl]-1,3-thiazol-5-yl}methyl)sulfanyl]phenoxy}propanoic acid ¹H NMR (CD₃OD) 400 MHz δ 8.15(d, 2H, J=8.00 Hz), 7.81(d, 2H, J=8.00 Hz), 7.25(d, 1H, J=2.21 Hz), 7.15(dd, 1H, J=8.55, 2.21 Hz), 6.70(d, 1H, J=8.55 Hz), 4.68(q, 1H, J=6.53 Hz), 4.30(s, 2H), 3.60(s, 2H), 3.48(br s, 4H), 3.14(t, 2H, J=7.45 Hz), 2.73(t, 4H, J=5.10 Hz), 2.22(s, 3H), 1.63(d, 3H, J=6.53 Hz), 1.52(s, 2H), 0.93(t, 3H, J=7.45 Hz),
MS(ES⁻) M−H=635.3

2-{4-[({4-({4-[(Ethylamino)carbonyl]-1-piperazinyl]methyl)-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.15(d, 2H, J=8.28 Hz), 7.81(d, 2H, J=8.28 Hz), 7.25(d, 1H, J=2.48 Hz), 7.14(dd, 1H, J=8.28, 2.48 Hz), 6.70(d, 1H, J=8.28 Hz), 4.67(br s, 1H), 4.29(s, 2H), 3.56(s, 2H), 3.46(br s, 4H), 3.22(q, 2H, J=7.17 Hz), 2.68(t, 4H, J=4.92 Hz), 2.21(s, 3H), 1.61(d, 3H, J=6.35 Hz), 1.14(t, 3H, J=7.17 Hz),
MS(ES⁻) M−H=621.1

2-{2-Methyl-4-[({4-({4-[(methylamino)carbonyl]-1-piperazinyl}methyl)-2-]4-(trifluoromethyl)phenyl]-1,3-thiazol-5-yl}methyl)sulfanyl]phenoxy}propanoic acid ¹H NMR (CD₃OD) 400 MHz δ 8.05(d, 2H, J=8.20 Hz), 7.72(d, 2H, J=8.20 Hz), 7.17(d, 1H, J=2.22 Hz), 7.09(dd, 1H, J=8.37, 2.22 Hz), 6.61(d, 1H, J=8.37 Hz), 4.66(q, 1H, J=6.75 Hz), 4.20(s, 2H), 3.56(s, 2H), 3.42(br s, 4H), 2.69(m, 7H), 2.15(s, 3H), 1.58(d, 3H, J=6.75 Hz),
MS(ES⁻) M−H=607.0

2-{4-[({4-({4-[(Isopropylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.09(d, 2H, J=8.20 Hz), 7.75(d, 2H, J=8.20 Hz), 7.17(br s, 1H), 7.08(d, 1H, J=8.20 Hz), 6.64(d, 1H, J=8.20 Hz), 4.63(q, 1H, J=6.49 Hz), 4.23(s, 2H), 3.84(m, 1H), 3.46(m, 6H), 2.68(br s, 4H), 2.16(s, 3H), 1.57(d, 3H, J=6.49 Hz), 1.10(d, 6H, J=6.32 Hz),
MS(ES⁻) M−H=635.0

2-{4-[({4-({4-[(tert-Butylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.08(d, 2H, J=8.20 Hz), 7.75(d, 2H, J=8.20 Hz), 7.16(d, 1H, J=2.22 Hz), 7.07(dd, 1H, J=8.37, 2.22 Hz), 6.64(d, 1H, J=8.37 Hz), 4.61(q, 1H, J=6.75 Hz), 4.21(s, 2H), 3.44(m, 6H), 2.71(br s, 4H), 2.16(s, 3H), 1.55(d, 3H, J=6.75 Hz), 1.27(s, 9H),
MS(ES⁻) M−H=649.0

2-{2-Methyl-4-[({4-[(4-{[(2-phenylethyl)amino]carbonyl]-1-piperazinyl)methyl]-2-[4-(trifluoromethyl)phenyl]-1,3-thiazol-5-yl}methyl)sulfanyl]phenoxy}propanoic acid ¹H NMR (CD₃OD) 400 MHz δ 8.08(d, 2H, J=8.03 Hz), 7.75(d, 2H, J=8.03 Hz), 7.17(s, 7H), 6.64(d, 1H, J=8.55 Hz), 4.61(q, 1H, J=6.84 Hz), 4.24(s, 2H), 3.43(m, 9H), 2.76(t, 2H, J=7.52 Hz), 2.62(br s, 4H), 2.16(s, 3H), 1.56(d, 3H, J=6.67 Hz),
MS(ES⁻) M−H=697.0

2-{4-[({4-[(4-Benzoyl-1-piperazinyl]methyl]-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.03(d, 2H, J=8.28 Hz), 7.70(d, 2H, J=8.28 Hz), 7.42(m, 5H), 7.13(d, 1H, J=2.24 Hz), 7.07(dd, 1H, J=8.45, 2.24 Hz), 6.62(d, 1H, J=8.45 Hz), 4.61(q, 1H, J=6.78 Hz), 4.26(s, 2H), 3.83(br s, 4H), 3.62(s, 2H), 2.86(br s, 4H), 2.11(s, 3H), 1.53(d, 3H, J=6.78 Hz),
MS(ES⁻) M−H=653.7

2-{2-Methyl-4-[({4-{[4-(4-propoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400 MHz δ 8.11(d, 2H, J=7.69 Hz), 7.77(d, 2H, J=7.69 Hz), 7.15(s, 1H), 7.08(dd, 1H, J=8.61, 2.20 Hz), 6.93(d, 2H, J=8.97 Hz), 6.82(d, 2H, J=8.97 Hz), 6.67(d, 1H, J=8.61 Hz), 4.57(q, 1H, J=6.78 Hz), 4.24(s, 2H), 3.85(t, 2H, J=7.01 Hz), 3.55(s, 2H), 3.18(br s, 4H), 3.03(br s, 4H), 2.16(s, 3H), 1.73(m, 2H), 1.54(d, 3H, J=6.78 Hz), 1.00(t, 3H, J=7.01 Hz),

MS(ES⁻) M−H=684.0

2-{4-[({4-{[4-(4-Ethoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.11(d, 2H, J=8.06 Hz), 7.77(d, 2H, J=8.06 Hz), 7.15(s, 1H), 7.08(dd, 1H, J=8.42, 2.20 Hz), 6.92(d, 2H, J=8.97 Hz), 6.81(d, 2H, J=8.97 Hz), 6.67(d, 1H, J=8.42 Hz), 4.59(q, 1H, J=6.78 Hz), 4.24(s, 2H), 3.95(q, 2H, J=6.78 Hz), 3.54(s, 2H), 3.17(br s, 4H), 3.04(br s, 4H), 2.17(s, 3H), 1.55(d, 3H, J=6.78 Hz), 1.32(t, 3H, J=6.78 Hz),

MS(ES⁻) M−H=671.0

2-{2-Methyl-4-[({4-({4-[4-(trifluoromethoxy)phenyl]-1-piperazinyl}methyl)-2-[4-(trifluoromethyl)phenyl]-1,3-thiazol-5-yl}methyl)sulfanyl]phenoxy}propanoic acid ¹H NMR (CD₃OD) 400 MHz δ 8.10(d, 2H, J=8.28 Hz), 7.75(d, 2H, J=8.28 Hz), 7.15(d, 1H, J=2.24 Hz), 7.12(d, 2H, J=9.14 Hz), 7.08(dd, 1H, J=8.45, 2.24 Hz), 7.00(d, 2H, J=9.31 Hz), 6.66(d, 1H, J=8.45 Hz), 4.59(q, 1H, J=6.72 Hz), 4.24(s, 2H), 3.54(s, 2H), 3.27(m, 4H), 2.97(t, 4H, J=4.83 Hz), 2.16(s, 3H), 1.54(d, 3H, J=6.72 Hz),

MS(ES⁻) M−H=710.0

2-{4-[({4-{[4-(3,4-Dimethoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.17(d, 2H, J=8.28 Hz), 7.82(d, 2H, J=8.28 Hz), 7.20(br s, 1H), 7.12(br s, 1H), 6.89(d, 1H, J=8.83 Hz), 6.72(m, 2H), 6.55(dd, 1H, J=8.83, 2.76 Hz), 4.66(br s, 1H), 4.29(s, 2H), 3.84(s, 3H), 3.80(s, 3H), 3.57(s, 2H), 3.25(br s, 4H), 3.07(br s, 4H), 2.23(s, 3H), 1.61(br s, 3H),

MS(ES⁻) M−H=686.0

2-{4-[({4-{[4-(4-Hydroxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.14(br s, 2H), 7.80(br s, 2H), 7.24(br s, 1H), 7.12(br s, 1H), 6.92(br s, 2H), 6.76(br s, 2H), 6.63(sbr, 1H), 4.54(br s, 1H), 4.31(br s, 2H), 3.67(br s, 2H), 3.06(br s, 8H), 2.23(br s, 3H), 1.60(br s, 3H),

MS(ES⁻) M−H=642.3

2-{4-[({4-{[4-(3-Hydroxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.15(d, 2H, J=8.28 Hz), 7.81(d, 2H, J=8.28 Hz), 7.22(d, 1H, J=2.21 Hz), 7.15(dd, 1H, J=8.28, 2.21 Hz), 7.08(t, 1H, J=8.14 Hz), 6.71(d, 1H, J=8.28 Hz), 6.49(dd, 1H, J=4, 2.21 Hz), 6.45(t, 1H, J=2.21 Hz), 6.39(dd, 1H, J=8.14, 2.21 Hz), 4.74(q, 1H, J=6.81 Hz), 4.30(s, 2H), 3.85(s, 2H), 3.36(m, 4H), 3.24(m, 4H), 2.21(s, 3H), 1.61(d, 3H, J=6.81 Hz),

MS(ES⁻) M−H=642.0

2-{4-[({4-{[4-(2-Hydroxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.20(d, 2H, J=8.00 Hz), 7.80(d, 2H, J=8.00 Hz), 7.23(br s, 1H), 7.01(m, 3H), 6.82(m, 2H), 6.66(br s, 1H), 4.74(br s, 1H), 4.26(s, 2H), 3.56(s, 2H), 3.12(m, 8H), 2.19(s, 3H), 1.58(br s, 3H),

MS(ES⁻) M−H=642.1

2-{4-[({4-[(4-Butyryl-1-piperazinyl)methyl]-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.05(d, 2H, J=8.55 Hz), 7.72(d, 2H, J=8.55 Hz), 7.17(d, 1H, J=2.22 Hz), 7.08(d, 1H, J=8.55 Hz), 6.64(s, 1H), 4.56(q, 1H, J=6.55 Hz), 4.26(s, 2H), 3.54(br s, 4H), 3.38(s, 2H), 2.46(br s, 4H), 2.33(t, 2H, J=7.43 Hz), 2.16(s, 3H), 1.58(m, 5H), 0.93(t, 3H, J=7.43 Hz),

MS(ES⁻) M−H=620.0

2-{2-Methyl-4-[({4-[(4-pentanoyl-1-piperazinyl]methyl}-2-[4-(trifluoromethyl)phenyl]-1,3-thiazol-5-yl}methyl)sulfanylphenoxy}propanoic acid ¹H NMR (CD₃OD) 400 MHz δ 8.06(d, 2H, J=8.20 Hz), 7.74(d, 2H, J=8.20 Hz), 7.17(d, 1H, J=2.22 Hz), 7.10(dd, 1H, J=8.20, 2.22 Hz), 6.65(d, 1H, J=8.20 Hz), 4.68(q, 1H, J=6.75 Hz), 4.25(s, 2H), 3.56(br s, 4H), 3.40(s, 2H), 2.56(br s, 4H), 2.36(t, 2H, J=7.35 Hz), 2.16(s, 3H), 1.54(m, 5H), 1.34(m, 2H), 0.90(t, 3H, J=7.35 Hz),

MS(ES⁻) M−H=634.0

2-{4-[({4-{[4-(Methoxyacetyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.07(d, 2H, J=8.37 Hz), 7.75(d, 2H, J=8.37 Hz), 7.18(d, 1H, J=2.20 Hz), 7.11(d, 1H, J=8.37 Hz), 6.65(d, 1H, J=8.37 Hz), 4.68(q, 1H, J=6.72 Hz), 4.26(s, 2H), 4.12(s, 2H), 3.57(br s, 2H), 3.46(br s, 2H), 3.39(s, 2H), 3.35(s, 3H), 2.53(t, 4H, J=4.79 Hz), 2.16(s, 3H), 1.56(d, 3H, J=6.72 Hz),

MS(ES⁻) M−H=622.0

2-{4-[({4-[(4-Isobutyryl-1-piperazinyl)methyl]-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.10(d, 2H, J=8.28 Hz), 7.76(d, 2H, J=8.28 Hz), 7.20(d, 1H, J=2.21 Hz), 7.13(dd, 1H, J=8.55, 2.21 Hz), 6.69(d, 1H, J=8.55 Hz), 4.67(q, 1H, J=6.81 Hz), 4.31(s, 2H), 3.76(br s, 4H), 3.69(s, 2H), 2.92(m, 5H), 2.20(s, 3H), 1.59(d, 3H, J=6.81 Hz), 1.10(d, 6H, J=6.62 Hz),

MS(ES⁻) M−H=620.4

2-{4-[({4-{[4-(2,2-Dimethylpropanoyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300 MHz δ 8.10(d, 2H, J=8.28 Hz), 7.76(d, 2H, J=8.28 Hz), 7.19(d, 1H, J=2.21 Hz), 7.13(dd, 1H, J=8.28, 2.21 Hz), 6.69(d, 1H, J=8.28 Hz), 4.68(q, 1H, J=6.71 Hz), 4.32(s, 2H), 3.83(br s, 4H), 3.71(s, 2H), 2.98(t, 4H, J=4.83 Hz), 2.20(s, 3H), 1.60(d, 3H, J=6.71 Hz), 1.28(s, 9H),
MS(ES⁻) M−H=634.2

2-Methyl-2-[4-({[2-[4-(trifluoromethyl)phenyl]-4-({4-[3-(trifluoromethyl)phenyl]-1-piperazinyl}methyl)-1,3-thiazol-5-yl]methyl}sulfanyl)phenoxy]propanoic acid ¹H NMR (CD₃OD) 400 MHz δ 8.10(d, 2H, J=8.06 Hz), 7.76(d, 2H, J=8.06 Hz), 7.40(t, 1H, J=7.69 Hz), 7.28(d, 2H, J=8.79 Hz), 7.18(s, 2H), 7.09(d, 1H, J=7.69 Hz), 6.81(d, 2H, J=8.79 Hz), 4.31(s, 2H), 3.59(s, 2H), 3.31(t, 4H, J=4.94 Hz), 2.88(t, 4H, J=4.94 Hz), 1.54(s, 6H),
MS(ES⁻)M−H=694.5
CHN Analysis (Theoretical % C=56.97, % H=4.49, % N=6.04; Found % C=56.69, % H=4.66, % N=5.77)

{4-[({4-{[4-(tert-Butoxycarbonyl)-1-piperazinyl]methyl}-2-[4-(trifluoromethyl)phenyl]-1,3-thiazol-5-yl}methyl)sulfanyl]-2-methylphenoxy}acetic acid ¹H NMR (CD₃OD) 400 MHz δ 8.05(d, 2H, J=8.28 Hz), 7.73(d, 2H, J=8.28 Hz), 7.18(s, 1H), 7.11(br s, 1H), 6.66(br s, 1H), 4.54(s, 2H), 4.26(s, 2H), 3.42(m, 6H), 2.50(br s, 4H), 2.19(s, 3H), 1.43(s, 9H),
MS(ES⁻) M−H=636.5

{2-Methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}acetic acid ¹H NMR (CD₃OD) 400 MHz δ 8.21(s, 1H), 8.09(d, 3H, J=8.10 Hz), 7.80(s, 1H), 7.75(d, 2H, J=8.28 Hz), 7.19(d, 1H, J=2.07 Hz), 7.13(dd, 1H, J=8.45, 2.24 Hz), 6.70(d, 1H, J=8.45 Hz), 4.57(s, 2H), 4.27(s, 2H), 3.66(br s, 4H), 3.53(s, 2H), 2.77(br s, 4H), 2.17(s, 3H),
MS(ES⁻) M−H=612.4

{4-[({4-{[4-(2-Methoxyphenyl)-1-piperazinyl]methyl}-2-[4-(trifluoromethyl)phenyl]-1,3-thiazol-5-yl}methyl)sulfanyl]-2-methylphenoxy}acetic acid ¹H NMR (CD₃OD) 400 MHz δ 8.10(d, 2H, J=8.28 Hz), 7.75(d, 2H, J=8.28 Hz), 7.18(d, 1H, J=2.20 Hz), 7.02(s, 2H), 6.92(dd, 2H, J=8.10, 2.20 Hz), 6.86(s, 1H), 6.62(d, 1H, J=8.45 Hz), 4.48(s, 2H), 4.25(s, 2H), 3.81(s, 3H), 3.55(s, 2H), 3.11(br s, 4H), 2.96(br s, 4H), 2.17(s, 3H),
MS(ES⁻) M−H=640.5

{4-[({4-{[4-(3-Methoxyphenyl)-1-piperazinyl]methyl}-2-[4-(trifluoromethyl)phenyl]-1,3-thiazol-5-yl}methyl)sulfanyl]-2-methylphenoxy}acetic acid ¹H NMR (CD₃OD) 400 MHz δ 8.10(d, 2H, J=8.28 Hz), 7.75(d, 2H, J=8.28 Hz), 7.18(d, 1H, J=2.24 Hz), 7.10(s, 2H), 6.67(d, 1H, J=8.23 Hz), 6.53(dd, 1H, J=8.28, 2.24 Hz), 6.47(t, 1H, J=2.24 Hz), 6.43(dd, 1H, J=8.28, 2.24 Hz), 4.52(s, 2H), 4.25(s, 2H), 3.72(s, 3H), 3.58(s, 2H), 3.24(t, 4H, J=5.09 Hz), 2.98(t, 4H, J=5.09 Hz), 2.17(s, 3H),
MS(ES⁻) M−H=642.0

2-Methyl-2-[(4-[({4-{[4-(phenoxycarbonyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400 MHz δ 8.07(d, 2H, J=8.28 Hz), 7.73(d, 2H, J=8.28 Hz), 7.34(t, 2H, J=7.59 Hz), 7.27(d, 2H, J=8.45 Hz), 7.18(t, 1H, J=7.59 Hz), 7.06(d, 2H, J=7.59 Hz), 6.80(d, 2H, J=8.45 Hz), 4.33(s, 2H), 3.68(br s, 2H), 3.53(br s, 2H), 3.44(s, 2H), 2.56(br s, 4H), 1.52(s, 6H),
CHN Analysis 1MeOH (Theoretical % C=58.02, % H=5.16, % N=5.97; Found % C=58.33, % H=5.09, % N=5.72)

2-{4-[({4-{[4-(tert-Butoxycarbonyl)-1-piperazinyl]methyl}-2-[4-(trifluoromethyl)phenyl]-1,3-thiazol-5-yl}methyl)sulfanyl]phenoxy}-2-methylpropanoic acid ¹H NMR (CD₃OD) 400 MHz δ 8.04(d, 2H, J=8.28 Hz), 7.71(d, 2H, J=8.28 Hz), 7.22(d, 2H, J=8.10 Hz), 6.78(d, 2H, J=8.10 Hz), 4.27(s, 2H), 3.40(m, 6H), 2.49(br s, 4H), 1.50(s, 6H), 1.41(s, 9H),
MS(ES⁻) M−H=650.5

2-Methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400 MHz δ 8.21(s, 1H), 8.07(m, 3H), 7.79(s, 1H), 7.73(d, 2H, J=8.28 Hz), 7.25(d, 2H, J=8.10 Hz), 6.79(d, 2H, J=8.10 Hz), 4.30(s, 2H), 3.65(br s, 4H), 3.53(s, 2H), 2.72(br s, 4H), 1.53(s, 6H),
MS(ES⁻) M−H=627.6

2-{4-[({4-{[4-(2-Methoxyphenyl)-1-piperazinyl]methyl}-2-[4-(trifluoromethyl)phenyl]-1,3-thiazol-5-yl}methyl)sulfanyl]phenoxy}-2-methylpropanoic acid ¹H NMR (CD₃OD) 400 MHz δ 8.10(d, 2H, J=8.28 Hz), 7.74(d, 2H, J=8.28 Hz), 7.21(d, 2H, J=8.42 Hz), 7.00(m, 1H), 6.92(m, 2H), 6.86(m, 1H), 6.78(d, 2H, J=8.42 Hz), 4.27(s, 2H), 3.81(s, 3H), 3.59(s, 2H), 3.14(br s, 4H), 3.01(br s, 4H), 1.51(s, 6H),
MS(ES⁻) M−H=656.0

2-{4-[({4-{[4-(Ethoxycarbonyl)-1-piperazinyl]methyl}-2-[4-(trifluoromethyl)phenyl]-1,3-thiazol-5-yl}methyl)sulfanyl]phenoxy}-2-methylpropanoic acid ¹H NMR (CD₃OD) 400 MHz δ 8.05(d, 2H, J=8.10 Hz), 7.72(d, 2H, J=8.10 Hz), 7.24(d, 2H, J=8.42 Hz), 6.79(d, 2H, J=8.42 Hz), 4.30(s, 2H), 4.09(q, 2H, J=7.16 Hz), 3.44(m, 6H), 2.50(s, 4H), 1.52(s, 6H), 1.21(t, 3H, J=7.16 Hz),
MS(ES⁻) M−H=621.7

2-{4-[({4-{[4-(4-Isopropoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400 MHz δ 8.13(d, 2H, J=8.06 Hz), 7.79(d, 2H, J=8.06 Hz), 7.13(m, 2H), 6.92(d, 2H, J=8.97

Hz), 6.81(d, 2H, J=8.97 Hz), 6.67(d, 1H, J=8.42 Hz), 4.61(q, 1H, J=6.78 Hz), 4.46(m, 1H), 4.25(s, 2H), 3.56(s, 2H), 3.19(br s, 4H), 3.06(br s, 4H), 2.17(s, 3H), 1.55(d, 3H, J=6.78 Hz), 1.24(d, 6H, J=6.87 Hz),

MS(ES⁻) M–H=685.0

[4-({[4-(1,1'-Biphenyl]-4-ylmethyl)-2-(4-{trifluoromethyl}phenyl)-1,3-thiazol-5-yl]methyl}sulfanyl)-2-methylphenoxy]acetic acid TLC(5% MeOH/CH₂Cl₂) R$_f$=0.16
MS(ES⁻) M–H=603

{2-Methyl-4-[({2-(4-trifluoromethyl}phenyl)-4-[4-(3-thienyl)benzyl]-1,3-thiazol-5-yl}methyl)sulfanyl]phenoxy}acetic acid ¹H NMR (CDCl₃) 300 MHz δ 7.93(d, 2H, J=8.23 Hz), 7.61(d, 2H, J=8.23 Hz), 7.44(d, 2H, J=8.23 Hz), 7.36(s, 1H), 7.29(m, 2H), 7.08(m, 3H), 6.54(d, 1H, J=8.23 Hz), 4.52(s, 2H), 4.06(s, 2H), 3.90(s, 2H), 2.15(s, 3H),
TLC(5% MeOH/CH₂Cl₂) R$_f$=0.18
MS(ES⁻) M–H=609

[4-({[4-Benzyl-2-(4-{trifluoromethyl}phenyl)-1,3-thiazol-5-yl]methyl}sulfanyl)phenoxy]acetic acid ¹H NMR (CD₃OD) 300 MHz δ 8.04(d, 2H, J=8.23 Hz), 7.75(d, 2H, J=8.23 Hz), 7.34(d, 2H, J=8.76 Hz), 7.20(m, 5H), 6.88(d, 2H, J=9.76 Hz), 4.66(s, 2H), 4.25(s, 2H), 3.93(s, 2H),
MS(ES⁻) M–H=513.86
TLC(20% MeOH/CH₂Cl₂) R$_f$=0.37

2-[4-({[4-Benzyl-2-(4-{trifluoromethyl}phenyl)-1,3-thiazol-5-yl]methyl}sulfanyl)phenoxy]propanoic acid ¹H NMR (CDCl₃) 300 MHz δ 8.02(d, 2H, J=8.23 Hz), 7.69(d, 2H, J=8.23 Hz), 7.26(m, 7H), 6.83(d, 2H, J=8.76 Hz), 4.80(q, 1H, J=6.72 Hz), 4.14(s, 2H), 3.90(m, 2H), 1.68(d, 3H, J=6.72 Hz),
MS(ES⁻) M–H=528.43
TLC(20% MeOH/CH₂Cl₂) R$_f$=0.60

[2-Methyl-4-({[2-(4-{trifluoromethyl}phenyl)-4-(2-phenylethyl)-1,3-thiazol-5-yl]methyl}sulfanyl)phenoxy]acetic acid ¹H (CDCl₃) 300 MHz δ 7.99(d, 2H, J=8.79 Hz), 7.67(d, 2H, J=8.93 Hz), 7.18(m, 8H), 6.60(d, 1H, J=8.51 Hz), 4.64(s, 2H), 3.85(s, 2H), 2.90(m, 2H), 2.80(m, 2H), 2.23(s, 3H),

[4-({[4-[(Benzyloxy)methyl]-2-(4-trifluoromethyl}phenyl)-1,3-thiazol-5-yl]methyl}sulfanyl)-2-methylphenoxy]acetic acid ¹H (CDCl₃) 300 MHz δ 7.99(d, 2H, J=8.79 Hz), 7.67(d, 2H, J=8.79 Hz), 7.33(m, 4H), 7.28(s, 2H), 7.18(dd, 1H, J=2.33, 0.55 Hz), 7.08(ddd, 1H, J=8.38, 2.33, 0.55 Hz), 6.56(d, 1H, J=8.38 Hz), 4.63(s, 2H), 4.53(s, 2H), 4.39(s, 2H), 4.19(s, 2H), 2.21(s, 3H),

[2-Methyl-4-({[2-(4-{trifluoromethyl}phenyl)-4-(3-phenylpropyl)-1,3-thiazol-5-yl]methyl}sulfanyl)phenoxy]acetic acid ¹H NMR (CDCl₃) 300 MHz δ 7.82(m, 2H), 7.50(m, 2H), 6.94(m, 8H), 3.95(s, 2H), 2.55(m, 4H), 1.99(m, 7H),

{2-Methyl-4-]({2-(4-{trifluoromethyl}phenyl)-4-[(2-phenylethoxy)methyl]-1,3-thiazol-5-yl}methyl)sulfanyl]phenoxy}acetic acid ¹H NMR (CDCl₃) 300 MHz δ 7.92(m, 2H), 7.62(m, 2H), 7.20(m, 7H), 7.05(br s, 1H), 4.55(s, 2H), 4.38(s, 2H), 4.09(s, 2H), 3.66(br s, 2H), 2.87(br s, 2H), 2.17(s, 3H),
TLC(5% MeOH/Dichloromethane) R$_f$=0.65

[4-({[4-(4-Bromobenzyl)-2-(4-{trifluoromethyl}phenyl)-1,3-thiazol-5-yl]methyl}sulfanyl)-2-methylphenoxy]acetic acid ¹H NMR (CDCl₃) 400 MHz δ 7.82(d, 2H, J=8.20 Hz), 7.53(d, 2H, J=8.20 Hz), 7.22(d, 2H, J=8.55 Hz), 7.05(m, 1H), 6.97(dd, 1H, J=8.37, 2.39 Hz), 6.88(d, 2H, J=8.55 Hz), 6.47(d, 1H, J=8.37 Hz), 4.47(s, 2H), 3.72(s, 2H), 3.36(s, 2H), 2.08(s, 3H),
TLC(5% MeOH/CH₂Cl₂) R$_f$=0.16

[4-({[4-Benzyl-2-(4-{triflurormethyl}phenyl)-1,3-thiazol-5-yl]methyl}sulfanyl)-2-methylphenoxy]acetic acid ¹H (CDCl₃) 300 MHz δ 7.97(d, 2H, J=8.79 Hz), 7.64(d, 2H, J=9.48 Hz), 7.21(m, 8H), 6.58(d, 1H, J=8.38 Hz), 4.65(s, 2H), 4.11(s, 2H), 3.93(s, 2H), 2.22(s, 3H),
MS(ES⁺) M+H=529.99

2-{4-[({4-{[3-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H NMR (CDCl₃) 400 MHz δ 8.01(d, 2H, J=8.03 Hz), 7.68(m, 3H), 7.43(m, 1H), 7.36(t, 1H, J=8.03 Hz), 7.20(d, 2H, J=8.89 Hz), 7.05(dd, 1H, J=8.20, 2.39 Hz), 6.79(d, 2H, J=8.89 Hz), 4.76(q, 1H, J=6.78 Hz), 4.66(d, 1H, J□.28 Hz), 4.36(d, 1H, J□.28 Hz), 4.24(d, 1H, J□.70 Hz), 4.15(d, 1H, J□.70 Hz), 2.71(s, 3H), 1.67(m, 3H),
MS(ES⁺) M+H=628.0

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400 MHz δ 9.03(br s, 1H), 7.96(d, 2H, J=8.20 Hz), 7.67(d, 2H, J=8.20 Hz), 7.15(d, 2H, J=8.72 Hz), 6.81(m, 6H), 4.12(s, 2H), 3.73(s, 3H), 3.50(s, 2H), 3.27(brs, 4H), 3.15(br s, 4H), 1.63(s, 6H),
HPLC(C-18, 3 μm) 1% MeOH/0–90% CH₃CN/Water (0.1% TFA)/(50 mM Et₃N/TFA) 4 min run R$_t$=2.89 min

2-(4-{[(4-{[4-(4-Methoxyphenyl)-1-piperazinyl]methyl}-2-phenyl-1,3-thiazol-5-yl)methyl]sulfanyl}phenoxy)-2-methylpropanoic acid ¹H NMR (CDCl₃) 400 MHz δ 7.87(m, 2H), 7.44(m, 3H), 7.15(d, 2H, J=8.55 Hz), 6.82(m, 6H), 4.08(s, 2H), 3.73(s, 3H), 3.46(s, 2H), 3.31(m, 4H), 3.18(m, 4H), 1.65(s, 6H),
HPLC(C-18, 3 μm) 1% MeOH/0–90% CH₃CN/Water (0.1% TFA)/(50 mM Et₃N/TFA) 4 min run R_t=2.74 min

{4-[({4-{[4-(4-Methoxyphenyl)-1-piperazinyl]methyl}-2-[4-(trifluoromethyl)phenyl]-1,3-thiazol-5-yl}methyl)sulfanyl]phenoxy}acetic acid ¹H NMR (CDCl₃) 400 MHz δ 10.00(s, 1H), 7.96(d, 2H, J=8.20 Hz), 7.66(d, 2H, J=8.20 Hz), 7.27(d, 2H, J=8.72 Hz), 6.82(m, 6H), 4.51(s, 2H), 4.22(s, 2H), 3.80(s, 2H), 3.72(s, 3H), 3.21(m, 8H),
HPLC(C-18, 3 μm) 1% MeOH/0–90% CH₃CN/Water (0.1% TFA)/(50 mM Et₃N/TFA) 4 min run R_t=2.74 min

(4-{[(4-{[4-(4-Methoxyphenyl)-1-piperazinyl]methyl}-2-phenyl]-1,3-thiazol-5-yl)methyl]sulfanyl}phenoxy)acetic acid ¹H NMR (CDCl₃) 400 MHz δ 9.49(br s, 1H), 7.86(m, 2H), 7.42(m, 3H), 7.24(d, 2H, J=8.55 Hz), 6.80(m, 6H), 4.50(s, 2H), 4.22(s, 2H), 3.81(s, 2H), 3.71(s, 3H), 3.24(m, 8H),
HPLC(C-18, 3 μm) 1% MeOH/0–90% CH₃CN/Water (0.1% TFA)/(50 mM Et₃N/TFA) 4 min run R_t=2.55 min

2-{4-[({4-{[4-(4-Methoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CDCl₃) 400 MHz δ 9.31(s, 1H), 7.96(d, 2H, J=8.20 Hz), 7.68(d, 2H, J=8.20 Hz), 7.18(d, 2H, J=8.55 Hz), 6.82(m, 6H), 4.73(q, 1H, J=6.67 Hz), 4.16(d, 1H, J□.87 Hz), 4.10(d, 1H, J□.87 Hz), 3.72(s, 3H), 3.58(d, 1H, J□.53 Hz), 3.51(d, 1H, J□.53 Hz), 3.24(m, 8H), 1.59(d, 3H, J=6.67 Hz),
HPLC(C-18, 3 μm) 1% MeOH/0–90% CH₃CN/Water (0.1% TFA)/(50 mM Et₃N/TFA) 4 min run R_t=2.80 min

2-(4-{[(4-{[4-(4-Methoxyphenyl)-1-piperazinyl]methyl}-2-phenyl-1,3-thiazol-5-yl)methyl]sulfanyl}phenoxy)propanoic acid ¹H NMR (CDCl₃) 400 MHz 68.42(s, 1H), 7.84(m, 2H), 7.40(m, 3H), 7.17(d, 2H, J=8.72 Hz), 6.81(m, 6H), 4.69(q, 1H, J=6.67 Hz), 4.11(d, 1H, J□.18 Hz), 4.07(d, 1H, J□.18 Hz), 3.73(s, 3H), 3.57(d, 1H, J□.87 Hz), 3.49(d, 1H, J□.87 Hz), 3.18(m, 8H), 1.59(d, 3H, J=6.67 Hz),
HPLC(C-18, 3 μm) 1% MeOH/0–90% CH₃CN/Water (0.1% TFA)/(50 mM Et₃N/TFA) 4 min run R_t=2.63 min

{4-[({4-{[3-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}acetic acid ¹H NMR (CDCl₃) 400 MHz δ 10.17(s, 1H), 8.02(d, 2H, J=8.20 Hz), 7.67(m, 3H), 7.46(m, 1H), 7.36(t, 1H, J=7.95 Hz), 7.22(d, 2H, J=8.72 Hz), 7.06(dd, 1H, J=8.37, 2.39 Hz), 6.79(d, 2H, J=8.72 Hz), 4.69(s, 2H), 4.58(s, 2H), 4.22(s, 2H), 2.73(s, 3H),
MS(ES⁺) M+H=614.00

2-Methyl-2-{4-]({4-{[4-(5-methyl-1,2,4-oxadiazol-3-yl)phenoxy]methyl}-2-]4-(trifluoromethyl)phenyl]-1,3-thiazol-5-yl}methyl)sulfanyl]phenoxy}propanoic acid ¹H (CDCl₃) 400 MHz δ 7.98(d, 2H, J=8.03 Hz), 7.92(d, 2H, J=9.06 Hz), 7.67(d, 2H, J=8.03 Hz), 7.18(d, 2H, J=9.06 Hz), 6.96(d, 2H, J=8.75 Hz), 6.74(d, 2H, J=8.75 Hz), 4.98(s, 2H), 4.29(s, 2H), 2.66(s, 3H), 1.57(s, 6H)
MS(ES⁻) M−H=640.00

2-Methyl-2-(4-[({4-{[4-(5-methyl-1,2,4-oxadiazol-3-yl)phenoxy]methyl}-2-phenyl-1,3-thiazol-5-yl)methyl]sulfanyl}phenoxy)propanoic acid ¹H NMR (CDCl₃) 400 MHz 67.93(d, 2H, J=9.06 Hz), 7.86(m, 2H), 7.42(m, 3H), 7.17(d, 2H, J=8.72 Hz), 6.96(d, 2H, J=9.06 Hz), 6.73(d, 2H, J=8.72 Hz), 4.92(s, 2H), 4.27(s, 2H), 2.66(s, 3H), 1.57(s, 6H),
MS(ES⁻) M−H=571.50

{4-[({4-{[4-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}acetic acid ¹H NMR (CDCl₃) 400 MHz δ 7.98(d, 2H, J=8.20 Hz), 7.93(d, 2H, J=9.06 Hz), 7.66(d, 2H, J=8.20 Hz), 7.28(d, 2H, J=8.89 Hz), 6.96(d, 2H, J=9.06 Hz), 6.76(d, 2H, J=8.89 Hz), 4.86(s, 2H), 4.60(s, 2H), 4.25(s, 2H), 2.62(s, 3H),
MS(ES⁻) M−H=611.80

(4-{[(4-{[4-(5-Methyl-1,2,4-oxadiazol-3-yl)phenoxy]methyl}-2-phenyl-1,3-thiazol-5-yl)methyl]sulfanyl}phenoxy)acetic acid ¹H NMR (CDCl₃) 400 MHz 7.92(d, 2H, J=9.06 Hz), 7.83(m, 2H), 7.39(m, 3H), 7.23(d, 2H, J=8.90 Hz), 6.95(d, 2H, J=9.06 Hz), 6.76(d, 2H, J=8.90 Hz), 4.70(s, 2H), 4.54(s, 2H), 4.18(s, 2H), 2.60(s, 3H),
MS(ES⁺) M+H=546.20

2-{4-[({4-{[4-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H NMR (CDCl₃) 400 MHz 67.97(d, 2H, J=8.20 Hz), 7.92(d, 2H, J=8.89 Hz), 7.65(d, 2H, J=8.20 Hz), 7.22(d, 2H, J=8.89 Hz), 6.94(d, 2H, J=8.89 Hz), 6.73(d, 2H, J=8.89 Hz), 4.86(d, 1H, J□.79 Hz), 4.80(d, 1H, J□.96 Hz), 4.66(q, 1H, J=6.89 Hz), 4.26(d, 1H, J□.87 Hz), 4.20(d, 1H, J□.87 Hz), 2.62(s, 3H), 1.58(d, 3H, J=6.89 Hz),
MS(ES⁻) M−H=626.00

2-(4-{[(4-{[4-(5-Methyl-1,2,4-oxadiazol-3-yl)phenoxy]methyl}-2-phenyl-1,3-thiazol-5-yl)methyl]sulfanyl}phenoxy)propanoic acid ¹H NMR (CDCl₃) 400 MHz δ 7.93(d, 2H, J=9.06 Hz), 7.85(m, 2H), 7.41(m, 3H), 7.24(d, 2H, J=8.89 Hz), 6.95(d, 2H, J=9.06 Hz), 6.74(d, 2H, J=8.89 Hz), 4.82(s, 2H), 4.68(q, 1H, J=6.89 Hz), 4.25(d, 1H, J□.87 Hz), 4.19(d, 1H, J□.87 Hz), 2.64(s, 3H), 1.61(d, 3H, J=6.89 Hz),
MS(ES⁻) M−H=558.30

2-{4-[({4-{[4-(4-Acetylphenyl)-1-piperazinyl]methyl}-2-[4-(trifluoromethyl)phenyl]-1,3-thiazol-5-yl}methyl)sulfanyl]phenoxy}-2-methylpropanoic acid $^1$H NMR (CD$_3$OD) 400 MHz δ 8.04(d, 2H, J=8.10 Hz), 7.85(d, 2H, J=9.14 Hz), 7.72(d, 2H, J=8.10 Hz), 7.25(d, 2H, J=8.79 Hz), 6.93(d, 2H, J=9.14 Hz), 6.81(d, 2H, J=8.79 Hz), 4.32(s, 2H), 3.47(s, 2H), 3.35(t, 4H, J=4.91 Hz), 2.59(t, 4H, J=4.91 Hz), 2.47(s, 3H), 1.47(s, 6H),
MS(ES$^-$) M−H=668.1

2-{4-[({4-{[4-(4-Chlorophenyl)-1-piperazinyl]methyl}-2-[4-(trifluoromethyl)phenyl]-1,3-thiazol-5-yl}methyl)sulfanyl]phenoxy}-2-methylpropanoic acid $^1$H NMR (CD$_3$OD) 400 MHz δ 8.05(d, 2H, J=8.10 Hz), 7.73(d, 2H, J=8.10 Hz), 7.24(d, 2H, J=8.79 Hz), 7.15(d, 2H, J=8.97 Hz), 6.90(d, 2H, J=8.97 Hz), 6.80(d, 2H, J=8.79 Hz), 4.30(s, 2H), 3.57(s, 2H), 3.18(t, 4H, J=5.00 Hz), 2.77(t, 4H, J=5.00 Hz), 1.49(s, 6H),
CHN Analysis: Theory (C, 58.04%; H, 4.72%; N, 6.35%) Found (C, 57.65%; H, 4.80%; N, 6.13%)

2-{4-[({4-{[4-(3-Methoxyphenyl)-1-piperazinyl]methyl}-2-[4-(trifluoromethyl)phenyl]-1,3-thiazol-5-yl}methyl)sulfanyl]phenoxy}-2-methylpropanoic acid $^1$H NMR (CD$_3$OD) 400 MHz δ 7.98(d, 2H, J=7.93 Hz), 7.63(d, 2H, J=7.93 Hz), 7.12(m, 3H), 6.73(m, 2H), 6.47(m, 1H), 6.38(m, 2H), 4.18(s, 2H), 3.70(s, 3H), 3.50(s, 2H), 3.14(br s, 4H), 2.76(sbr, 4H), 1.49(s, 6H),
CHN Analysis: Theory (C, 60.26%; H, 5.21%; N, 6.39%) Found (C, 59.83%; H, 5.29%; N, 6.32%)

2-(4-{[(2-(4-Fluorophenyl)-4-{[4-(phenoxycarbonyl)-1-piperazinyl]methyl}-1,3-thiazol-5-yl)methyl]sulfanyl}-2-methylphenoxy)-2-methylpropanoic acid $^1$H NMR (CDCl$_3$) 400 MHz δ 7.93(m, 2H), 7.35(m, 3H), 7.19(m, 4H), 7.08(m, 2H), 6.69(br s, 1H), 4.27(s, 2H), 3.60(br s, 4H), 3.39(s, 2H), 2.54(br s, 4H), 2.14(s, 3H), 1.55(s, 6H),
MS(ES$^-$) M−H=634.1

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid $^1$H NMR (CD$_3$OD) 400 MHz δ 8.05(br s, 2H), 7.66(d, 2H, J=8.28 Hz), 7.15(s, 1H), 6.84(m, 6H), 4.19(s, 2H), 3.44(s, 2H) 3.69(s, 3H), 3.10(m, 4H), 2.82(br s, 4H), 2.10(s, 3H), 1.52(s, 6H),
MS(ES$^+$) M+H=672.2

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-methylphenoxy}-2-methylpropanoic acid $^1$H NMR (CD$_3$OD) 400 MHz δ 7.97(d, 2H, J=8.10 Hz), 7.80(d, 2H, J=8.42 Hz), 7.65(d, 2H, J=8.10 Hz), 7.16(br s, 1H), 7.01(br s, 1H), 6.84(d, 2H, J=8.42 Hz), 6.60(br s, 1H), 4.23(s, 2H), 3.44(s, 2H), 3.27(br s, 4H), 2.55(br s, 4H), 2.44(s, 3H), 2.11(s, 3H), 1.52(s, 6H),
MS(ES$^+$) M+H=684.2

2-{4-[({4-{[4-(3-Methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid $^1$H NMR (CD$_3$OD) 400 MHz δ 7.96(d, 2H, J=8.10 Hz), 7.61(d, 2H, J=8.10 Hz), 7.03(m, 3H), 6.38(m, 4H), 4.18(s, 2H), 3.69(s, 3H), 3.33(s, 2H), 3.11(m, 4H), 2.66(br s, 4H), 2.09(s, 3H), 1.50(s, 6H),
MS(ES$^-$) M−H=670.0

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-methylphenoxy}-2-methylpropanoic acid $^1$H NMR (CD$_3$OD) 400 MHz δ 8.08(d, 2H, J=8.24 Hz), 7.73(d, 2H, J=8.24 Hz), 7.18(br s, 1H), 7.04(br s, 1H), 6.92(m, 4H), 6.72(br s, 1H), 4.26(s, 2H), 3.58(s, 2H), 3.14(br s, 4H), 2.84(br s, 4H), 2.10(s, 3H), 1.60(s, 6H),
MS(ES$^-$) M−H=658.4

2-Methyl-2-{2-methyl-4-[({4-{[4-(phenoxycarbonyl)-1-piperazinyl]methyl}-2-]4-(trifluoromethyl)phenyl]-1,3-thiazol-5-yl}methyl)sulfanyl]phenoxy}propanoic acid $^1$H NMR (CD$_3$OD) 400 MHz δ 8.04(br s, 2H), 7.71(br s, 2H), 7.34(m, 2H), 7.19(m, 3H), 7.04(m, 3H), 4.28(s, 2H), 3.65(s, 2H), 3.45(br s, 4H), 2.47(br s, 4H), 2.12(s, 3H), 1.61(s, 6H),
MS(ES$^-$) M−H=684.0

2-[4-({[4-{[4-(4-Acetylphenyl)-1-piperazinyl]methyl}-2-(4-fluorophenyl)-1,3-thiazol-5-yl]methyl}sulfanyl)-2-methylphenoxy]-2-methylpropanoic acid $^1$H NMR (CD$_3$OD) 400 MHz δ 7.93(m, 2H), 7.86(d, 2H, J=9.16 Hz), 7.18(m, 3H), 7.07(br s, 1H), 6.95(d, 2H, J=9.16 Hz), 6.69(br s, 1H), 4.23(s, 2H), 3.42(m, 6H), 2.69(br s, 4H), 2.49(s, 3H), 2.13(s, 3H), 1.56(s, 6H),
MS(ES$^-$) M−H=632.3

2-(4-{[(2-(4-Fluorophenyl)-4-{[4-(3-methoxyphenyl)-1-piperazinyl]methyl}-1,3-thiazol-5-yl)methyl]sulfanyl}-2-methylphenoxy)-2-methylpropanoic acid $^1$H NMR (CD$_3$OD) 400 MHz δ 7.96(m, 2H), 7.19(m, 3H), 7.12(t, 1H, J=8.24 Hz), 7.01(br s, 1H), 6.66(br s, 1H), 6.54(dd, 1H, J=8.24, 2.20 Hz), 6.47(t, 1H, J=2.20 Hz), 6.43(dd, 1H, J=8.24, 2.20 Hz), 4.20(s, 2H), 3.73(s, 3H), 3.55(s, 2H), 3.24(br s, 4H), 2.91(br s, 4H), 2.13(s, 3H), 1.56(s, 6H),
MS(ES$^-$) M−H=620.0

2-[4-({[4-{[4-(Ethoxycarbonyl)-1-piperazinyl]methyl}-2-(4-fluorophenyl)-1,3-thiazol-5-yl]methyl}sulfanyl)-2-methylphenoxy]-2-methylpropanoic acid $^1$H NMR (CD$_3$OD) 400 MHz δ 7.94(m, 2H), 7.19(m, 3H), 7.00(br s, 1H), 6.66(br s, 1H), 4.23(s, 2H), 4.09(q, 2H, J=7.05 Hz), 3.48(m, 6H), 2.49(br s, 4H), 2.13(s, 3H), 1.56(s, 6H), 1.23(t, 3H, J=7.05 Hz),
MS(ES$^-$) M–H=586.2

2-(4-{[(2-(4-Fluorophenyl)-4-{[4-(isopropoxycarbonyl)-1-piperazinyl]methyl}-1,3-thiazol-5-yl)methyl]sulfanyl}-2-methylphenoxy)-2-methylpropanoic acid $^1$H NMR (CDCl$_3$) 400 MHz δ 7.90(m, 2H), 7.18(m, 3H), 7.07(br s, 1H), 6.74(br s, 1H), 4.64(m, 1H), 4.26(s, 2H), 3.44(t, 4H, J=4.58 Hz), 3.36(s, 2H), 2.43(br s, 4H), 2.13(s, 3H), 1.55(s, 6H), 1.22(d, 6H, J=6.23 Hz),
MS(ES$^-$) M–H=600.0

2-{2-methyl-4-[({4-]4-(trifluoromethoxy)benzyl]-2-[4-(trifluoromethyl)phenyl]-1,3-thiazol-5-yl}methyl)sulfanyl]phenoxy}propanoic acid From ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate (0.167 g, 0.25 mmol), 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid (0.066 g, 41%) was obtained as a white solid.

$^1$H NMR (CD$_3$OD): δ 8.05 (d, 2H), 7.77 (d, 2H), 7.20 (m, 6H), 6.71 (d, 1H), 4.80 (q, 1H), 4.25 (s, 2H), 3.93 (s, 2H), 2.20 (s, 3H), 1.60 (d, 3H); $^{19}$F NMR (CD$_3$OD): δ –59.87 (s) –64.72 (s); MS m/z 628 (M+1); Anal. Calcd. for C$_{29}$H$_{23}$FNOS$_2$: C, 55.5; H, 3.69; N, 2.23%; found: C, 55.27; H, 3.80; N, 2.21%.

{2-methyl-4-[({4-[4-(trifluoromethoxy)benzyl]-2-[4-(trifluoromethyl)phenyl]-1,3-thiazol-5-yl}methyl)sulfanyl]phenoxy}acetic acid From methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate (0.15 g, 0.24 mmol), {2-methyl-4-[({4-[4-(trifluoromethoxy)benzyl]-2-[4-(trifluoromethyl)phenyl]-1,3-thiazol-5-yl}methyl)sulfanyl]phenoxy}acetic acid (0.053 g, 36%) was obtained as a white solid.

$^1$H NMR (CD$_3$OD): δ 8.05 (d, 2H), 7.77 (d, 2H), 7.20 (m, 6H), 6.71 (d, 1H), 4.70 (s, 2H), 4.27 (s, 2H), 3.94 (s, 2H), 2.20 (s, 3H); $^{19}$F NMR (CD$_3$OD): 6–59.88 (s)-64.72 (s); MS m/z 614 (M+1); Anal. Calcd. for C$_{28}$H$_{21}$F$_6$NO$_4$S$_2$: C, 54.81; H, 3.45; N, 2.28%; found: C, 54.64; H, 3.46; N, 2.23%.

2-{2-methyl-4-[({4-(3-thienylmethyl)-2-[4-(trifluoromethyl)phenyl]-1,3-thiazol-5-yl}methyl)sulfanyl]phenoxy}propanoic acid From ethyl 2-{2-methyl-4-[({4-(3-thienylmethyl)-2-[4-(trifluoromethyl)phenyl]-1,3-thiazol-5-yl}methyl)sulfanyl]phenoxy}propanoate (0.255 g, 0.44 mmol), 2-{2-methyl-4-[({4-(3-thienylmethyl)-2-[4-(trifluoromethyl)phenyl]-1,3-thiazol-5-yl}methyl)sulfanyl]phenoxy}propanoic acid (0.058 g, 24%) was obtained as a white solid.

$^1$H NMR (CD$_3$OD): δ 8.05 (d, 2H), 7.77 (d, 2H), 7.33 (t, 1H), 7.18 (m, 2H), 6.95 (m, 2H), 6.69 (d, 1H), 4.80 (q, 1H), 4.22 (s, 2H), 3.95 (s, 2H), 2.20 (s, 3H), 1.61 (d, 3H); MS m/z 550 (M+1); HPLC RT 4.056 (C18 4.2×100 mm, 0–100% ACN/H$_2$O (0.1% TFA), 6 min @ 2 ml/min @254/220 nm). Anal. Calcd. for C$_{26}$H$_{22}$F$_3$NO$_3$S$_3$: C, 56.82; H, 4.03; N, 2.55%; found: C, 56.84; H, 4.16; N, 2.53%.

{2-methyl-4-[({4-(3-thienylmethyl)-2-[4-(trifluoromethyl)phenyl]-1,3-thiazol-5-yl}methyl)sulfanyl]phenoxy}acetic acid From methyl {2-methyl-4-[({4-(3-thienylmethyl)-2-[4-(trifluoromethyl)phenyl]-1,3-thiazol-5-yl}methyl)sulfanyl]phenoxy}acetate (0.259 g, 0.47 mmol), {2-methyl-4-[({4-(3-thienylmethyl)-2-[4-(trifluoromethyl)phenyl]-1,3-thiazol-5-yl}methyl)sulfanyl]phenoxy}acetic acid (0.138 g, 55%) was obtained as a white solid.

$^1$H NMR (CD$_3$OD): δ 8.05 (d, 2H), 7.77 (d, 2H), 7.33 (t, 1H), 7.18 (m, 2H), 6.95 (m, 2H), 6.69 (d, 1H), 4.70 (s, 2H), 4.24 (s, 2H), 3.95 (s, 2H), 2.21 (s, 3H); MS m/z 536 (M+1); HPLC RT 3.979 (C18 4.2×100 mm, 0–100% ACN/H$_2$O (0.1% TFA), 6 min @ 2 ml/min @254/220 nm). Anal. Calcd. for C$_{25}$H$_{20}$F$_3$NO$_3$S$_3$: C, 56.06; H, 3.76; N, 2.61%; found: C, 55.90; H, 3.88; N, 2.62%.

2-{4-[({4-(2-furylmethyl)-2-[4-(trifluoromethyl)phenyl]-1,3-thiazol-5-yl}methyl)sulfanyl]-2-methylphenoxy}propanoic acid From ethyl 2-{4-[({4-(2-furylmethyl)-2-[4-(trifluoromethyl)phenyl]-1,3-thiazol-5-yl}methyl)sulfanyl]-2-methylphenoxy}propanoate (0.091 g, 0.16 mmol), 2-{4-[({4-(2-furylmethyl)-2-[4-(trifluoromethyl)phenyl]-1,3-thiazol-5-yl}methyl)sulfanyl]-2-methylphenoxy}propanoic acid (0.019 g, 22%) was obtained as a white solid.

$^1$H NMR (CD$_3$OD): δ 8.05 (d, 2H), 7.77 (d, 2H), 7.37 (s, 1H), 7.21 (s, 1H), 7.17 (d, 1H), 6.72 (d, 1H), 6.31 (s, 1H), 5.99 (s, 1H), 4.80 (q, 1H), 4.22 (s, 2H), 3.97 (s, 2H), 2.22 (s, 3H), 1.63 (d, 3H); MS m/z 534 (M+1); HPLC RT 3.929 (C18 4.2×100 mm, 0–100% ACN/H$_2$O (0.1% TFA), 6 min @ 2 ml/min @254/220 nm). Anal. Calcd. for C$_{26}$H$_{22}$F$_3$NO$_4$S$_2$: C, 58.53; H, 4.16; N, 2.62%; found: C, 58.04; H, 4.76; N, 2.47%

2-{4-[({4-(3-furylmethyl)-2-[4-(trifluoromethyl)phenyl]-1,3-thiazol-5-yl}methyl)sulfanyl]-2-methylphenoxy}propanoic acid From ethyl 2-{4-[({4-(3-furylmethyl)-2-[4-(trifluoromethyl)phenyl]-1,3-thiazol-5-yl}methyl)sulfanyl]-2-methylphenoxy}propanoate (0.177 g, 0.32 mmol), 2-{4-[({4-(3-furylmethyl)-2-[4-(trifluoromethyl)phenyl]-1,3-thiazol-5-yl}methyl)sulfanyl]-2-methylphenoxy}propanoic acid (0.030 g, 18%) was obtained as a white solid.

$^1$H NMR (CD$_3$OD): δ 8.05 (d, 2H), 7.77 (d, 2H), 7.39 (s, 1H), 7.20 (m, 3H), 6.70 (d, 1H), 6.29 (s, 1H), 4.80 (q, 1H), 4.22 (s, 2H), 3.70 (s, 2H), 2.20 (s, 3H), 1.62 (d, 3H); MS m/z 534 (M+1); HPLC RT 3.966 (C18 4.2×100 mm, 0–100% ACN/H$_2$O (0.1% TFA), 6 min @ 2 ml/min @254/220 nm). Anal. Calcd. for C$_{26}$H$_{22}$F$_3$NO$_4$S$_2$: C, 58.53; H, 4.16; N, 2.62%; found: C, 58.38; H, 4.30; N, 2.54%

2-{2-methyl-4-[({4-(2-thienylmethyl)-2-[4-(trifluoromethyl)phenyl]-1,3-thiazol-5-yl}methyl)sulfanyl]phenoxy}propanoic acid From ethyl 2-{4-[({4-(2-thienylmethyl)-2-[4-(trifluoromethyl)phenyl]-1,3-thiazol-5-yl}methyl)sulfanyl]-2-methylphenoxy}propanoate (0.21 g, 0.36 mmol), 2-{2-methyl-4-[({4-(2-thienylmethyl)-2-[4-(trifluoromethyl)phenyl]-1,3-thiazol-5-yl}methyl)sulfanyl]phenoxy}propanoic acid (0.019 g, 10%) was obtained as a white solid.

$^1$H NMR (CD$_3$OD): δ 8.05 (d, 2H), 7.77 (d, 2H), 7.20 (m, 3H), 6.91 (t, 1H), 6.79 (s, 1H), 6.69 (d, 1H), 4.80 (q, 1H), 4.24 (s, 2H), 4.09 (s, 2H), 2.20 (s, 3H), 1.62 (d, 3H); MS m/z 550 (M+1); HPLC RT 4.074 (C18 4.2×100 mm, 0–100% ACN/H$_2$O (0.1% TFA), 6 min @ 2 ml/min @254/220 nm).

2-methyl-2-{4-[({4-[4-(trifluoromethoxy)benzyl]-2-[4-(trifluoromethyl)phenyl]-1,3-thiazol-5-yl}methyl)sulfanyl]phenoxy}propanoic acid From ethyl 2-methyl-2-{4-[({4-[4-(trifluoromethoxy)benzyl]-2-[4-(trifluoromethyl)phenyl]-1,3-thiazol-5-yl}methyl)sulfanyl]phenoxy}propanoate (0.210 g, 0.32 mmol), 2-methyl-2-{4-[({4-[4-(trifluoromethoxy)benzyl]-2-[4-(trifluoromethyl)phenyl]-1,3-thiazol-5-yl}methyl)sulfanyl]phenoxy}propanoic acid (0.035 g, 17%) was obtained as a cream solid.

$^1$H NMR (CD$_3$Cl$_3$): δ 8.05 (d, 2H), 7.77 (d, 2H), 7.28 (d, 2H), 7.22 (d, 2H), 7.13 (d, 2H), 6.86 (d, 2H), 4.19 (s, 2H), 3.96 (s, 2H), 1.63 (s, 6H); $^{19}$F NMR (CD$_3$Cl$_3$): δ-58.26 (s)-63.16 (s); MS m/z 628 (M+1); HPLC RT 4.526 (C18 4.2×100 mm, 0–100% ACN/H$_2$O (0.1% TFA), 6 min @ 2 ml/min @254/220 nm). Anal. Calcd. for C$_{29}$H$_{23}$F$_6$NO$_4$S$_2$: C, 55.5; H, 3.69; N, 2.23%; found: C, 55.78; H, 3.83; N, 2.10%

{2-Methyl-4-[({4-[(4-methyl-2-thienyl)methyl]-2-[4-(trifluoromethyl)phenyl]-1,3-thiazol-5-yl}methyl)sulfanyl]phenoxy}acetic acid From ethyl {2-methyl-4-[({4-[(4-methyl-2-thienyl)methyl]-2-[4-(trifluoromethyl)phenyl]-1,3-thiazol-5-yl}methyl)sulfanyl]phenoxy}acetate (0.13 g, 0.23 mmol), {2-methyl-4-[({4-[(4-methyl-2-thienyl)methyl]-2-[4-(trifluoromethyl)phenyl]-1,3-thiazol-5-yl}methyl)sulfanyl]phenoxy}acetic acid (0.011 g, 9%) was obtained as a cream solid.

$^1$H NMR (CD$_3$Cl$_3$): δ 8.01 (d, 2H), 7.68 (d, 2H), 7.24 (s, 1H), 7.15 (d, 2H), 6.72 (s, 1H), 6.64 (d, 1H), 4.75 (s, 2H), 4.19 (s, 2H), 4.05 (s, 2H), 2.20 (s, 3H), 2.29 (s, 3H); MS m/z 550 (M+1); HPLC RT 4.366 (C18 4.2×100 mm, 0–100% ACN/H$_2$O (0.1% TFA), 6 min @ 2 ml/min @254/220 nm).

{4-[({4-(2,4-difluorobenzyl)-2-[4-(trifluoromethyl)phenyl]-1,3-thiazol-5-yl}methyl)sulfanyl}-2-methylphenoxy]acetic acid From ethyl {4-[({4-(2,4-difluorobenzyl)-2-[4-(trifluoromethyl)phenyl]-1,3-thiazol-5-yl}methyl)sulfanyl]-2-methylphenoxy}acetate, (0.1 g, 0.17 mmol), {4-[({4-(2,4-difluorobenzyl)-2-[4-(trifluoromethyl)phenyl]-1,3-thiazol-5-yl}methyl)sulfanyl]-2-methylphenoxy}acetic acid (0.027 g, 28%) was obtained as a cream solid.

$^1$H NMR (CD$_3$Cl$_3$): δ 7.99 (d, 2H), 7.68 (d, 2H), 7.22 (s, 1H), 7.13 (m, 2H), 6.79 (m, 2H), 6.62 (d, 1H), 4.70 (s, 2H), 4.20 (s, 2H), 3.86 (s, 2H), 2.23 (s, 3H); $^{19}$F NMR (CD$_3$Cl$_3$): δ-63.15 (s)-114.03 (s)-114.06 (s); MS m/z 566 (M+1); HPLC RT 4.356 (C18 4.2×100 mm, 0–100% ACN/H$_2$O (0.1% TFA), 6 min @ 2 ml/min @254/220 nm). Anal. Calcd. for C$_{27}$H$_{20}$F$_5$NO$_3$S$_2$.0.5H$_2$O: C, 56.44; H, 3.68; N, 2.44%; found: C, 56.40; H, 3.79; N, 2.20%

{4-[({4-(4-methoxybenzyl)-2-[4-(trifluoromethyl)phenyl]-1,3-thiazol-5-yl}methyl)sulfanyl]-2-methylphenoxy}acetic acid From ethyl {4-[({4-(4-methoxybenzyl)-2-[4-(trifluoromethyl)phenyl]-1,3-thiazol-5-yl}methyl)sulfanyl]-2-methylphenoxy}acetate (0.160 g 0.27 mmol), {4-[({4-(4-methoxybenzyl)-2-[4-(trifluoromethyl)phenyl]-1,3-thiazol-5-yl}methyl)sulfanyl]-2-methylphenoxy}acetic acid (0.005 g, 3%) was obtained as a cream solid.

$^1$H NMR (CD$_3$Cl$_3$): δ 8.01 (d, 2H), 7.68 (d, 2H), 7.23 (s, 1H), 7.11 (m, 3H), 6.82 (d, 2H), 6.62 (d, 1H), 4.90 (s, 2H), 4.17 (s, 2H), 3.90 (s, 2H), 3.80 (s, 3H), 2.25 (s, 3H); MS m/z 560.

2-Methyll-2-{4-[({4-[(4-methyl-2-thienyl)methyl]-2-[4-(trifluoromethyl)phenyl]-1,3-thiazol-5-yl}methyl)sulfanyl]phenoxy}propanoic acid From ethyl 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoate (0.17 g 0.29 mmol), 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoic acid (0.002 g, 1.2%) was obtained as a cream solid.

$^1$H NMR (CD$_3$Cl$_3$): δ 8.01 (d, 2H), 7.78 (d, 2H), 7.28 (d, 2H), 6.86 (d 2H), 6.73 (s, 1H), 6.63 (s, 1H), 4.18 (s, 2H), 3.99 (s, 2H), 2.21(s, 3H), 1.63 (s, 6H); MS m/z 564 (M+1); HPLC RT 4.413 (C18 4.2×100 mm, 0–100% ACN/H$_2$O (0.1% TFA), 6 min @ 2 ml/min @254/220 nm).

The following is an alternative procedure for the synthesis of Ethyl 2-{4-[({4-(hydroxymethyl)-2-[4-(trifluoromethyl)phenyl]-1,3-thiazol-5-yl}methyl)sulfanyl]phenoxy}-2-methylpropanoate

Ethyl 2-[4-(chlorosulfonyl)phenoxy]-2-methylpropanoate

Cool a solution of the ethyl 2-methyl-2-phenoxypropanoate, (1.0 wt, 1.0 eq), in dichloromethane (7.5 vols) to 0° C. with stirring under a nitrogen atmosphere. Slowly add neat chlorosulfonic acid (0.78 wt, 1.4 eq) to the reaction mixture at a rate such that the reaction temperature never rises above 5.0° C. The addition typically takes 30 minutes to complete. Following the completion of the addition, stir the reaction mixture at 0–1° C. Follow the course of the reaction by HPLC. The reaction is typically complete after 30 minutes. At this point, slowly treat the reaction mixture with DMF (1.75 L) (1.40 wt, 4.0 eq). The addition of DMF to the reaction mixture is very exothermic. Adjust the rate of addition so that the reaction temperature never rises above 10.0° C. The addition of DMF to the reaction mixture takes approximately 30 minutes. Following the completion of the DMF addition, re-cool the reaction mixture to 0.5 to 1° C. Treat the cooled reaction mixture with neat thionyl chloride (619 mL, 1.01 kg) (0.86 wt, 1.5 eq). Adjust the rate of addition so that the process temperature never reaches 5.0° C. The addition of thionyl chloride to the reaction mixture is not very exothermic at all. Hence, the addition of thionyl chloride is typically complete in 5 minutes. Following the completion of the DMF addition, warm the reaction mixture to 20° C. with stirring. Follow the course of the reaction via HPLC. After 2.0 h, the reaction is typically complete. At this point, cool the reaction mixture to 0–1° C. and carefully treat the reaction mixture with water (8.8 L) (7.5 vols). [Note: The addition of water may be somewhat exothermic depending upon how much unreacted thionyl chloride is left in the reaction mixture.] Separate the organic layer and wash the organic layer with aqueous 0.1N HCl solution (2×7.5 vols). Separate the organic layer, concentrate the organic layer to a minimum stir volume, treat the organic layer with isopropyl acetate (1×5.0 vols) and then concentrate the resulting solution via vacuum distillation to afford the titled compound as a translucent bronze colored oil.

Yield (% theory): 85–98%.

$^1$H NMR (400 MHz, CDCl$_3$) δ 7.90 (2H, bd), 6.90 (2H, bd), 4.22 (2H, q, J=7.0 Hz), 1.67 (6H, s), 1.20 (3H, t, J=7.0 Hz)

Diethyl 2-[4-(trifluoromethyl)phenyl]-1,3-thiazole-4,5-dicarboxylate

Heat a solution of the 4-fluorobenzenecarbothioamide, (1.0 wt, 1.0 eq), in absolute ethanol (3 vols) to 50° C. with stirring under a nitrogen atmosphere. Add diethyl 2-chloro-3-oxosuccinate (1.2 wt, 1.1 eq), in one portion. Some warming is seen during the addition which is typically complete in less then 30 minutes. After the addition is complete, heat the reaction mixture to about 68° C. Hold the reaction mixture at 67–69° C. for 6 h and then cool the reaction mixture to ambient temperature overnight. Dilute the resulting yellow hazy solution slowly with aqueous 50% ethanol solution (3 vols), stir at ambient temperature for 4 h, and then cool the reaction mixture to <5° C. Filter the solids. Wash the wet cake with aqueous 50% ethanol solution (3 vols) and dry at 45° C. to constant weight to afford the title compound as an off-white to white colored solid.

Yield (% theory): 78–83%.

$^1$H NMR (300 MHz, CDCl$_3$) δ 8.14 (2H, d, J=8.2 Hz), 7.76 (2H, d, J=8.2 Hz), 4.52 (2H, q, J=7.1 Hz), 4.43 (2H, q, J=7.1 Hz), 1.47 (3H, t, J=7.1 Hz), 1.42 (3H, t, J=7.1 Hz).

{5-Hydroxymethyl-2-[4-(trifluoromethyl)phenyl]-1,3-thiazol-4-yl}methanol

To a suspension of lithium aluminum hydride (0.14 wt) in THF (3.4 vols), add a solution of the diethyl 2-[4-(trifluoromethyl)phenyl]-1,3-thiazole-4,5-dicarboxylate (1.0 wt, 1.0 eq), dissolved in THF (2 vols) at a rate such that the temperature of the reaction mixture is maintained at below −10° C. The addition time is 1.5–3.0 hr. After the addition is complete, stir the reaction mixture at ambient temperature for 18 h. Quench the reaction by adding aqueous 16% sulfuric acid (2.4 vols). Charge ethyl acetate (5 vols) with stirring to the reaction mixture followed with water (5 vols). Filter the resulting two phase mixture through celite (0.4 wt). Separate the layers and wash the organic layer with water (4×4 vols) and with brine (2×4 vol). Reduce the total volume of the reaction mixture via vacuum distillation to leave the solid suspended in ethyl acetate (1–1.5 vols). Dilute the slurry with dichloromethane (5 vols) and stir the suspension for at least 6 h. Filter the tan-colored solid. Wash the wet cake with dichloromethane (2 vols) and dry the wet cake at 45° C. under mild vacuum to afford the title compound as an off-white solid.

Yield (% theory): 65–85%.

$^1$H NMR (300 MHz, CD$_3$OD) δ 8.15(2H, d, J=8.3 Hz), 7.79(2H, d, J=8.3 Hz), 4.92 (2H, s), 4.90 (2H, s), 4.77(2H, s).

Ethyl 2-{4-[({4-(hydroxymethyl)-2-[4-(trifluoromethyl)phenyl]-1,3-thiazol-5-yl}methyl)-sulfanyl]phenoxy}-2-methylpropanoate To a stirred suspension of zinc dust (0.75 wt, 3.5 eq) in isopropyl acetate (5 vols), add a solution of DME (0.5 vol) and water (0.5 eq). Heat the resulting solution from room temperature to 40° C. Treat the reaction mixture with a solution of ethyl 2-[4-(chlorosulfonyl)phenoxy]-2-methylpropanoate (1.0 wt, 1.0 eq) and dichlorodimethylsilane (0.32 wt, 0.75 eq) in isopropyl acetate (3 vols) over a period of 2 h as this addition is mildly exothermic. After the addition is complete, increase the process temperature to 60° C. Treat the suspension at 60° C. slowly with neat dichlorodimethylsilane (0.95 wt, 2.3 eq) over a period of 1 h. When the reduction of the sulfonylchloride is deemed complete (by HPLC), treat the reaction mixture with {5-Hydroxymethyl-2-[4-(trifluoromethyl)phenyl]-1,3-thiazol-4-yl}methanol (1.04 wt, 1.1 eq) in one portion at 60° C. After the addition is complete, increase the process temperature to 89° C. and stir the reaction mixture at this temperature for 3 to 5 h then cool to ambient temperature. Filter the reaction mixture to remove unreacted zinc residue, wash the filtrate with water (2×8 vols) and concentrate the organic layer to about 3.5 volumes via vacuum distillation at 40–45° C. Dissolve the resultant, somewhat syrupy, residue in ethanol (2 vols) and treat the resulting solution with iso-octane (2 vols). Cool the clear yellow-tinted solution to ambient temperature to induce crystallization of the product. Collect the solid via filtration. Wash the wet cake with iso-octane/EtOH (9:1, 1 vol) and dry under vacuum (~21 Torr) at 60° C. for 12 h to afford the title compound as an off-white solid.

Yield (% theory): 45–55%.

$^1$H NMR (400 MHz, CDCl$_3$) δ 7.96 (2H, d, J=8.5 Hz), 7.66 (2H, d, J=8.5 Hz), 7.24 (2H, d, J=8.8 Hz), 6.74 (2H, d, J=8.8 Hz), 4.45 (2H, d, J=3.5 Hz), 4.19 (2H, q, J=7.2 Hz), 4.16 (2H, s), 2.30 (1H, br s), 1.57 (6H, s), 1.20 (3H, t, J=7.2 Hz).

The following intermediates and ligands were prepared for the binding and transfection assays described below:

i) 2-{2-methyl-4-[({4-methyl-2-[4-(trifluoromethyl)phenyl]-1,3-thiazol-5-yl}methyl)sulfanyl]phenoxy}acetic acid This compound was used as a PPARdelta reference in the transfection assays described below and was prepared according to the following method:

Intermediate A

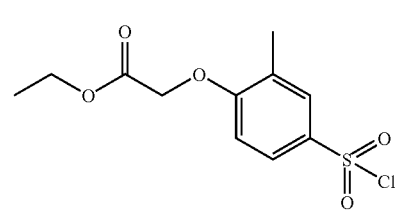

Chlorosulfonic acid (15 mL) was cooled to 0° C. then 10.0 g (0.05M) of ethyl (2-methylphenoxyacetate was added over 10 m. The reaction mixture was stirred at 0–5° C. for 30 m, the bath was removed and stirring continued for 2 h. The reaction mixture was poured into ice, forming a white solid which was washed with ice water and dried under high vacuum affording the title compound (12.846 g, 86%).

Intermediate B:

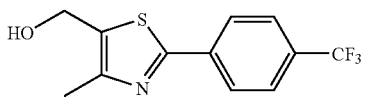

To a well stirred solution of LiAlH$_4$ (1.52 g, 40 mmol) in dry THF (50 mL) at 0° C., was slowly added a solution of ethyl 4-methyl-2-[4-(trifluoromethyl)phenyl]-thiazole-5-carboxylate (12.6 g, 40 mmol) in dry THF (50 mL). The mixture was stirred at room temperature for 2 hs. The reaction was quenched by slow addition at 0° C. of water (2 mL), 5N NaOH (2 mL) and water (6 mL). The precipitate was filtered, washed with EtOAc, MeOH, CH$_2$Cl$_2$ and THF. After evaporation, a yellow solid was obtained, that was crystallyzed from MeOH-water to afford intermediate 1 depicted above (9.90 g, 36 mmol, 90%) as a yellow solid mp 120–122° C.

Intermediate C:

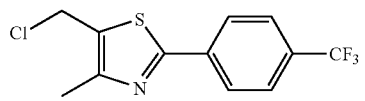

To a cold (0° C.) stirred solution of intermediate 1 (8.2 g, 30 mmol) and Et$_3$N (6.07 g, 8.36 mL, 60 mmol), in dry CH$_2$Cl$_2$ (120 mL) was slowly added MeSO$_2$Cl (5.49 g, 3.71 mL, 48 mmol). After 2 hs at 0° C. more Et$_3$N (6 mmol) and MeSO$_2$Cl (4.8 mmol) were added. After 2 more h a tLc (hexane:EtOAc, 1:1) showed complete reaction. The reaction mixture was diluted with CH$_2$Cl$_2$ (120 mL) and washed with NaHCO$_3$ (sat.) (2×240 mL) and water (2×240 mL), dried, filtered and evaporated to afford intermediate 2 (8.0 g, 27 mmol, 90%) as a yellow solid.

2-{2-methyl-4-[({4-methyl-2-[4-(trifluoromethyl) phenyl]-1,3-thiazol-5-yl}methyl)sulfanyl] phenoxy}acetic acid

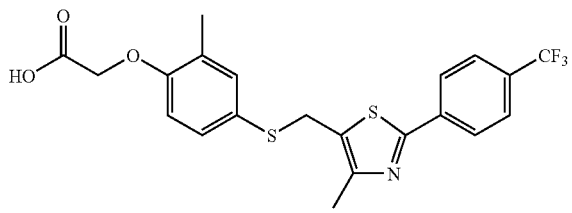

Intermediate A (4.68 g, 16 mM) was refluxed with 9.6 g of tin powder in ethanol (20 mL) and dioxane/HCl (20 mL). After 3 h the reaction mixture was poured into ice and CH$_2$Cl$_2$ (200 mL) and filtered. The phases were separated and the aqueous layer was extracted 2×50 mL CH$_2$Cl$_2$. The combined organic layers were dried (MgSO$_4$), filtered and evaporated to yield 3.5 g (97%). This material readily forms disulfides and therefore was used immediately. It was dissolved in acetonitrile (50 mL) with intermediate C (4.0 g, 14.0 mM) and Cs$_2$CO$_3$ (10.1 g, 31.0 mM) and stirred for 1 h then diluted with ether (200 mL) and water (200 mL). The phases were separated and the organic phase was washed 2×NaOH 0.1N (50 mL), dried (MgSO$_4$), filtered and evaporated to afford crude product (6.57 g,) which was slurried in hexane:ether (1:1) and filtered to yield pure intermediate D (5.0 g, 74%). This material was hydrolyzed as described below to prepare the title compound. A solution of the corresponding ester (Intermediate D) (1 mmol) in THF (10 mL) (in some cases few drops of MeOH were added to help solubility), was treated with 1N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

Binding Assay:

Compounds were tested for their ability to bind to hPPAR gamma hPPARalpha or PPARdelta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand (3H-BRL 49653 for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 (see Brown, P. J et al. *Chem. Biol.*, 4, 909–918 (1997). For the structure and synthesis of this ligand) for PPAR delta) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent Ki values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. *Anal. Biochem.*, 257, 112–119 (1998)).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), *J. Biol. Chem.*, 270, 12953–6 (1995). The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the beta-galactosidase activity as an internal standard (see, for example, Kliewer, S. A., et. al. Cell 83, 813–819 (1995)). Rosiglitazone (BRL 49653) was used as a positive control in the hPPAR gamma assay. The positive control for PPAR delta assays was 2-{2-methyl-4-[({4-methyl-2-{trifluoromethyl)phenyl]-1,3-thiazol-5-yl}methyl)sulfanyl]phenoxy}acetic acid.

The positive control in the hPPARalpha transfection assay was 2-[4-(2-(3-(4-fluorophenyl)-1-heptylureido)ethyl)-phenoxy]-2-methylpropionic acid, which can be prepared as described in Brown, Peter J., et. al. *Synthesis* Issue 7, 778–782 (1997), or patent publication WO 9736579.

All of the above examples of this invention were agonists of at least one hPPAR subtype.

What is claimed:
1. A compound of the structure:

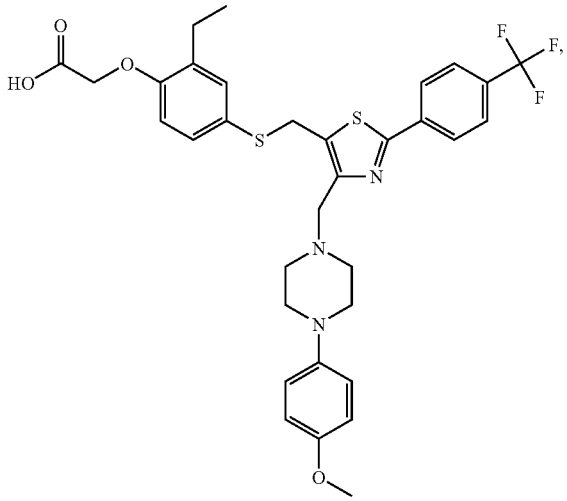

also known as {2-Ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid, or a salt thereof.

2. A pharmaceutical composition comprising a compound according to claim 1, and a pharmaceutically acceptable diluent or carrier.

3. A method of treating a disease or condition in a patient, wherein the disease or condition is selected from dyslipidemia, syndrome X, hypercholesteremia, atherosclerosis, arteriosclerosis, hypertriglyceridemia, type II diabetes mellitus, type I diabetes, insulin resistance, hyperlipidemia, inflammation, psoriasis, and obesity, comprising the administration of a therapeutically effective amount of a compound according to claim 1.

* * * * *

UNITED STATES PATENT AND TRADEMARK OFFICE
CERTIFICATE OF CORRECTION

PATENT NO. : 7,229,998 B2  Page 1 of 1
APPLICATION NO. : 11/550060
DATED : June 12, 2007
INVENTOR(S) : Cadilla et al.

It is certified that error appears in the above-identified patent and that said Letters Patent is hereby corrected as shown below:

On the Title page:

Item (63) should read as follows:

(63)           Related U.S. Application Data
    Continuation of application No. 10/451,295 filed October 31, 2003,
    now abandoned, which is a 371 application of PCT/US01/51056 filed
    December 19, 2001.

Item (56) should read as follows:

(56)           References Cited

-- FOREIGN PATENT DOCUMENTS
    WO        00/08002      2/2000
    WO        02/062774    8/2002
    WO        01/00603      1/2001
    WO        01/40207      6/2001
    WO        02/50048      6/2002 --

Signed and Sealed this

Sixth Day of April, 2010

David J. Kappos
*Director of the United States Patent and Trademark Office*